(12) United States Patent
Moini et al.

(10) Patent No.: US 8,383,065 B2
(45) Date of Patent: *Feb. 26, 2013

(54) TEST MODULE WITH INTEGRAL PHOTOSENSOR FOR ELECTROCHEMILUMINESCENT DETECTION OF HYBRIDIZATION

(75) Inventors: Alireza Moini, Rozelle (AU); Mehdi Azimi, Rozelle (AU); Kia Silverbrook, Rozelle (AU)

(73) Assignee: Silverbrook Research Pty Ltd

( * ) Notice: Subject to any disclaimer, the term of this patent is extended or adjusted under 35 U.S.C. 154(b) by 0 days.

This patent is subject to a terminal disclaimer.

(21) Appl. No.: 13/150,057

(22) Filed: Jun. 1, 2011

(65) Prior Publication Data
US 2011/0312719 A1 Dec. 22, 2011

Related U.S. Application Data

(60) Provisional application No. 61/356,018, filed on Jun. 17, 2010, provisional application No. 61/437,686, filed on Jan. 30, 2011.

(51) Int. Cl.
*B01L 3/00* (2006.01)

(52) U.S. Cl. ......... 422/507; 422/52; 422/73; 422/82.01; 422/82.05; 422/82.06; 422/82.07; 422/82.08; 422/82.09; 422/82.11; 422/407; 422/502; 422/503; 422/504; 436/17; 436/43; 436/63; 436/94; 436/149; 436/164; 436/172; 436/174; 436/177; 436/517; 436/518; 436/805; 436/809; 435/4; 435/6.1; 435/6.11; 435/6.12; 435/7.1; 435/7.92; 435/29; 435/288.5; 506/30; 250/214.1; 250/251; 250/459.1; 250/573; 250/576; 530/408; 714/752

(58) Field of Classification Search ............. 422/52, 422/73, 82.01, 82.05, 82.06, 82.07, 82.08, 422/82.09, 82.11, 407, 501, 502, 503, 504, 507; 436/17, 43, 63, 94, 149, 164, 172, 174, 436/177, 517, 518, 805, 809; 435/4, 6.1, 435/6.11, 6.12, 7.1, 7.92, 29, 288.5; 250/214.1, 250/251, 459.1, 573, 576; 506/30; 530/408; 714/752

See application file for complete search history.

(56) References Cited

U.S. PATENT DOCUMENTS

| | | | |
|---|---|---|---|
| 5,527,710 A | 6/1996 | Nacamulli et al. | |
| 6,207,369 B1 | 3/2001 | Wohlstadter et al. | |
| 7,815,868 B1 | 10/2010 | Jones et al. | |
| 2003/0143591 A1 | 7/2003 | Davies et al. | |
| 2003/0186222 A1 | 10/2003 | Paul, III | |
| 2004/0115794 A1 | 6/2004 | Brubaker | |
| 2007/0074972 A1 | 4/2007 | Nassef et al. | |
| 2008/0176757 A1 | 7/2008 | Hassibi et al. | |

OTHER PUBLICATIONS

Dill, Kilian et al, "Microarrays: Preparation, Microfluidics, Detection Methods, and Biological Applications", Springer, New York, 2008, ISBN 0387727167, 9780387727165.
U.S. Appl. No. 13/149,971, filed Dec. 22, 2011, Silverbrook, Kia.
U.S. Appl. No. 13/149,973, filed Dec. 22, 2011, Silverbrook, Kia.
U.S. Appl. No. 13/149,975, filed Dec. 22, 2011, Moini, Alireza.
U.S. Appl. No. 13/149,979, filed Dec. 22, 2011, Azimi, Mehdi.

(Continued)

*Primary Examiner* — Dennis M White

(57) ABSTRACT

A test module for detecting target nucleic acid sequences in a fluid, the test module having an outer casing having a receptacle for receiving the fluid containing the target nucleic acid sequences, electrochemiluminescent (ECL) probes having an ECL luminophore for emitting photons when in an excited state and a functional moiety for quenching photon emission from the ECL luminophore by resonant energy transfer, electrodes for receiving an electrical pulse to excite the ECL luminophores, and, a detection photosensor for exposure to the photons emitted by the ECL luminophores.

19 Claims, 107 Drawing Sheets

OTHER PUBLICATIONS

U.S. Appl. No. 13/149,981, filed Dec. 22, 2011, Silverbrook, Kia.
U.S. Appl. No. 13/149,984, filed Dec. 22, 2011, Moini, Alireza.
U.S. Appl. No. 13/149,986, filed Dec. 22, 2011, Azimi, Mehdi.
U.S. Appl. No. 13/149,990, filed Dec. 22, 2011, Silverbrook, Kia.
U.S. Appl. No. 13/149,995, filed Dec. 22, 2011, Azimi, Mehdi.
U.S. Appl. No. 13/150,001, filed Dec. 22, 2011, Silverbrook, Kia.
U.S. Appl. No. 13/150,006, filed Dec. 22, 2011, Azimi, Mehdi.
U.S. Appl. No. 13/150,008, filed Dec. 22, 2011, Silverbrook, Kia.
U.S. Appl. No. 13/150,011, filed Dec. 22, 2011, Azimi, Mehdi.
U.S. Appl. No. 13/150,017, filed Dec. 22, 2011, Silverbrook, Kia.
U.S. Appl. No. 13/150,021, filed Dec. 22, 2011, Azimi, Mehdi.
U.S. Appl. No. 13/150,024, filed Dec. 22, 2011, Moini, Alireza.
U.S. Appl. No. 13/150,030, filed Dec. 22, 2011, Azimi, Mehdi.
U.S. Appl. No. 13/150,033, filed Dec. 22, 2011, Silverbrook, Kia.
U.S. Appl. No. 13/150,038, filed Dec. 22, 2011, Azimi, Mehdi.
U.S. Appl. No. 13/150,041, filed Dec. 22, 2011, Silverbrook, Kia.
U.S. Appl. No. 13/150,046, filed Dec. 22, 2011, Silverbrook, Kia.
U.S. Appl. No. 13/150,057, filed Dec. 22, 2011, Moini, Alireza.
U.S. Appl. No. 13/150,061, filed Dec. 22, 2011, Azimi, Mehdi.
U.S. Appl. No. 13/150,064, filed Dec. 22, 2011, Silverbrook, Kia.
U.S. Appl. No. 13/150,068, filed Dec. 22, 2011, Azimi, Mehdi.
U.S. Appl. No. 13/150,073, filed Dec. 22, 2011, Silverbrook, Kia.
U.S. Appl. No. 13/150,077, filed Dec. 22, 2011, Azimi, Mehdi.
U.S. Appl. No. 13/150,084, filed Dec. 22, 2011, Moini, Alireza.
U.S. Appl. No. 13/150,088, filed Dec. 22, 2011, Azimi, Mehdi.
U.S. Appl. No. 13/150,091, filed Dec. 22, 2011, Azimi, Mehdi.
U.S. Appl. No. 13/150,093, filed Dec. 22, 2011, Facer, Geoffrey.
U.S. Appl. No. 13/150,095, filed Dec. 22, 2011, Azimi, Mehdi.
U.S. Appl. No. 13/150,239, filed Dec. 22, 2011, Facer, Geoffrey R.
U.S. Appl. No. 13/150,248, filed Dec. 22, 2011, Azimi, Mehdi.
U.S. Appl. No. 13/150,251, filed Dec. 22, 2011, Facer, Geoffrey R.
U.S. Appl. No. 13/150,255, filed Dec. 22, 2011, Azimi, Mehdi.
U.S. Appl. No. 13/150,257, filed Dec. 22, 2011, Moini, Alireza.
U.S. Appl. No. 13/150,258, filed Dec. 22, 2011, Moini, Alireza.
U.S. Appl. No. 13/150,259, filed Dec. 22, 2011, Facer, Geoffrey R.
U.S. Appl. No. 13/150,260, filed Dec. 22, 2011, Silverbrook, Kia.
U.S. Appl. No. 13/150,261, filed Dec. 22, 2011, Silverbrook, Kia.
U.S. Appl. No. 13/150,262, filed Dec. 22, 2011, Moini, Alireza.
U.S. Appl. No. 13/150,263, filed Dec. 22, 2011, Azimi, Mehdi.
U.S. Appl. No. 13/150,264, filed Dec. 22, 2011, Facer, Geoffrey R.
U.S. Appl. No. 13/150,266, filed Dec. 22, 2011, Facer, Geoffrey R.
U.S. Appl. No. 13/150,267, filed Dec. 22, 2011, Azimi, Mehdi.
U.S. Appl. No. 13/150,268, filed Dec. 22, 2011, Moini, Alireza.
U.S. Appl. No. 13/150,270, filed Dec. 22, 2011, Silverbrook, Kia.
U.S. Appl. No. 13/150,272, filed Aug. 3, 2012, Azimi, Mehdi.
Wang et al ("A Controllable Solid-State RU(bpy)32+ Electrochemiluminescence Film Based on Conformation Change of Ferrocene-Labeled DNA Molecular Beacon", Langmuir, Jan. 29, 2008, 24, pp. 2200-2205).
Tokuda et al. ("Optical and electrochemical dual-image CMOS sensor for on-chip biomolecular sensing applications" Sensors and Actuators A, Oct. 10, 2006, 135, 315-322).
Miao et al ("Electrogenerated Chemiluminescence Determination of Immobilized DNA and C-Reactive Protein on Au (111) Electrodes Using Tris(2,2'-bipyridyl)ruthenium(II) Labels" Anal. Chem. 2003, 75, 5825-5834).
Fiaccabrino et al ("On Chip Detection of Electrogenerated Chemiluminescence of Ru(bpy)—at Pt Interdigitated Microelectrode Arrays" International Conference on Solid-state Sensors and Actuators, Chicago, Jun. 16-19, 1997, pp. 171-174).
Mastrangelo et al ("Microfabricated Devices for Genetic Diagnostics" Proceedings of the IEEE, vol. 86, No. 8, Aug. 1998).
Man et al ("Microfluidic Plastic Capillaries on Silicon Substrates: A new Inexpensive Technology for Bioanalysis Chips" Presented at the 1997 MEMS Conference, Jan. 26-30, 1997, Nagoya, Japan p. 1-6).
Eltoukhy et al, "A 0.18-m CMOS Bioluminescence Detection Lab-on-Chip" Journal of Solid-State Circuits, Vol. 41, No. 3, Mar. 2006, pp. 651-662.
Wilson et al, "Photoluminescence and electrochemiluminescence of a Ru(II)(bpy) 3-quencher dual-labeled oligonucleotide probe", Chem.Commun., 2003, 2710-2711.

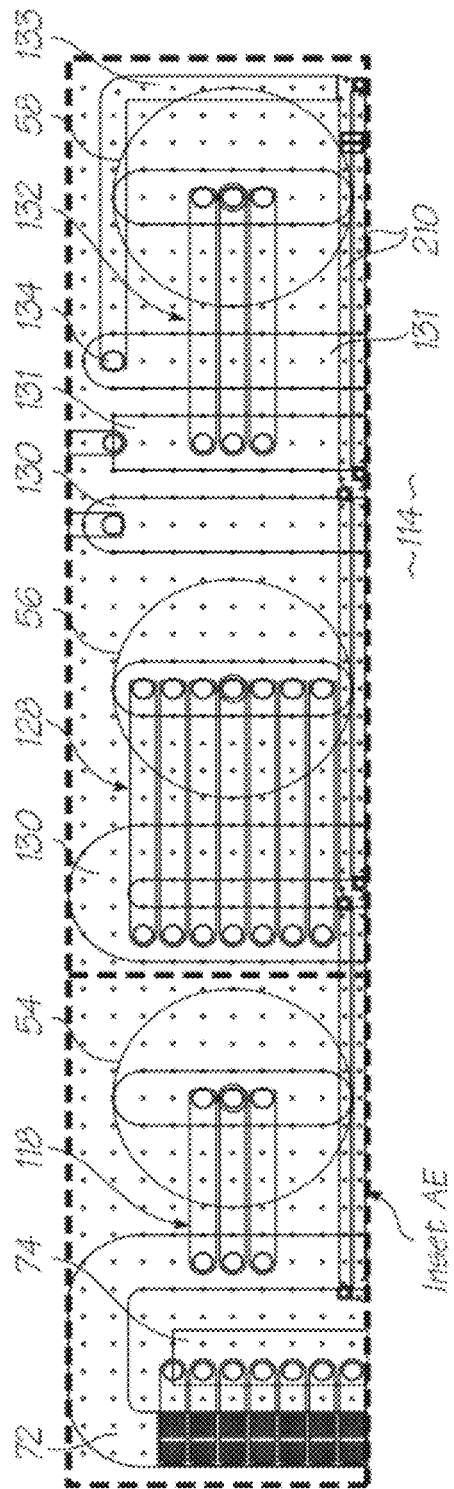
FIG. 13 (Inset AA)
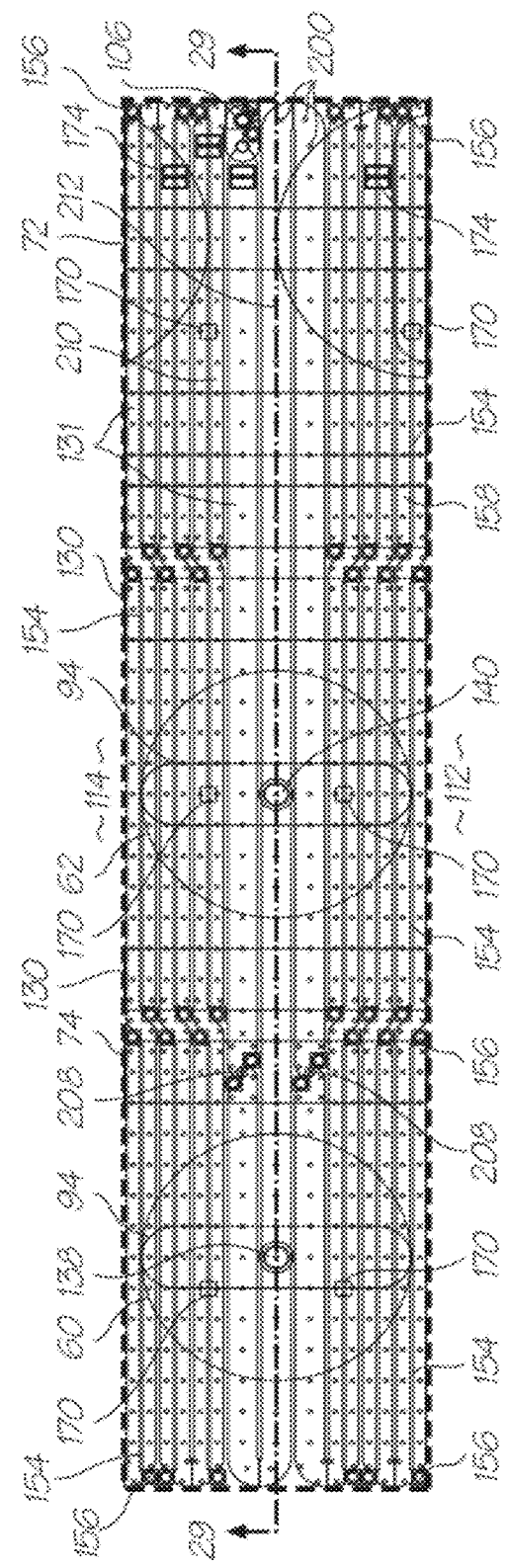
FIG. 14 (Inset AB)

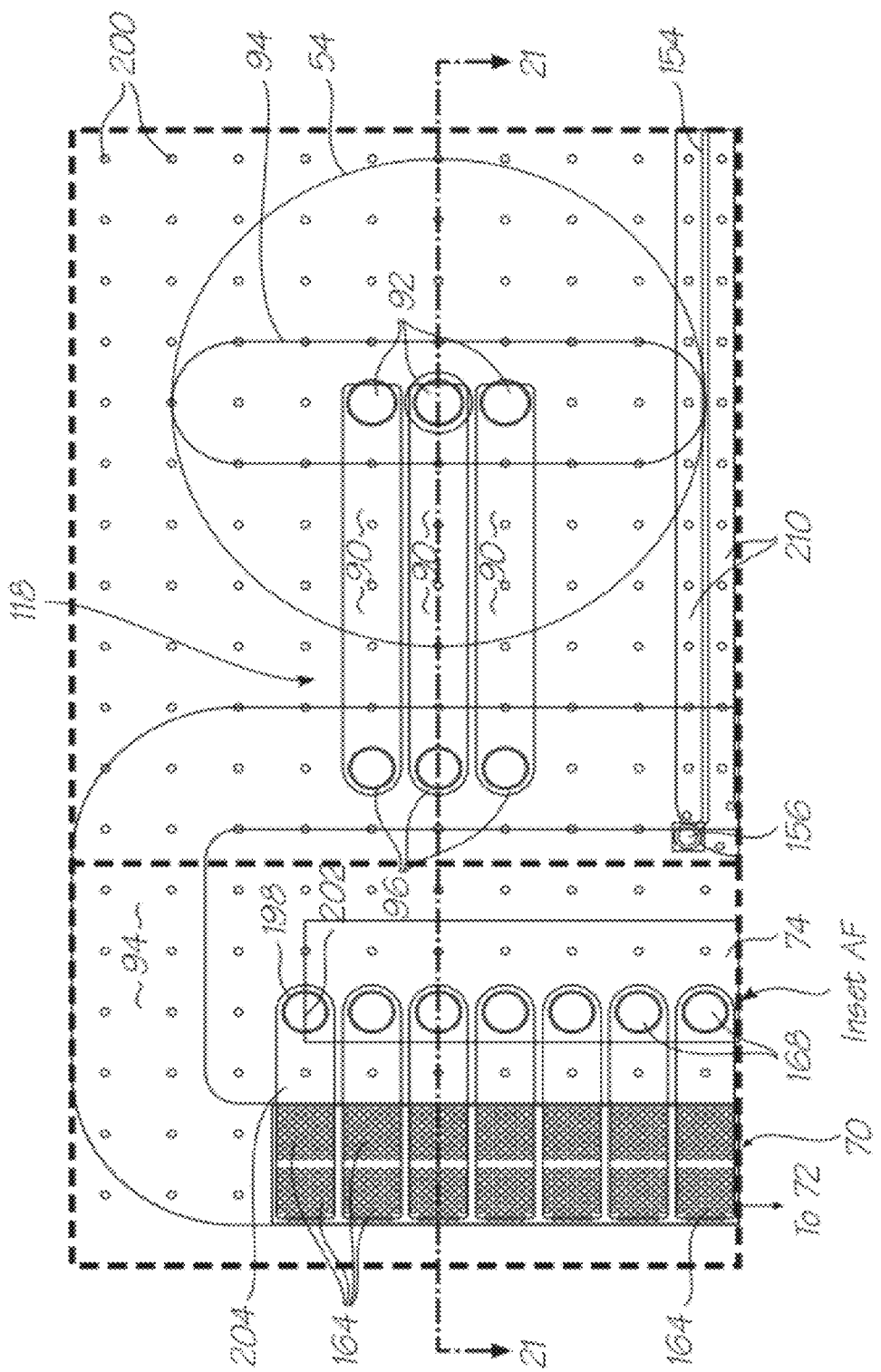
FIG. 15 (Inset AE)

(Inset AE)

(Inset AE)

(Inset AE)

(Inset AE)

(Inset AE)

(Inset AE)

(Inset AB)

(Inset AB)

(Inset AI)

(Inset AB)

(Inset AB)

(Inset AB)

(Inset AB)

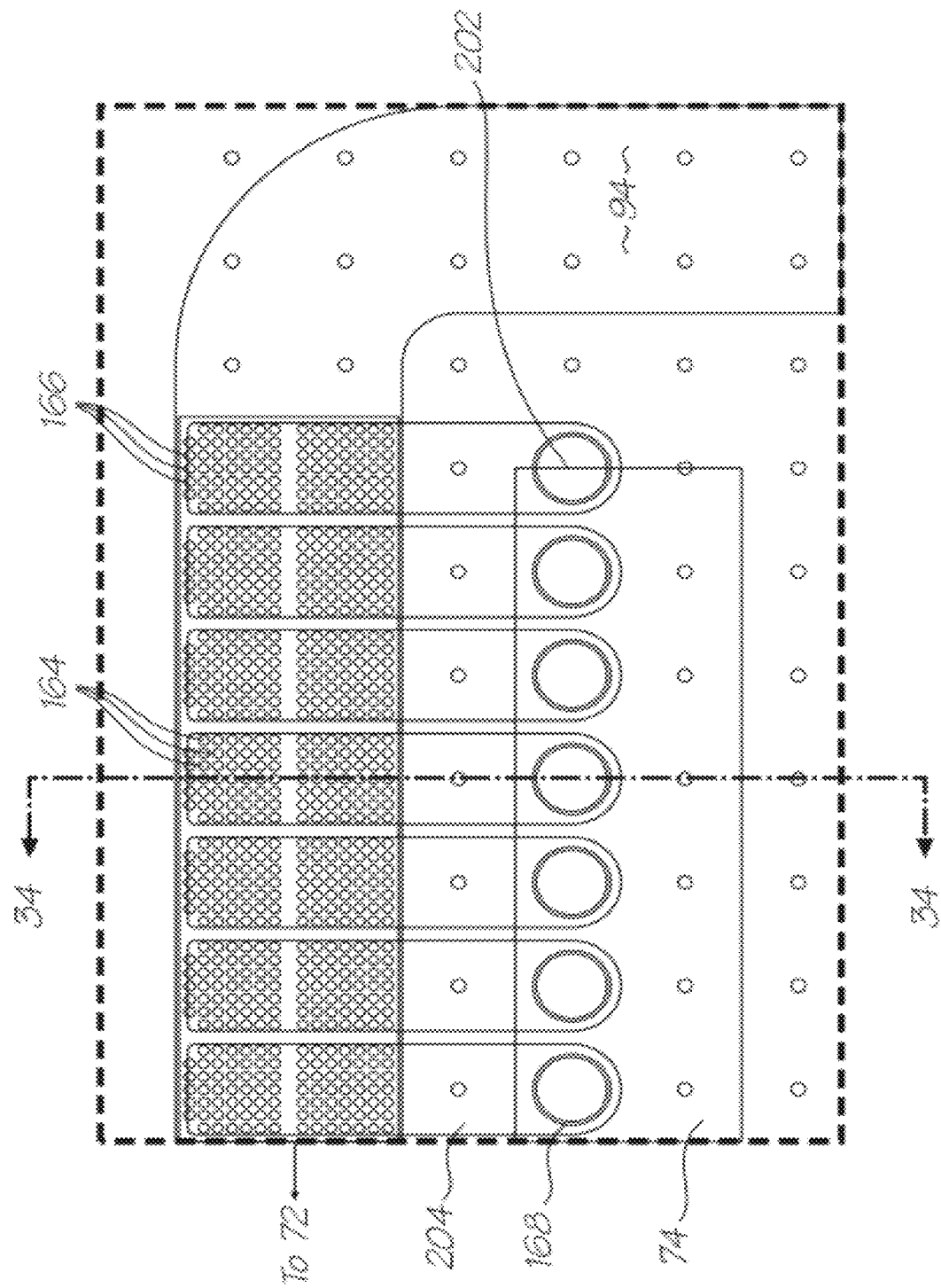
FIG. 33 (Inset AF)

FIG. 35 (Inset AC)

(Inset AC)

(Inset AC)

(Inset AK)

(Inset AC)

(Inset AC)

(Inset AC)

(Inset AL)

(Inset AC)

(Inset AM)

(Inset AC)

(Inset AN)

(Inset AC)

(Inset AC)

(Inset AC)

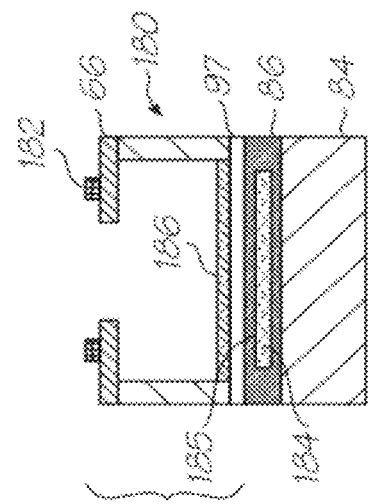
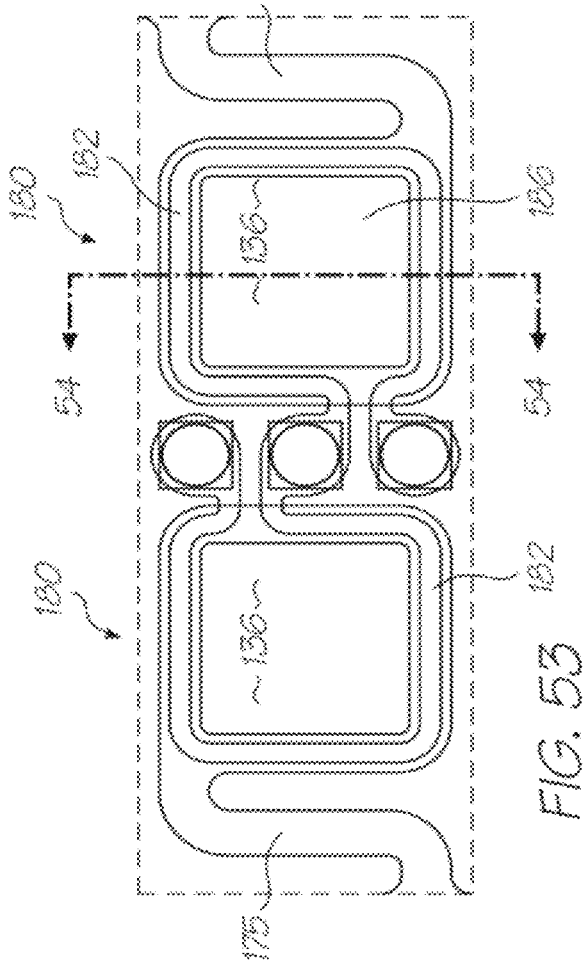
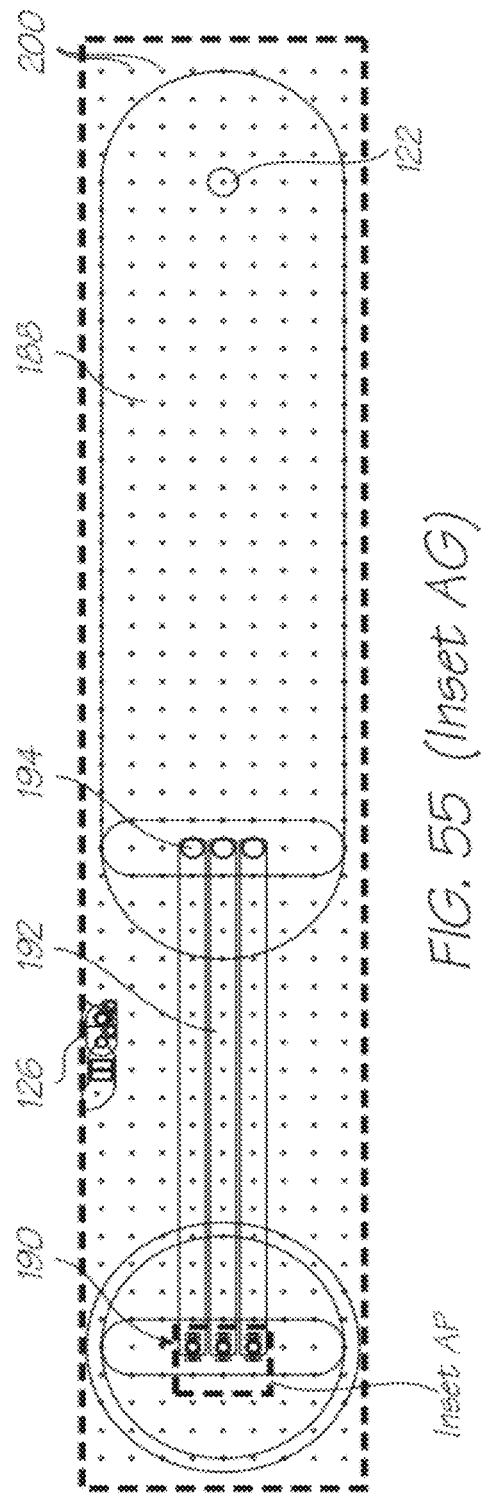

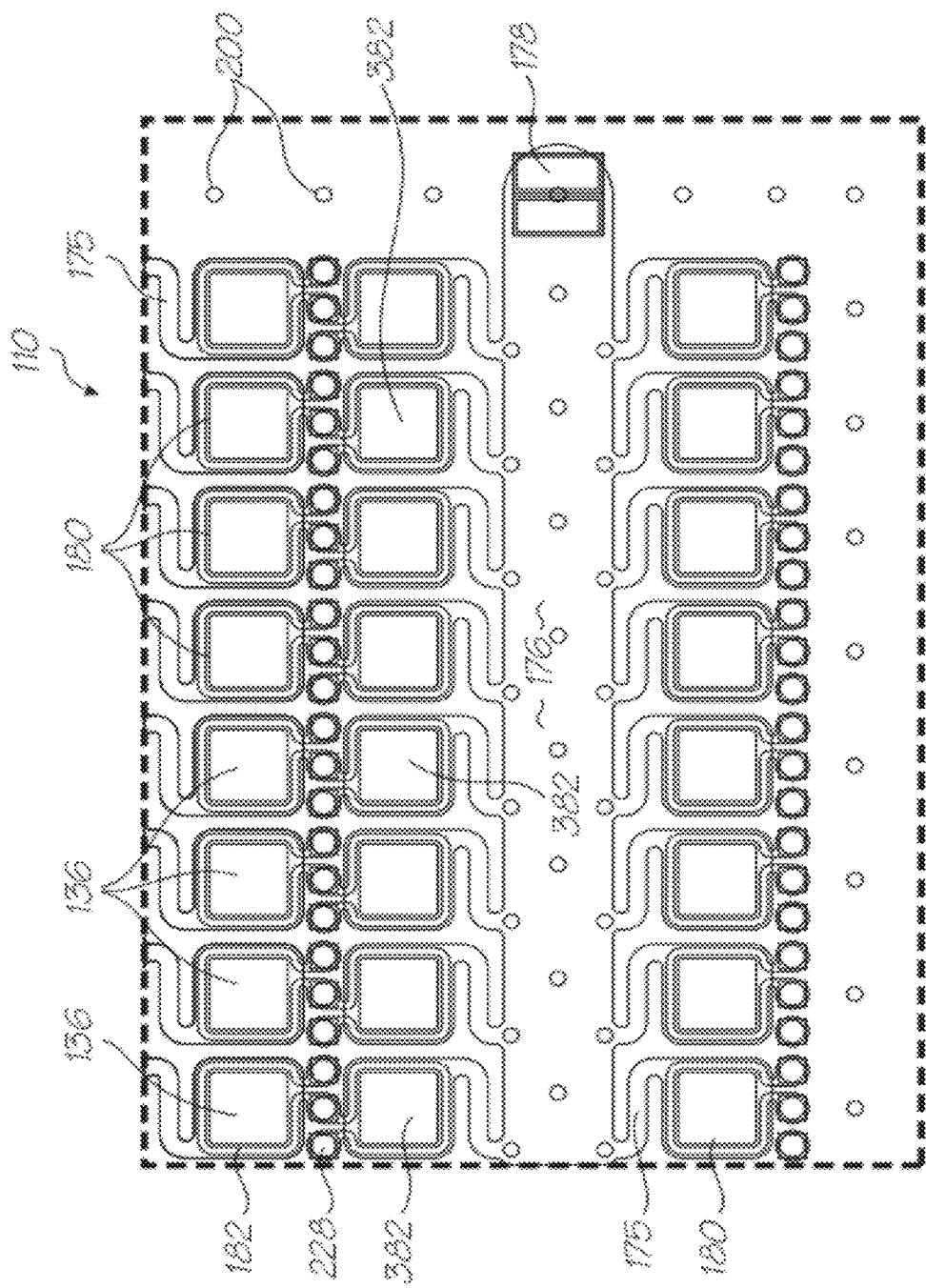
FIG. 56 (Inset AD)

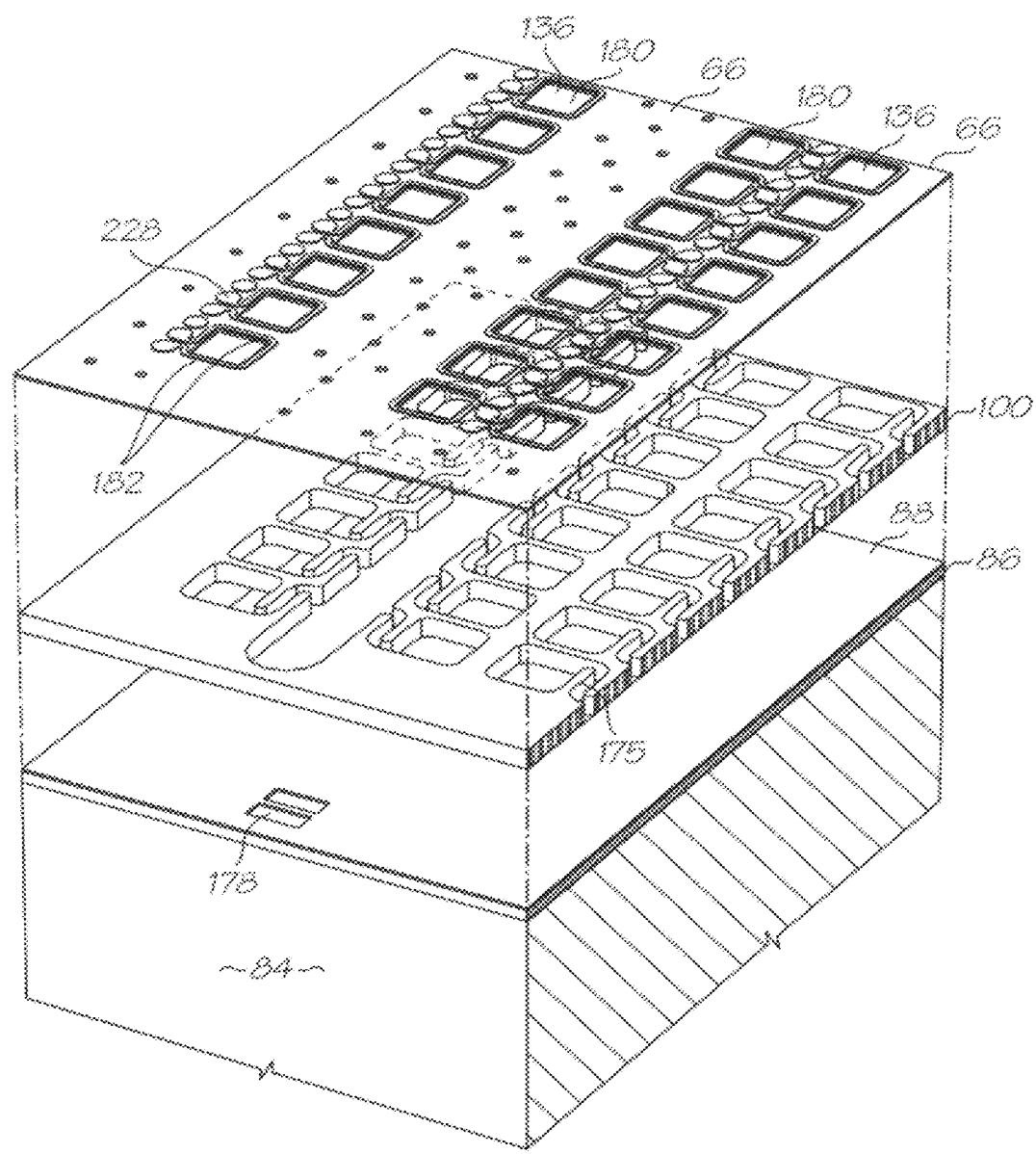
FIG. 57 (Inset AD)

(Inset AH)

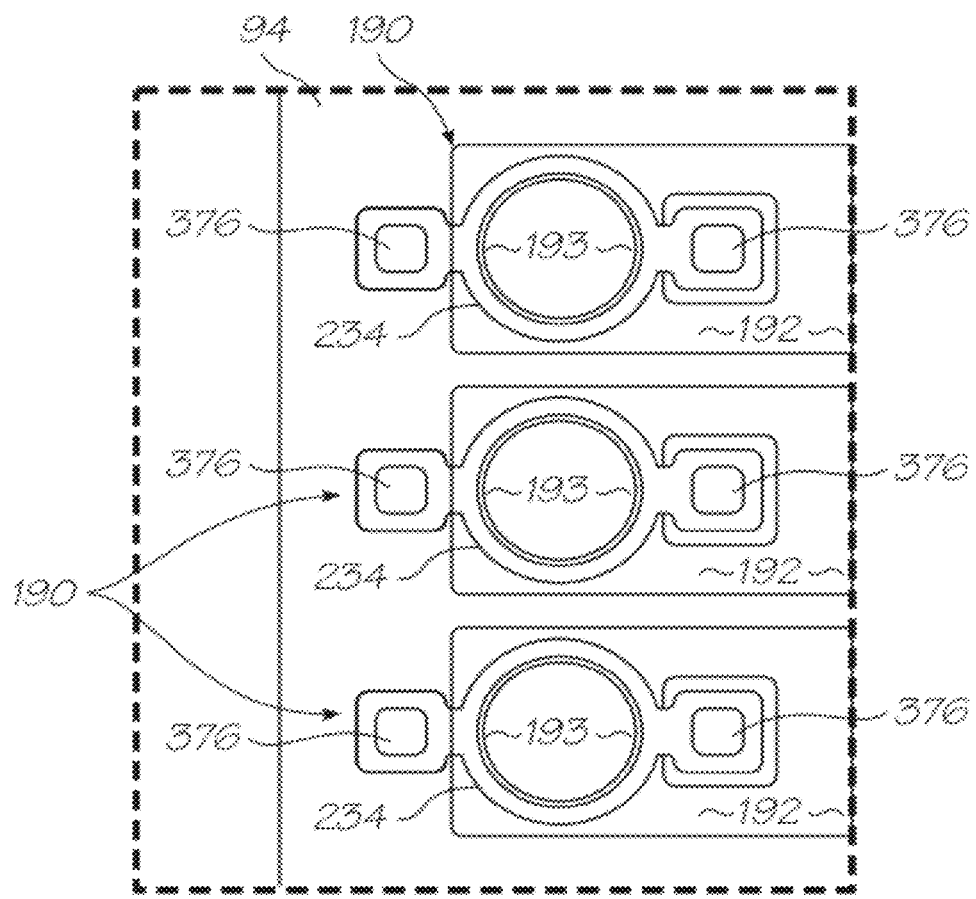
FIG. 61 (Inset AP)
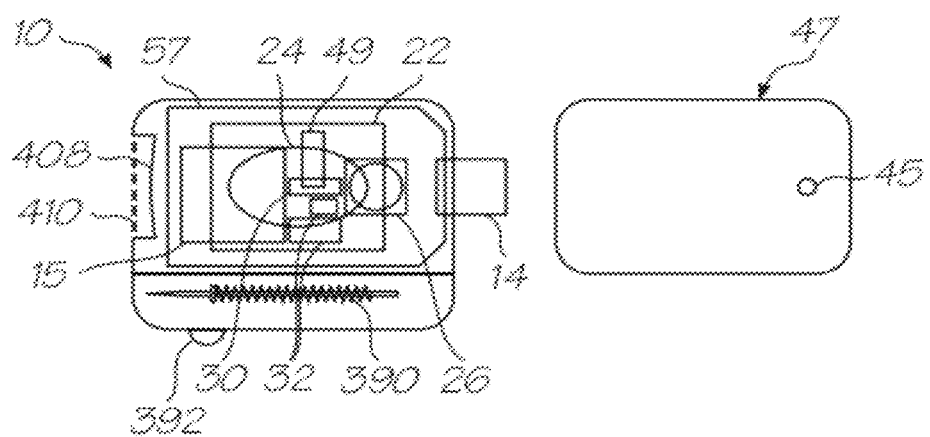
FIG. 63

FIG. 66 (Inset CA)

FIG. 67 (Inset CA)

FIG. 68 (Inset CE)

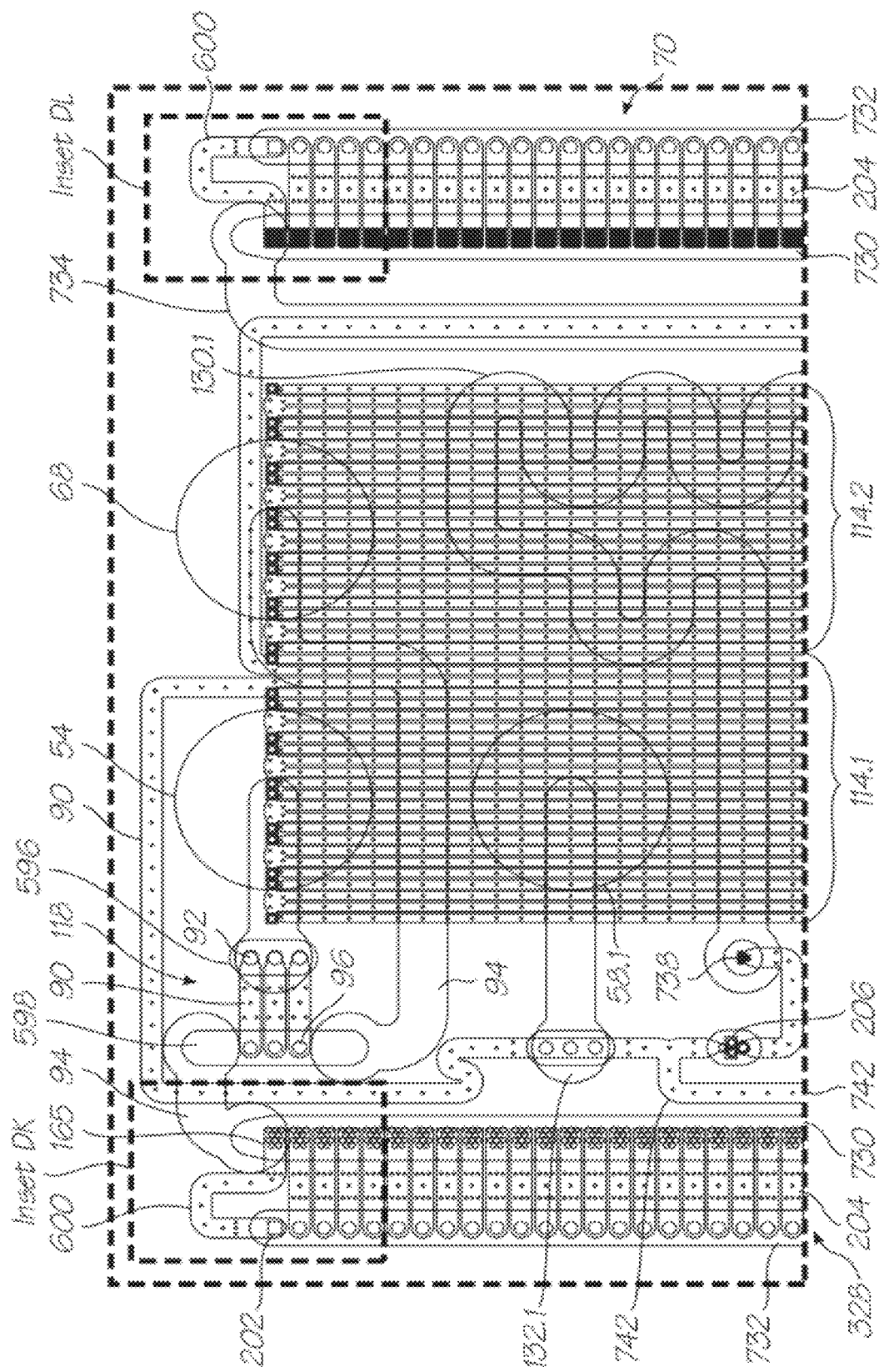
FIG. 82 (Inset DA)

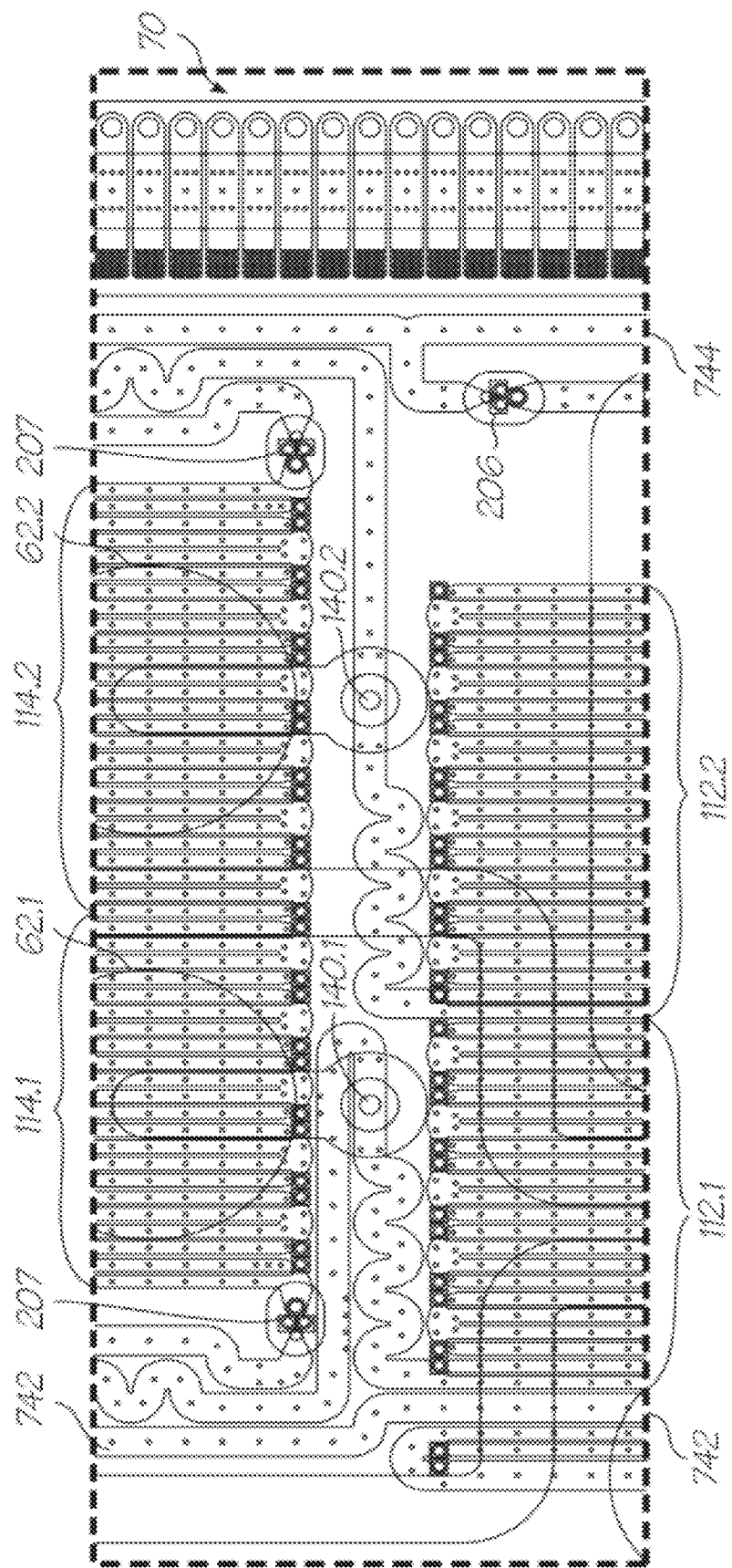
FIG. 83 (Inset DB)

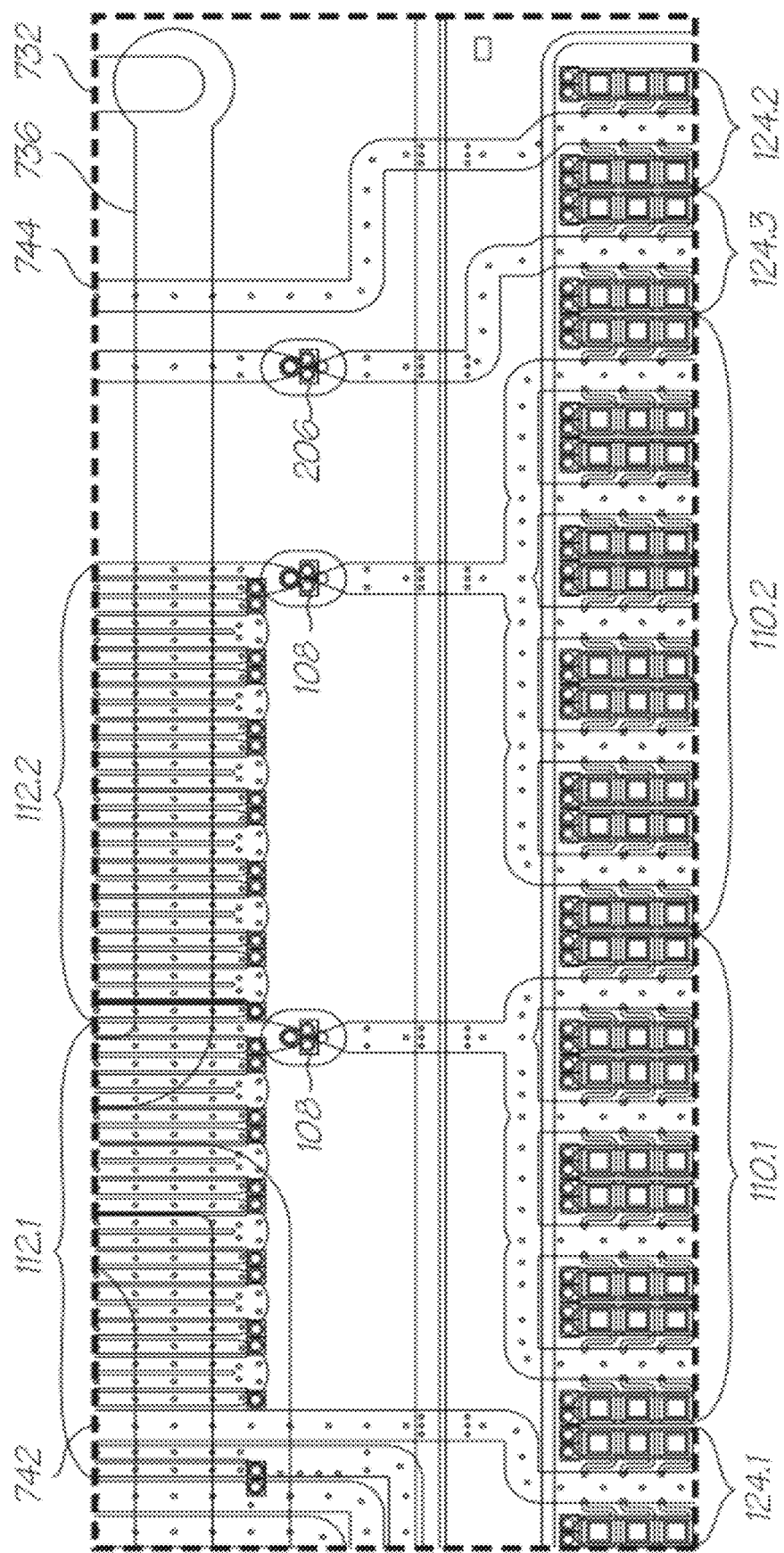
FIG. 84 (Inset DC)

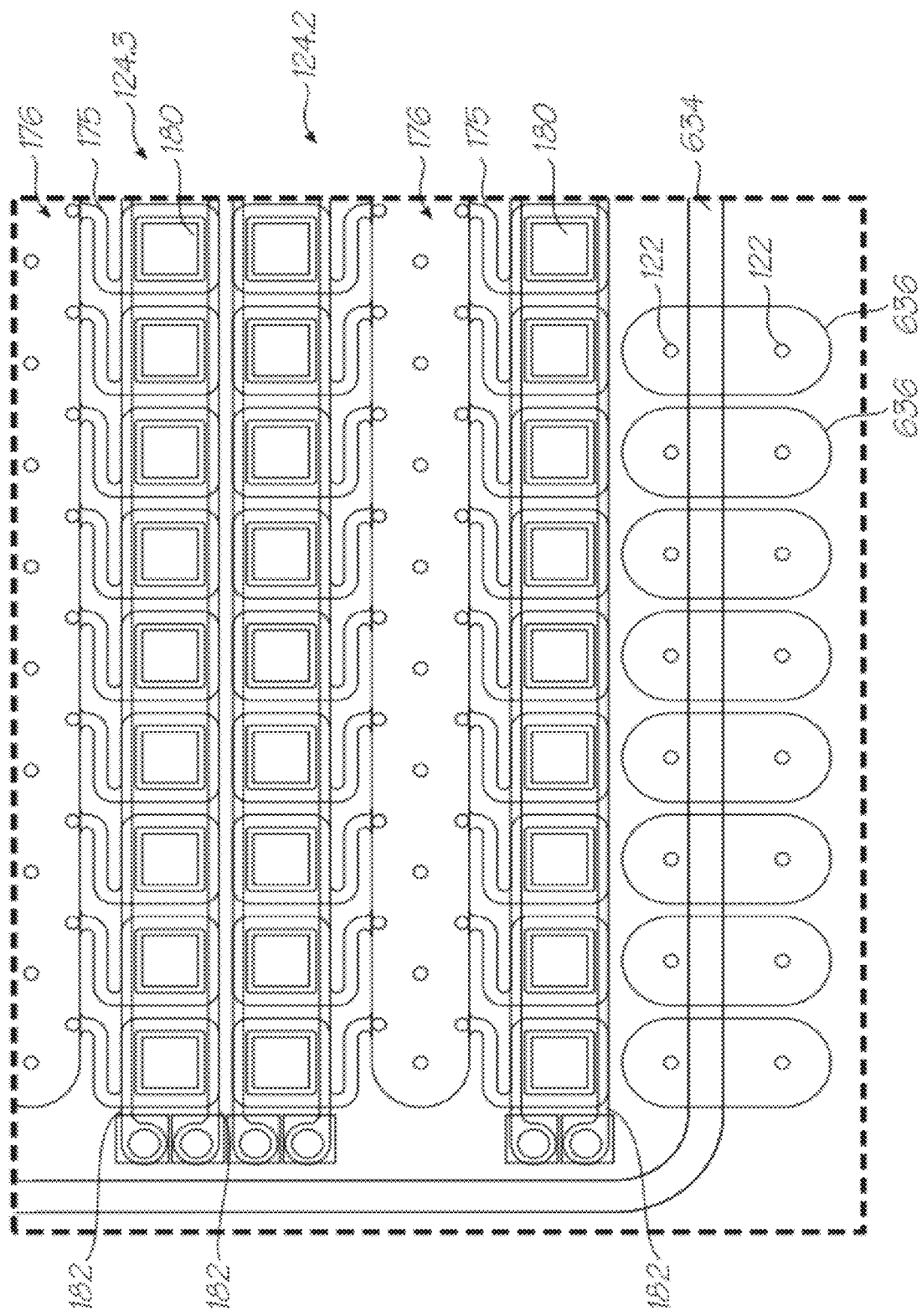
FIG. 85 (Inset DD)

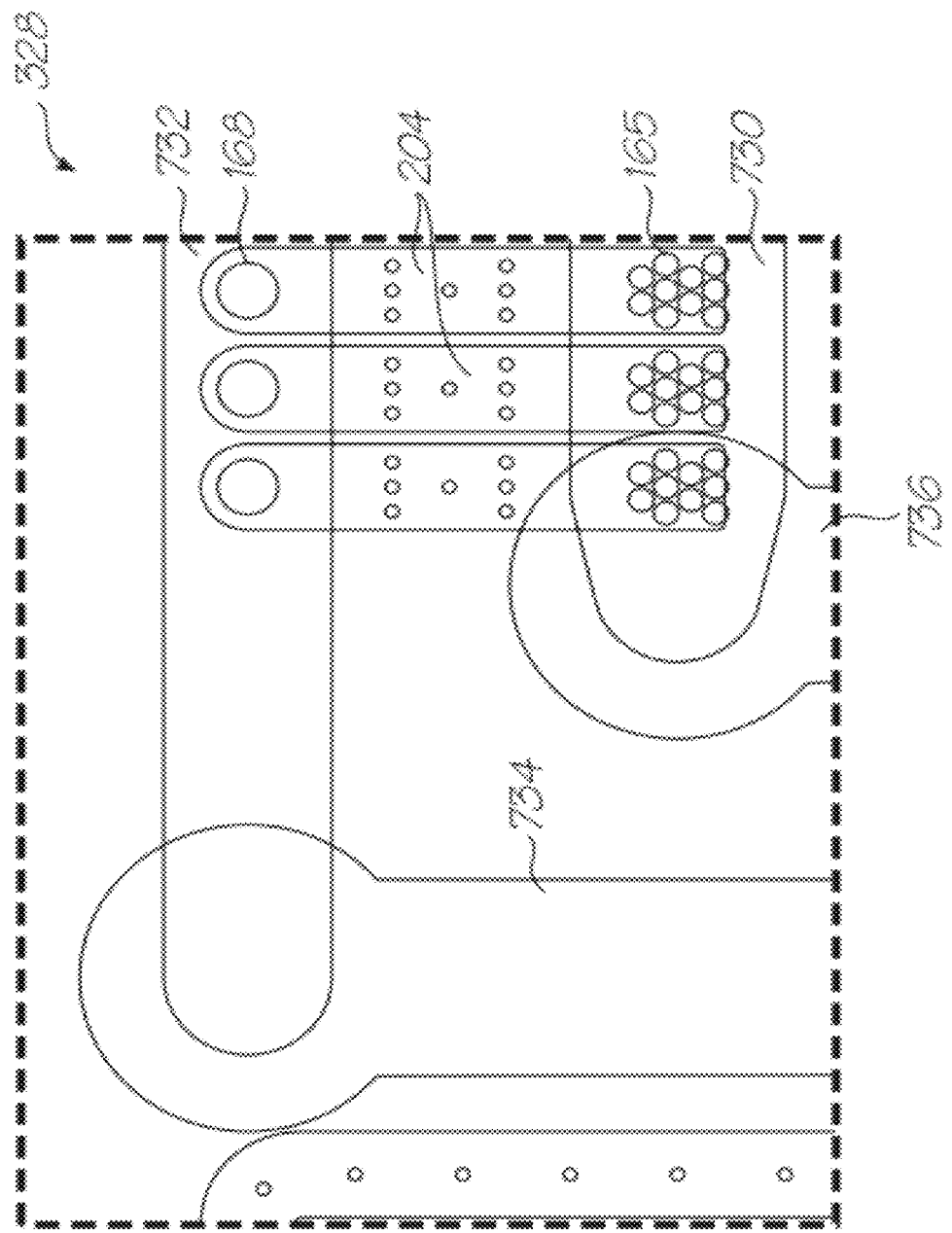
FIG. 86 (Inset DE)

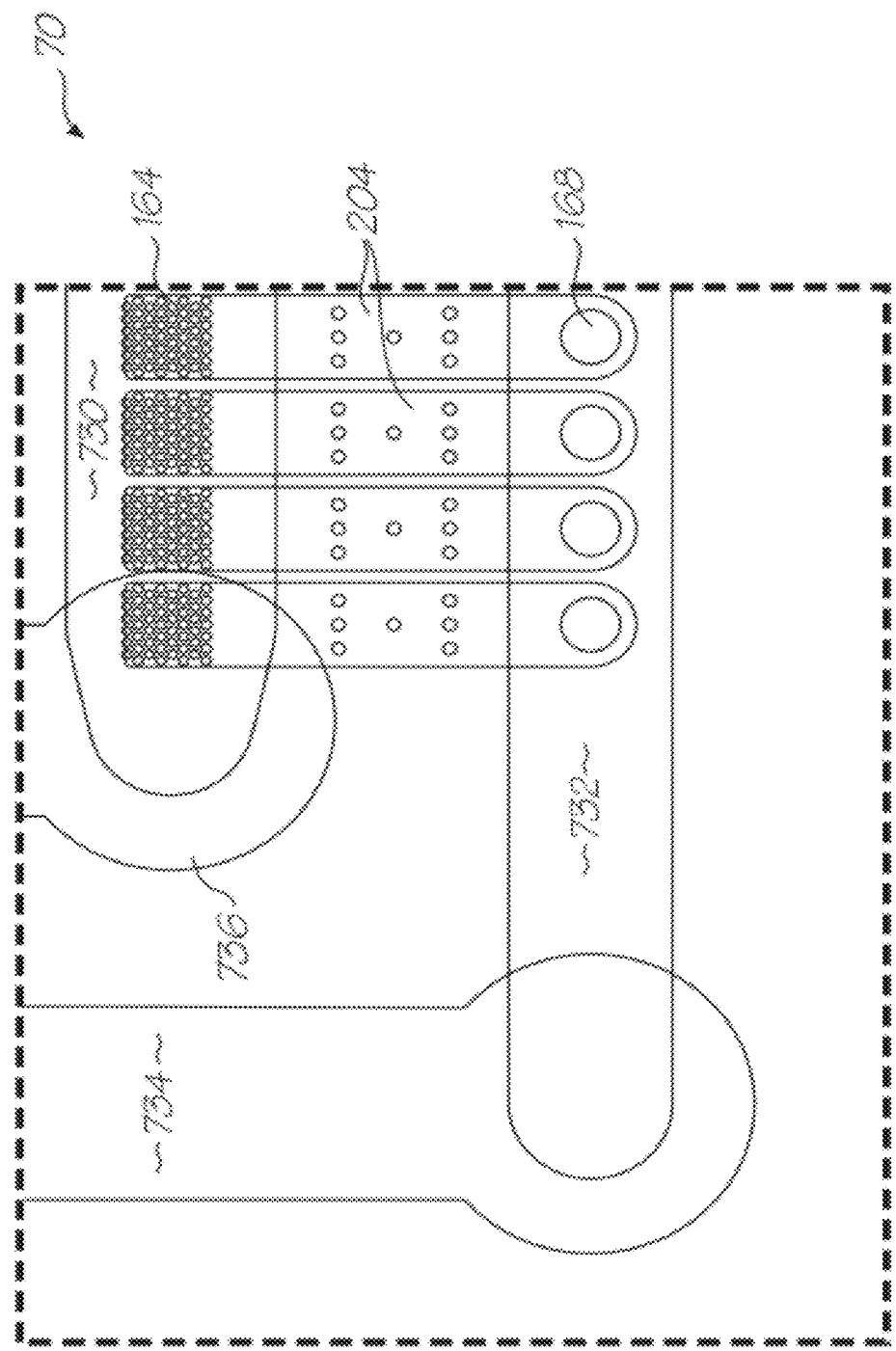
FIG. 87 (Inset DF)

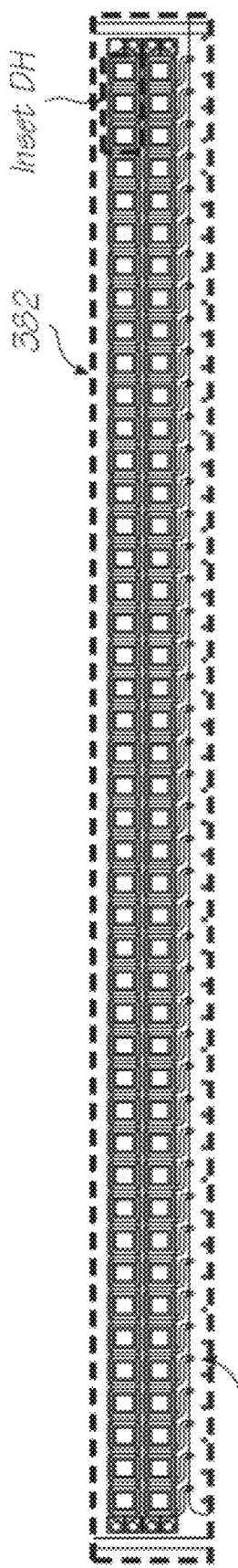
FIG. 88 (Inset DG)
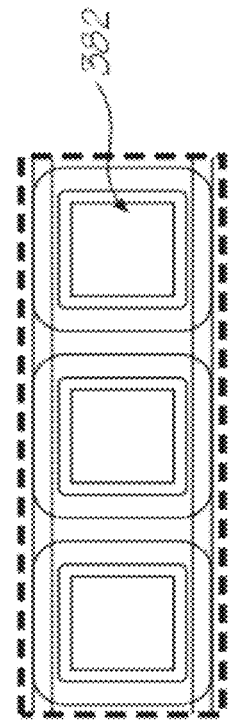
FIG. 89 (Inset DH)

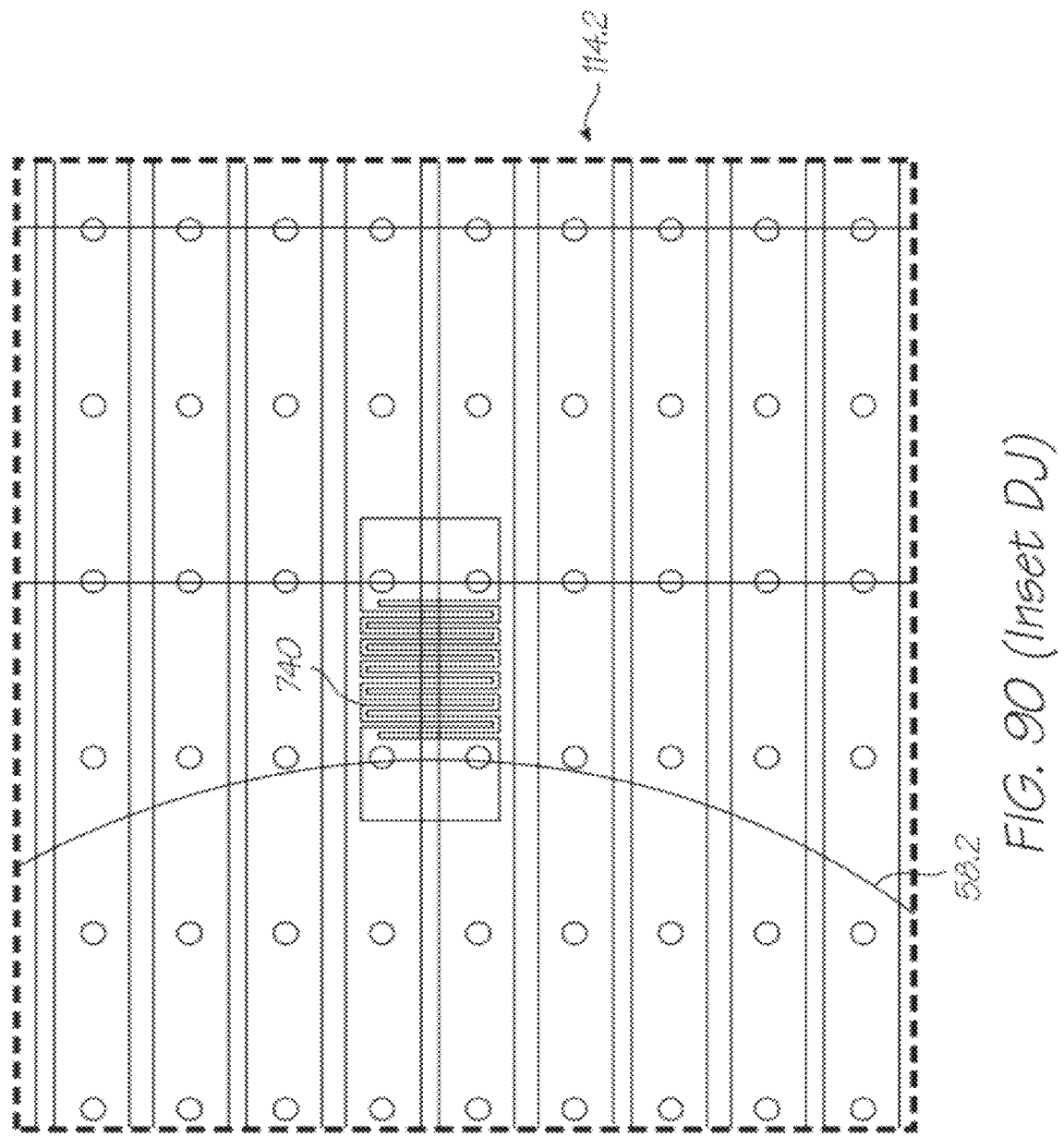

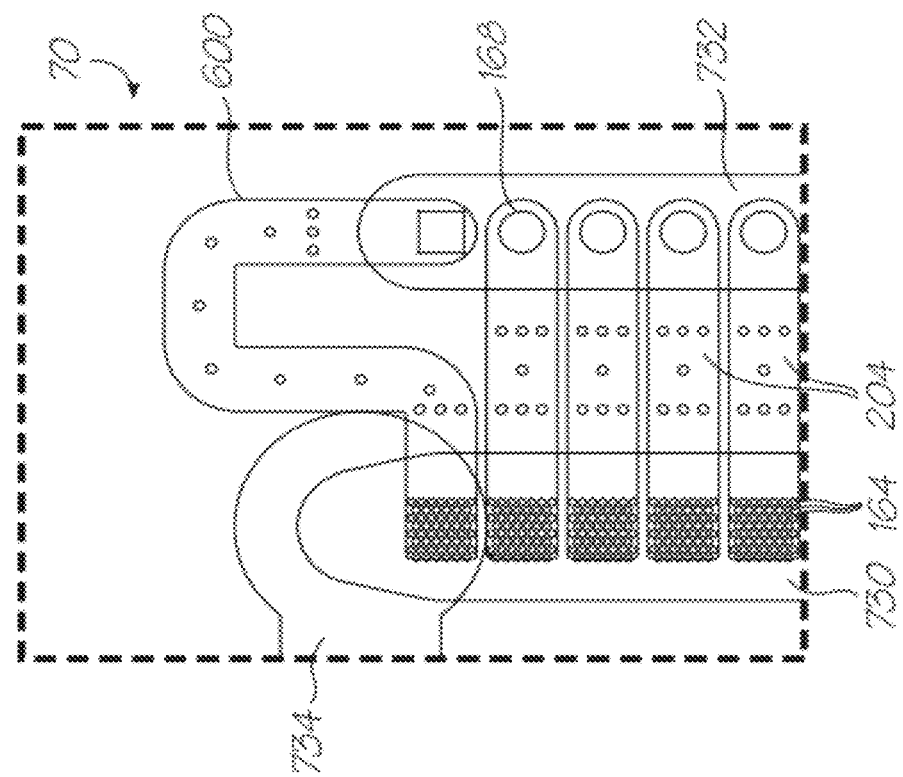
FIG. 92 (Inset DL)
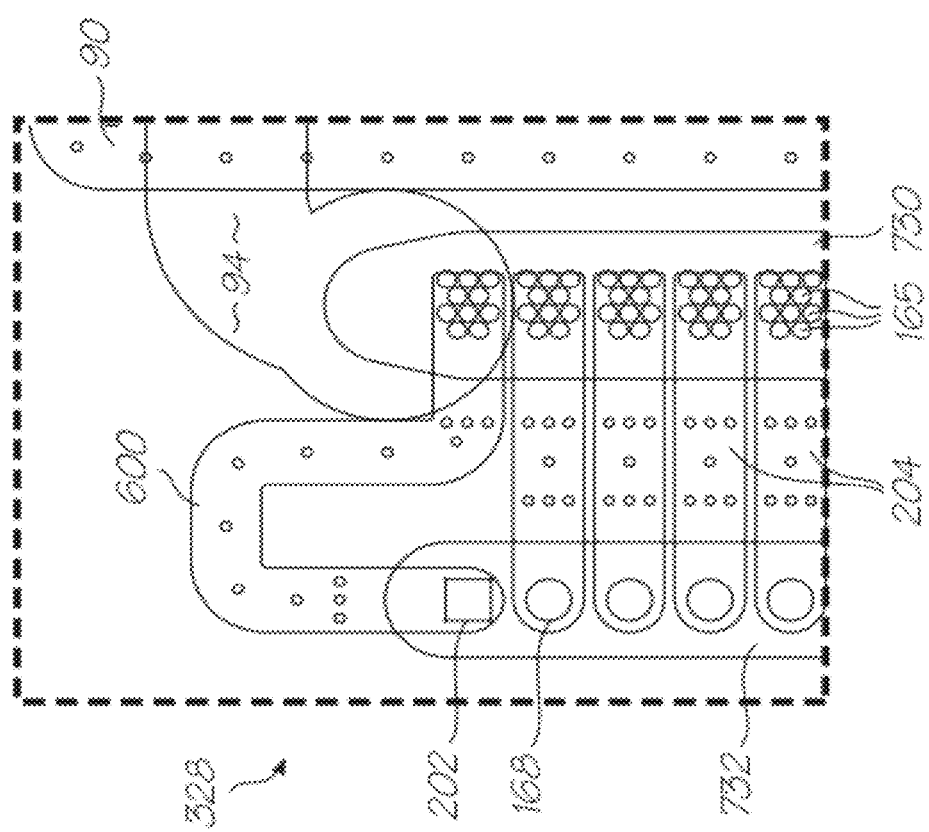
FIG. 91 (Inset DK)

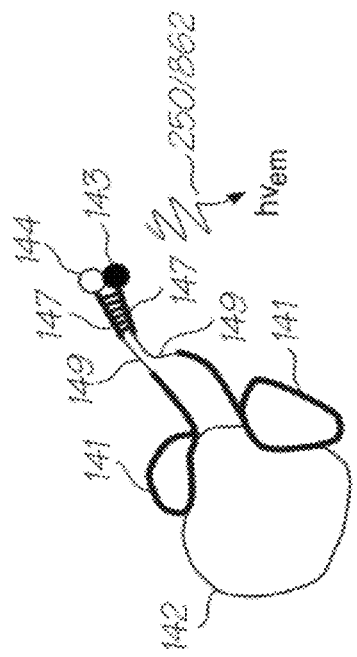
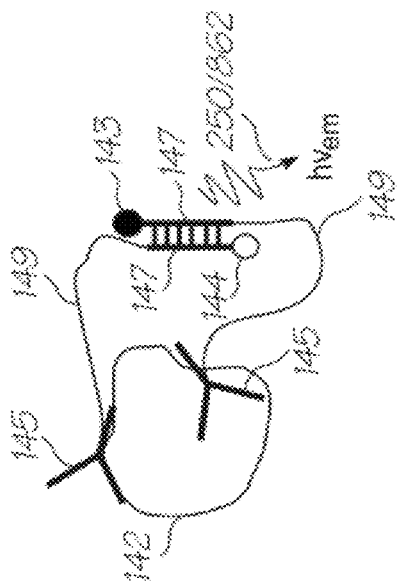
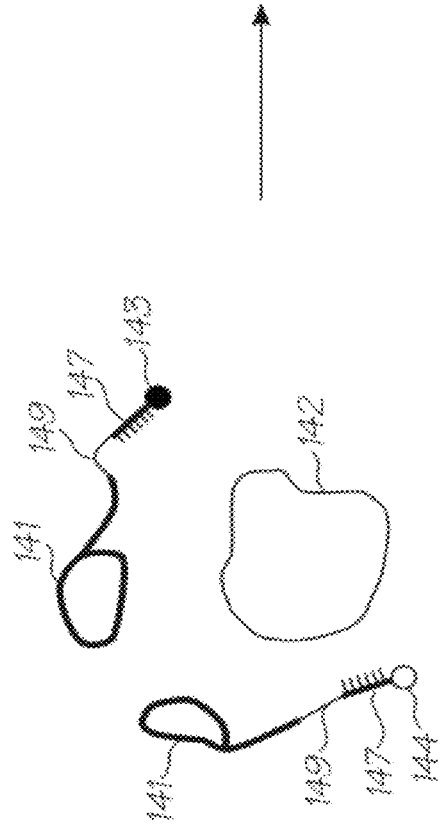
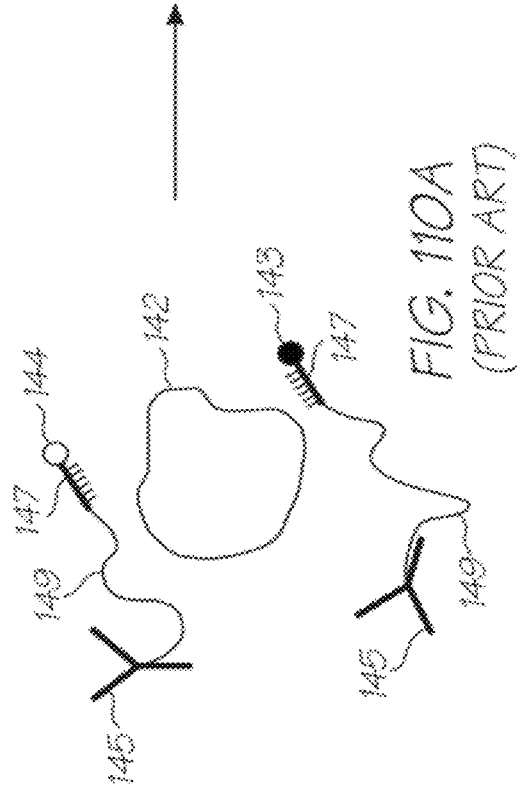
FIG. 109A (PRIOR ART)
FIG. 109B (PRIOR ART)
FIG. 110A (PRIOR ART)
FIG. 110B (PRIOR ART)

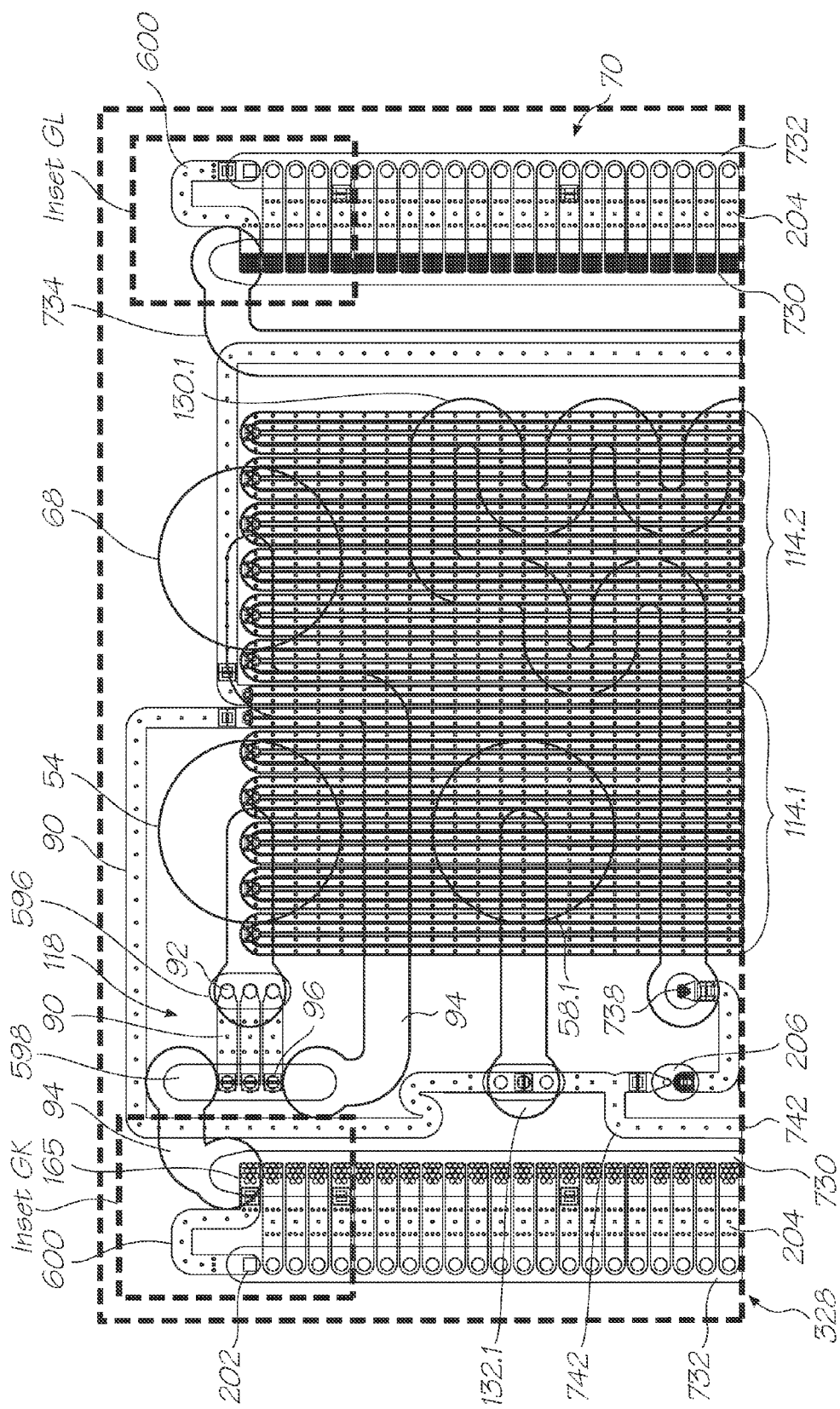
FIG. 117 (Inset GA)

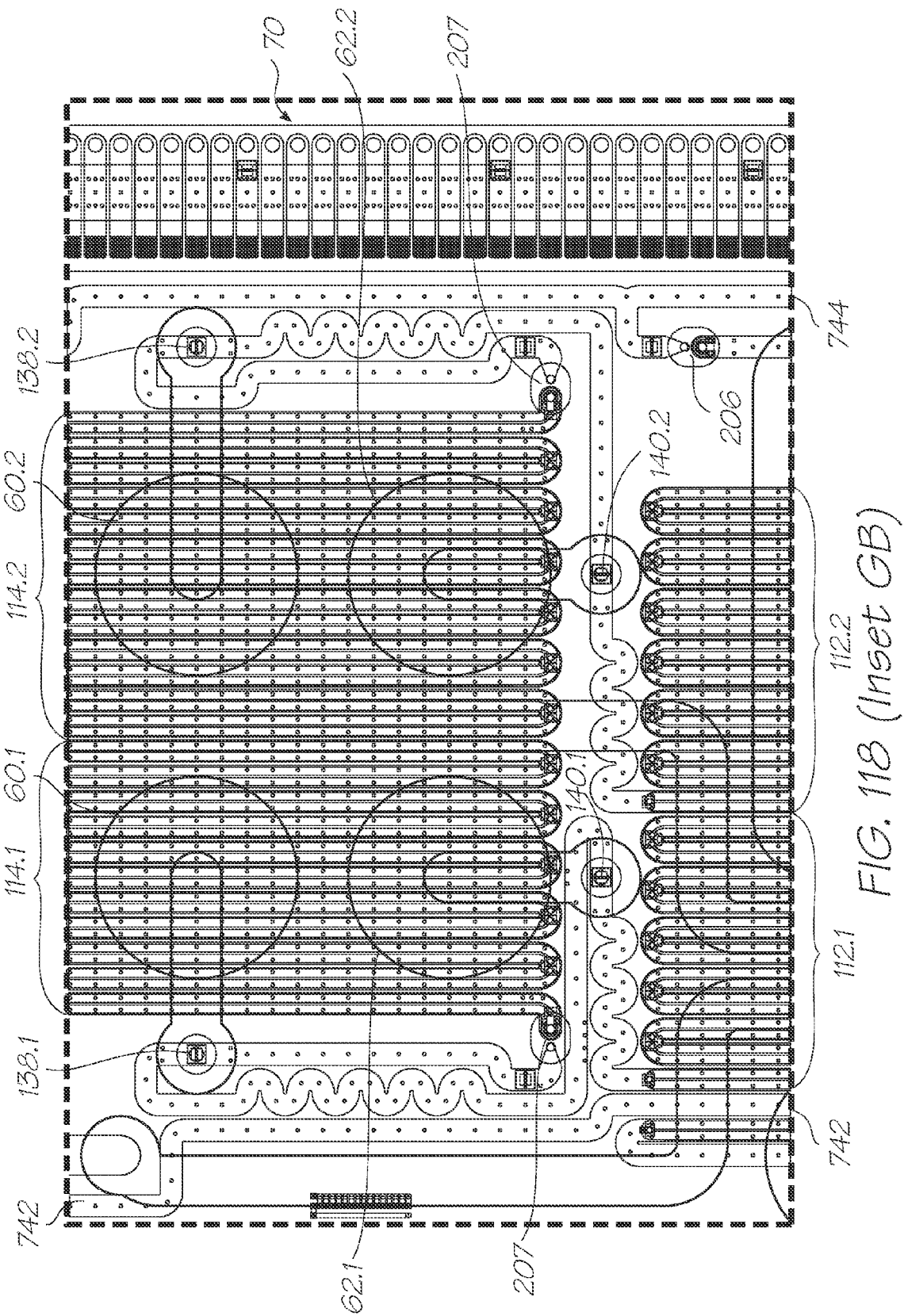
FIG. 118 (Inset GB)

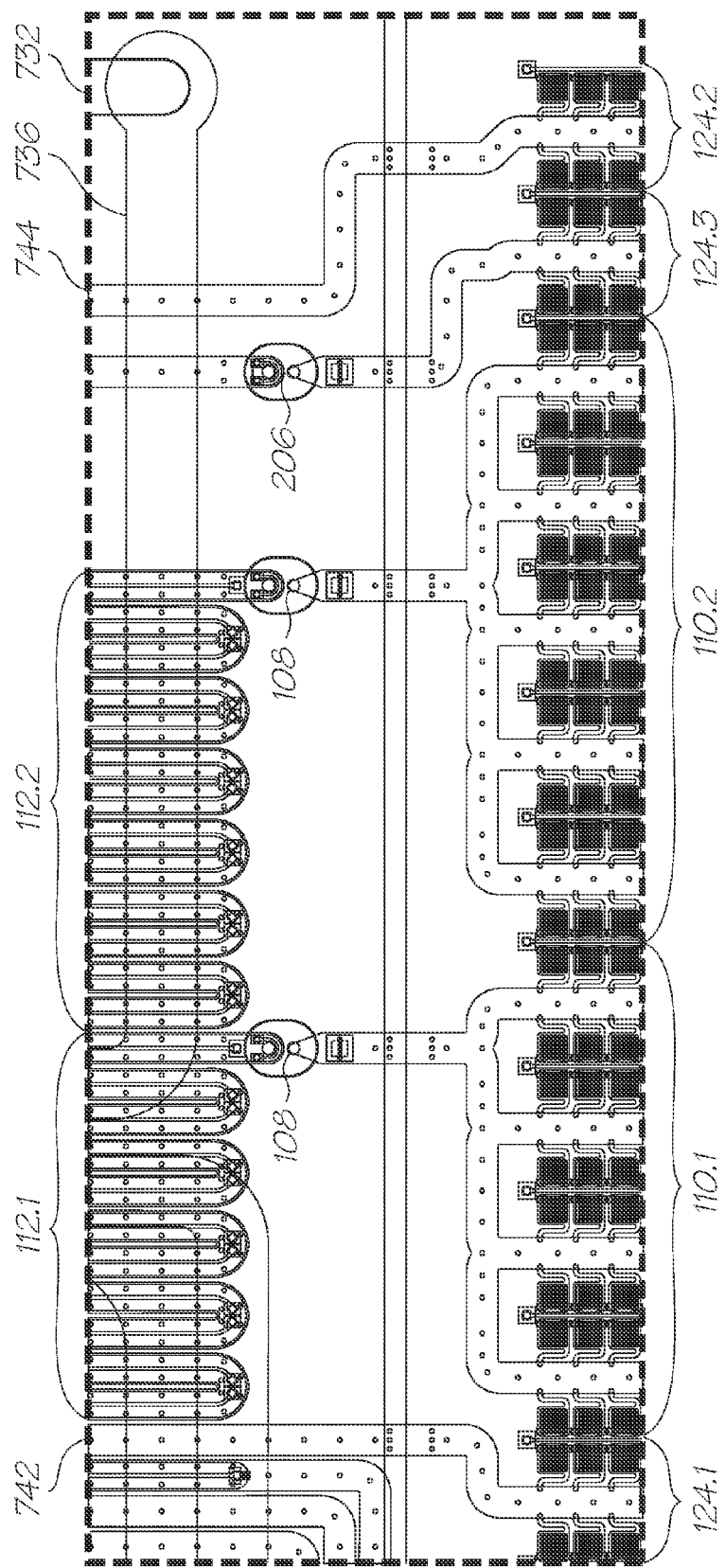
FIG. 119 (Inset GC)

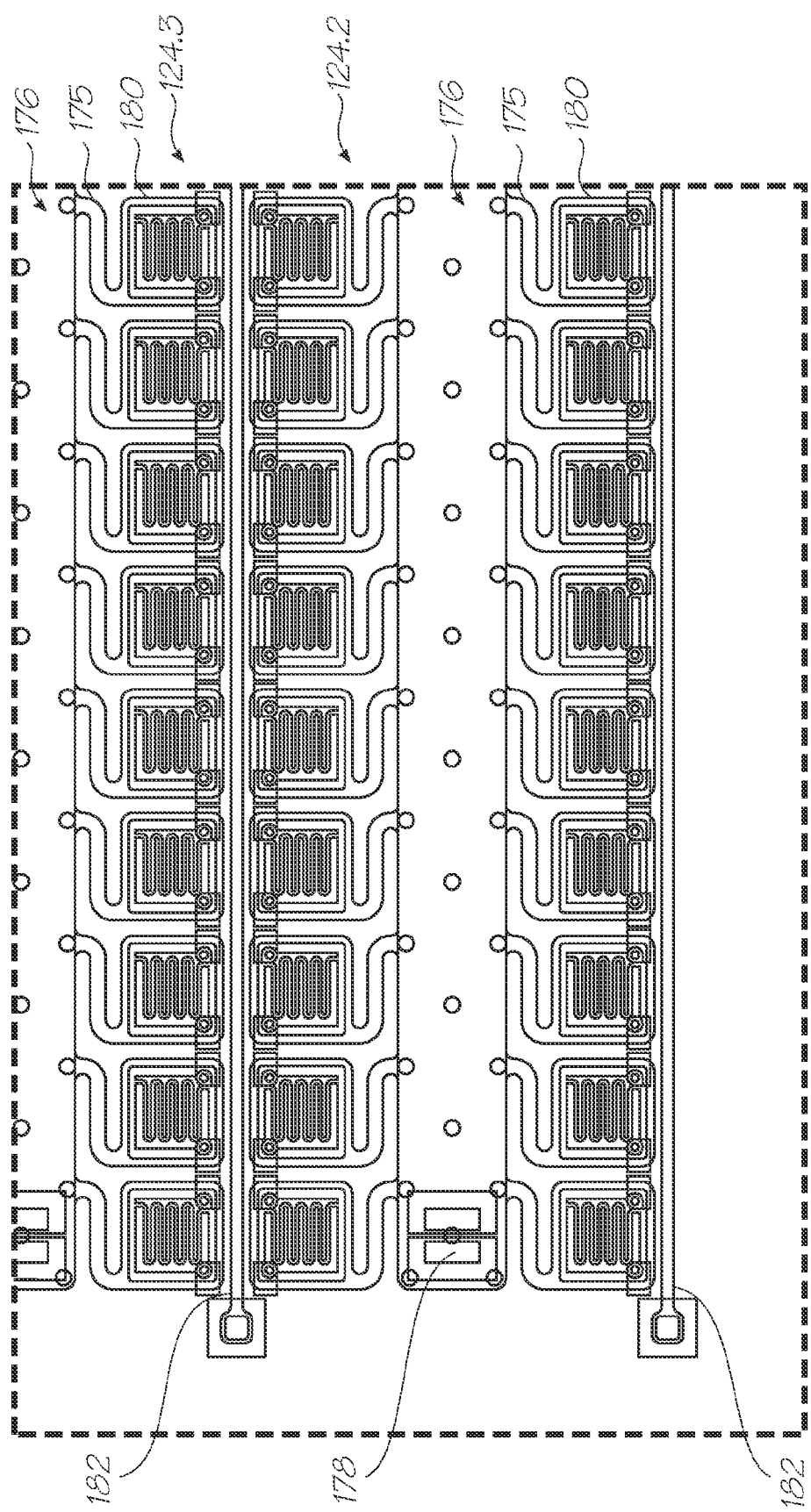
FIG. 120 (Inset GD)

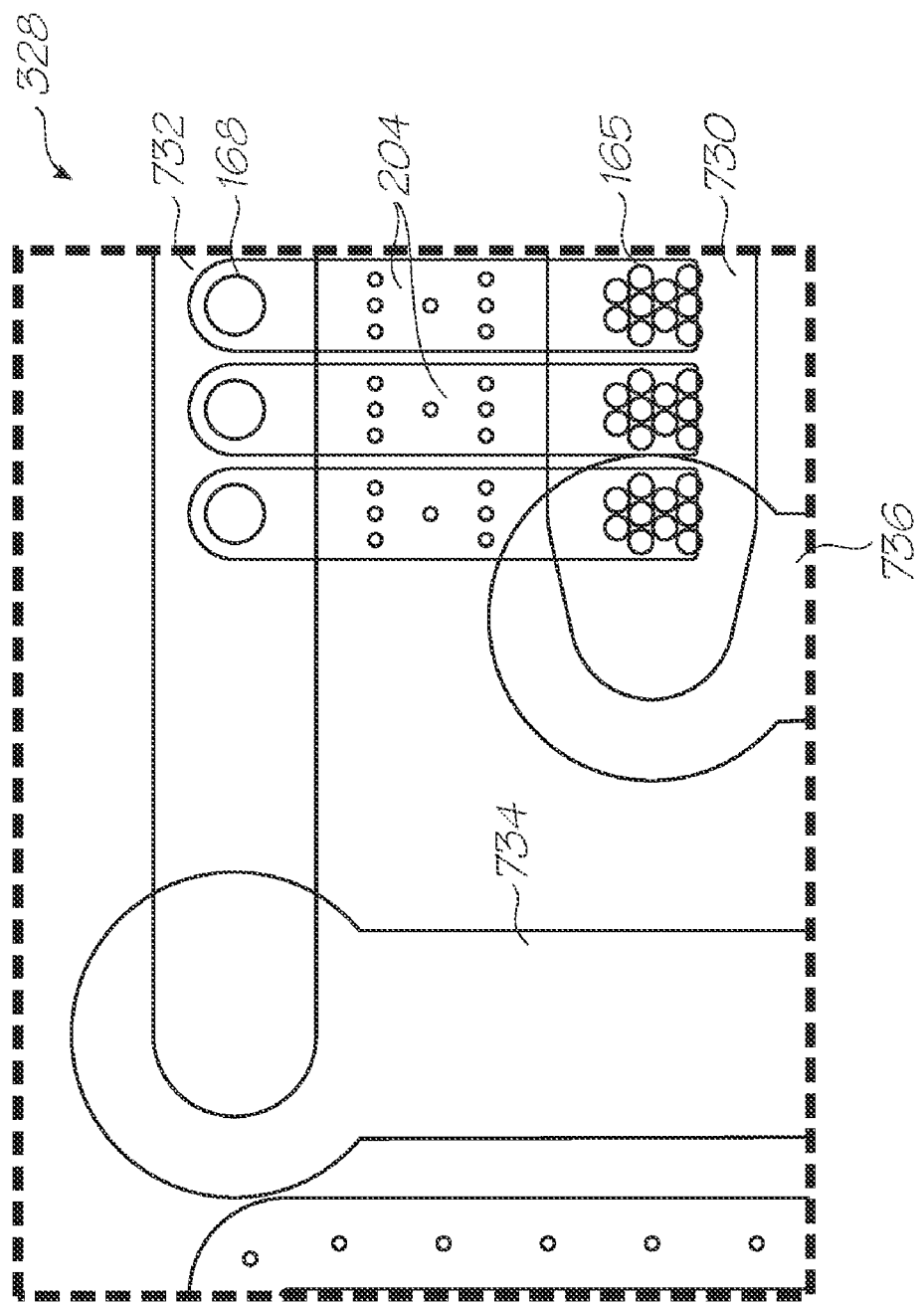
FIG. 121 (Inset GE)

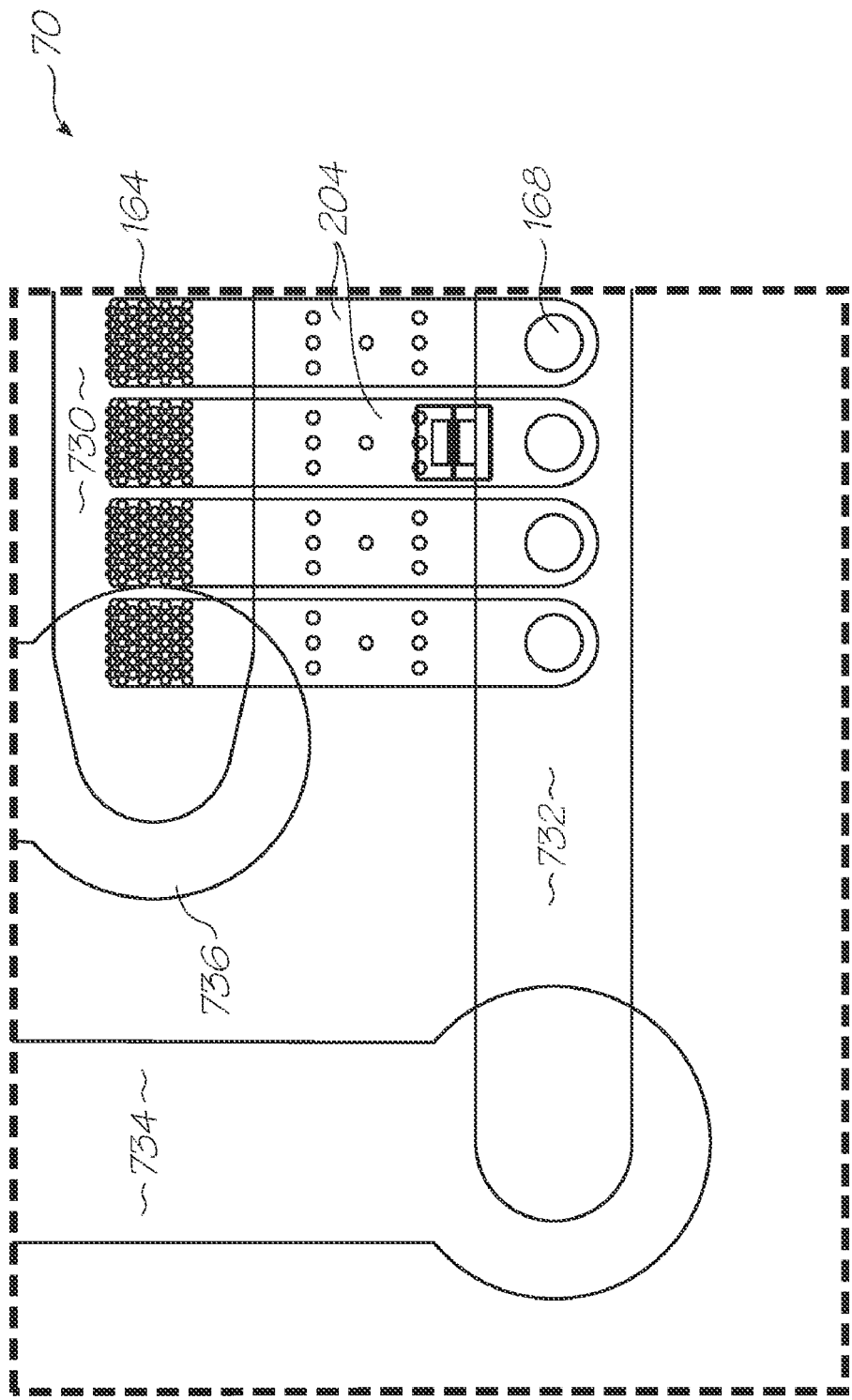
FIG. 122 (Inset GF)

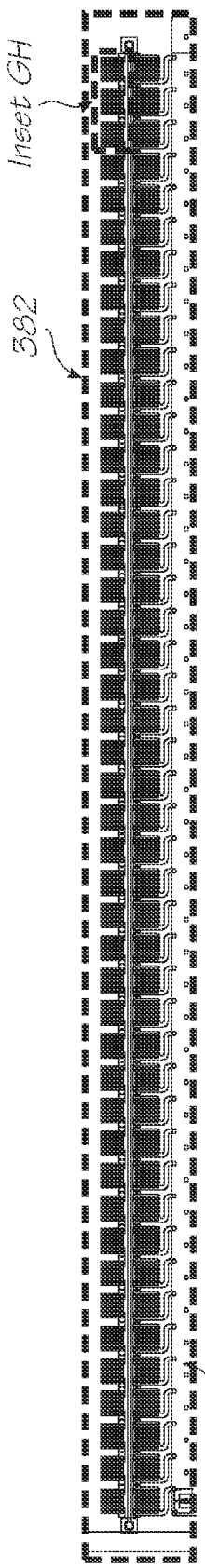
FIG. 123 (Inset GG)
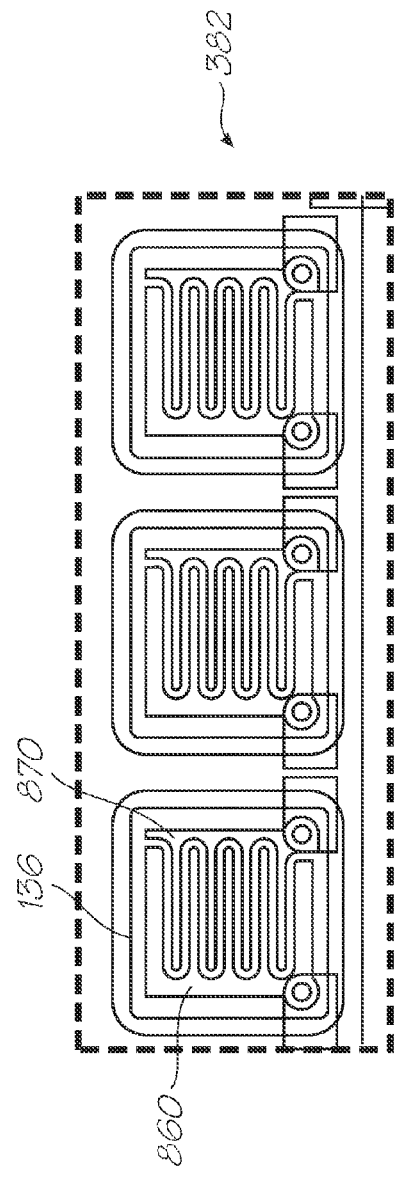
FIG. 124 (Inset GH)

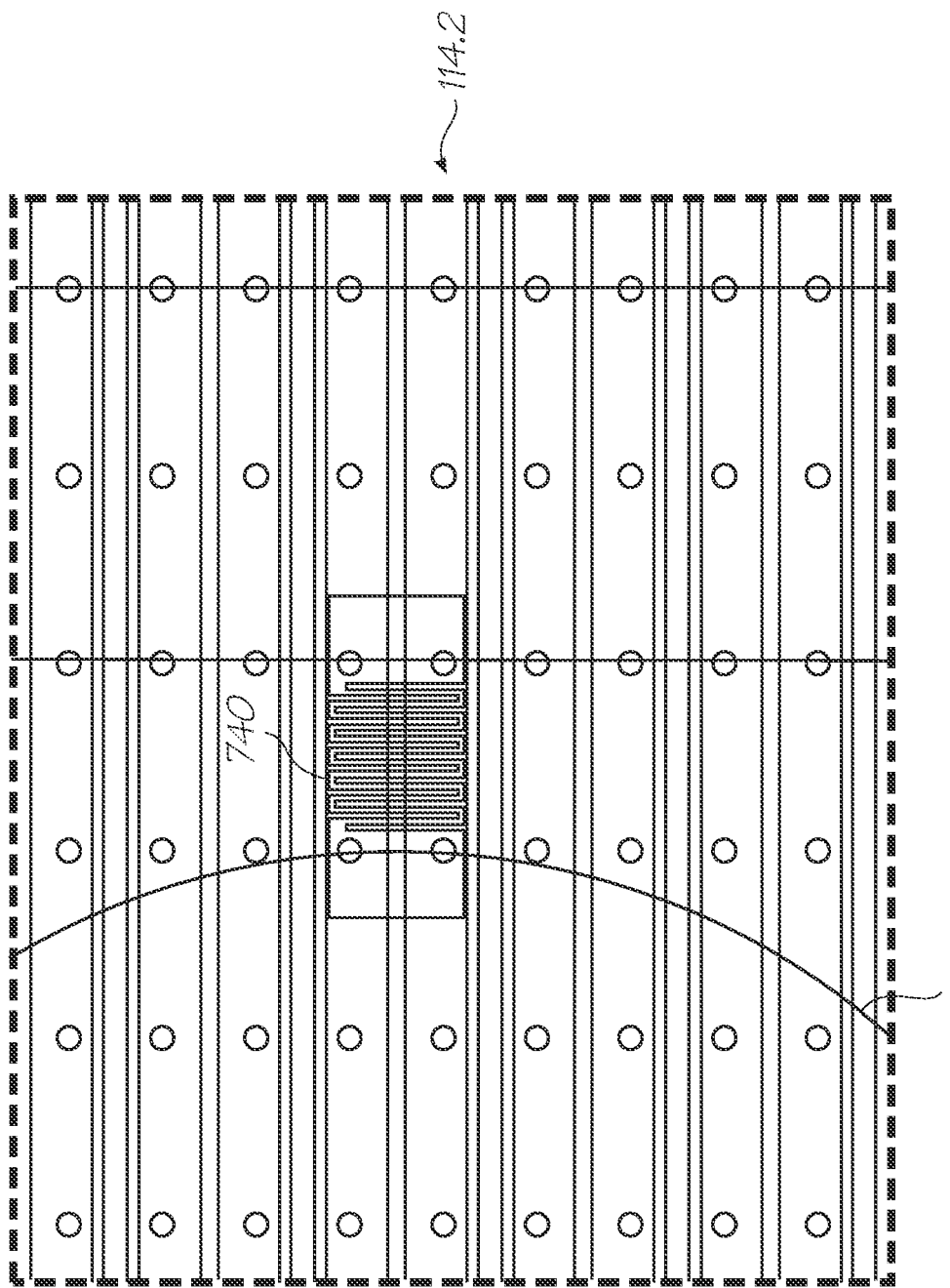
FIG. 125 (Inset GJ)

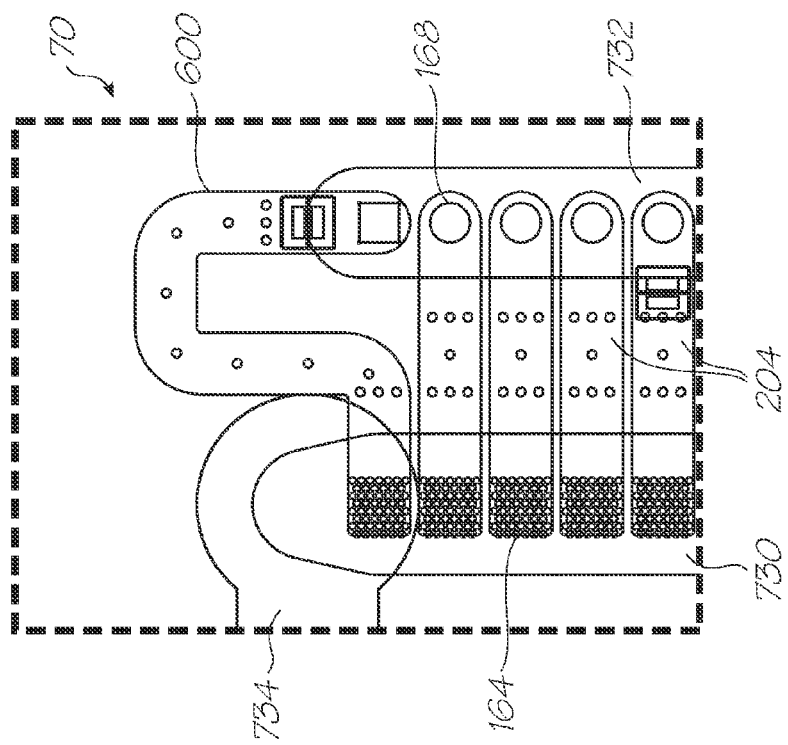
FIG. 127 (Inset GL)
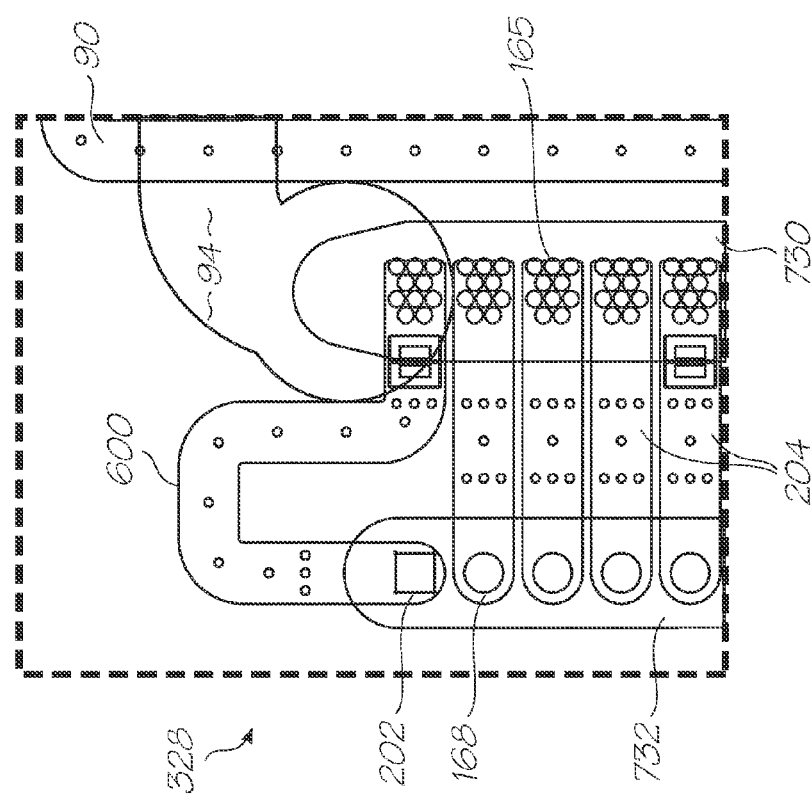
FIG. 126 (Inset GK)

TEST MODULE WITH INTEGRAL PHOTOSENSOR FOR ELECTROCHEMILUMINESCENT DETECTION OF HYBRIDIZATION

FIELD OF THE INVENTION

The present invention relates to diagnostic devices that use microsystems technologies (MST). In particular, the invention relates to microfluidic and biochemical processing and analysis for molecular diagnostics.

CO-PENDING APPLICATIONS

The following applications have been filed by the Applicant which relate to the present application:

| | | | | |
|---|---|---|---|---|
| GBS001US | GBS002US | GBS003US | GBS005US | GBS006US |
| GSR001US | GSR002US | GAS001US | GAS002US | GAS003US |
| GAS004US | GAS006US | GAS007US | GAS008US | GAS009US |
| GAS010US | GAS012US | GAS013US | GAS014US | GAS015US |
| GAS016US | GAS017US | GAS018US | GAS019US | GAS020US |
| GAS021US | GAS022US | GAS023US | GAS024US | GAS025US |
| GAS026US | GAS027US | GAS028US | GAS030US | GAS031US |
| GAS032US | GAS033US | GAS034US | GAS035US | GAS036US |
| GAS037US | GAS038US | GAS039US | GAS040US | GAS041US |
| GAS042US | GAS043US | GAS044US | GAS045US | GAS046US |
| GAS047US | GAS048US | GAS049US | GAS050US | GAS054US |
| GAS055US | GAS056US | GAS057US | GAS058US | GAS059US |
| GAS060US | GAS061US | GAS062US | GAS063US | GAS065US |
| GAS066US | GAS067US | GAS068US | GAS069US | GAS070US |
| GAS080US | GAS081US | GAS082US | GAS083US | GAS084US |
| GAS085US | GAS086US | GAS087US | GAS088US | GAS089US |
| GAS090US | GAS091US | GAS092US | GAS093US | GAS094US |
| GAS095US | GAS096US | GAS097US | GAS098US | GAS099US |
| GAS100US | GAS101US | GAS102US | GAS103US | GAS104US |
| GAS105US | GAS106US | GAS108US | GAS109US | GAS110US |
| GAS111US | GAS112US | GAS113US | GAS114US | GAS115US |
| GAS117US | GAS118US | GAS119US | GAS120US | GAS121US |
| GAS122US | GAS123US | GAS124US | GAS125US | GAS126US |
| GAS127US | GAS128US | GAS129US | GAS130US | GAS131US |
| GAS132US | GAS133US | GAS134US | GAS136US | GAS137US |
| GAS138US | GAS139US | GAS140US | GAS141US | GAS142US |
| GAS143US | GAS144US | GAS146US | GAS147US | GRR001US |
| GRR002US | GRR003US | GRR004US | GRR005US | GRR006US |
| GRR007US | GRR008US | GRR009US | GRR010US | GVA001US |
| GVA002US | GVA004US | GVA005US | GVA006US | GVA007US |
| GVA008US | GVA009US | GVA010US | GVA011US | GVA012US |
| GVA013US | GVA014US | GVA015US | GVA016US | GVA017US |
| GVA018US | GVA019US | GVA020US | GVA021US | GVA022US |
| GHU001US | GHU002US | GHU003US | GHU004US | GHU006US |
| GHU007US | GHU008US | GWM001US | GWM002US | GDI001US |
| GDI002US | GDI003US | GDI004US | GDI005US | GDI006US |
| GDI007US | GDI009US | GDI010US | GDI011US | GDI013US |
| GDI014US | GDI015US | GDI016US | GDI017US | GDI019US |
| GDI023US | GDI028US | GDI030US | GDI039US | GDI040US |
| GDI041US | GPC001US | GPC002US | GPC003US | GPC004US |
| GPC005US | GPC006US | GPC007US | GPC008US | GPC009US |
| GPC010US | GPC011US | GPC012US | GPC014US | GPC017US |
| GPC018US | GPC019US | GPC023US | GPC027US | GPC028US |
| GPC029US | GPC030US | GPC031US | GPC033US | GPC034US |
| GPC035US | GPC036US | GPC037US | GPC038US | GPC039US |
| GPC040US | GPC041US | GPC042US | GPC043US | GLY001US |
| GLY002US | GLY003US | GLY004US | GLY005US | GLY006US |
| GIN001US | GIN002US | GIN003US | GIN004US | GIN005US |
| GIN006US | GIN007US | GIN008US | GMI001US | GMI002US |
| GMI005US | GMI008US | GLE001US | GLE002US | GLE003US |
| GLE004US | GLE005US | GLE006US | GLE007US | GLE008US |
| GLE009US | GLE010US | GLE011US | GLE012US | GLE013US |
| GLE014US | GLA001US | GGA001US | GGA003US | GRE001US |
| GRE002US | GRE003US | GRE004US | GRE005US | GRE006US |
| GRE007US | GCF001US | GCF002US | GCF003US | GCF004US |
| GCF005US | GCF006US | GCF007US | GCF008US | GCF009US |
| GCF010US | GCF011US | GCF012US | GCF013US | GCF014US |
| GCF015US | GCF016US | GCF020US | GCF021US | GCF022US |
| GCF023US | GCF024US | GCF025US | GCF027US | GCF028US |
| GCF029US | GCF030US | GCF031US | GCF032US | GCF033US |
| GCF034US | GCF035US | GCF036US | GCF037US | GSA001US |
| GSA002US | GSE001US | GSE002US | GSE003US | GSE004US |
| GDA001US | GDA002US | GDA003US | GDA004US | GDA005US |
| GDA006US | GDA007US | GPK001US | GMO001US | GMV001US |
| GMV002US | GMV003US | GMV004US | GRD001US | GRD002US |
| GRD003US | GRD004US | GPD001US | GPD003US | GPD004US |
| GPD005US | GPD006US | GPD007US | GPD008US | GPD009US |
| GPD010US | GPD011US | GPD012US | GPD013US | GPD014US |
| GPD015US | GPD016US | GPD017US | GAL001US | GPA001US |
| GPA003US | GPA004US | GPA005US | GSS001US | GSL001US |
| GCA001US | GCA002US | GCA003US | | |

The disclosures of these co-pending applications are incorporated herein by reference. The above applications have been identified by their filing docket number, which will be substituted with the corresponding application number, once assigned.

BACKGROUND OF THE INVENTION

Molecular diagnostics has emerged as a field that offers the promise of early disease detection, potentially before symptoms have manifested. Molecular diagnostic testing is used to detect:
  Inherited disorders
  Acquired disorders
  Infectious diseases
  Genetic predisposition to health-related conditions.

With high accuracy and fast turnaround times, molecular diagnostic tests have the potential to reduce the occurrence of ineffective health care services, enhance patient outcomes, improve disease management and individualize patient care. Many of the techniques in molecular diagnostics are based on the detection and identification of specific nucleic acids, both deoxyribonucleic acid (DNA) and ribonucleic acid (RNA), extracted and amplified from a biological specimen (such as blood or saliva). The complementary nature of the nucleic acid bases allows short sequences of synthesized DNA (oligonucleotides) to bond (hybridize) to specific nucleic acid sequences for use in nucleic acid tests. If hybridization occurs, then the complementary sequence is present in the sample. This makes it possible, for example, to predict the disease a person will contract in the future, determine the identity and virulence of an infectious pathogen, or determine the response a person will have to a drug.

Nucleic Acid Based Molecular Diagnostic Test

A nucleic acid based test has four distinct steps:
  1. Sample preparation
  2. Nucleic acid extraction
  3. Nucleic acid amplification (optional)
  4. Detection Many sample types are used for genetic analysis, such as blood, urine, sputum and tissue samples. The diagnostic test determines the type of sample required as not all samples are representative of the disease process. These samples have a variety of constituents, but usually only one of these is of interest. For example, in blood, high concentrations of erythrocytes can inhibit the detection of a pathogenic organism. Therefore a purification and/or concentration step at the beginning of the nucleic acid test is often required.

Blood is one of the more commonly sought sample types. It has three major constituents: leukocytes (white blood cells), erythrocytes (red blood cells) and thrombocytes (platelets). The thrombocytes facilitate clotting and remain active in vitro. To inhibit coagulation, the specimen is mixed with an agent such as ethylenediaminetetraacetic acid (EDTA) prior to purification and concentration. Erythrocytes are usually removed from the sample in order to concentrate the target cells. In humans, erythrocytes account for approximately 99% of the cellular material but do not carry DNA as they have no nucleus. Furthermore, erythrocytes contain components such as haemoglobin that can interfere with the downstream nucleic acid amplification process (described below). Removal of erythrocytes can be achieved by differentially lysing the erythrocytes in a lysis solution, leaving remaining cellular material intact which can then be separated from the sample using centrifugation. This provides a concentration of the target cells from which the nucleic acids are extracted.

The exact protocol used to extract nucleic acids depends on the sample and the diagnostic assay to be performed. For example, the protocol for extracting viral RNA will vary considerably from the protocol to extract genomic DNA. However, extracting nucleic acids from target cells usually involves a cell lysis step followed by nucleic acid purification. The cell lysis step disrupts the cell and nuclear membranes, releasing the genetic material. This is often accomplished using a lysis detergent, such as sodium dodecyl sulfate, which also denatures the large amount of proteins present in the cells.

The nucleic acids are then purified with an alcohol precipitation step, usually ice-cold ethanol or isopropanol, or via a solid phase purification step, typically on a silica matrix in a column, resin or on paramagnetic beads in the presence of high concentrations of a chaotropic salt, prior to washing and then elution in a low ionic strength buffer. An optional step prior to nucleic acid precipitation is the addition of a protease which digests the proteins in order to further purify the sample.

Other lysis methods include mechanical lysis via ultrasonic vibration and thermal lysis where the sample is heated to 94° C. to disrupt cell membranes.

The target DNA or RNA may be present in the extracted material in very small amounts, particularly if the target is of pathogenic origin. Nucleic acid amplification provides the ability to selectively amplify (that is, replicate) specific targets present in low concentrations to detectable levels.

The most commonly used nucleic acid amplification technique is the polymerase chain reaction (PCR). PCR is well known in this field and comprehensive description of this type of reaction is provided in E. van Pelt-Verkuil et al., Principles and Technical Aspects of PCR Amplification, Springer, 2008.

PCR is a powerful technique that amplifies a target DNA sequence against a background of complex DNA. If RNA is to be amplified (by PCR), it must be first transcribed into cDNA (complementary DNA) using an enzyme called reverse transcriptase. Afterwards, the resulting cDNA is amplified by PCR.

PCR is an exponential process that proceeds as long as the conditions for sustaining the reaction are acceptable. The components of the reaction are:

1. pair of primers—short single strands of DNA with around 10-30 nucleotides complementary to the regions flanking the target sequence
2. DNA polymerase—a thermostable enzyme that synthesizes DNA
3. deoxyribonucleoside triphosphates (dNTPs)—provide the nucleotides that are incorporated into the newly synthesized DNA strand
4. buffer—to provide the optimal chemical environment for DNA synthesis PCR typically involves placing these reactants in a small tube (~10-50 microliters) containing the extracted nucleic acids. The tube is placed in a thermal cycler; an instrument that subjects the reaction to a series of different temperatures for varying amounts of time. The standard protocol for each thermal cycle involves a denaturation phase, an annealing phase, and an extension phase. The extension phase is sometimes referred to as the primer extension phase. In addition to such three-step protocols, two-step thermal protocols can be employed, in which the annealing and extension phases are combined. The denaturation phase typically involves raising the temperature of the reaction to 90-95° C. to denature the DNA strands; in the annealing phase, the temperature is lowered to ~50-60° C. for the primers to anneal; and then in the extension phase the temperature is raised to the optimal DNA polymerase activity temperature of 60-72° C. for primer extension. This process is repeated cyclically around 20-40 times, the end result being the creation of millions of copies of the target sequence between the primers.

There are a number of variants to the standard PCR protocol such as multiplex PCR, linker-primed PCR, direct PCR, tandem PCR, real-time PCR and reverse-transcriptase PCR, amongst others, which have been developed for molecular diagnostics.

Multiplex PCR uses multiple primer sets within a single PCR mixture to produce amplicons of varying sizes that are specific to different DNA sequences. By targeting multiple genes at once, additional information may be gained from a single test-run that otherwise would require several experiments. Optimization of multiplex PCR is more difficult though and requires selecting primers with similar annealing temperatures, and amplicons with similar lengths and base composition to ensure the amplification efficiency of each amplicon is equivalent.

Linker-primed PCR, also known as ligation adaptor PCR, is a method used to enable nucleic acid amplification of essentially all DNA sequences in a complex DNA mixture without the need for target-specific primers. The method firstly involves digesting the target DNA population with a suitable restriction endonuclease (enzyme). Double-stranded oligonucleotide linkers (also called adaptors) with a suitable overhanging end are then ligated to the ends of target DNA fragments using a ligase enzyme. Nucleic acid amplification is subsequently performed using oligonucleotide primers which are specific for the linker sequences. In this way, all fragments of the DNA source which are flanked by linker oligonucleotides can be amplified.

Direct PCR describes a system whereby PCR is performed directly on a sample without any, or with minimal, nucleic acid extraction. It has long been accepted that PCR reactions are inhibited by the presence of many components of unpurified biological samples, such as the haem component in blood. Traditionally, PCR has required extensive purification of the target nucleic acid prior to preparation of the reaction mixture. With appropriate changes to the chemistry and sample concentration, however, it is possible to perform PCR with minimal DNA purification, or direct PCR. Adjustments to the PCR chemistry for direct PCR include increased buffer strength, the use of polymerases which have high activity and processivity, and additives which chelate with potential polymerase inhibitors.

Tandem PCR utilises two distinct rounds of nucleic acid amplification to increase the probability that the correct amplicon is amplified. One form of tandem PCR is nested PCR in which two pairs of PCR primers are used to amplify a single locus in separate rounds of nucleic acid amplification. The first pair of primers hybridize to the nucleic acid sequence at regions external to the target nucleic acid sequence. The second pair of primers (nested primers) used in the second round of amplification bind within the first PCR product and produce a second PCR product containing the target nucleic acid, that will be shorter than the first one. The logic behind this strategy is that if the wrong locus were amplified by mistake during the first round of nucleic acid amplification, the probability is very low that it would also be amplified a second time by a second pair of primers and thus ensures specificity.

Real-time PCR, or quantitative PCR, is used to measure the quantity of a PCR product in real time. By using a fluorophore-containing probe or fluorescent dyes along with a set of standards in the reaction, it is possible to quantitate the starting amount of nucleic acid in the sample. This is particularly useful in molecular diagnostics where treatment options may differ depending on the pathogen load in the sample.

Reverse-transcriptase PCR (RT-PCR) is used to amplify DNA from RNA. Reverse transcriptase is an enzyme that reverse transcribes RNA into complementary DNA (cDNA), which is then amplified by PCR. RT-PCR is widely used in expression profiling, to determine the expression of a gene or to identify the sequence of an RNA transcript, including transcription start and termination sites. It is also used to amplify RNA viruses such as human immunodeficiency virus or hepatitis C virus.

Isothermal amplification is another form of nucleic acid amplification which does not rely on the thermal denaturation of the target DNA during the amplification reaction and hence does not require sophisticated machinery. Isothermal nucleic acid amplification methods can therefore be carried out in primitive sites or operated easily outside of a laboratory environment. A number of isothermal nucleic acid amplification methods have been described, including Strand Displacement Amplification, Transcription Mediated Amplification, Nucleic Acid Sequence Based Amplification, Recombinase Polymerase Amplification, Rolling Circle Amplification, Ramification Amplification, Helicase-Dependent Isothermal DNA Amplification and Loop-Mediated Isothermal Amplification.

Isothermal nucleic acid amplification methods do not rely on the continuing heat denaturation of the template DNA to produce single stranded molecules to serve as templates for further amplification, but instead rely on alternative methods such as enzymatic nicking of DNA molecules by specific restriction endonucleases, or the use of an enzyme to separate the DNA strands, at a constant temperature.

Strand Displacement Amplification (SDA) relies on the ability of certain restriction enzymes to nick the unmodified strand of hemi-modified DNA and the ability of a 5'-3' exonuclease-deficient polymerase to extend and displace the downstream strand. Exponential nucleic acid amplification is then achieved by coupling sense and antisense reactions in which strand displacement from the sense reaction serves as a template for the antisense reaction. The use of nickase enzymes which do not cut DNA in the traditional manner but produce a nick on one of the DNA strands, such as N. Alw1, N. BstNB1 and Mly1, are useful in this reaction. SDA has been improved by the use of a combination of a heat-stable restriction enzyme (Ava1) and heat-stable Exo-polymerase (Bst polymerase). This combination has been shown to increase amplification efficiency of the reaction from $10^8$ fold amplification to $10^{10}$ fold amplification so that it is possible using this technique to amplify unique single copy molecules.

Transcription Mediated Amplification (TMA) and Nucleic Acid Sequence Based Amplification (NASBA) use an RNA polymerase to copy RNA sequences but not corresponding genomic DNA. The technology uses two primers and two or three enzymes, RNA polymerase, reverse transcriptase and optionally RNase H (if the reverse transcriptase does not have RNase activity). One primer contains a promoter sequence for RNA polymerase. In the first step of nucleic acid amplification, this primer hybridizes to the target ribosomal RNA (rRNA) at a defined site. Reverse transcriptase creates a DNA copy of the target rRNA by extension from the 3' end of the promoter primer. The RNA in the resulting RNA:DNA duplex is degraded by the RNase activity of the reverse transcriptase if present or the additional RNase H. Next, a second primer binds to the DNA copy. A new strand of DNA is synthesized from the end of this primer by reverse transcriptase, creating a double-stranded DNA molecule. RNA polymerase recognizes the promoter sequence in the DNA template and initiates transcription. Each of the newly synthesized RNA amplicons re-enters the process and serves as a template for a new round of replication.

In Recombinase Polymerase Amplification (RPA), the isothermal amplification of specific DNA fragments is achieved by the binding of opposing oligonucleotide primers to template DNA and their extension by a DNA polymerase. Heat is not required to denature the double-stranded DNA (dsDNA) template. Instead, RPA employs recombinase-primer complexes to scan dsDNA and facilitate strand exchange at cognate sites. The resulting structures are stabilised by single-stranded DNA binding proteins interacting with the displaced template strand, thus preventing the ejection of the primer by branch migration. Recombinase disassembly leaves the 3' end of the oligonucleotide accessible to a strand displacing DNA polymerase, such as the large fragment of Bacillus subtilis Pol I (Bsu), and primer extension ensues. Exponential nucleic acid amplification is accomplished by the cyclic repetition of this process.

Helicase-dependent amplification (HDA) mimics the in vivo system in that it uses a DNA helicase enzyme to generate single-stranded templates for primer hybridization and subsequent primer extension by a DNA polymerase. In the first step of the HDA reaction, the helicase enzyme traverses along the target DNA, disrupting the hydrogen bonds linking the two strands which are then bound by single-stranded binding proteins. Exposure of the single-stranded target region by the helicase allows primers to anneal. The DNA polymerase then extends the 3' ends of each primer using free deoxyribonucleoside triphosphates (dNTPs) to produce two DNA replicates. The two replicated dsDNA strands independently enter the next cycle of HDA, resulting in exponential nucleic acid amplification of the target sequence.

Other DNA-based isothermal techniques include Rolling Circle Amplification (RCA) in which a DNA polymerase extends a primer continuously around a circular DNA template, generating a long DNA product that consists of many repeated copies of the circle. By the end of the reaction, the polymerase generates many thousands of copies of the circular template, with the chain of copies tethered to the original target DNA. This allows for spatial resolution of target and rapid nucleic acid amplification of the signal. Up to $10^{12}$ copies of template can be generated in 1 hour. Ramification amplification is a variation of RCA and utilizes a closed circular probe (C-probe) or padlock probe and a DNA polymerase with a high processivity to exponentially amplify the C-probe under isothermal conditions.

Loop-mediated isothermal amplification (LAMP), offers high selectivity and employs a DNA polymerase and a set of four specially designed primers that recognize a total of six distinct sequences on the target DNA. An inner primer containing sequences of the sense and antisense strands of the target DNA initiates LAMP. The following strand displacement DNA synthesis primed by an outer primer releases a single-stranded DNA. This serves as template for DNA synthesis primed by the second inner and outer primers that hybridize to the other end of the target, which produces a stem-loop DNA structure. In subsequent LAMP cycling one inner primer hybridizes to the loop on the product and initiates displacement DNA synthesis, yielding the original stem-loop DNA and a new stem-loop DNA with a stem twice as long. The cycling reaction continues with accumulation of $10^9$ copies of target in less than an hour. The final products are stem-loop DNAs with several inverted repeats of the target and cauliflower-like structures with multiple loops formed by annealing between alternately inverted repeats of the target in the same strand.

After completion of the nucleic acid amplification, the amplified product must be analysed to determine whether the anticipated amplicon (the amplified quantity of target nucleic acids) was generated. The methods of analyzing the product range from simply determining the size of the amplicon through gel electrophoresis, to identifying the nucleotide composition of the amplicon using DNA hybridization.

Gel electrophoresis is one of the simplest ways to check whether the nucleic acid amplification process generated the anticipated amplicon. Gel electrophoresis uses an electric field applied to a gel matrix to separate DNA fragments. The negatively charged DNA fragments will move through the matrix at different rates, determined largely by their size. After the electrophoresis is complete, the fragments in the gel can be stained to make them visible. Ethidium bromide is a commonly used stain which fluoresces under UV light.

The size of the fragments is determined by comparison with a DNA size marker (a DNA ladder), which contains DNA fragments of known sizes, run on the gel alongside the amplicon. Because the oligonucleotide primers bind to specific sites flanking the target DNA, the size of the amplified product can be anticipated and detected as a band of known size on the gel. To be certain of the identity of the amplicon, or if several amplicons have been generated, DNA probe hybridization to the amplicon is commonly employed.

DNA hybridization refers to the formation of double-stranded DNA by complementary base pairing. DNA hybridization for positive identification of a specific amplification product requires the use of a DNA probe around 20 nucleotides in length. If the probe has a sequence that is complementary to the amplicon (target) DNA sequence, hybridization will occur under favourable conditions of temperature, pH and ionic concentration. If hybridization occurs, then the gene or DNA sequence of interest was present in the original sample.

Optical detection is the most common method to detect hybridization. Either the amplicons or the probes are labelled to emit light through fluorescence or electrochemiluminescence. These processes differ in the means of producing excited states of the light-producing moieties, but both enable covalent labelling of nucleotide strands. In electrochemiluminescence (ECL), light is produced by luminophore molecules or complexes upon stimulation with an electric current. In fluorescence, it is illumination with excitation light which leads to emission.

Fluorescence is detected using an illumination source which provides excitation light at a wavelength absorbed by the fluorescent molecule, and a detection unit. The detection unit comprises a photosensor (such as a photomultiplier tube or charge-coupled device (CCD) array) to detect the emitted signal, and a mechanism (such as a wavelength-selective filter) to prevent the excitation light from being included in the photosensor output. The fluorescent molecules emit Stokes-shifted light in response to the excitation light, and this emitted light is collected by the detection unit. Stokes shift is the frequency difference or wavelength difference between emitted light and absorbed excitation light.

ECL emission is detected using a photosensor which is sensitive to the emission wavelength of the ECL species being employed. For example, transition metal-ligand complexes emit light at visible wavelengths, so conventional photodiodes and CCDs are employed as photosensors. An advantage of ECL is that, if ambient light is excluded, the ECL emission can be the only light present in the detection system, which improves sensitivity.

Microarrays allow for hundreds of thousands of DNA hybridization experiments to be performed simultaneously. Microarrays are powerful tools for molecular diagnostics with the potential to screen for thousands of genetic diseases or detect the presence of numerous infectious pathogens in a single test. A microarray consists of many different DNA probes immobilized as spots on a substrate. The target DNA (amplicon) is first labelled with a fluorescent or luminescent molecule (either during or after nucleic acid amplification) and then applied to the array of probes. The microarray is incubated in a temperature controlled, humid environment for a number of hours or days while hybridization between the probe and amplicon takes place. Following incubation, the microarray must be washed in a series of buffers to remove unbound strands. Once washed, the microarray surface is dried using a stream of air (often nitrogen). The stringency of the hybridization and washes is critical. Insufficient stringency can result in a high degree of nonspecific binding. Excessive stringency can lead to a failure of appropriate binding, which results in diminished sensitivity. Hybridization is recognized by detecting light emission from the labelled amplicons which have formed a hybrid with complementary probes.

Fluorescence from microarrays is detected using a microarray scanner which is generally a computer controlled inverted scanning fluorescence confocal microscope which typically uses a laser for excitation of the fluorescent dye and a photosensor (such as a photomultiplier tube or CCD) to detect the emitted signal. The fluorescent molecules emit Stokes-shifted light (described above) which is collected by the detection unit.

The emitted fluorescence must be collected, separated from the unabsorbed excitation wavelength, and transported to the detector. In microarray scanners, a confocal arrangement is commonly used to eliminate out-of-focus information by means of a confocal pinhole situated at an image plane. This allows only the in-focus portion of the light to be detected. Light from above and below the plane of focus of the object is prevented from entering the detector, thereby increasing the signal to noise ratio. The detected fluorescent photons are converted into electrical energy by the detector which is subsequently converted to a digital signal. This digital signal translates to a number representing the intensity of fluorescence from a given pixel. Each feature of the array is made up of one or more such pixels. The final result of a scan is an image of the array surface. The exact sequence and position of every probe on the microarray is known, and so the hybridized target sequences can be identified and analysed simultaneously.

More information regarding fluorescent probes can be found at: http://www.premierbiosoft.com/tech_notes/FRET-_probe.html and http://www.invitrogen.com/site/us/en/home/References/Molecular-Probes-The-Handbook/Technical-Notes-and-Product-Highlights/Fluorescence-Resonance-Energy-Transfer-FRET.html Point-of-Care Molecular Diagnostics Despite the advantages that molecular diagnostic tests offer, the growth of this type of testing in the clinical laboratory has been slower than expected and remains a minor part of the practice of laboratory medicine. This is primarily due to the complexity and costs associated with nucleic acid testing compared with tests based on methods not involving nucleic acids. The widespread adaptation of molecular diagnostics testing to the clinical setting is intimately tied to the development of instrumentation that significantly reduces the cost, provides a rapid and automated assay from start (specimen processing) to finish (generating a result) and operates without major intervention by personnel.

A point-of-care technology serving the physician's office, the hospital bedside or even consumer-based, at home, would offer many advantages including:

rapid availability of results enabling immediate facilitation of treatment and improved quality of care.

ability to obtain laboratory values from testing very small samples.

reduced clinical workload.

reduced laboratory workload and improved office efficiency by reducing administrative work.

improved cost per patient through reduced length of stay of hospitalization, conclusion of outpatient consultation at the first visit, and reduced handling, storing and shipping of specimens.

facilitation of clinical management decisions such as infection control and antibiotic use.

Lab-on-a-Chip (LOC) Based Molecular Diagnostics

Molecular diagnostic systems based on microfluidic technologies provide the means to automate and speed up molecular diagnostic assays. The quicker detection times are primarily due to the extremely low volumes involved, automation, and the low-overhead inbuilt cascading of the diagnostic process steps within a microfluidic device. Volumes in the nanoliter and microliter scale also reduce reagent consumption and cost. Lab-on-a-chip (LOC) devices are a common form of microfluidic device. LOC devices have MST structures within a MST layer for fluid processing integrated onto a single supporting substrate (usually silicon). Fabrication using the VLSI (very large scale integrated) lithographic techniques of the semiconductor industry keeps the unit cost of each LOC device very low. However, controlling fluid flow through the LOC device, adding reagents, controlling reaction conditions and so on necessitate bulky external plumbing and electronics. Connecting a LOC device to these external devices effectively restricts the use of LOC devices for molecular diagnostics to the laboratory setting. The cost of the external equipment and complexity of its operation precludes LOC-based molecular diagnostics as a practical option for point-of-care settings.

In view of the above, there is a need for a molecular diagnostic system based on a LOC device for use at point-of-care.

SUMMARY OF THE INVENTION

Accordingly, the present invention provides a test module for detecting target nucleic acid sequences in a fluid, the test module comprising:

an outer casing having a receptacle for receiving the fluid containing the target nucleic acid sequences;

electrochemiluminescent (ECL) probes having an ECL luminophore for emitting photons when in an excited state and a functional moiety for quenching photon emission from the ECL luminophore by resonant energy transfer;

electrodes for receiving an electrical pulse to excite the ECL luminophores; and, a detection photosensor for exposure to the photons emitted by the ECL luminophores.

Preferably, the test module also has a lab-on-a-chip (LOC) device with circuitry for providing the electrical pulse to the electrodes wherein the detection photosensor is incorporated into the circuitry and the ECL probes, the electrodes, and the control circuitry are integrated into the LOC device.

Preferably, the LOC device has a supporting substrate for supporting the circuitry which in turn supports the electrodes and the ECL probes.

Preferably, the circuitry has layers of CMOS circuitry deposited on the supporting substrate for providing the electrodes with an electrical pulse.

Preferably, the electrical pulse has duration less than 0.69 seconds.

Preferably, the electrical pulse has a current of 0.1 nanoamperes to 69.0 nanoamperes.

Preferably, the test module also has:

a communication interface for the circuitry to transmit data to an external device.

Preferably, the test module also has an array of hybridization chambers containing the ECL probes for different target nucleic acid sequences wherein the CMOS circuitry has memory for storing the identity data relating to the ECL probes in each of the hybridization chambers.

Preferably, the hybridization chambers have a volume less than 900,000 cubic microns.

Preferably, the hybridization chambers have a volume less than 200,000 cubic microns.

Preferably, the communication interface is a universal serial bus (USB) connection such that the outer casing is configured as a USB drive.

Preferably, the detection photosensor is an array of detection photodiodes positioned in registration with the hybridization chambers.

Preferably, the test module also has at least one calibration source for providing a calibration emission, and at least one calibration photodiode for sensing the calibration emission wherein the CMOS circuitry has a differential circuit for subtracting the calibration photodiode output from the output of one or more of the detection photodiodes.

Preferably, the test module also has a plurality of the calibration sources and a corresponding plurality of the calibration photodiodes in registration with the calibration sources respectively.

Preferably, the calibration sources are calibration probes without an ECL luminophore.

Preferably, the test module also has a plurality of calibration chambers containing the calibration sources distributed throughout the array of hybridization chambers, wherein during use, output from any one of the detection photodiodes is compared to output from the calibration photodiode most proximate to that detection photodiode.

Preferably, the calibration sources are calibration probes and the calibration chambers are configured to seal the calibration probes from the fluid containing the target nucleic acid sequences.

Preferably, each of the calibration chambers are surrounded by a three-by-three square of the hybridization chambers.

Preferably, the detection photodiodes are less than 1600 microns from the hybridization chambers.

Preferably, the ECL probes have a stem-and-loop structure with a loop portion containing the sequence complementary to the target nucleic acid sequence, the loop portion being positioned between the functional moiety for quenching photon emission from the ECL luminophore, and the ECL luminophore, such that hybridization with the target nucleic acid sequence opens the loop portion and moves the ECL luminophore away from the functional moiety.

The integrated image sensor with the driver for excitation of electrochemiluminescence luminophores obviate the need for an expensive external imaging system and provides for a mass-producible inexpensive integrated solution with low system component-count that is a compact, light, and highly portable system. The integrated image sensor increases the readout sensitivity by benefiting from large angle of light collection and obviates the need for optical components in the optical collection train.

The electrochemiluminescence-based assay target detection obviates any need, of the assay system, for an excitation light source, excitation optics, and optical filter elements, in turn, providing for a more compact and more inexpensive assay system. The absence of the requirement for the rejection of any excitation light also simplifies the detector circuitry, making the assay system even more inexpensive.

BRIEF DESCRIPTION OF THE DRAWINGS

Preferred embodiments of the present invention will now be described by way of example only with reference to the accompanying drawings, in which:

FIG. 13 is an enlarged view of Inset AA shown in FIG. 6;

FIG. 14 is an enlarged view of Inset AB shown in FIG. 6;

FIG. 15 is an enlarged view of Inset AE shown in FIG. 13;

FIG. 32 is a schematic section view of the boiling-initiated valve taken through line 33-33 shown in FIG. 31;

FIG. 33 is an enlarged view of Inset AF shown in FIG. 15;

FIG. 53 is a further enlarged plan view of two hybridization chambers in isolation;

FIG. 54 is schematic section view of a single hybridization chamber;

FIG. 55 is an enlarged view of the humidifier illustrated in Inset AG shown in FIG. 6;

FIG. 56 is an enlarged view of Inset AD shown in FIG. 52;

FIG. 57 is an exploded perspective view of the LOC device within Inset AD;

FIG. 61 is an enlarged view of the evaporator shown in Inset AP of FIG. 55;

FIG. 63 is a schematic representation of a test module with a lancet;

FIG. 78 is a plan view of LOC variant X showing the structures of the CMOS+MST device in isolation;

FIG. 82 is an enlarged view of Inset DA shown in FIG. 81;
FIG. 83 is an enlarged view of Inset DB shown in FIG. 81;
FIG. 84 is an enlarged view of Inset DC shown in FIG. 81;
FIG. 85 is an enlarged view of Inset DD shown in FIG. 81;
FIG. 86 is an enlarged view of Inset DE shown in FIG. 81;
FIG. 87 is an enlarged view of Inset DF shown in FIG. 81;
FIG. 88 is an enlarged view of Inset DG shown in FIG. 81;
FIG. 89 is an enlarged view of Inset DH shown in FIG. 81;
FIG. 90 is an enlarged view of Inset DJ shown in FIG. 81;
FIG. 91 is an enlarged view of Inset DK shown in FIG. 81;
FIG. 92 is an enlarged view of Inset DL shown in FIG. 81.

FIGS. 109A and 109B are diagrams illustrating binding of two aptamers to a protein to produce a detectable signal;

FIGS. 110A and 110B are diagrams illustrating binding of two antibodies to a protein to produce a detectable signal;

FIG. 117 is an enlarged view of Inset GA shown in FIG. 116;
FIG. 118 is an enlarged view of Inset GB shown in FIG. 116;
FIG. 119 is an enlarged view of Inset GC shown in FIG. 116;
FIG. 120 is an enlarged view of Inset GD shown in FIG. 116;
FIG. 121 is an enlarged view of Inset GE shown in FIG. 116;
FIG. 122 is an enlarged view of Inset GF shown in FIG. 116;
FIG. 123 is an enlarged view of Inset GG shown in FIG. 116;
FIG. 124 is an enlarged view of Inset GH shown in FIG. 116;
FIG. 125 is an enlarged view of Inset GJ shown in FIG. 116;
FIG. 126 is an enlarged view of Inset GK shown in FIG. 116;
FIG. 127 is an enlarged view of Inset GL shown in FIG. 116;

FIG. 138 is an enlarged view of the hybridization chamber of LOC variant L;

DETAILED DESCRIPTION OF THE PREFERRED EMBODIMENTS

Overview

Figure 1:
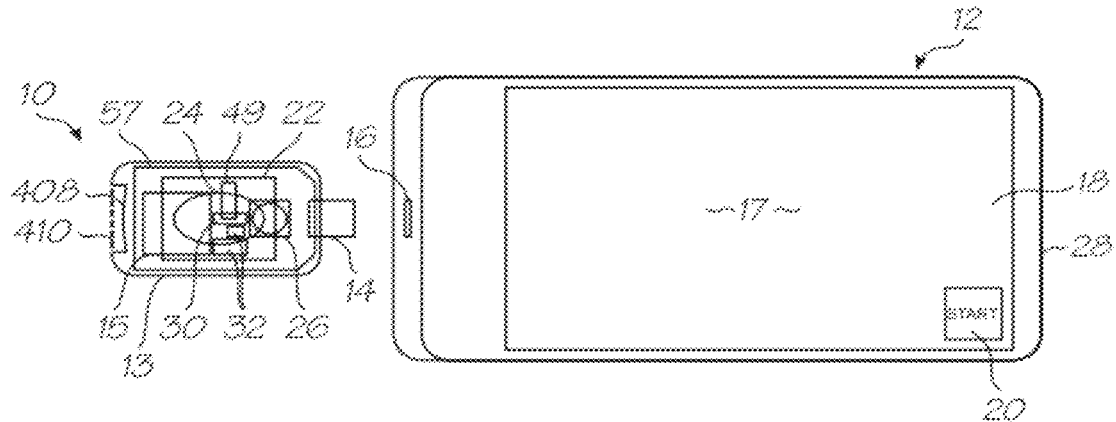
FIG. 1 shows a test module and test module reader configured for fluorescence detection.

This overview identifies the main components of a molecular diagnostic system that incorporates embodiments of the present invention. Comprehensive details of the system architecture and operation are set out later in the specification.

Referring to FIGS. 1, 2, 3, 104 and 105, the system has the following top level components:

Test modules 10 and 11 are the size of a typical USB memory key and very cheap to produce. Test modules 10 and 11 each contain a microfluidic device, typically in the form of a lab-on-a-chip (LOC) device 30 preloaded with reagents and typically more than 1000 probes for the molecular diagnostic assay (see FIGS. 1 and 104). Test module 10 schematically shown in FIG. 1 uses a fluorescence-based detection technique to identify target molecules, while test module 11 in FIG. 104 uses an electrochemiluminescence-based detection technique. The LOC device 30 has an integrated photosensor 44 for fluorescence or electrochemiluminescence detection (described in detail below). Both test modules 10 and 11 use a standard Micro-USB plug 14 for power, data and control, both have a printed circuit board (PCB) 57, and both have external power supply capacitors 32 and an inductor 15. The test modules 10 and 11 are both single-use only for mass production and distribution in sterile packaging ready for use.

The outer casing 13 has a macroreceptacle 24 for receiving the biological sample and a removable sterile sealing tape 22, preferably with a low tack adhesive, to cover the macroreceptacle prior to use. A membrane seal 408 with a membrane guard 410 forms part of the outer casing 13 to reduce dehumidification within the test module while providing pressure relief from small air pressure fluctuations. The membrane guard 410 protects the membrane seal 408 from damage.

Figure 3:
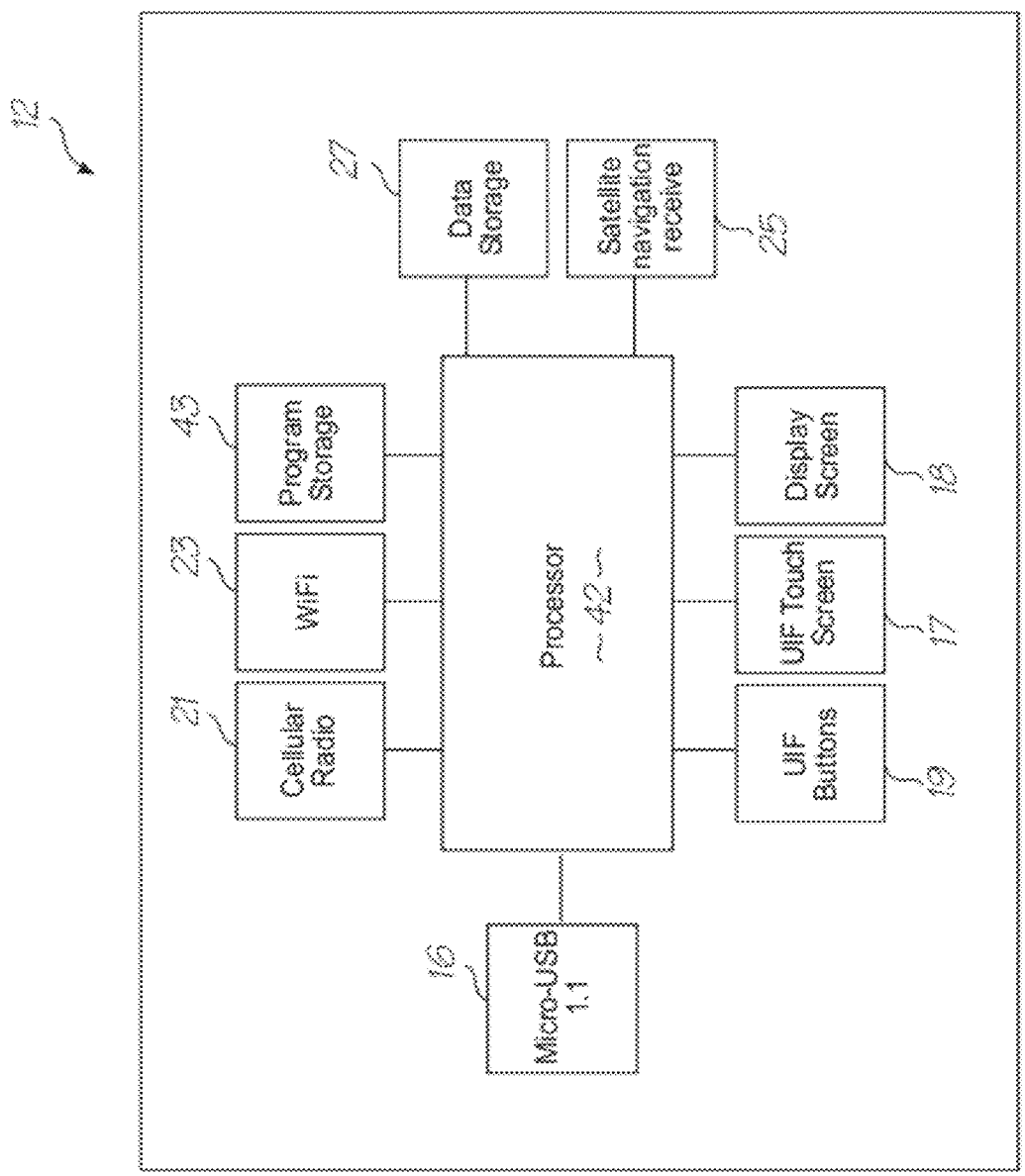
FIG. 3 is a schematic overview of the electronic components in the test module reader.
Figure 104:
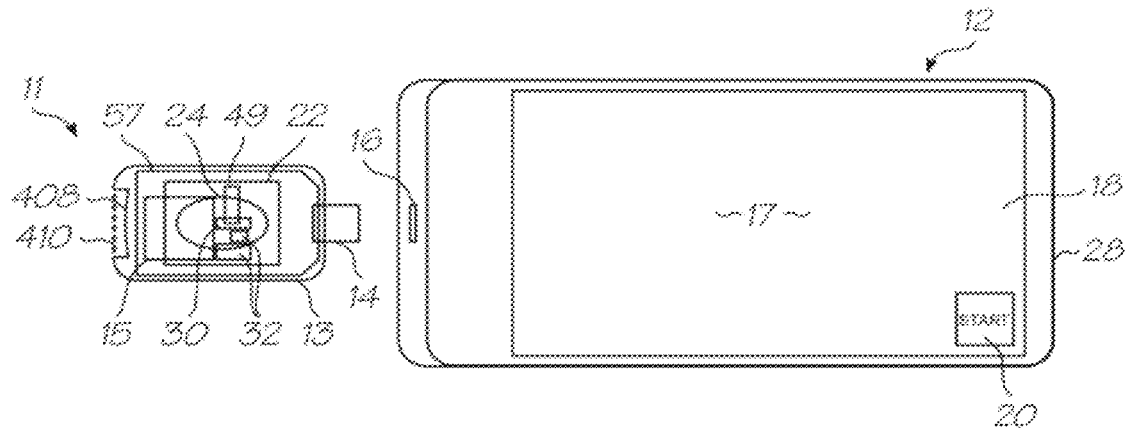
FIG. 104 shows a test module and test module reader configured for use with ECL detection.

Test module reader 12 powers the test module 10 or 11 via Micro-USB port 16. The test module reader 12 can adopt many different forms and a selection of these are described later. The version of the reader 12 shown in FIGS. 1, 3 and 104 is a smart phone embodiment. A block diagram of this reader 12 is shown in FIG. 3. Processor 42 runs application software from program storage 43. The processor 42 also interfaces with the display screen 18 and user interface (UI) touch screen 17 and buttons 19, a cellular radio 21, wireless network connection 23, and a satellite navigation system 25. The cellular radio 21 and wireless network connection 23 are used for communications. Satellite navigation system 25 is used for updating epidemiological databases with location data. The location data can, alternatively, be entered manually via the touch screen 17 or buttons 19. Data storage 27 holds genetic and diagnostic information, test results, patient information, assay and probe data for identifying each probe and its array position. Data storage 27 and program storage 43 may be shared in a common memory facility. Application software installed on the test module reader 12 provides analysis of results, along with additional test and diagnostic information.

To conduct a diagnostic test, the test module 10 (or test module 11) is inserted into the Micro-USB port 16 on the test module reader 12. The sterile sealing tape 22 is peeled back and the biological sample (in a liquid form) is loaded into the sample macroreceptacle 24. Pressing start button 20 initiates testing via the application software. The sample flows into the LOC device 30 and the on-board assay extracts, incubates, amplifies and hybridizes the sample nucleic acids (the target) with presynthesized hybridization-responsive oligonucleotide probes. In the case of test module 10 (which uses fluorescence-based detection), the probes are fluorescently labelled and the LED 26 housed in the casing 13 provides the necessary excitation light to induce fluorescence emission from the hybridized probes (see FIGS. 1 and 2). In test module 11 (which uses electrochemiluminescence (ECL) detection), the LOC device 30 is loaded with ECL probes (discussed above) and the LED 26 is not necessary for generating the luminescent emission. Instead, electrodes 860 and 870 provide the excitation electrical current (see FIG. 105). The emission (fluorescent or luminescent) is detected using a photosensor 44 integrated into CMOS circuitry of each LOC device. The detected signal is amplified and converted to a digital output which is analyzed by the test module reader 12. The reader then displays the results.

The data may be saved locally and/or uploaded to a network server containing patient records. The test module 10 or 11 is removed from the test module reader 12 and disposed of appropriately.

Figure 106:
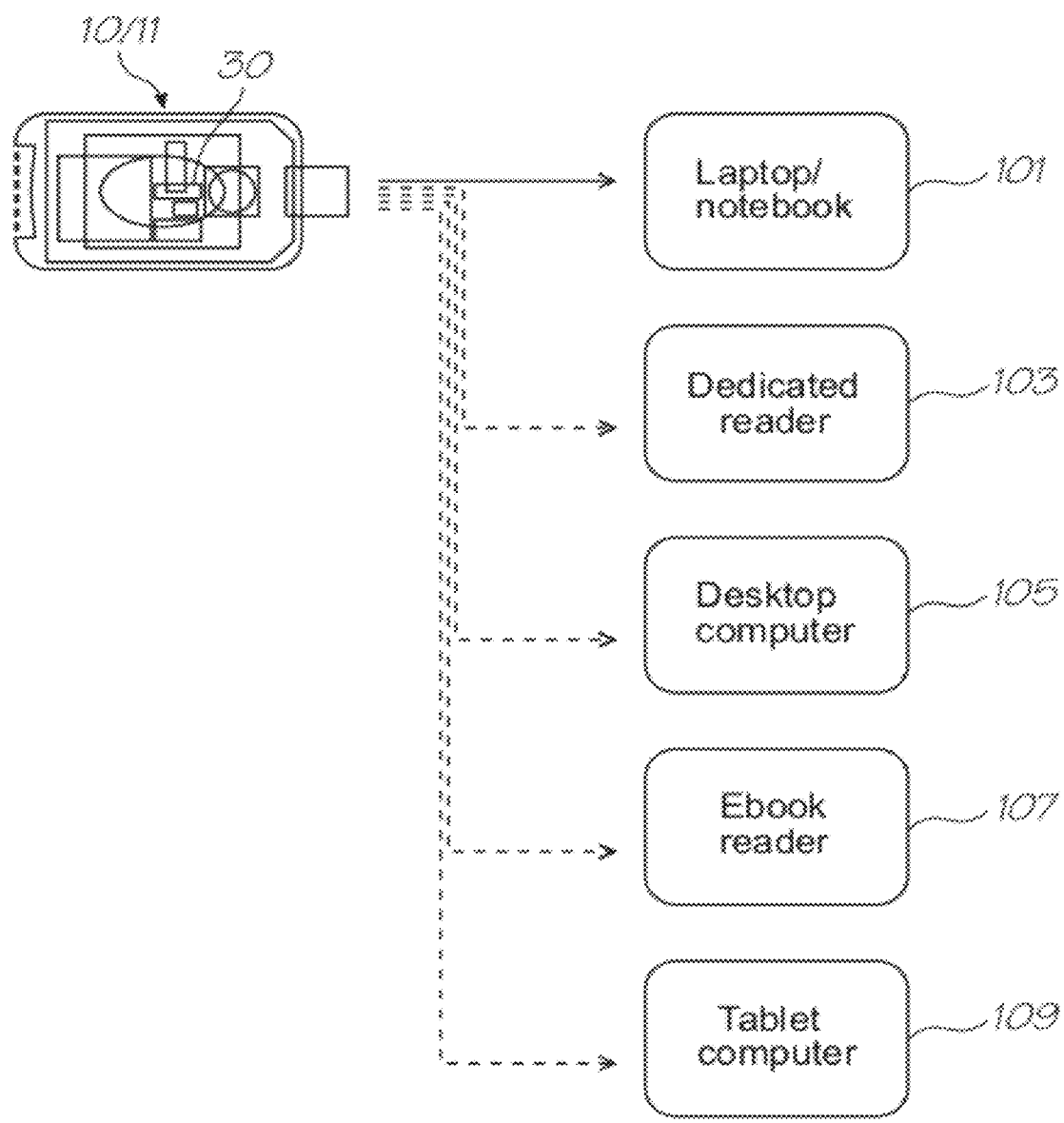
FIG. 106 shows a test module and alternative test module readers.

FIGS. 1, 3 and 104 show the test module reader 12 configured as a mobile phone/smart phone 28. In other forms, the test module reader is a laptop/notebook 101, a dedicated reader 103, an ebook reader 107, a tablet computer 109 or desktop computer 105 for use in hospitals, private practices or laboratories (see FIG. 106). The reader can interface with a range of additional applications such as patient records, billing, online databases and multi-user environments. It can also be interfaced with a range of local or remote peripherals such as printers and patient smart cards.

Figure 107:
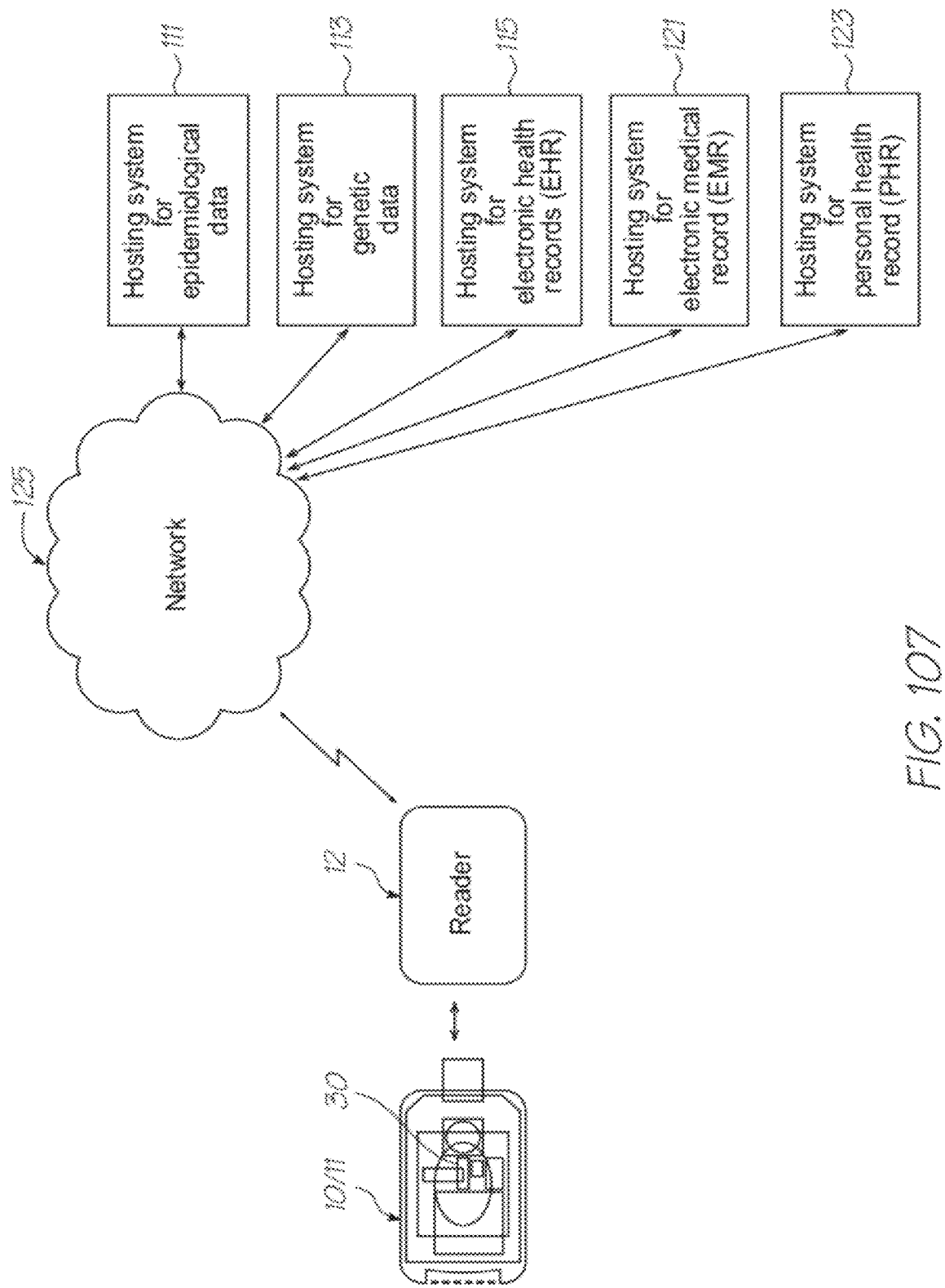
FIG. 107 shows a test module and test module reader along with the hosting system housing various databases.

Referring to FIG. 107, the data generated by the test module 10 can be used to update, via the reader 12 and network 125, the epidemiological databases hosted on the hosting system for epidemiological data 111, the genetic databases hosted on the hosting system for genetic data 113, the electronic health records hosted on the hosting system for electronic health records (EHR) 115, the electronic medical records hosted on the hosting system for electronic medical records (EMR) 121, and the personal health records hosted on the hosting system for personal health records (PHR) 123. Conversely, the epidemiological data hosted on the hosting system for epidemiological data 111, the genetic data hosted on the hosting system for genetic data 113, the electronic health records hosted on the hosting system for electronic health records (EHR) 115, the electronic medical records hosted on the hosting system for electronic medical records (EMR) 121, and the personal health records hosted on the hosting system for personal health records (PHR) 123, can be used to update, via network 125 and the reader 12, the digital memory in the LOC 30 of the test module 10.

Referring back to FIGS. 1, 2, 104 and 105 the reader 12 uses battery power in the mobile phone configuration. The mobile phone reader contains all test and diagnostic information preloaded. Data can also be loaded or updated via a number of wireless or contact interfaces to enable communications with peripheral devices, computers or online servers. A Micro-USB port 16 is provided for connection to a computer or mains power supply for battery recharge.

FIG. 63 shows an embodiment of the test module 10 used for tests that only require a positive or negative result for a particular target, such as testing whether a person is infected with, for example, H1N1 Influenza A virus. Only a purpose built USB power/indicator-only module 47 is adequate. No other reader or application software is necessary. An indicator 45 on the USB power/indicator-only module 47 signals positive or negative results. This configuration is well suited to mass screening.

Additional items supplied with the system may include a test tube containing reagents for pre-treatment of certain samples, along with spatula and lancet for sample collection. FIG. 63 shows an embodiment of the test module incorporating a spring-loaded, retractable lancet 390 and lancet release button 392 for convenience. A satellite phone can be used in remote areas.

Test Module Electronics

Figure 2:
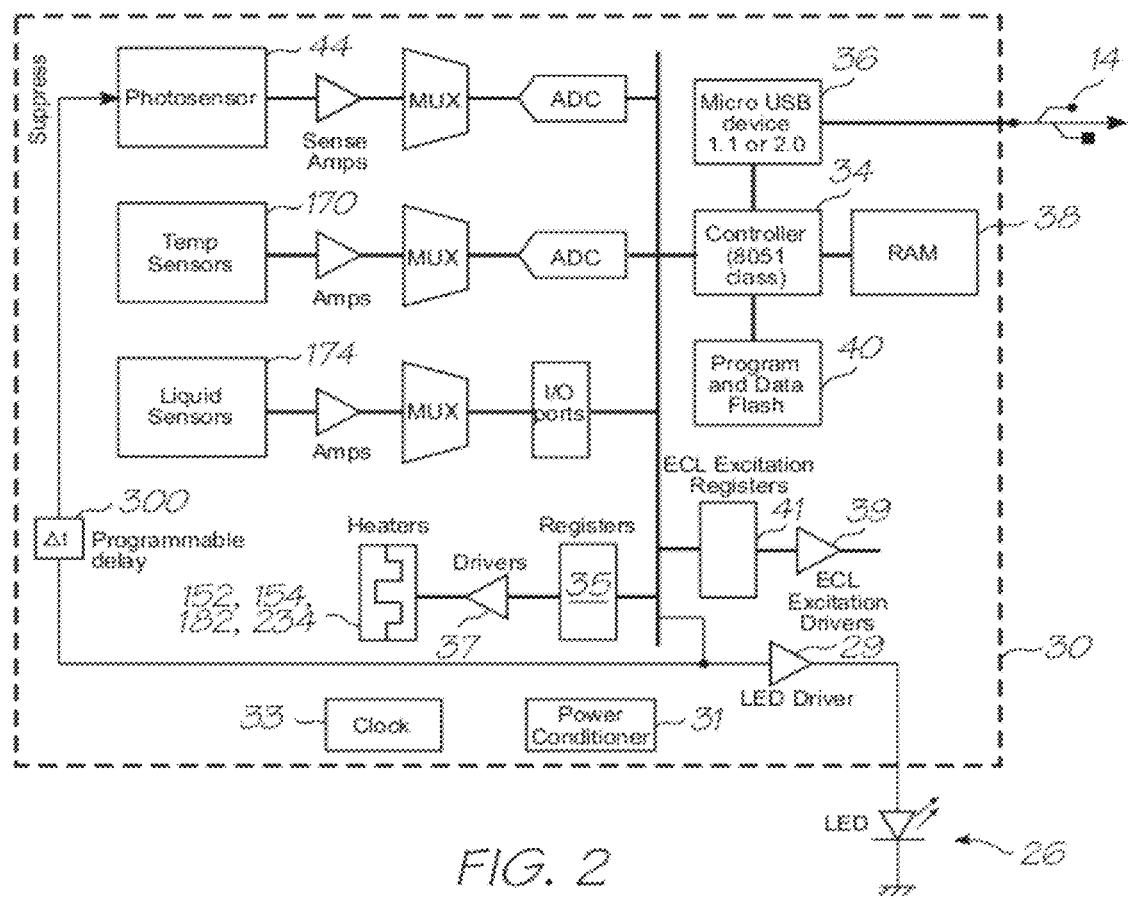
FIG. 2 is a schematic overview of the electronic components in the test module configured for fluorescence detection.
Figure 105:
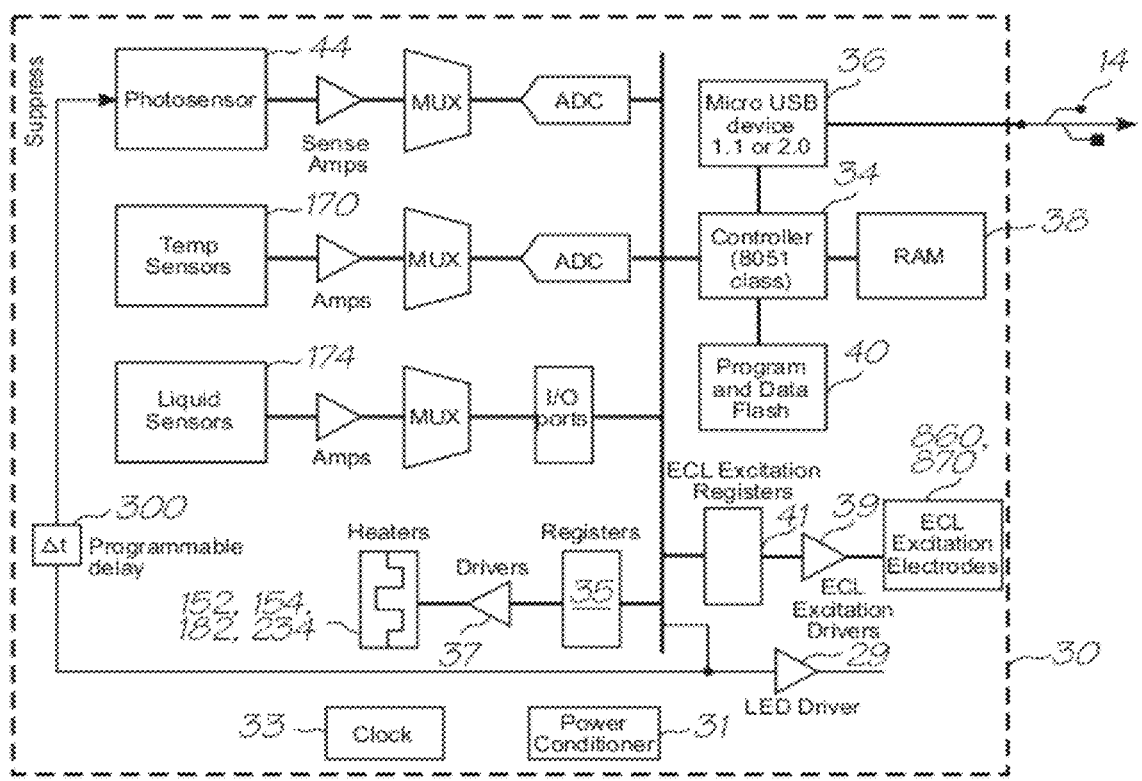
FIG. 105 is a schematic overview of the electronic components in the test module configured for use with ECL detection.

FIGS. 2 and 105 are block diagrams of the electronic components in the test modules 10 and 11, respectively. The CMOS circuitry integrated in the LOC device 30 has a USB device driver 36, a controller 34, a USB-compatible LED driver 29, clock 33, power conditioner 31, RAM 38 and program and data flash memory 40. These provide the control and memory for the entire test module 10 or 11 including the photosensor 44, the temperature sensors 170, the liquid sensors 174, and the various heaters 152, 154, 182, 234, together with associated drivers 37 and 39 and registers 35 and 41. Only the LED 26 (in the case of test module 10), external power supply capacitors 32 and the Micro-USB plug 14 are external to the LOC device 30. The LOC devices 30 include bond-pads for making connections to these external components. The RAM 38 and the program and data flash memory 40 have the application software and the diagnostic and test information (Flash/Secure storage, e.g. via encryption) for over 1000 probes. In the case of test module 11 configured for ECL detection, there is no LED 26 (see FIGS. 104 and 105). Data is encrypted by the LOC device 30 for secure storage and secure communication with an external device. The LOC devices 30 are loaded with electrochemiluminescent probes and the hybridization chambers each have a pair of ECL excitation electrodes 860 and 870.

Many types of test modules 10 are manufactured in a number of test forms, ready for off-the-shelf use. The differences between the test forms lie in the on board assay of reagents and probes.

Some examples of infectious diseases rapidly identified with this system include:
Influenza—Influenza virus A, B, C, Isavirus, Thogotovirus
Pneumonia—respiratory syncytial virus (RSV), adenovirus, metapneumovirus, *Streptococcus pneumoniae*, *Staphylococcus aureus*
Tuberculosis—*Mycobacterium tuberculosis*, *bovis*, *africanum*, *canetti*, and *microti*
*Plasmodium falciparum*, *Toxoplasma gondii* and other protozoan parasites
Typhoid—*Salmonella enterica* serovar *typhi*
Ebola virus
Human immunodeficiency virus (HIV)
Dengue Fever—Flavivirus
Hepatitis (A through E)
Hospital acquired infections—for example *Clostridium difficile*, Vancomycin resistant *Enterococcus*, and Methicillin resistant *Staphylococcus aureus*
Herpes simplex virus (HSV)
Cytomegalovirus (CMV)
Epstein-Ban virus (EBV)
Encephalitis—Japanese Encephalitis virus, Chandipura virus
Whooping cough—*Bordetella pertussis*
Measles—paramyxovirus
Meningitis—*Streptococcus pneumoniae* and *Neisseria meningitidis*
Anthrax—*Bacillus anthracis*

Some examples of genetic disorders identified with this system include:
Cystic fibrosis
Haemophilia
Sickle cell disease
Tay-Sachs disease
Haemochromatosis
Cerebral arteriopathy
Crohn's disease
Polycistic kidney disease
Congential heart disease
Rett syndrome A small selection of cancers identified by the diagnostic system include:
Ovarian
Colon carcinoma
Multiple endocrine neoplasia
Retinoblastoma
Turcot syndrome The above lists are not exhaustive and the diagnostic system can be configured to detect a much greater variety of diseases and conditions using nucleic acid and proteomic analysis.

Detailed Architecture of System Components

LOC Device

The LOC device 30 is central to the diagnostic system. It rapidly performs the four major steps of a nucleic acid based molecular diagnostic assay, i.e. sample preparation, nucleic acid extraction, nucleic acid amplification, and detection, using a microfluidic platform. The LOC device also has alternative uses, and these are detailed later. As discussed above, test modules 10 and 11 can adopt many different configurations to detect different targets Likewise, the LOC device 30 has numerous different embodiments tailored to the target(s) of interest. One form of the LOC device 30 is LOC device 301 for fluorescent detection of target nucleic acid sequences in the pathogens of a whole blood sample. For the purposes of illustration, the structure and operation of LOC device 301 is now described in detail with reference to FIGS. 4 to 26 and 27 to 57.

Figure 4:
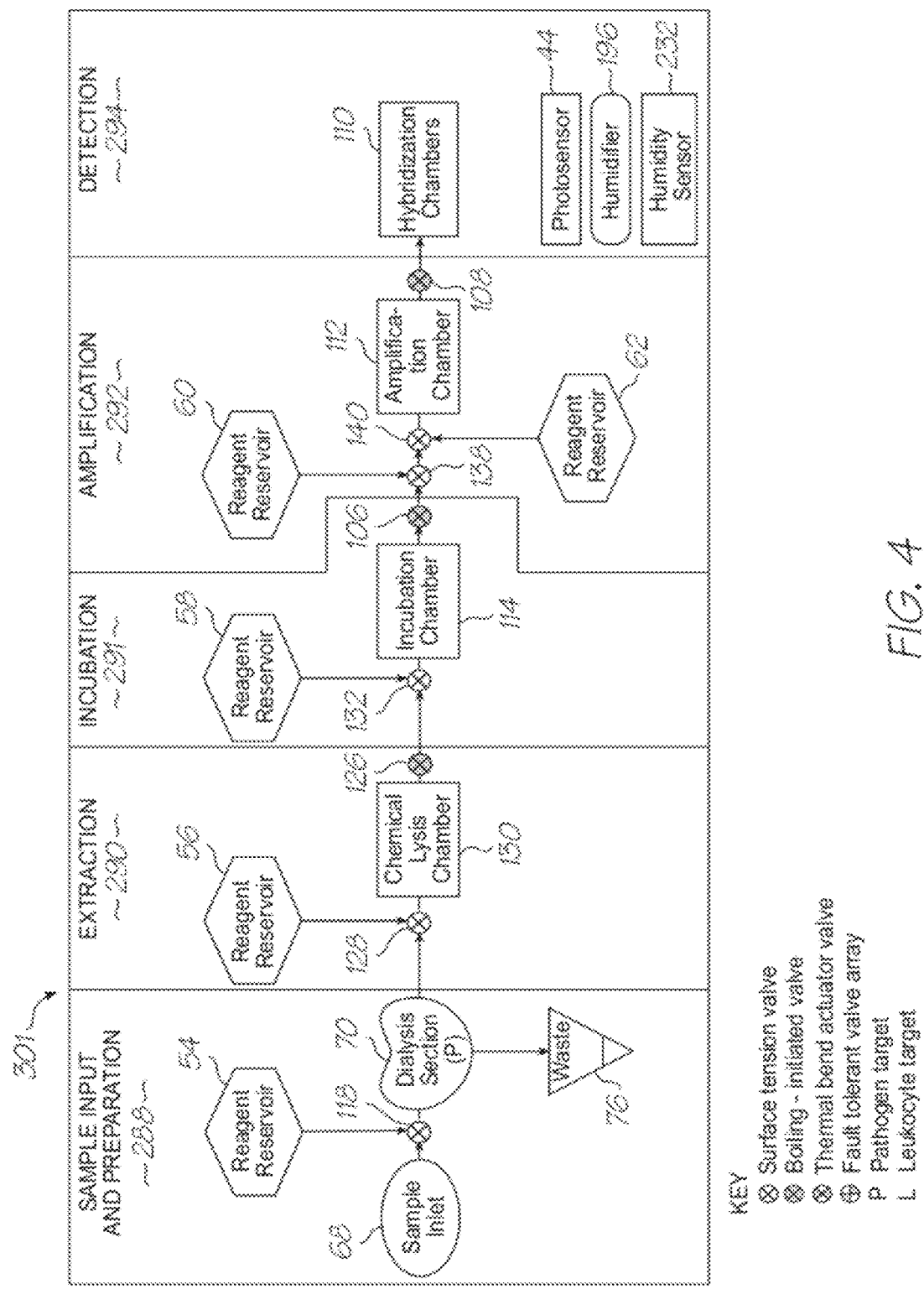
FIG. 4 is a schematic representation of the architecture of the LOC device.

FIG. 4 is a schematic representation of the architecture of the LOC device 301. For convenience, process stages shown in FIG. 4 are indicated with the reference numeral corresponding to the functional sections of the LOC device 301 that perform that process stage. The process stages associated with each of the major steps of a nucleic acid based molecular diagnostic assay are also indicated: sample input and preparation 288, extraction 290, incubation 291, amplification 292 and detection 294. The various reservoirs, chambers, valves and other components of the LOC device 301 will be described in more detail later.

Figure 5:
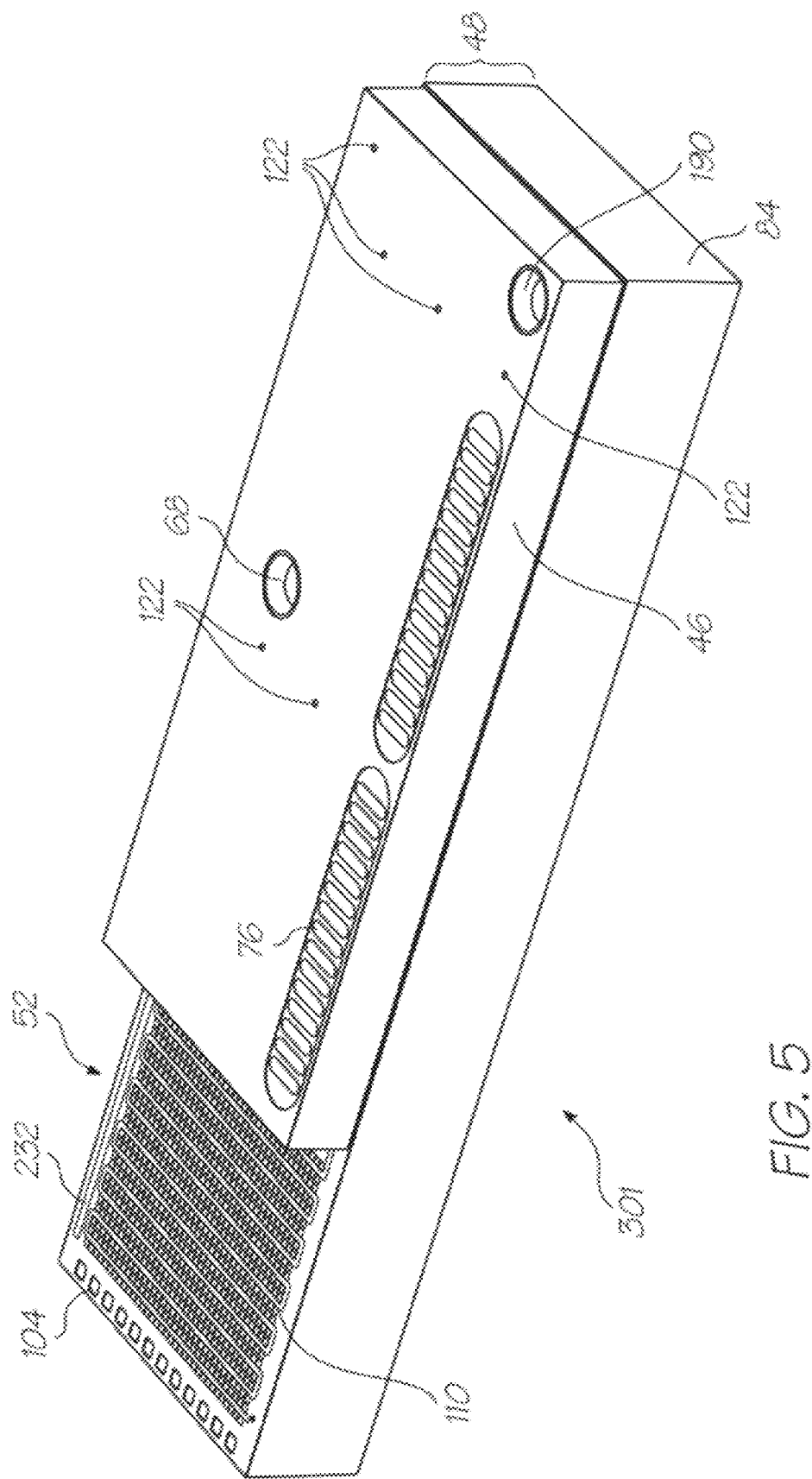
FIG. 5 is a perspective of the LOC device.

FIG. 5 is a perspective view of the LOC device 301. It is fabricated using high volume CMOS and MST (microsystems technology) manufacturing techniques. The laminar structure of the LOC device 301 is illustrated in the schematic (not to scale) partial section view of FIG. 12. The LOC device 301 has a silicon substrate 84 which supports the CMOS+MST chip 48, comprising CMOS circuitry 86 and an MST layer 87, with a cap 46 overlaying the MST layer 87. For the purposes of this patent specification, the term 'MST layer' is a reference to a collection of structures and layers that process the sample with various reagents. Accordingly, these structures and components are configured to define flow-paths with characteristic dimensions that will support capillary driven flow of liquids with physical characteristics similar to those of the sample during processing. In light of this, the MST layer and components are typically fabricated using surface micromachining techniques and/or bulk micromachining techniques. However, other fabrication methods can also produce structures and components dimensioned for capillary driven flows and processing very small volumes. The specific embodiments described in this specification show the MST layer as the structures and active components supported on the CMOS circuitry 86, but excluding the features of the cap 46. However, the skilled addressee will appreciate that the MST layer need not have underlying CMOS or indeed an overlying cap in order for it to process the sample.

The overall dimensions of the LOC device shown in the following figures are 1760 μm×5824 μm. Of course, LOC devices fabricated for different applications may have different dimensions.

Figure 6:
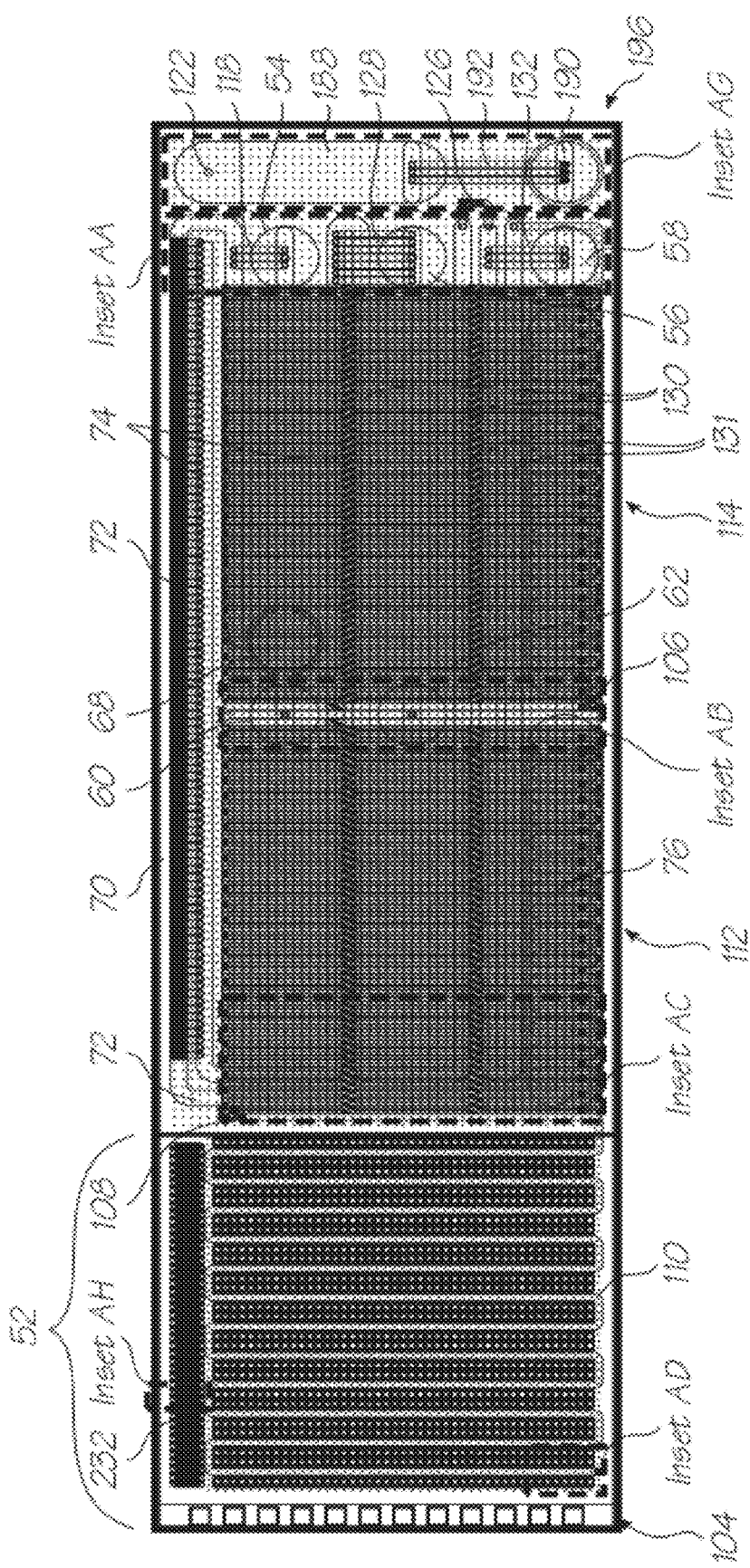
FIG. 6 is a plan view of the LOC device with features and structures from all layers superimposed on each other.
Figure 11:
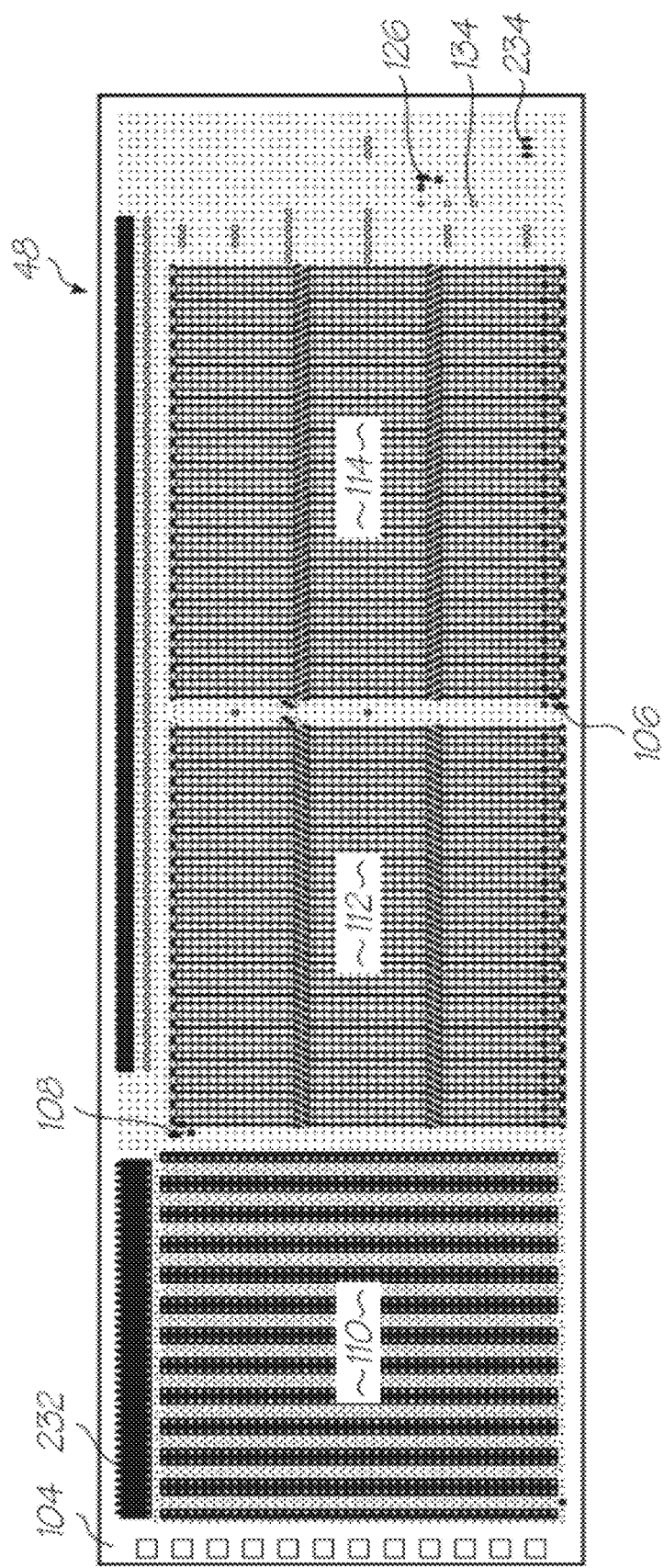
FIG. 11 is a plan view of the LOC device showing the structures of the CMOS+MST device in isolation.

FIG. 6 shows the features of the MST layer 87 superimposed with the features of the cap. Insets AA to AD, AG and AH shown in FIG. 6 are enlarged in FIGS. 13, 14, 35, 56, 55 and 58, respectively, and described in detail below for a comprehensive understanding of each structure within the LOC device 301. FIGS. 7 to 10 show the features of the cap 46 in isolation while FIG. 11 shows the CMOS+MST device 48 structures in isolation.

Laminar Structure

Figure 12:
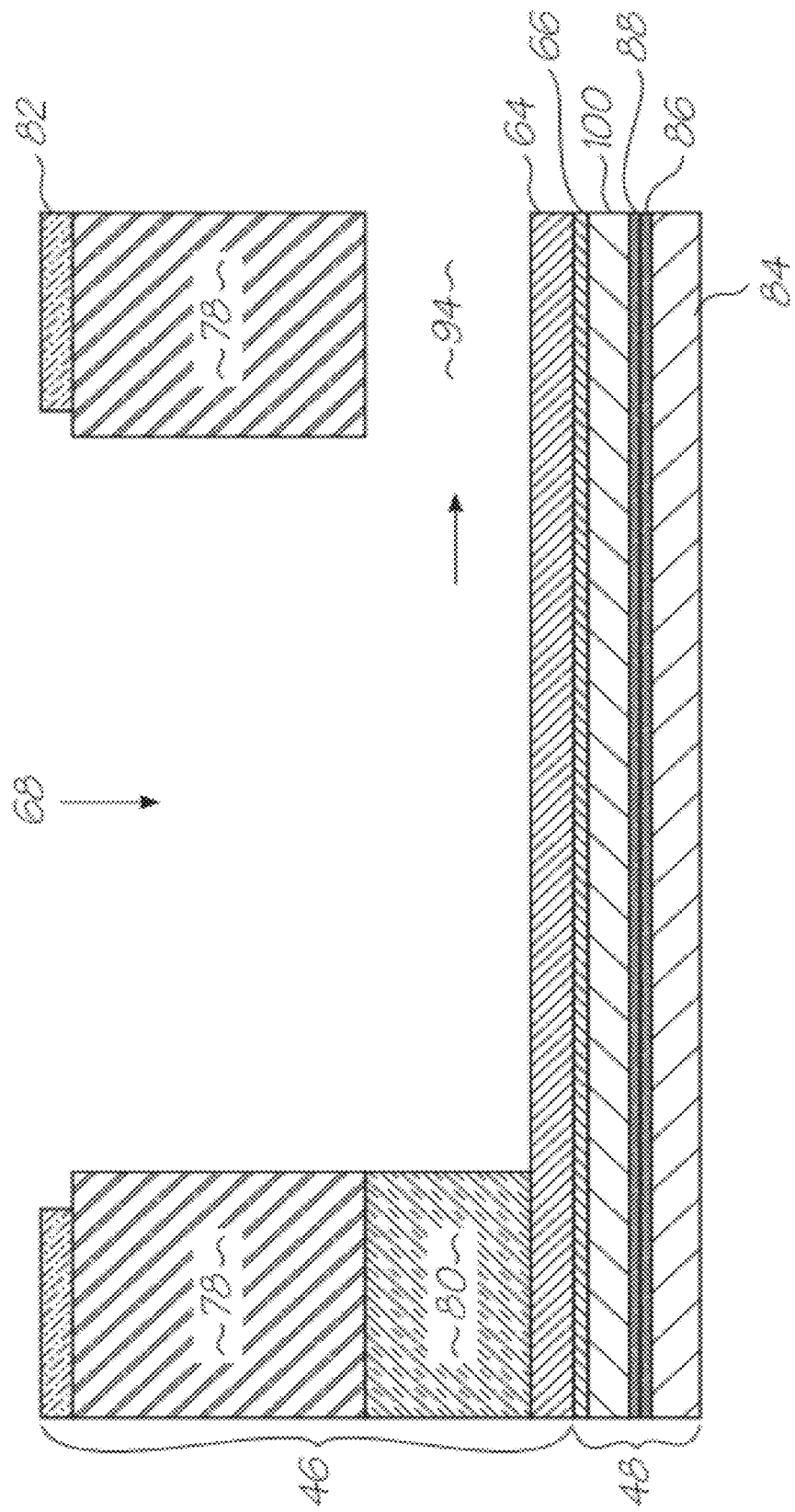
FIG. 12 is a schematic section view of the LOC device at the sample inlet.
Figure 22:
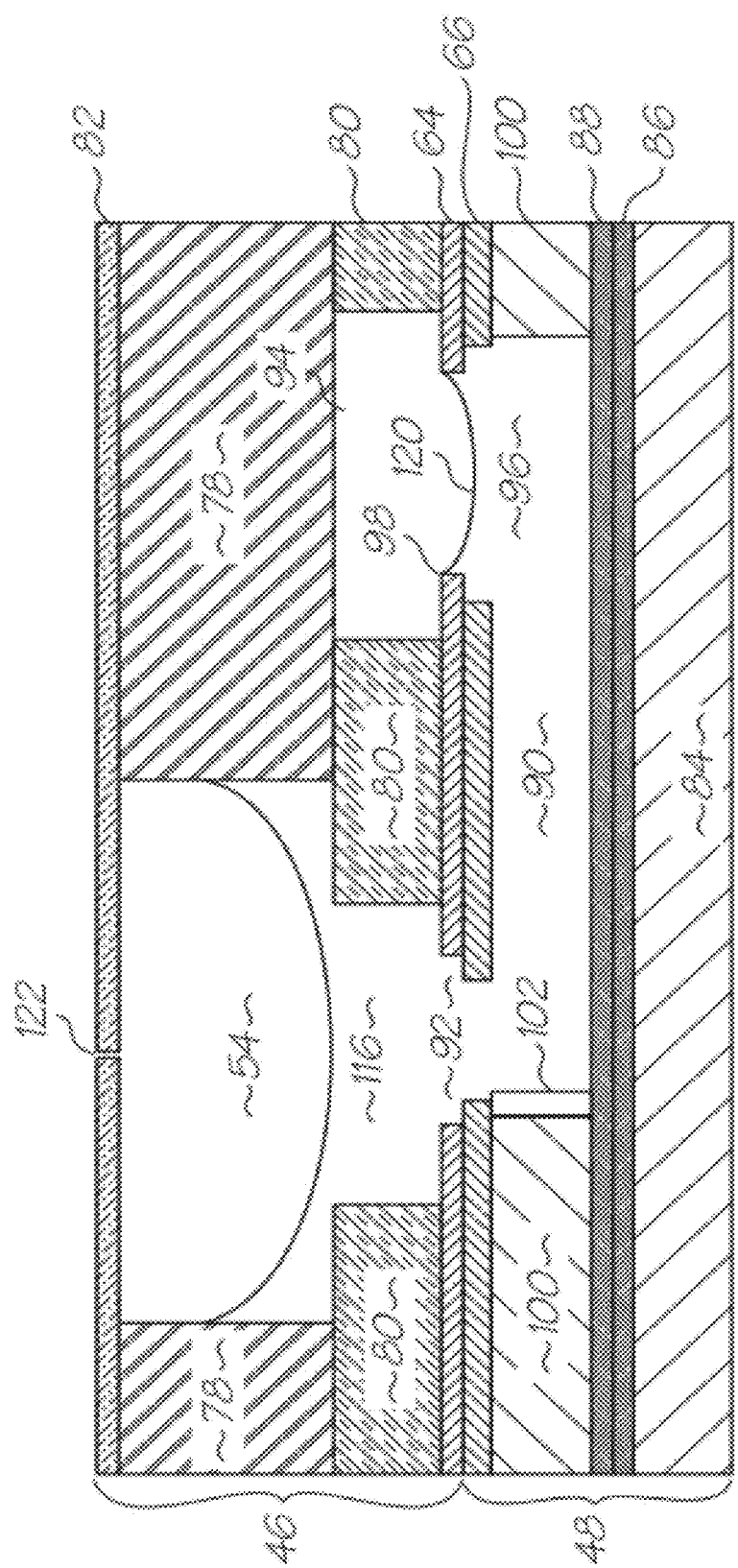
FIG. 22 is schematic section view of the lysis reagent reservoir shown in FIG. 21.

FIGS. 12 and 22 are sketches that diagrammatically show the laminar structure of the CMOS+MST device 48, the cap 46 and the fluidic interaction between the two. The figures are not to scale for the purposes of illustration. FIG. 12 is a schematic section view through the sample inlet 68 and FIG. 22 is a schematic section through the reservoir 54. As best shown in FIG. 12, the CMOS+MST device 48 has a silicon substrate 84 which supports the CMOS circuitry 86 that operates the active elements within the MST layer 87 above. A passivation layer 88 seals and protects the CMOS layer 86 from the fluid flows through the MST layer 87.

Fluid flows through both the cap channels 94 and the MST channels 90 (see for example FIGS. 7 and 16) in the cap layer 46 and MST channel layer 100, respectively. Cell transport occurs in the larger channels 94 fabricated in the cap 46, while biochemical processes are carried out in the smaller MST channels 90. Cell transport channels are sized so as to be able to transport cells in the sample to predetermined sites in the MST channels 90. Transportation of cells with sizes greater than 20 microns (for example, certain leukocytes) requires channel dimensions greater than 20 microns, and therefore a cross sectional area transverse to the flow of greater than 400 square microns. MST channels, particularly at locations in the LOC where transport of cells is not required, can be significantly smaller.

It will be appreciated that cap channel 94 and MST channel 90 are generic references and particular MST channels 90 may also be referred to as (for example) heated microchannels or dialysis MST channels in light of their particular function. MST channels 90 are formed by etching through a MST channel layer 100 deposited on the passivation layer 88 and patterned with photoresist. The MST channels 90 are enclosed by a roof layer 66 which forms the top (with respect to the orientation shown in the figures) of the CMOS+MST device 48.

Despite sometimes being shown as separate layers, the cap channel layer 80 and the reservoir layer 78 are formed from a unitary piece of material. Of course, the piece of material may also be non-unitary. This piece of material is etched from both sides in order to form a cap channel layer 80 in which the cap channels 94 are etched and the reservoir layer 78 in which the reservoirs 54, 56, 58, 60 and 62 are etched. Alternatively, the reservoirs and the cap channels are formed by a micromolding process. Both etching and micromolding techniques are used to produce channels with cross sectional areas transverse to the flow as large as 20,000 square microns, and as small as 8 square microns.

At different locations in the LOC device, there can be a range of appropriate choices for the cross sectional area of the channel transverse to the flow. Where large quantities of sample, or samples with large constituents, are contained in the channel, a cross-sectional area of up to 20,000 square microns (for example, a 200 micron wide channel in a 100 micron thick layer) is suitable. Where small quantities of liquid, or mixtures without large cells present, are contained in the channel, a very small cross sectional area transverse to the flow is preferable.

A lower seal 64 encloses the cap channels 94 and the upper seal layer 82 encloses the reservoirs 54, 56, 58, 60 and 62.

Figure 62:
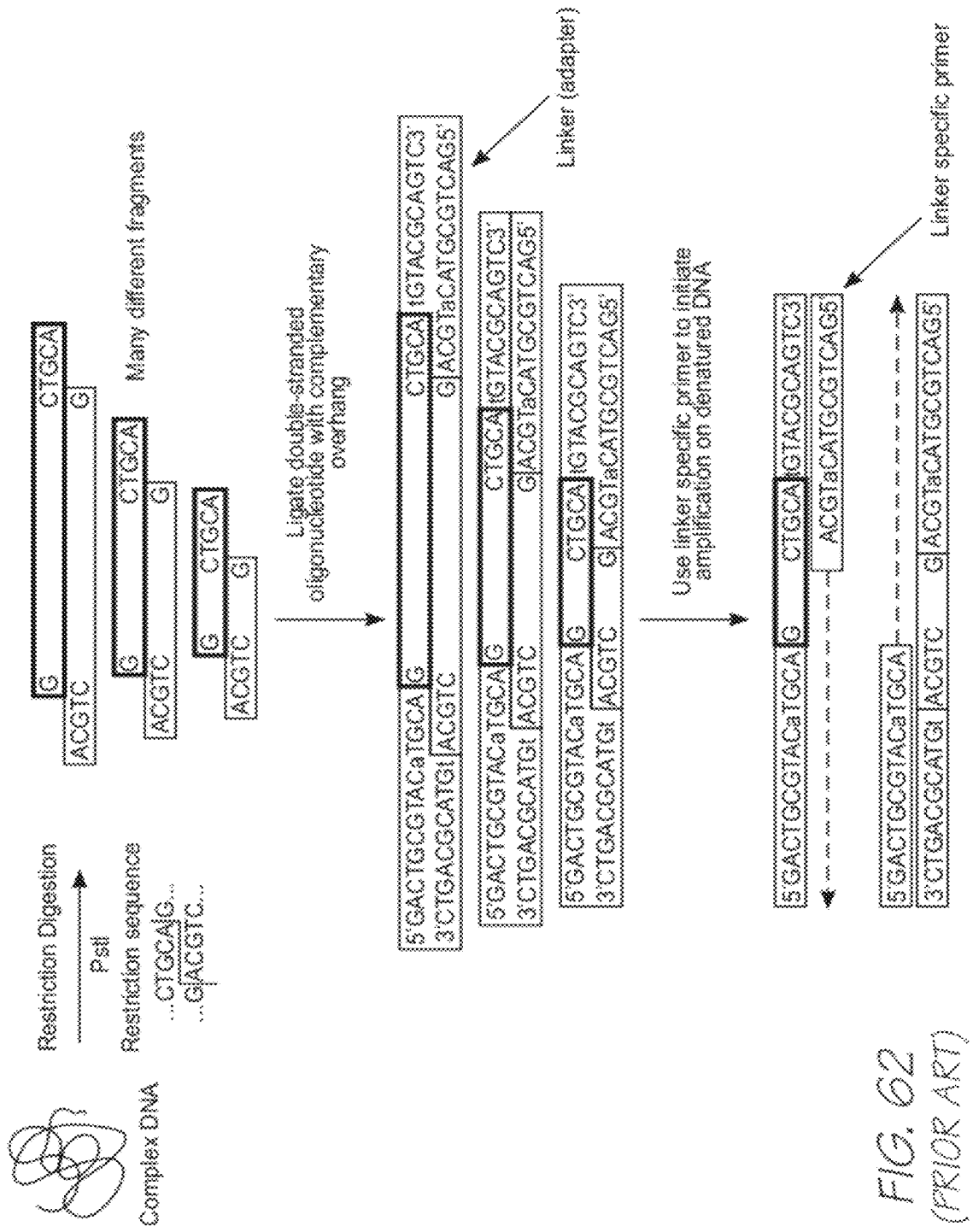
FIG. 62 is a diagram of linker-primed PCR.

The five reservoirs 54, 56, 58, 60 and 62 are preloaded with assay-specific reagents. In the embodiment described here, the reservoirs are preloaded with the following reagents, but other reagents can easily be substituted:

reservoir 54: anticoagulant with option to include erythrocyte lysis buffer
reservoir 56: lysis reagent
reservoir 58: restriction enzymes, ligase and linkers (for linker-primed PCR (see FIG. 62, extracted from T. Stachan et al., Human Molecular Genetics 2, Garland Science, NY and London, 1999))
reservoir 60: amplification mix (dNTPs, primers, buffer) and
reservoir 62: DNA polymerase.

The cap 46 and the CMOS+MST layers 48 are in fluid communication via corresponding openings in the lower seal 64 and the roof layer 66. These openings are referred to as uptakes 96 and downtakes 92 depending on whether fluid is flowing from the MST channels 90 to the cap channels 94 or vice versa.

The operation of the LOC device 301 is described below in a step-wise fashion with reference to analysing pathogenic DNA in a blood sample. Of course, other types of biological or non-biological fluid are also analysed using an appropriate set, or combination, of reagents, test protocols, LOC variants and detection systems. Referring back to FIG. 4, there are five major steps involved in analysing a biological sample, comprising sample input and preparation 288, nucleic acid extraction 290, nucleic acid incubation 291, nucleic acid amplification 292 and detection and analysis 294.

Figure 7:
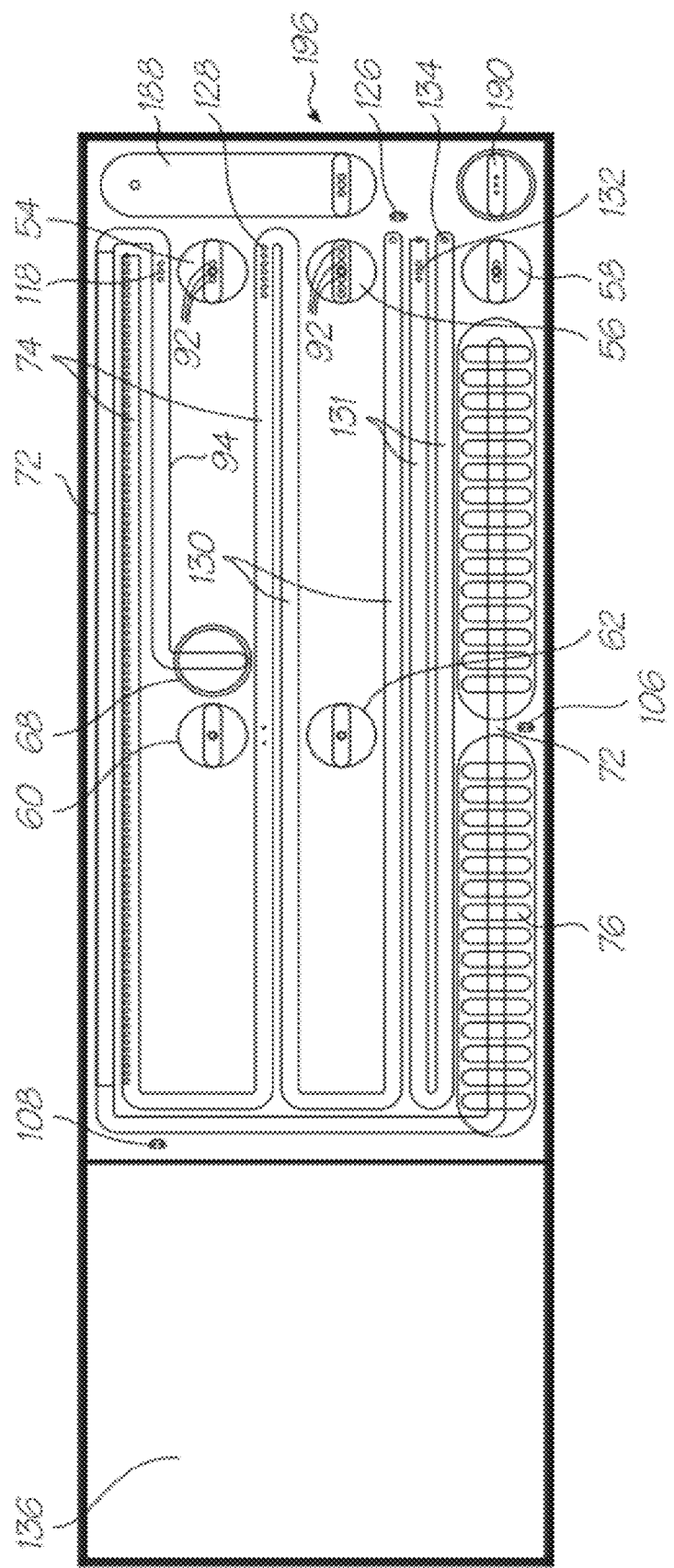
FIG. 7 is a plan view of the LOC device with the structures of the cap shown in isolation.
Figure 8:
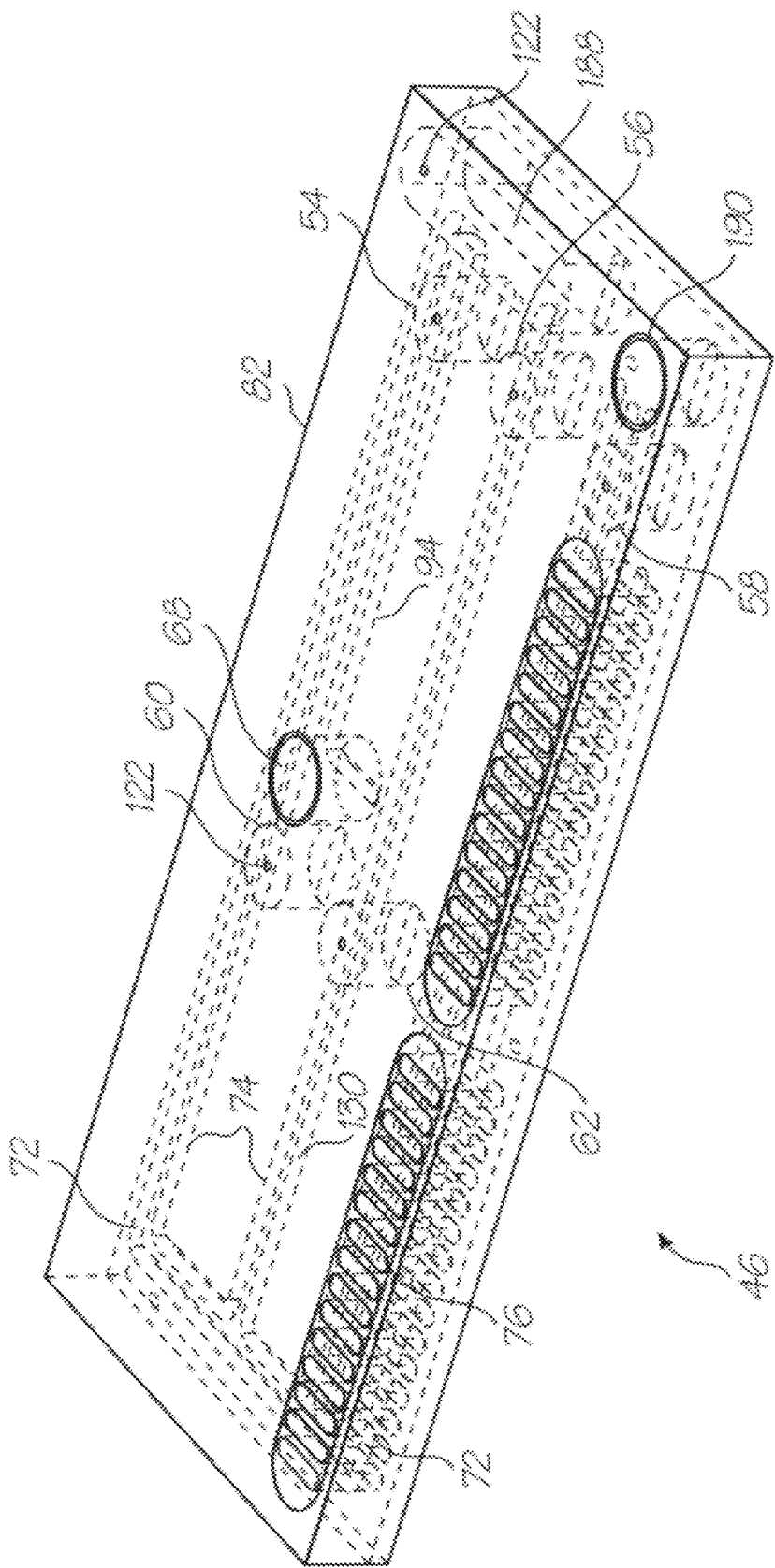
FIG. 8 is a top perspective of the cap with internal channels and reservoirs shown in dotted line.
Figure 9:
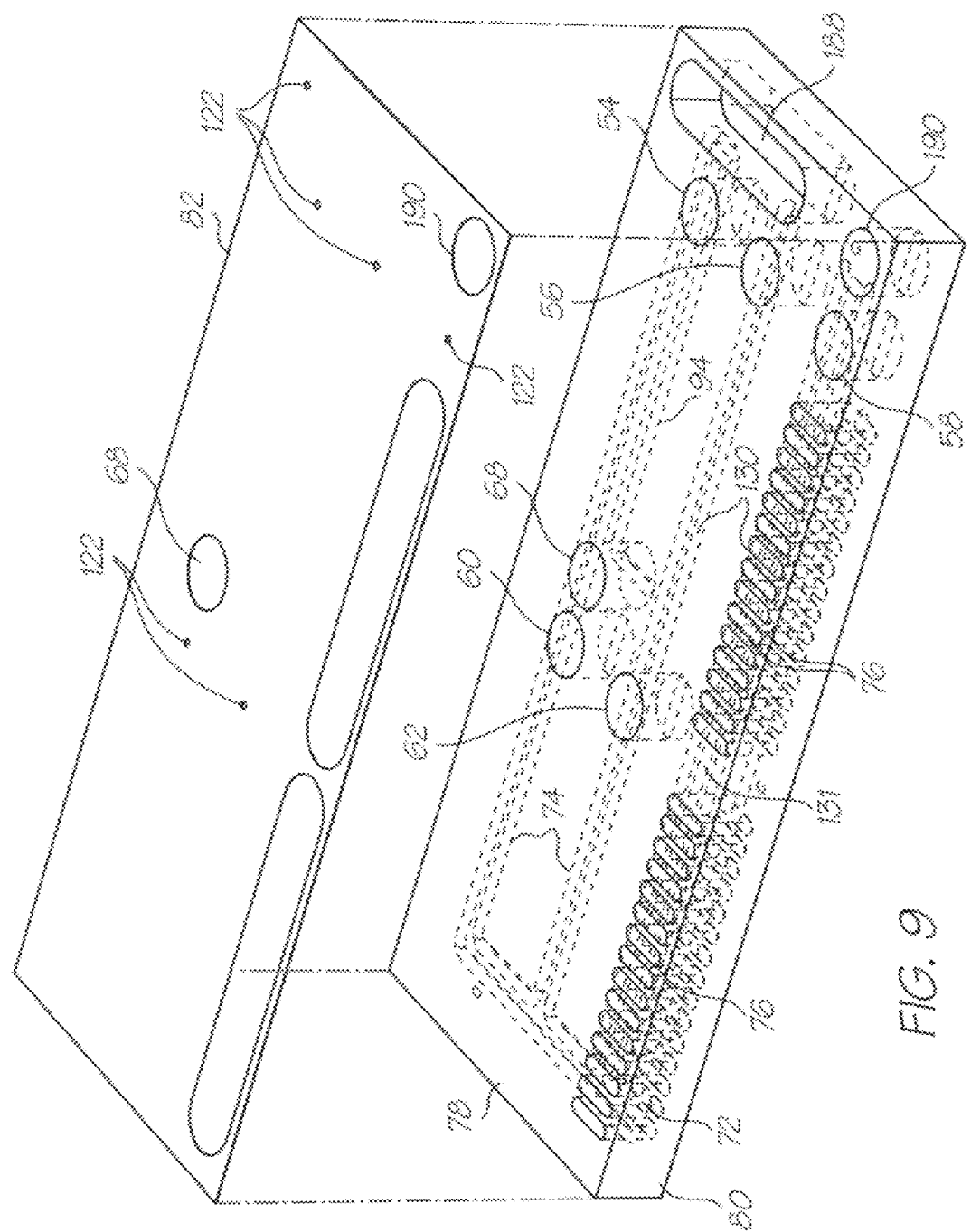
FIG. 9 is an exploded top perspective of the cap with internal channels and reservoirs shown in dotted line.
Figure 10:
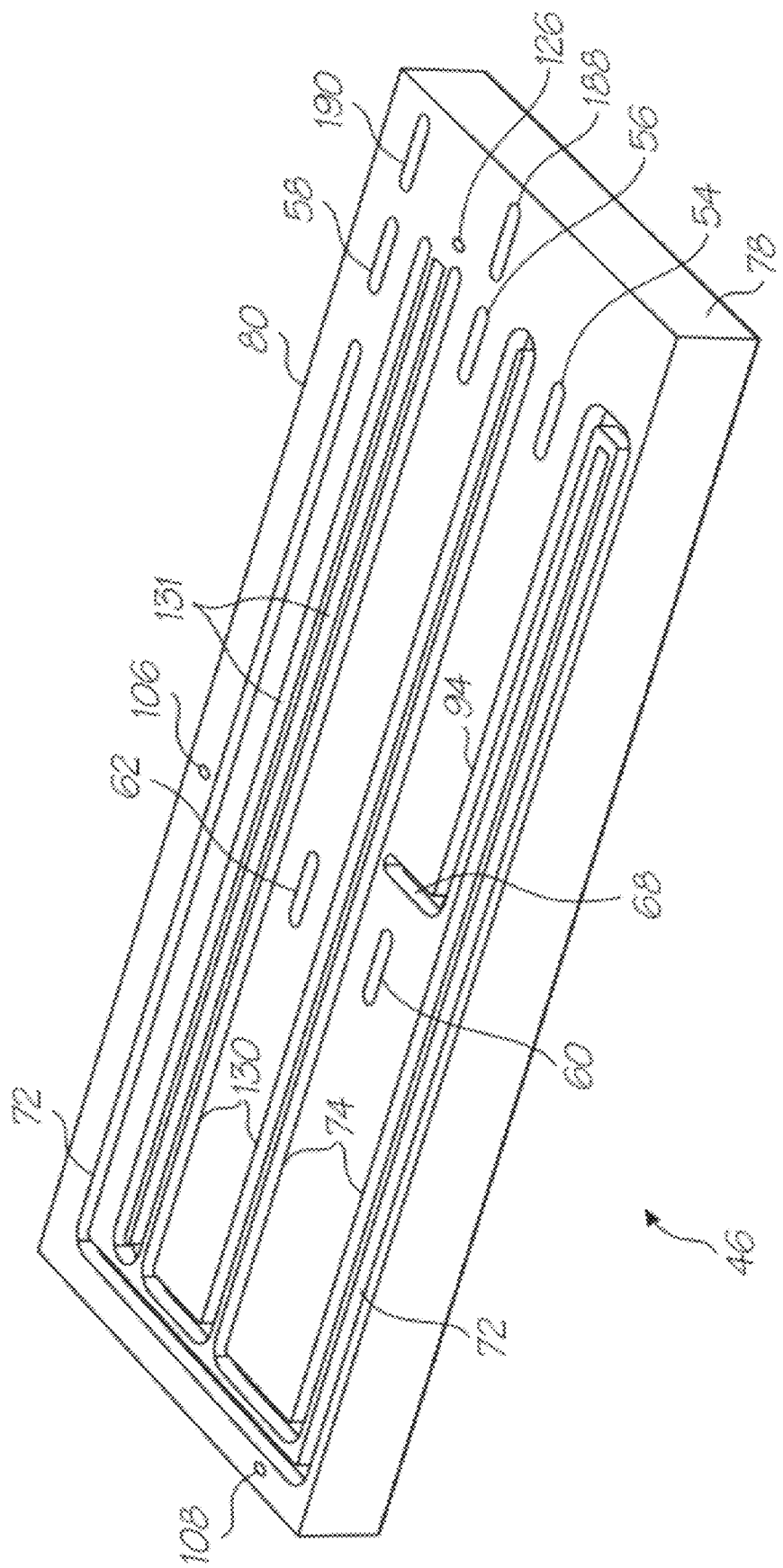
FIG. 10 is a bottom perspective of the cap showing the configuration of the top channels.

The sample input and preparation step 288 involves mixing the blood with an anticoagulant 116 and then separating pathogens from the leukocytes and erythrocytes with the pathogen dialysis section 70. As best shown in FIGS. 7 and 12, the blood sample enters the device via the sample inlet 68. Capillary action draws the blood sample along the cap channel 94 to the reservoir 54. Anticoagulant is released from the reservoir 54 as the sample blood flow opens its surface tension valve 118 (see FIGS. 15 and 22). The anticoagulant prevents the formation of clots which would block the flow.

As best shown in FIG. 22, the anticoagulant 116 is drawn out of the reservoir 54 by capillary action and into the MST channel 90 via the downtake 92. The downtake 92 has a capillary initiation feature (CIF) 102 to shape the geometry of the meniscus such that it does not anchor to the rim of the downtake 92. Vent holes 122 in the upper seal 82 allows air to replace the anticoagulant 116 as it is drawn out of the reservoir 54.

The MST channel 90 shown in FIG. 22 is part of a surface tension valve 118. The anticoagulant 116 fills the surface tension valve 118 and pins a meniscus 120 to the uptake 96 to a meniscus anchor 98. Prior to use, the meniscus 120 remains pinned at the uptake 96 so the anticoagulant does not flow into the cap channel 94. When the blood flows through the cap channel 94 to the uptake 96, the meniscus 120 is removed and the anticoagulant is drawn into the flow.

Figure 16:
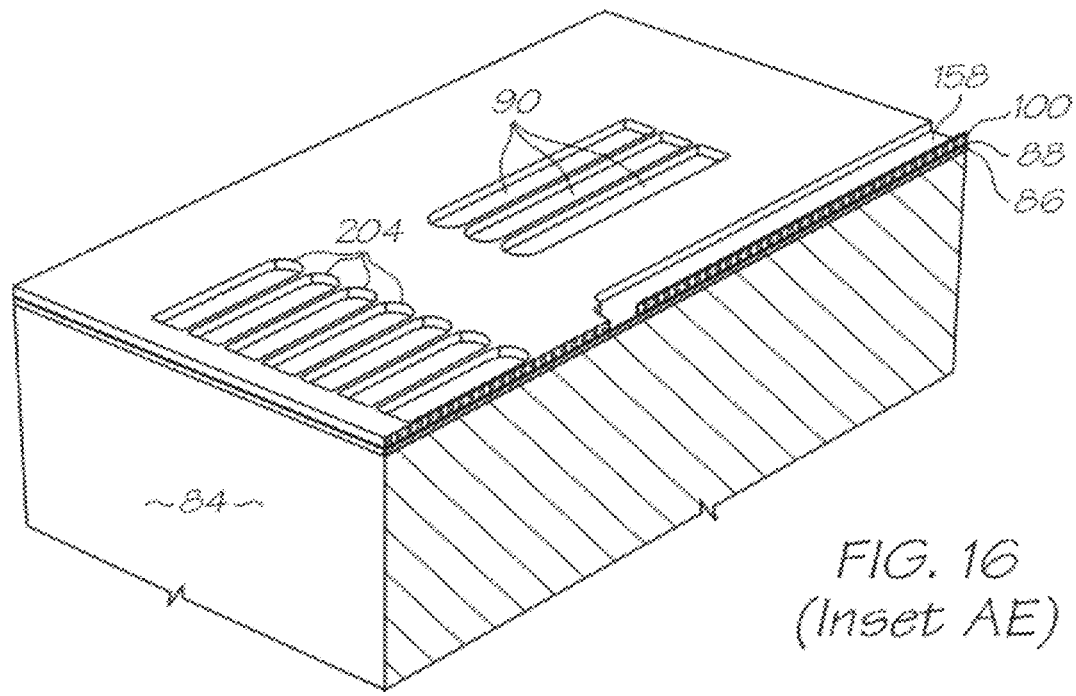
FIG. 16 is a partial perspective illustrating the laminar structure of the LOC device within Inset AE.
Figure 17:
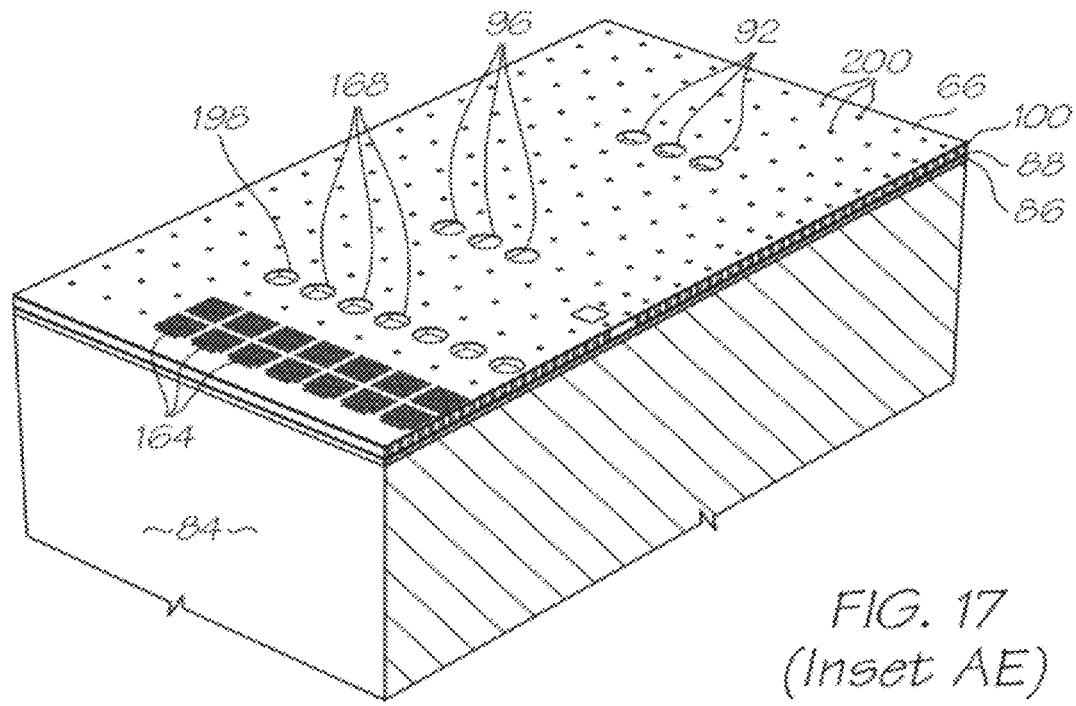
FIG. 17 is a partial perspective illustrating the laminar structure of the LOC device within Inset AE.
Figure 18:
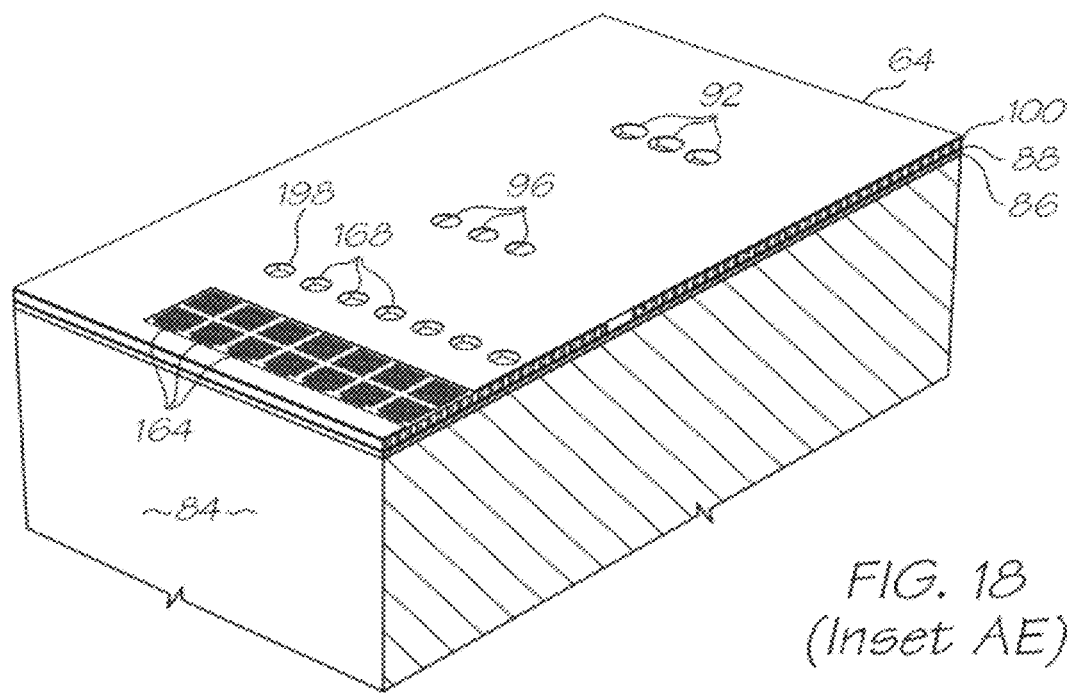
FIG. 18 is a partial perspective illustrating the laminar structure of the LOC device within Inset AE.
Figure 19:
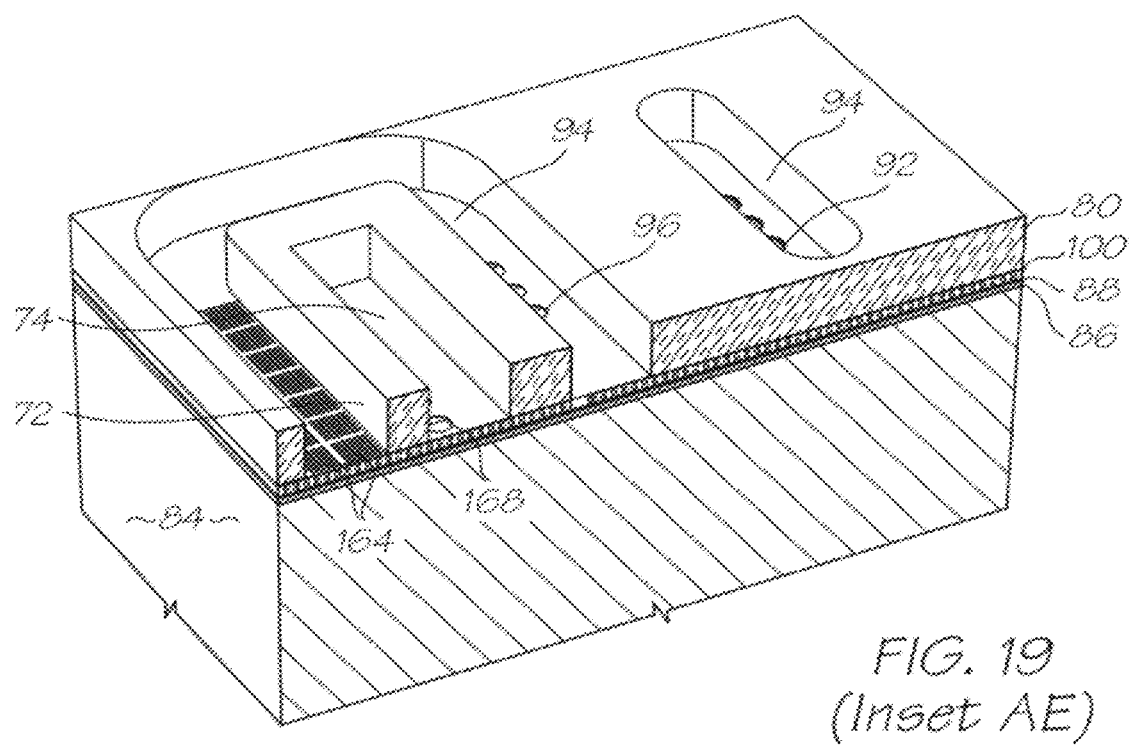
FIG. 19 is a partial perspective illustrating the laminar structure of the LOC device within Inset AE.
Figure 20:
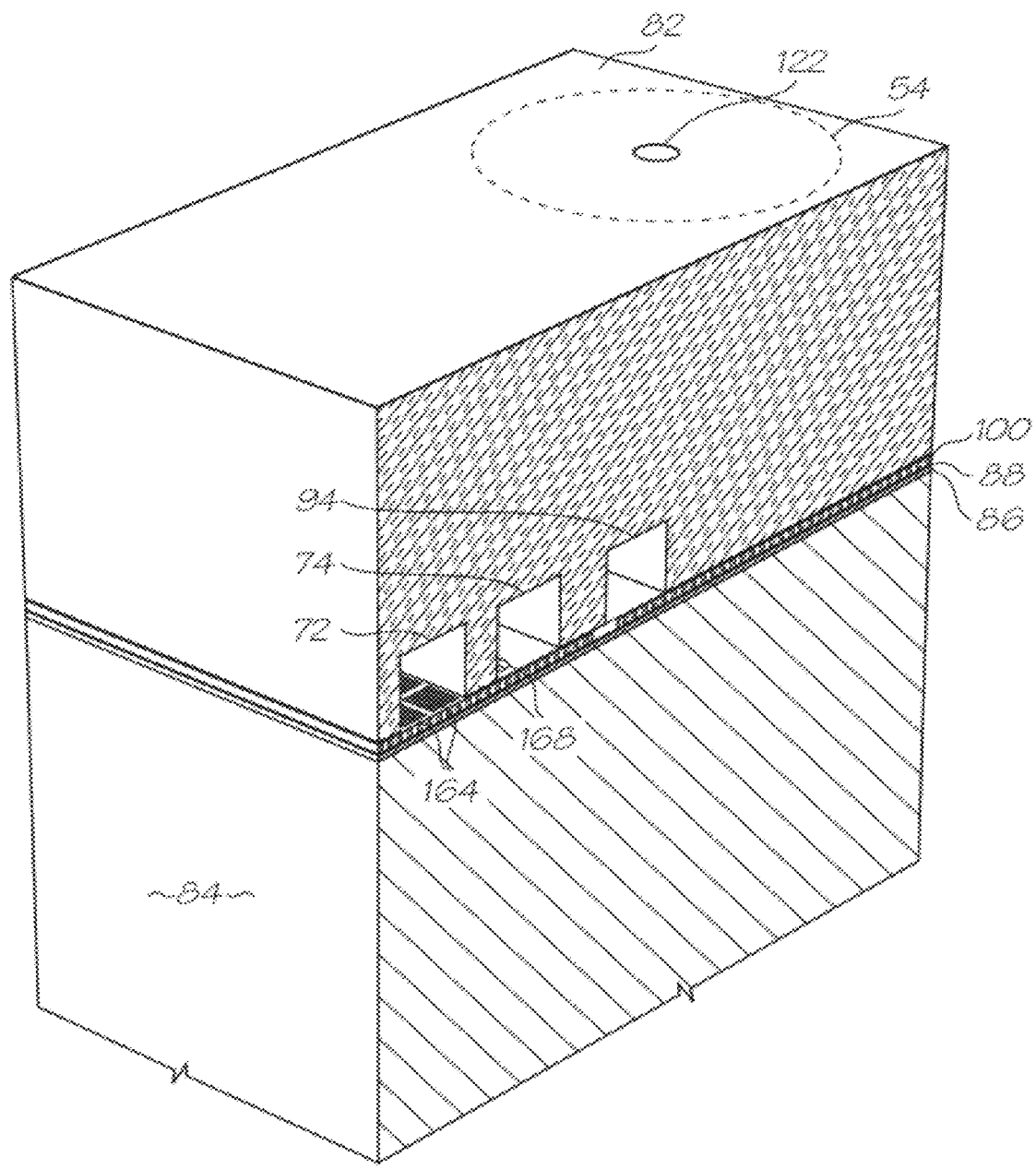
FIG. 20 is a partial perspective illustrating the laminar structure of the LOC device within Inset AE.
Figure 21:
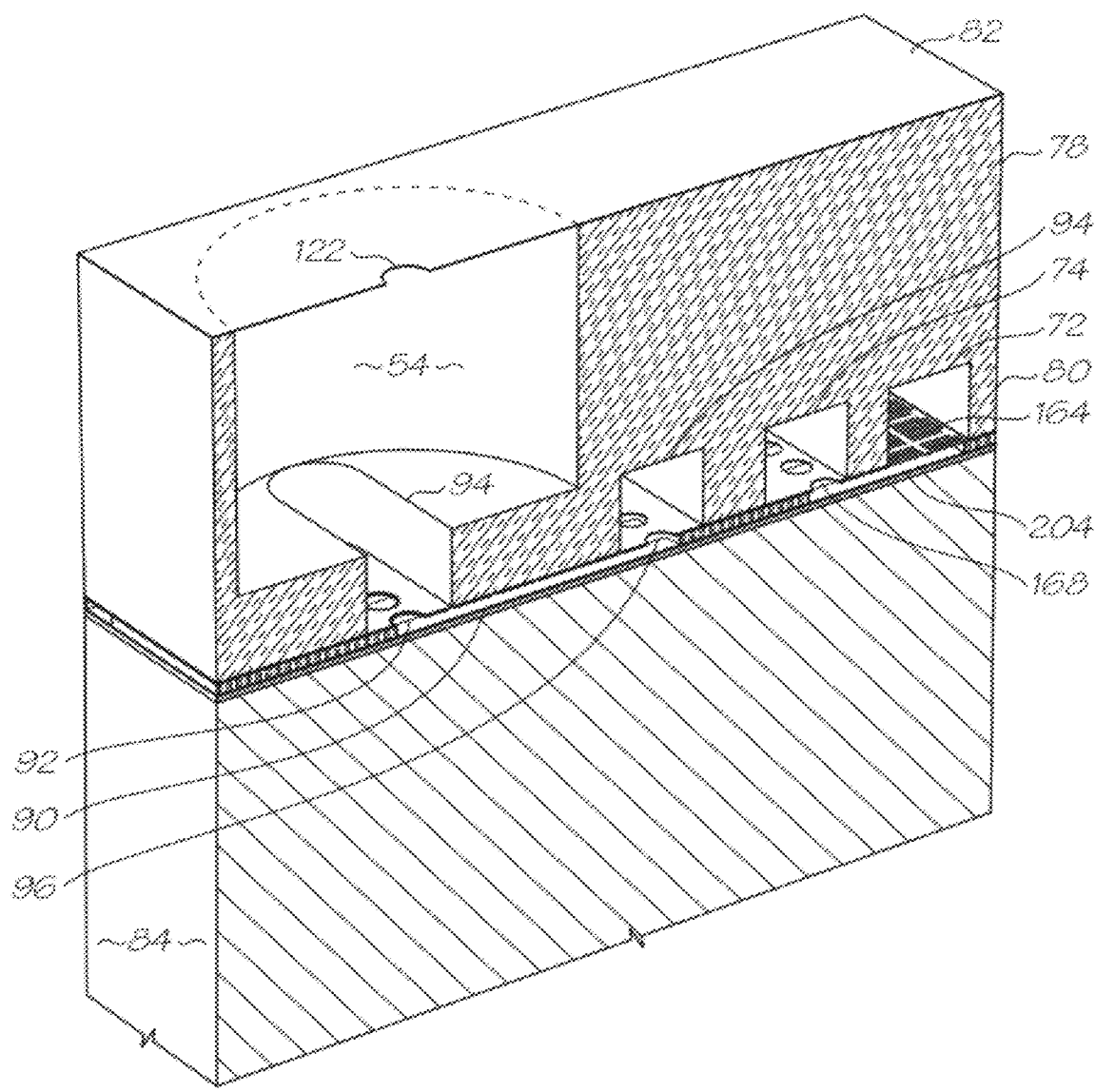
FIG. 21 is a partial perspective illustrating the laminar structure of the LOC device within Inset AE.

FIGS. 15 to 21 show Inset AE which is a portion of Inset AA shown in FIG. 13. As shown in FIGS. 15, 16 and 17, the surface tension valve 118 has three separate MST channels 90 extending between respective downtakes 92 and uptakes 96. The number of MST channels 90 in a surface tension valve can be varied to change the flow rate of the reagent into the sample mixture. As the sample mixture and the reagents mix together by diffusion, the flow rate out of the reservoir determines the concentration of the reagent in the sample flow. Hence, the surface tension valve for each of the reservoirs is configured to match the desired reagent concentration.

The blood passes into a pathogen dialysis section 70 (see FIGS. 4 and 15) where target cells are concentrated from the sample using an array of apertures 164 sized according to a predetermined threshold. Cells smaller than the threshold pass through the apertures while larger cells do not pass through the apertures. Unwanted cells, which may be either the larger cells withheld by the array of apertures 164 or the smaller cells that pass through the apertures, are redirected to a waste unit 76 while the target cells continue as part of the assay.

In the pathogen dialysis section 70 described here, the pathogens from the whole blood sample are concentrated for microbial DNA analysis. The array of apertures is formed by a multitude of 3 micron diameter holes 164 fluidically connecting the input flow in the cap channel 94 to a target channel 74. The 3 micron diameter apertures 164 and the dialysis uptake holes 168 for the target channel 74 are connected by a series of dialysis MST channels 204 (best shown in FIGS. 15 and 21). Pathogens are small enough to pass through the 3 micron diameter apertures 164 and fill the target channel 74 via the dialysis MST channels 204. Cells larger than 3 microns, such as erythrocytes and leukocytes, stay in the waste channel 72 in the cap 46 which leads to a waste reservoir 76 (see FIG. 7).

Other aperture shapes, sizes and aspect ratios can be used to isolate specific pathogens or other target cells such as leukocytes for human DNA analysis. Greater detail on the dialysis section and dialysis variants is provided later.

Referring again to FIGS. 6 and 7, the flow is drawn through the target channel 74 to the surface tension valve 128 of the lysis reagent reservoir 56. The surface tension valve 128 has seven MST channels 90 extending between the lysis reagent reservoir 56 and the target channel 74. When the menisci are unpinned by the sample flow, the flow rate from all seven of the MST channels 90 will be greater than the flow rate from the anticoagulant reservoir 54 where the surface tension valve 118 has three MST channels 90 (assuming the physical characteristics of the fluids are roughly equivalent). Hence the proportion of lysis reagent in the sample mixture is greater than that of the anticoagulant.

The lysis reagent and target cells mix by diffusion in the target channel 74 within the chemical lysis section 130. A boiling-initiated valve 126 stops the flow until sufficient time has passed for diffusion and lysis to take place, releasing the genetic material from the target cells (see FIGS. 6 and 7). The structure and operation of the boiling-initiated valves are described in greater detail below with reference to FIGS. 31 and 32. Other active valve types (as opposed to passive valves such as the surface tension valve 118) have also been developed by the Applicant which may be used here instead of the boiling-initiated valve. These alternative valve designs are also described later.

When the boiling-initiated valve 126 opens, the lysed cells flow into a mixing section 131 for pre-amplification restriction digestion and linker ligation.

Referring to FIG. 13, restriction enzymes, linkers and ligase are released from the reservoir 58 when the flow unpins the menisci at the surface tension valve 132 at the start of the mixing section 131. The mixture flows the length of the mixing section 131 for diffusion mixing. At the end of the mixing section 131 is downtake 134 leading into the incubator inlet channel 133 of the incubation section 114 (see FIG. 13). The incubator inlet channel 133 feeds the mixture into a serpentine configuration of heated microchannels 210 which provides an incubation chamber for holding the sample during restriction digestion and ligation of the linkers (see FIGS. 13 and 14).

Figure 23:
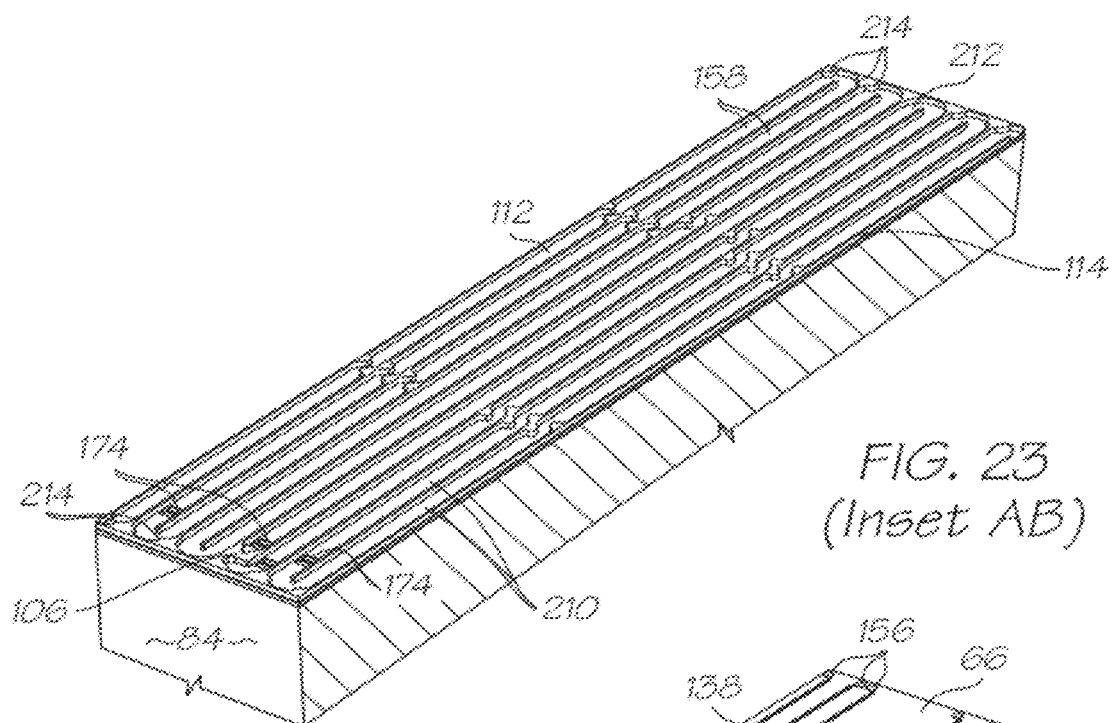
FIG. 23 is a partial perspective illustrating the laminar structure of the LOC device within Inset AB.
Figure 24:
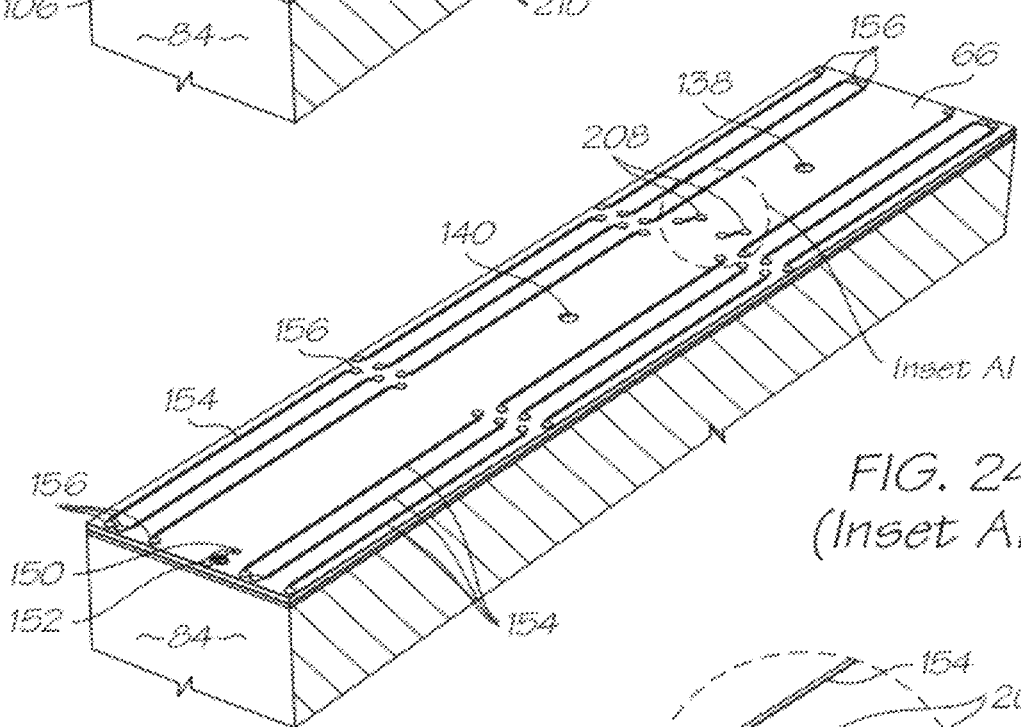
FIG. 24 is a partial perspective illustrating the laminar structure of the LOC device within Inset AB.

FIGS. 23, 24, 25, 26, 27, 28 and 29 show the layers of the LOC device 301 within Inset AB of FIG. 6. Each figure shows the sequential addition of layers forming the structures of the CMOS+MST layer 48 and the cap 46. Inset AB shows the end of the incubation section 114 and the start of the amplification section 112. As best shown in FIGS. 14 and 23, the flow fills the microchannels 210 of the incubation section 114 until reaching the boiling-initiated valve 106 where the flow stops while diffusion takes place. As discussed above, the microchannel 210 upstream of the boiling-initiated valve 106 becomes an incubation chamber containing the sample, restriction enzymes, ligase and linkers. The heaters 154 are then activated and held at constant temperature for a specified time for restriction digestion and linker ligation to occur.

The skilled worker will appreciate that this incubation step 291 (see FIG. 4) is optional and only required for some nucleic acid amplification assay types. Furthermore, in some instances, it may be necessary to have a heating step at the end of the incubation period to spike the temperature above the incubation temperature. The temperature spike inactivates the restriction enzymes and ligase prior to entering the amplification section 112. Inactivation of the restriction enzymes and ligase has particular relevance when isothermal nucleic acid amplification is being employed.

Figure 31:
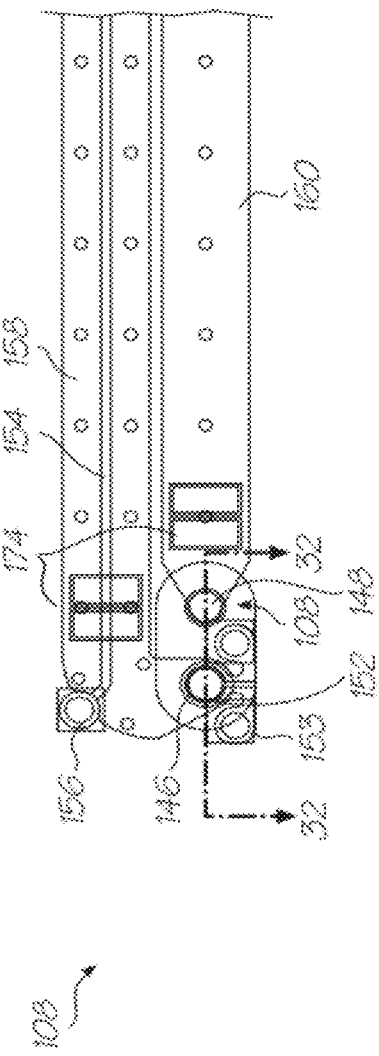
FIG. 31 show the features of a boiling-initiated valve in isolation.

Following incubation, the boiling-initiated valve 106 is activated (opened) and the flow resumes into the amplification section 112. Referring to FIGS. 31 and 32, the mixture fills the serpentine configuration of heated microchannels 158, which form one or more amplification chambers, until it reaches the boiling-initiated valve 108. As best shown in the schematic section view of FIG. 30, amplification mix (dNTPs, primers, buffer) is released from reservoir 60 and polymerase is subsequently released from reservoir 62 into the intermediate MST channel 212 connecting the incubation and amplification sections (114 and 112 respectively).

FIGS. 35 to 51 show the layers of the LOC device 301 within Inset AC of FIG. 6. Each figure shows the sequential addition of layers forming the structures of the CMOS+MST device 48 and the cap 46. Inset AC is at the end of the amplification section 112 and the start of the hybridization and detection section 52. The incubated sample, amplification mix and polymerase flow through the microchannels 158 to the boiling-initiated valve 108. After sufficient time for diffusion mixing, the heaters 154 in the microchannels 158 are activated for thermal cycling or isothermal amplification. The amplification mix goes through a predetermined number of thermal cycles or a preset amplification time to amplify sufficient target DNA. After the nucleic acid amplification process, the boiling-initiated valve 108 opens and flow resumes into the hybridization and detection section 52. The operation of boiling-initiated valves is described in more detail later.

Figure 52:
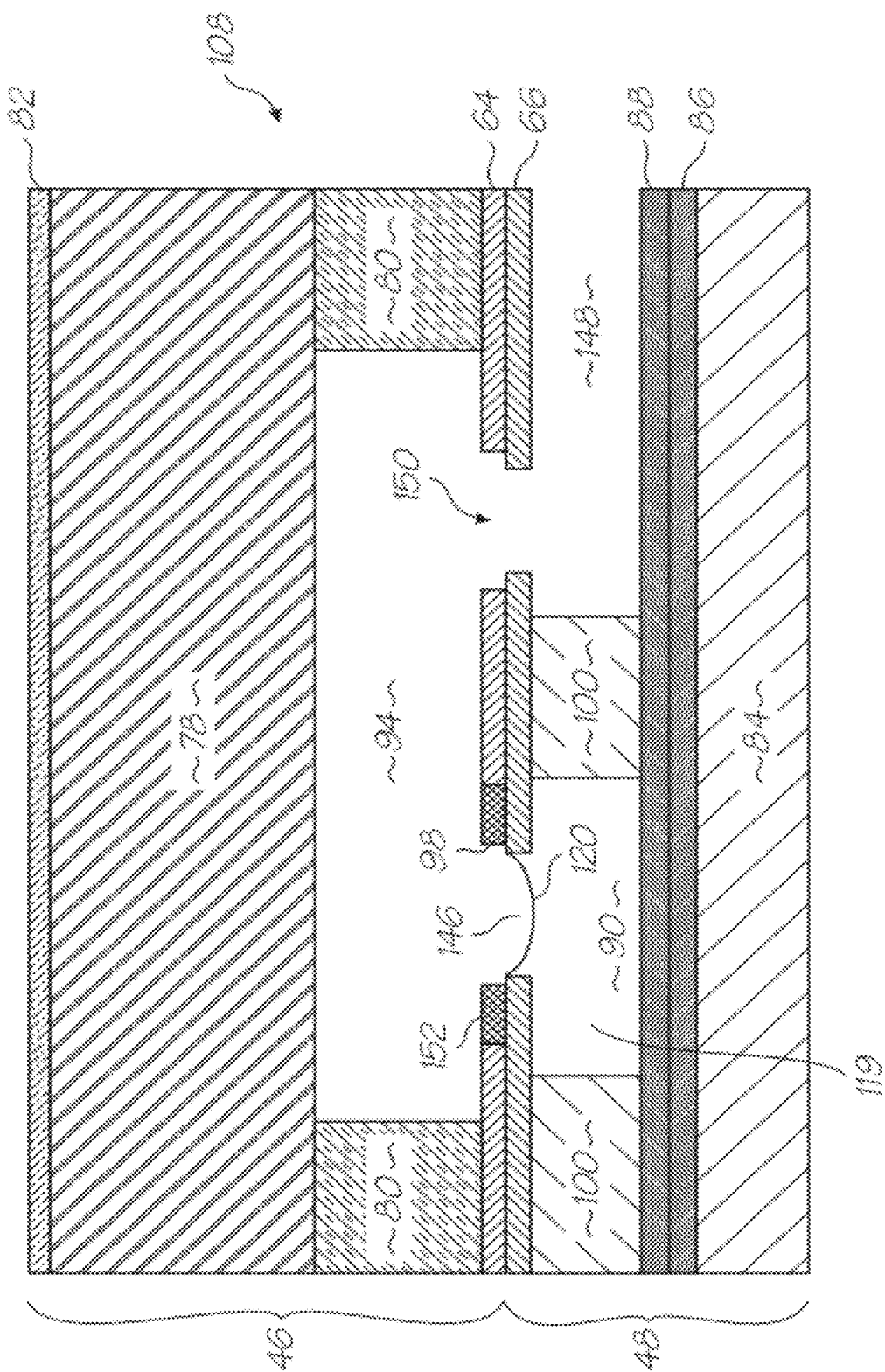
FIG. 52 is an enlarged plan view of the hybridization section.
Figure 34:
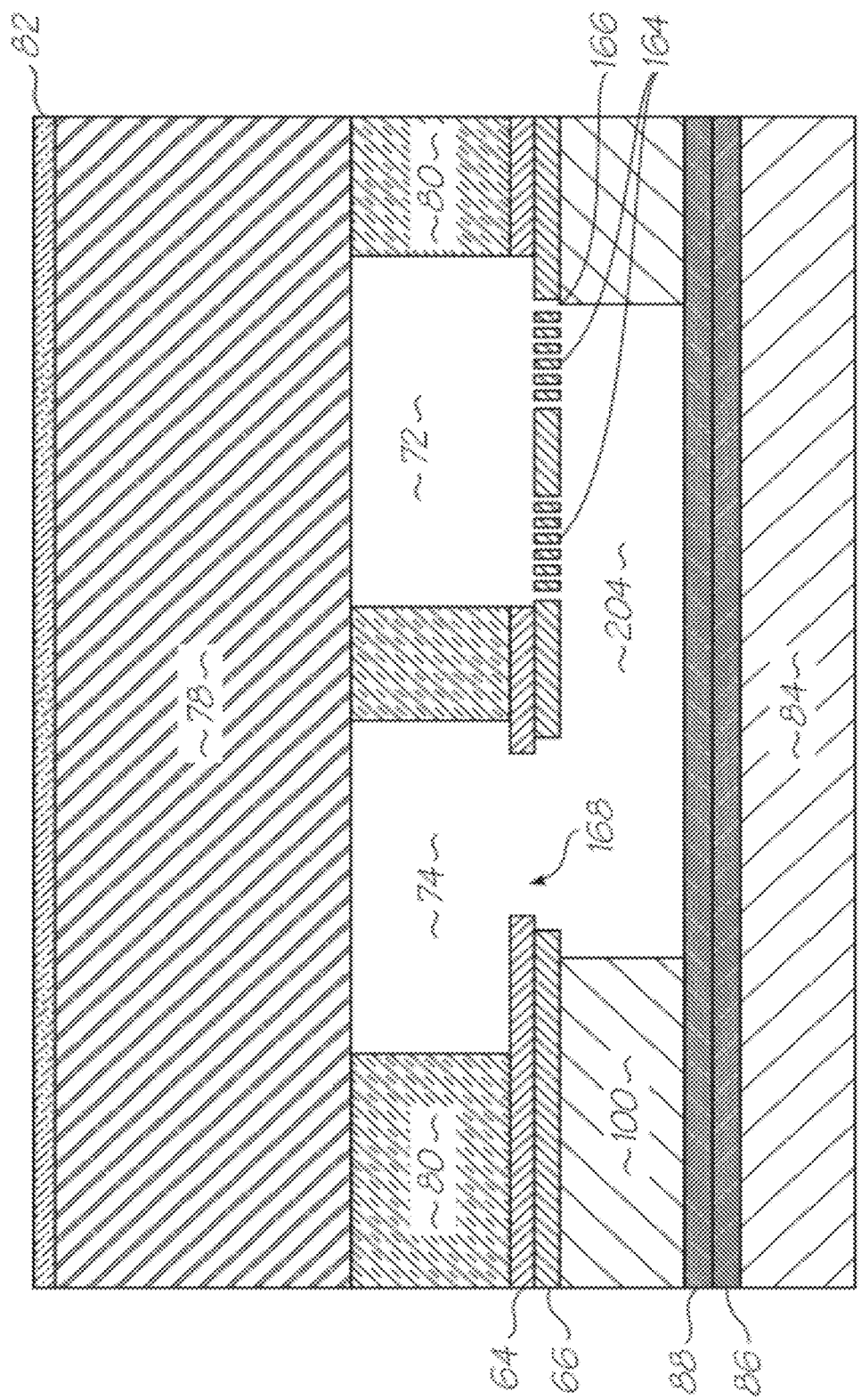
FIG. 34 is a schematic section view of the upstream end of the dialysis section taken through line 35-35 shown in FIG. 33.

As shown in FIG. 52, the hybridization and detection section 52 has an array of hybridization chambers 110. FIGS. 52, 53, 54 and 56 show the hybridization chamber array 110 and individual hybridization chambers 180 in detail. At the entrance to the hybridization chamber 180 is a diffusion barrier 175 which prevents diffusion of the target nucleic acid, probe strands and hybridized probes between the hybridization chambers 180 during hybridization so as to prevent erroneous hybridization detection results. The diffusion barriers 175 present a flow-path-length that is long enough to prevent the target sequences and probes diffusing out of one chamber and contaminating another chamber within the time taken for the probes and nucleic acids to hybridize and the signal to be detected, thus avoiding an erroneous result.

Another mechanism to prevent erroneous readings is to have identical probes in a number of the hybridization chambers. The CMOS circuitry 86 derives a single result from the photodiodes 184 corresponding to the hybridization chambers 180 that contain identical probes. Anomalous results can be disregarded or weighted differently in the derivation of the single result.

Figure 60:
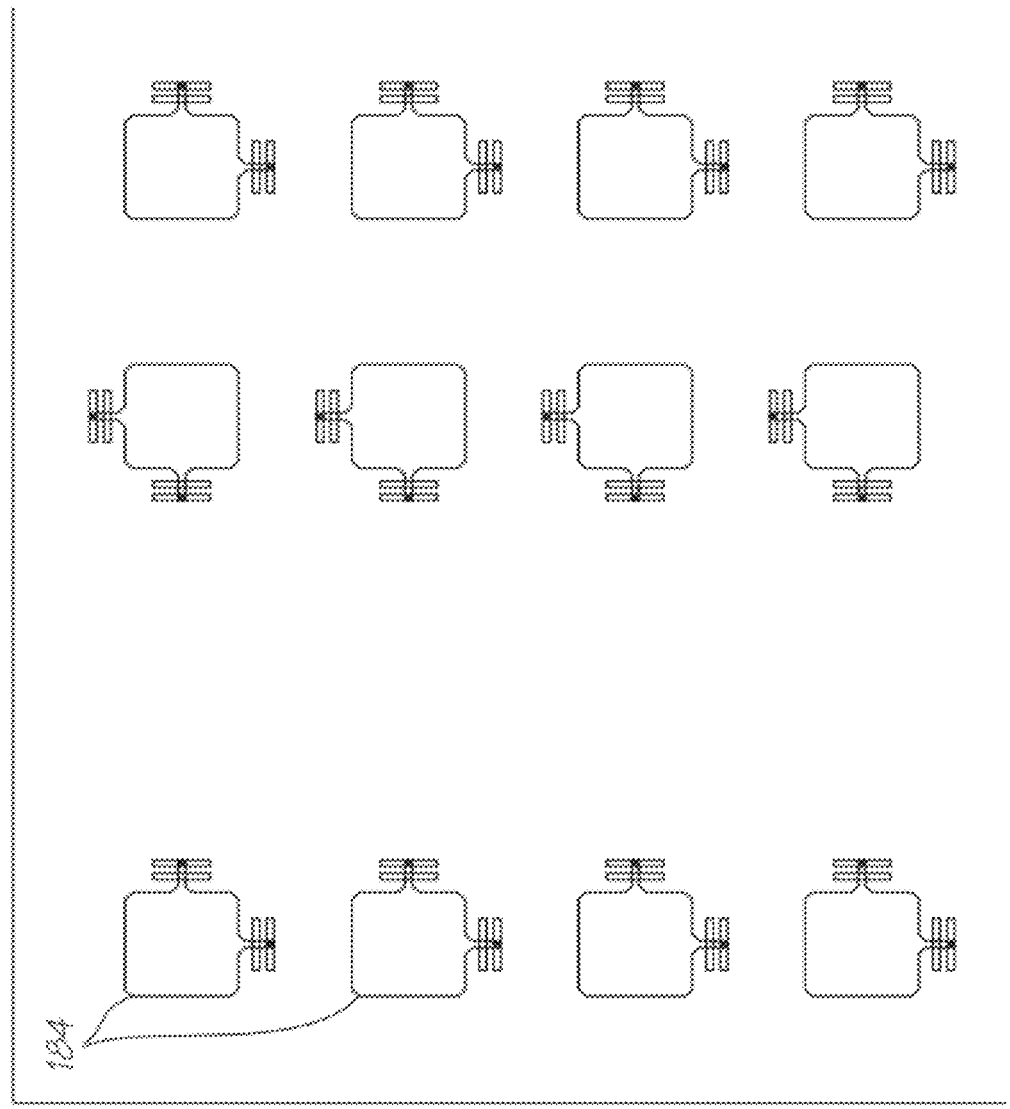
FIG. 60 is a schematic showing part of the photodiode array of the photo sensor.

The thermal energy required for hybridization is provided by CMOS-controlled heaters 182 (described in more detail below). After the heater is activated, hybridization occurs between complementary target-probe sequences. The LED driver 29 in the CMOS circuitry 86 signals the LED 26 located in the test module 10 to illuminate. These probes only fluoresce when hybridization has occurred thereby avoiding washing and drying steps that are typically required to remove unbound strands. Hybridization forces the stem-and-loop structure of the FRET probes 186 to open, which allows the fluorophore to emit fluorescent energy in response to the LED excitation light, as discussed in greater detail later. Fluorescence is detected by a photodiode 184 in the CMOS circuitry 86 underlying each hybridization chamber 180 (see hybridization chamber description below). The photodiodes 184 for all hybridization chambers and associated electronics collectively form the photosensor 44 (see FIG. 60). In other embodiments, the photosensor may be an array of charge coupled devices (CCD array). The detected signal from the photodiodes 184 is amplified and converted to a digital output which is analyzed by the test module reader 12. Further details of the detection method are described later.

Additional Details for the LOC Device
Modularity of the Design

The LOC device 301 has many functional sections, including the reagent reservoirs 54, 56, 58, 60 and 62, the dialysis section 70, lysis section 130, incubation section 114, and amplification section 112, valve types, the humidifier and humidity sensor. In other embodiments of the LOC device, these functional sections can be omitted, additional functional sections can be added or the functional sections can be used for alternative purposes to those described above.

For example, the incubation section 114 can be used as the first amplification section 112 of a tandem amplification assay system, with the chemical lysis reagent reservoir 56 being used to add the first amplification mix of primers, dNTPs and buffer and reagent reservoir 58 being used for adding the reverse transcriptase and/or polymerase. A chemical lysis reagent can also be added to the reservoir 56 along with the amplification mix if chemical lysis of the sample is desired or, alternatively, thermal lysis can occur in the incubation section by heating the sample for a predetermined time. In some embodiments, an additional reservoir can be incorporated immediately upstream of reservoir 58 for the mix of primers, dNTPs and buffer if there is a requirement for chemical lysis and a separation of this mix from the chemical lysis reagent is desired.

In some circumstances it may be desirable to omit a step, such as the incubation step 291. In this case, a LOC device can be specifically fabricated to omit the reagent reservoir 58 and incubation section 114, or the reservoir can simply not be loaded with reagents or the active valves, if present, not activated to dispense the reagents into the sample flow, and the incubation section then simply becomes a channel to transport the sample from the lysis section 130 to the amplification section 112. The heaters are independently operable and therefore, where reactions are dependent on heat, such as thermal lysis, programming the heaters not to activate during this step ensures thermal lysis does not occur in LOC devices that do not require it. The dialysis section 70 can be located at the beginning of the fluidic system within the microfluidic device as shown in FIG. 4 or can be located anywhere else within the microfluidic device. For example, dialysis after the amplification phase 292 to remove cellular debris prior to the hybridization and detection step 294 may be beneficial in some circumstances. Alternatively, two or more dialysis sections can be incorporated at any location throughout the LOC device. Similarly, it is possible to incorporate additional amplification sections 112 to enable multiple targets to be amplified in parallel or in series prior to being detected in the hybridization chamber arrays 110 with specific nucleic acid probes. For analysis of samples like whole blood, in which dialysis is not required, the dialysis section 70 is simply omitted from the sample input and preparation section 288 of the LOC design. In some cases, it is not necessary to omit the dialysis section 70 from the LOC device even if the analysis does not require dialysis. If there is no geometric hindrance to the assay by the existence of a dialysis section, a LOC with the dialysis section 70 in the sample input and preparation section can still be used without a loss of the required functionality.

Furthermore, the detection section 294 may encompass proteomic chamber arrays which are identical to the hybridization chamber arrays but are loaded with probes designed to conjugate or hybridize with sample target proteins present in non-amplified sample instead of nucleic acid probes designed to hybridize to target nucleic acid sequences.

It will be appreciated that the LOC devices fabricated for use in this diagnostic system are different combinations of functional sections selected in accordance with the particular LOC application. The vast majority of functional sections are common to many of the LOC devices and the design of additional LOC devices for new application is a matter of compiling an appropriate combination of functional sections from the extensive selection of functional sections used in the existing LOC devices.

Only a small number of the LOC devices are shown in this description and some more are shown schematically to illustrate the design flexibility of the LOC devices fabricated for this system. The person skilled in the art will readily recognise that the LOC devices shown in this description are not an exhaustive list and many additional LOC designs are a matter of compiling the appropriate combination of functional sections.

Sample Types

LOC variants can accept and analyze the nucleic acid or protein content of a variety of sample types in liquid form including, but not limited to, blood and blood products, saliva, cerebrospinal fluid, urine, semen, amniotic fluid, umbilical cord blood, breast milk, sweat, pleural effusion, tear, pericardial fluid, peritoneal fluid, environmental water samples and drink samples. Amplicon obtained from macroscopic nucleic acid amplification can also be analysed using the LOC device; in this case, all the reagent reservoirs will be empty or configured not to release their contents, and the dialysis, lysis, incubation and amplification sections will be used solely to transport the sample from the sample inlet 68 to the hybridization chambers 180 for nucleic acid detection, as described above.

For some sample types, a pre-processing step is required, for example semen may need to be liquefied and mucus may need to be pre-treated with an enzyme to reduce the viscosity prior to input into the LOC device.

Sample Input

Referring to FIGS. 1 and 12, the sample is added to the macroreceptacle 24 of the test module 10. The macroreceptacle 24 is a truncated cone which feeds into the inlet 68 of the LOC device 301 by capillary action. Here it flows into the 64 µm wide×60 µm deep cap channel 94 where it is drawn towards the anticoagulant reservoir 54, also by capillary action.

Reagent Reservoirs

The small volumes of reagents required by the assay systems using microfluidic devices, such as LOC device 301, permit the reagent reservoirs to contain all reagents necessary for the biochemical processing with each of the reagent reservoirs having a small volume. This volume is easily less than 1,000,000,000 cubic microns, in the vast majority of cases less than 300,000,000 cubic microns, typically less than 70,000,000 cubic microns and in the case of the LOC device 301 shown in the drawings, less than 20,000,000 cubic microns.

Dialysis Section

Referring to FIGS. 15 to 21, 33 and 34, the pathogen dialysis section 70 is designed to concentrate pathogenic target cells from the sample. As previously described, a plurality of apertures in the form of 3 micron diameter holes 164 in the roof layer 66 filter the target cells from the bulk of the sample. As the sample flows past the 3 micron diameter apertures 164, microbial pathogens pass through the holes into a series of dialysis MST channels 204 and flow back up into the target channel 74 via 16 µm dialysis uptake holes 168 (see FIGS. 33 and 34). The remainder of the sample (erythrocytes and so on) stay in the cap channel 94. Downstream of the pathogen dialysis section 70, the cap channel 94 becomes the waste channel 72 leading to the waste reservoir 76. For biological samples of the type that generate a substantial amount of waste, a foam insert or other porous element 49 within the outer casing 13 of the test module 10 is configured to be in fluid communication with the waste reservoir 76 (see FIG. 1).

The pathogen dialysis section 70 functions entirely on capillary action of the fluid sample. The 3 micron diameter apertures 164 at the upstream end of the pathogen dialysis section 70 have capillary initiation features (CIFs) 166 (see FIG. 33) so that the fluid is drawn down into the dialysis MST channel 204 beneath. The first uptake hole 198 for the target channel 74 also has a CIF 202 (see FIG. 15) to avoid the flow simply pinning a meniscus across the dialysis uptake holes 168.

Figure 71:
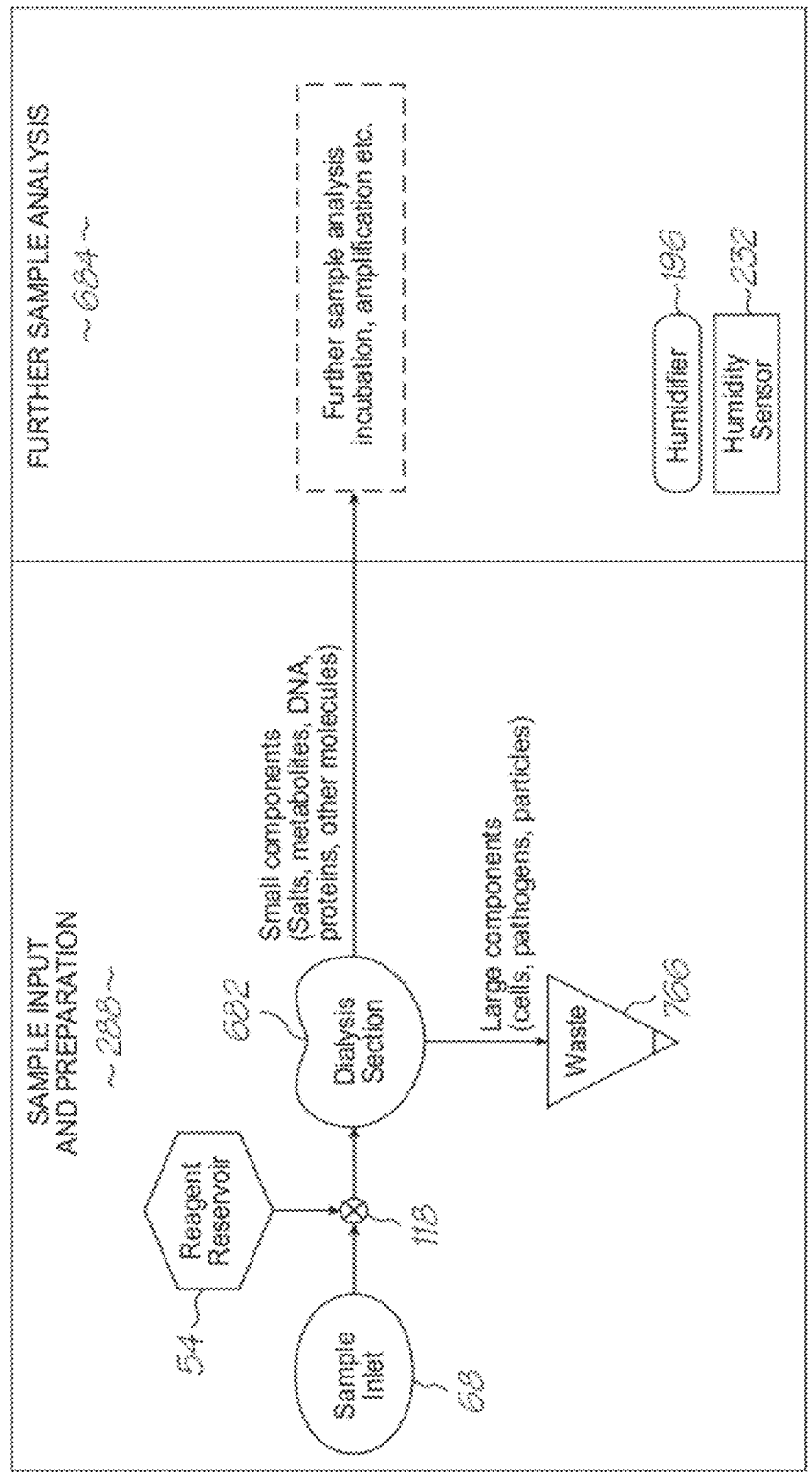
FIG. 71 is a schematic illustration of the architecture of LOC variant XLI.

The small constituents dialysis section 682 schematically shown in FIG. 71 can have a similar structure to the pathogen dialysis section 70. The small constituents dialysis section separates any small target cells or molecules from a sample by sizing (and, if necessary, shaping) apertures suitable for allowing the small target cells or molecules to pass into the target channel and continue for further analysis. Larger sized cells or molecules are removed to a waste reservoir 766. Thus, the LOC device 30 (see FIGS. 1 and 104) is not limited to separating pathogens that are less than 3 µm in size, but can be used to separate cells or molecules of any size desired.

Lysis Section

Referring back to FIGS. 7, 11 and 13, the genetic material in the sample is released from the cells by a chemical lysis process. As described above, a lysis reagent from the lysis reservoir 56 mixes with the sample flow in the target channel 74 downstream of the surface tension valve 128 for the lysis reservoir 56. However, some diagnostic assays are better suited to a thermal lysis process, or even a combination of chemical and thermal lysis of the target cells. The LOC device 301 accommodates this with the heated microchannels 210 of the incubation section 114. The sample flow fills the incubation section 114 and stops at the boiling-initiated valve 106. The incubation microchannels 210 heat the sample to a temperature at which the cellular membranes are disrupted.

In some thermal lysis applications, an enzymatic reaction in the chemical lysis section 130 is not necessary and the thermal lysis completely replaces the enzymatic reaction in the chemical lysis section 130.

Boiling-Initiated Valve

As discussed above, the LOC device 301 has three boiling-initiated valves 126, 106 and 108. The location of these valves is shown in FIG. 6. FIG. 31 is an enlarged plan view of the boiling-initiated valve 108 in isolation at the end of the heated microchannels 158 of the amplification section 112.

The sample flow 119 is drawn along the heated microchannels 158 by capillary action until it reaches the boiling-initiated valve 108. The leading meniscus 120 of the sample flow pins at a meniscus anchor 98 at the valve inlet 146. The geometry of the meniscus anchor 98 stops the advancing meniscus to arrest the capillary flow. As shown in FIGS. 31 and 32, the meniscus anchor 98 is an aperture provided by an uptake opening from the MST channel 90 to the cap channel 94. Surface tension in the meniscus 120 keeps the valve closed. An annular heater 152 is at the periphery of the valve inlet 146. The annular heater 152 is CMOS-controlled via the boiling-initiated valve heater contacts 153.

To open the valve, the CMOS circuitry 86 sends an electrical pulse to the valve heater contacts 153. The annular heater 152 resistively heats until the liquid sample 119 boils. The boiling unpins the meniscus 120 from the valve inlet 146 and initiates wetting of the cap channel 94. Once wetting the cap channel 94 begins, capillary flow resumes. The fluid sample 119 fills the cap channel 94 and flows through the valve downtake 150 to the valve outlet 148 where capillary driven flow continues along the amplification section exit channel 160 into the hybridization and detection section 52. Liquid sensors 174 are placed before and after the valve for diagnostics.

It will be appreciated that once the boiling-initiated valves are opened, they cannot be re-closed. However, as the LOC device 301 and the test module 10 are single-use devices, re-closing the valves is unnecessary.

Incubation Section and Nucleic Acid Amplification Section

FIGS. 6, 7, 13, 14, 23, 24, 25, 35 to 45, 50 and 51 show the incubation section 114 and the amplification section 112. The incubation section 114 has a single, heated incubation microchannel 210 etched in a serpentine pattern in the MST channel layer 100 from the downtake opening 134 to the boiling-initiated valve 106 (see FIGS. 13 and 14). Control over the temperature of the incubation section 114 enables enzymatic reactions to take place with greater efficiency. Similarly, the amplification section 112 has a heated amplification microchannel 158 in a serpentine configuration leading from the boiling-initiated valve 106 to the boiling-initiated valve 108 (see FIGS. 6 and 14). These valves arrest the flow to retain the target cells in the heated incubation or amplification microchannels 210 or 158 while mixing, incubation and nucleic acid amplification takes place. The serpentine pattern of the microchannels also facilitates (to some extent) mixing of the target cells with reagents.

Figure 51:
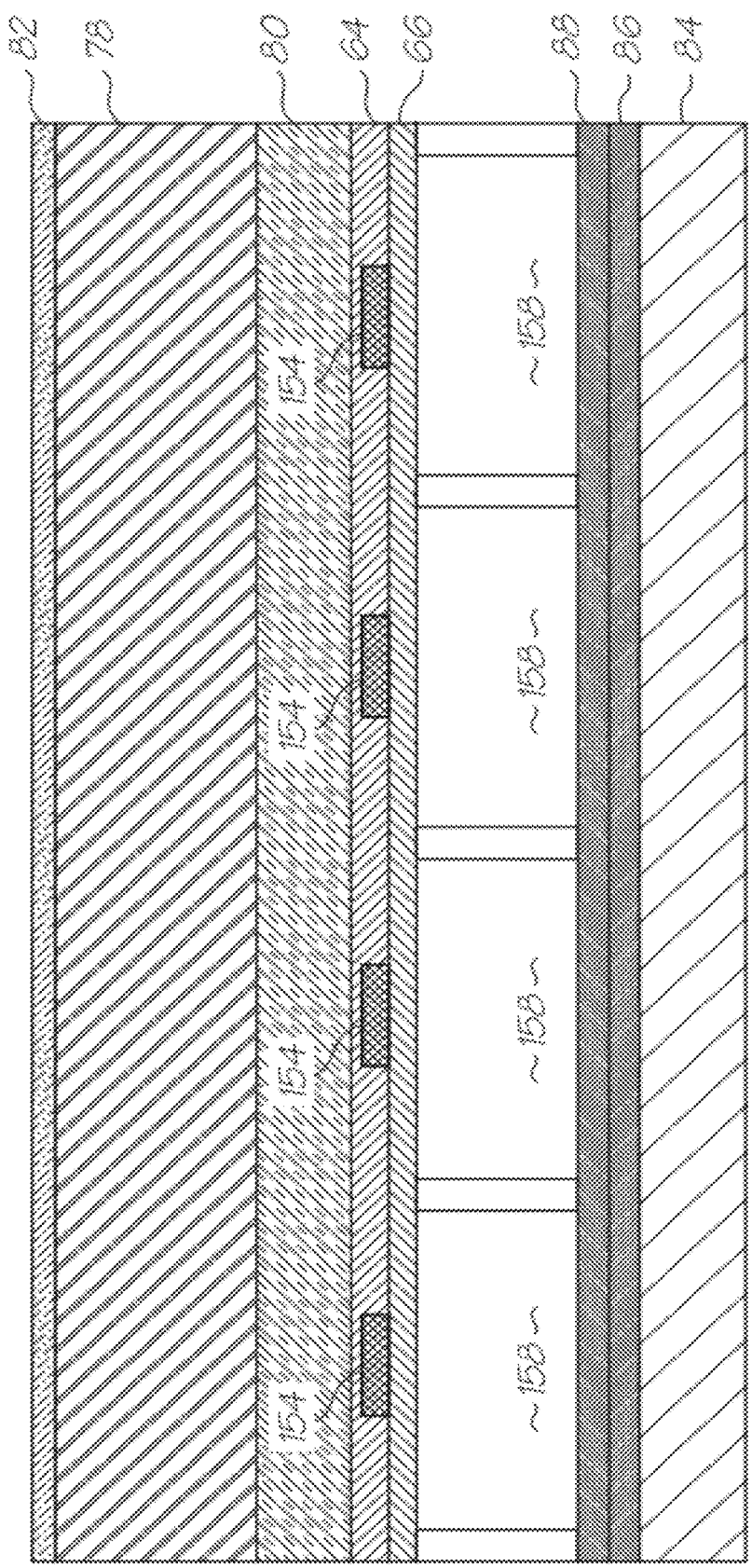
FIG. 51 is a schematic section view of the amplification section.
Figure 52:
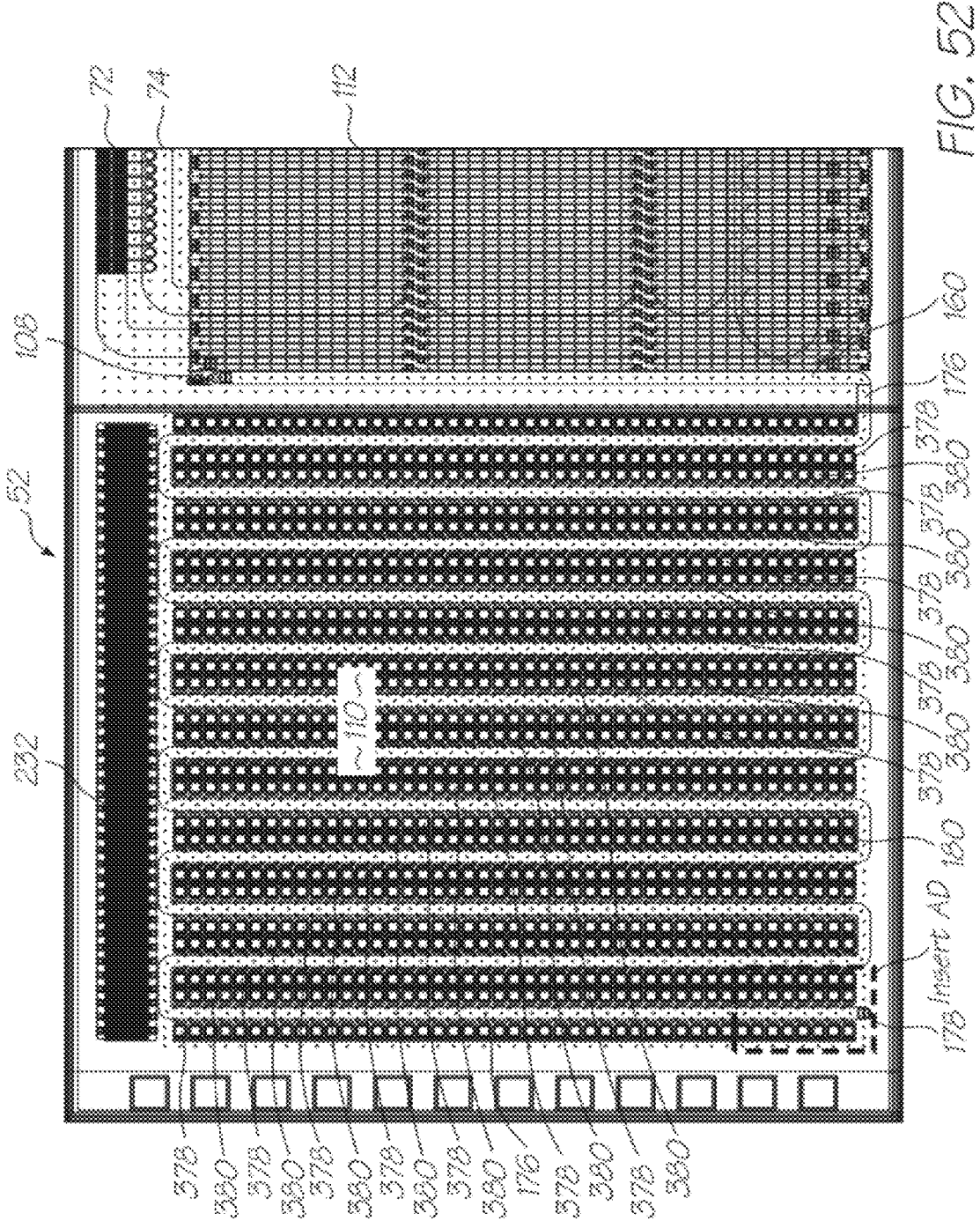
Figure 58:
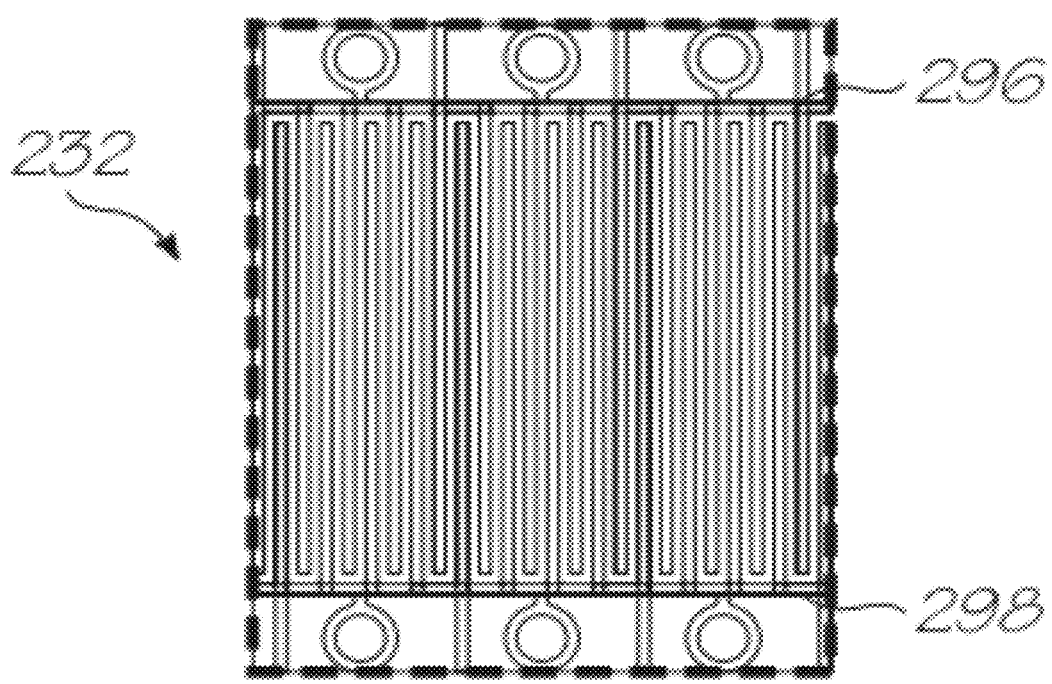
FIG. 58 is an enlarged plan view of the humidity sensor shown in Inset AH of FIG. 6.

In the incubation section 114 and the amplification section 112, the sample cells and the reagents are heated by the heaters 154 controlled by the CMOS circuitry 86 using pulse width modulation (PWM). Each meander of the serpentine configuration of the heated incubation microchannel 210 and amplification microchannel 158 has three separately operable heaters 154 extending between their respective heater contacts 156 (see FIG. 14) which provides for the two-dimensional control of input heat flux density. As best shown in FIG. 51, the heaters 154 are supported on the roof layer 66 and embedded in the lower seal 64. The heater material is TiAl but many other conductive metals would be suitable. The elongate heaters 154 are parallel with the longitudinal extent of each channel section that forms the wide meanders of the serpentine shape. In the amplification section 112, each of the wide meanders can operate as separate PCR chambers via individual heater control.

The small volumes of amplicon required by the assay systems using microfluidic devices, such as LOC device 301, permit low amplification mixture volumes for amplification in amplification section 112. This volume is easily less than 400 nanoliters, in the vast majority of cases less than 170 nanoliters, typically less than 70 nanoliters and in the case of the LOC device 301, between 2 nanoliters and 30 nanoliters.

Increased Rates of Heating and Greater Diffusive Mixing

The small cross section of each channel section increases the heating rate of the amplification fluid mix. All the fluid is kept a relatively short distance from the heater 154. Reducing the channel cross section (that is the amplification microchannel 158 cross section) to less than 100,000 square microns achieves appreciably higher heating rates than that provided by more 'macro-scale' equipment. Lithographic fabrication techniques allow the amplification microchannel 158 to have a cross sectional area transverse to the flow-path less than 16,000 square microns which gives substantially higher heating rates. Feature sizes on the order of 1 micron are readily achievable with lithographic techniques. If very little amplicon is needed (as is the case in the LOC device 301), the cross sectional area can be reduced to less than 2,500 square microns. For diagnostic assays with 1,000 to 2,000 probes on the LOC device, and a requirement of 'sample-in, answer out' in less than 1 minute, a cross sectional area transverse to the flow of between 400 square microns and 1 square micron is adequate.

The heater element in the amplification microchannel 158 heats the nucleic acid sequences at a rate more than 80 Kelvin (K) per second, in the vast majority of cases at a rate greater than 100 K per second. Typically, the heater element heats the nucleic acid sequences at a rate more than 1,000 K per second and in many cases, the heater element heats the nucleic acid sequences at a rate more than 10,000 K per second. Commonly, based on the demands of the assay system, the heater element heats the nucleic acid sequences at a rate more than 100,000 K per second, more than 1,000,000 K per second more than 10,000,000 K per second, more than 20,000,000 K per second, more than 40,000,000 K per second, more than 80,000,000 K per second and more than 160,000,000 K per second.

A small cross-sectional area channel is also beneficial for diffusive mixing of any reagents with the sample fluid. Before diffusive mixing is complete, diffusion of one liquid into the other is greatest near the interface between the two. Concentration decreases with distance from the interface. Using microchannels with relatively small cross sections transverse to the flow direction, keeps both fluid flows close to the interface for more rapid diffusive mixing. Reducing the channel cross section to less than 100,000 square microns achieves appreciably higher mixing rates than that provided by more 'macro-scale' equipment. Lithographic fabrication techniques allows microchannels with a cross sectional area transverse to the flow-path less than 16000 square microns which gives significantly higher mixing rates. If small volumes are needed (as is the case in the LOC device 301), the cross sectional area can be reduced to less than 2500 square microns. For diagnostic assays with 1000 to 2000 probes on the LOC device, and a requirement of 'sample-in, answer out' in less than 1 minute, a cross sectional area transverse to the flow of between 400 square microns and 1 square micron is adequate.

Short Thermal Cycle Times

Keeping the sample mixture proximate to the heaters, and using very small fluid volumes allows rapid thermal cycling during the nucleic acid amplification process. Each thermal cycle (i.e. denaturing, annealing and primer extension) is completed in less than 30 seconds for target sequences up to 150 base pairs (bp) long. In the vast majority of diagnostic assays, the individual thermal cycle times are less than 11 seconds, and a large proportion are less than 4 seconds. LOC devices 30 with some of the most common diagnostic assays have thermal cycles time between 0.45 seconds to 1.5 seconds for target sequences up to 150 bp long. Thermal cycling at this rate allows the test module to complete the nucleic acid amplification process in much less than 10 minutes; often less than 220 seconds. For most assays, the amplification section generates sufficient amplicon in less than 80 seconds from the sample fluid entering the sample inlet. For a great many assays, sufficient amplicon is generated in 30 seconds.

Upon completion of a preset number of amplification cycles, the amplicon is fed into the hybridization and detection section 52 via the boiling-initiated valve 108.

Hybridization Chambers

FIGS. 52, 53, 54, 56 and 57 show the hybridization chambers 180 in the hybridization chamber array 110. The hybridization and detection section 52 has a 24×45 array 110 of hybridization chambers 180, each with hybridization-responsive FRET probes 186, heater element 182 and an integrated photodiode 184. The photodiode 184 is incorporated for detection of fluorescence resulting from the hybridization of a target nucleic acid sequence or protein with the FRET probes 186. Each photodiode 184 is independently controlled by the CMOS circuitry 86. Any material between the FRET probes 186 and the photodiode 184 must be transparent to the emitted light. Accordingly, the wall section 97 between the probes 186 and the photodiode 184 is also optically transparent to the emitted light. In the LOC device 301, the wall section 97 is a thin (approximately 0.5 micron) layer of silicon dioxide.

Incorporation of a photodiode 184 directly beneath each hybridization chamber 180 allows the volume of probe-target hybrids to be very small while still generating a detectable fluorescence signal (see FIG. 54). The small amounts permit small volume hybridization chambers. A detectable amount of probe-target hybrid requires a quantity of probe, prior to hybridization, which is easily less than 270 picograms (corresponding to 900,000 cubic microns), in the vast majority of cases less than 60 picograms (corresponding to 200,000 cubic microns), typically less than 12 picograms (corresponding to 40,000 cubic microns) and in the case of the LOC device 301 shown in the accompanying figures, less than 2.7 picograms (corresponding to a chamber volume of 9,000 cubic microns). Of course, reducing the size of the hybridization chambers allows a higher density of chambers and therefore more probes on the LOC device. In LOC device 301, the hybridization section has more than 1,000 chambers in an area of 1,500 microns by 1,500 microns (i.e. less than 2,250 square microns per chamber). Smaller volumes also reduce the reaction times so that hybridization and detection is faster. An additional advantage of the small amount of probe required in each chamber is that only very small quantities of probe solution need to be spotted into each chamber during production of the LOC device. Embodiments of the LOC device according to the invention can be spotted using a probe solution volume of 1 picoliter or less.

After nucleic acid amplification, boiling-initiated valve 108 is activated and the amplicon flows along the flow-path 176 and into each of the hybridization chambers 180 (see FIGS. 52 and 56). An end-point liquid sensor 178 indicates when the hybridization chambers 180 are filled with amplicon and the heaters 182 can be activated.

After sufficient hybridization time, the LED 26 (see FIG. 2) is activated. The opening in each of the hybridization chambers 180 provides an optical window 136 for exposing the FRET probes 186 to the excitation radiation (see FIGS. 52, 54 and 56). The LED 26 is illuminated for a sufficiently long time in order to induce a fluorescence signal from the probes with high intensity. During excitation, the photodiode 184 is shorted. After a pre-programmed delay 300 (see FIG. 2), the photodiode 184 is enabled and fluorescence emission is detected in the absence of the excitation light. The incident light on the active area 185 of the photodiode 184 (see FIG. 54) is converted into a photocurrent which can then be measured using CMOS circuitry 86.

The hybridization chambers 180 are each loaded with probes for detecting a single target nucleic acid sequence. Each hybridization chambers 180 can be loaded with probes to detect over 1,000 different targets if desired. Alternatively, many or all the hybridization chambers can be loaded with the same probes to detect the same target nucleic acid repeatedly. Replicating the probes in this way throughout the hybridization chamber array 110 leads to increased confidence in the results obtained and the results can be combined by the photodiodes adjacent those hybridization chambers to provide a single result if desired. The person skilled in the art will recognise that it is possible to have from one to over 1,000 different probes on the hybridization chamber array 110, depending on the assay specification.

Hybridization Chambers with Electrochemiluminescence Detection

FIGS. 97, 120, 138 and 139 show the hybridization chambers 180 used in an ECL variant of the LOC device, LOC variant L 729. In this embodiment of the LOC device, a 24×45 array 110 of hybridization chambers 180, each with hybridization-responsive ECL probes 237, is positioned in registration with a corresponding array of photodiodes 184 integrated into the CMOS. In a similar fashion to the LOC devices configured for fluorescence detection, each photodiode 184 is incorporated for detection of ECL resulting from the hybridization of a target nucleic acid sequence or protein with an ECL probe 237. Each photodiode 184 is independently controlled by the CMOS circuitry 86. Again, the transparent wall section 97 between the probes 186 and the photodiode 184 is transparent to the emitted light.

Figure 97:
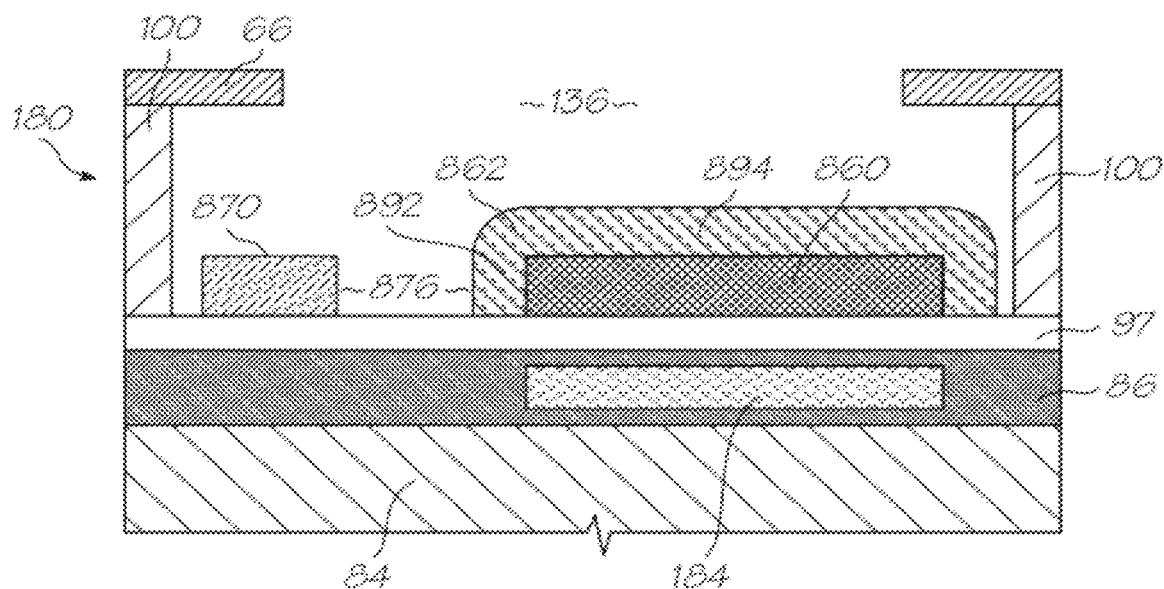
FIG. 97 is a schematic partial cross-section of the anode and cathode in the hybridization chamber.

A photodiode 184 closely adjacent each hybridization chamber 180 allows the amount of probe-target hybrids to be very small while still generating a detectable ECL signal (see FIG. 97). The small amounts permit small volume hybridization chambers. A detectable amount of probe-target hybrid requires a quantity of probe, prior to hybridization, which is easily less than 270 picograms (corresponding to a chamber volume of 900,000 cubic microns), in the vast majority of cases less than 60 picograms (corresponding to 200,000 cubic microns), typically less than 12 picograms (corresponding to 40,000 cubic microns) and in the case of the LOC device shown in the drawings less than 2.7 picograms (corresponding to a chamber volume of 9,000 cubic microns). Of course, reducing the size of the hybridization chambers allows a higher density of chambers and therefore more probes on the LOC device. In the LOC device shown, the hybridization section has more than 1,000 chambers in an area of 1,500 microns by 1,500 microns (i.e. less than 2,250 square microns per chamber). Smaller volumes also reduce the reaction times so that hybridization and detection is faster. An additional advantage of the small amount of probe required in each chamber is that only very small quantities of probe solution need be spotted into each chamber during production of the LOC device. In the case of the LOC device shown in the drawings, the required amount of probe can be spotted using a solution volume of 1 picoliter or less.

Figure 139:
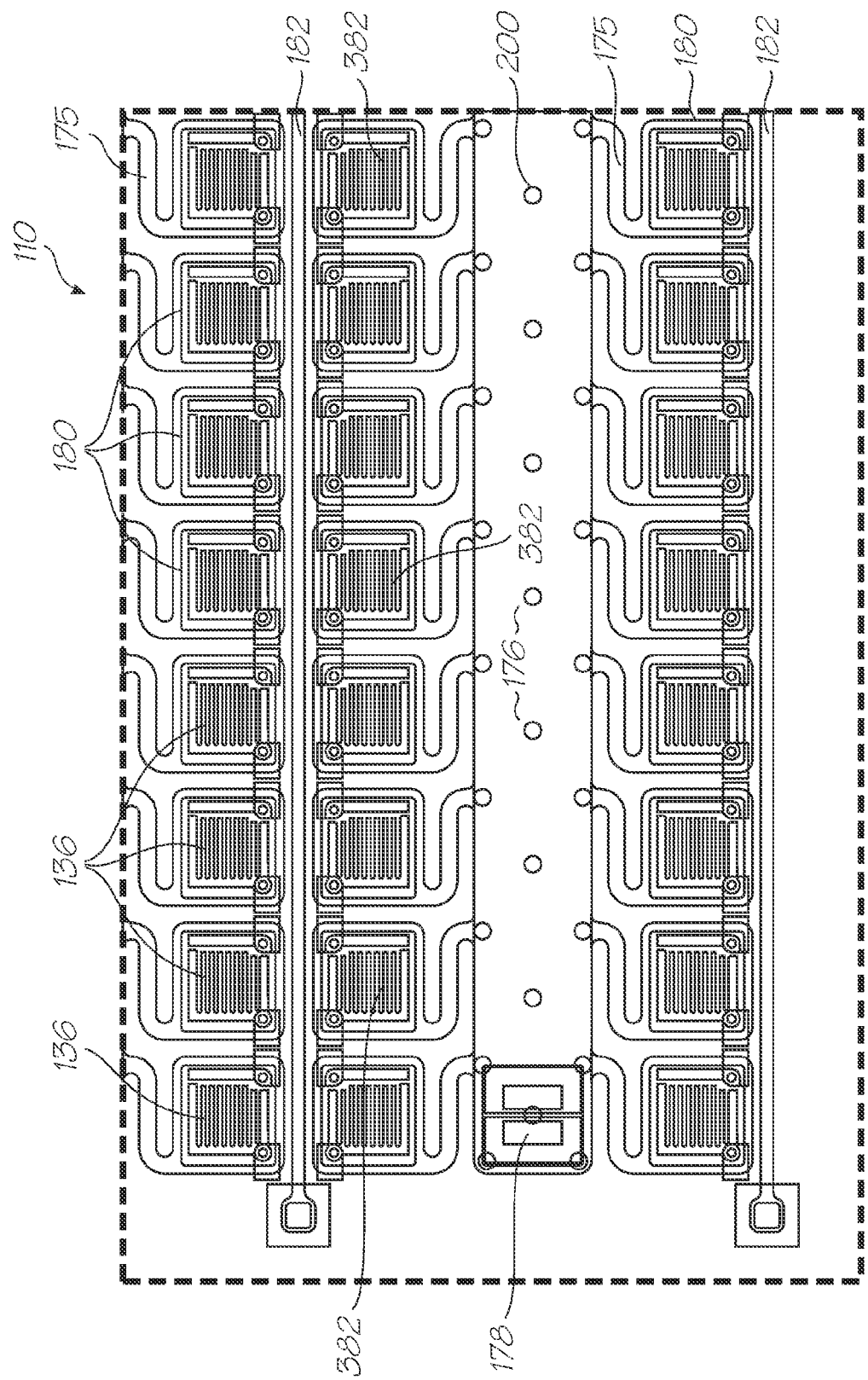
FIG. 139 is an enlarged view of the hybridization chamber array of LOC variant L showing the distribution of calibration chambers.

After nucleic acid amplification, the boiling-initiated valve 108 is activated and the amplicon flows along the flow-path 176 and into each of the hybridization chambers 180 (see FIGS. 52 and 139). An end-point liquid sensor 178 indicates when the hybridization chambers 180 are filled with amplicon so that the heaters 182 can be activated.

After sufficient hybridization time, the photodiode 184 is enabled ready for collection of the ECL signal. Then the ECL excitation drivers 39 (see FIG. 105) activate the ECL electrodes 860 and 870 for a predetermined length of time. The photodiode 184 remains active for a short time after cessation of the ECL excitation current to maximize the signal-to-noise ratio. For example, if the photodiode 184 remains active for five times the decay lifetime of the luminescent emission, then the signal will have decayed to less than one percent of the initial value. The incident light on the photodiode 184 is converted into a photocurrent which can then be measured using CMOS circuitry 86.

Proteomic Assay Chambers

Figure 81:
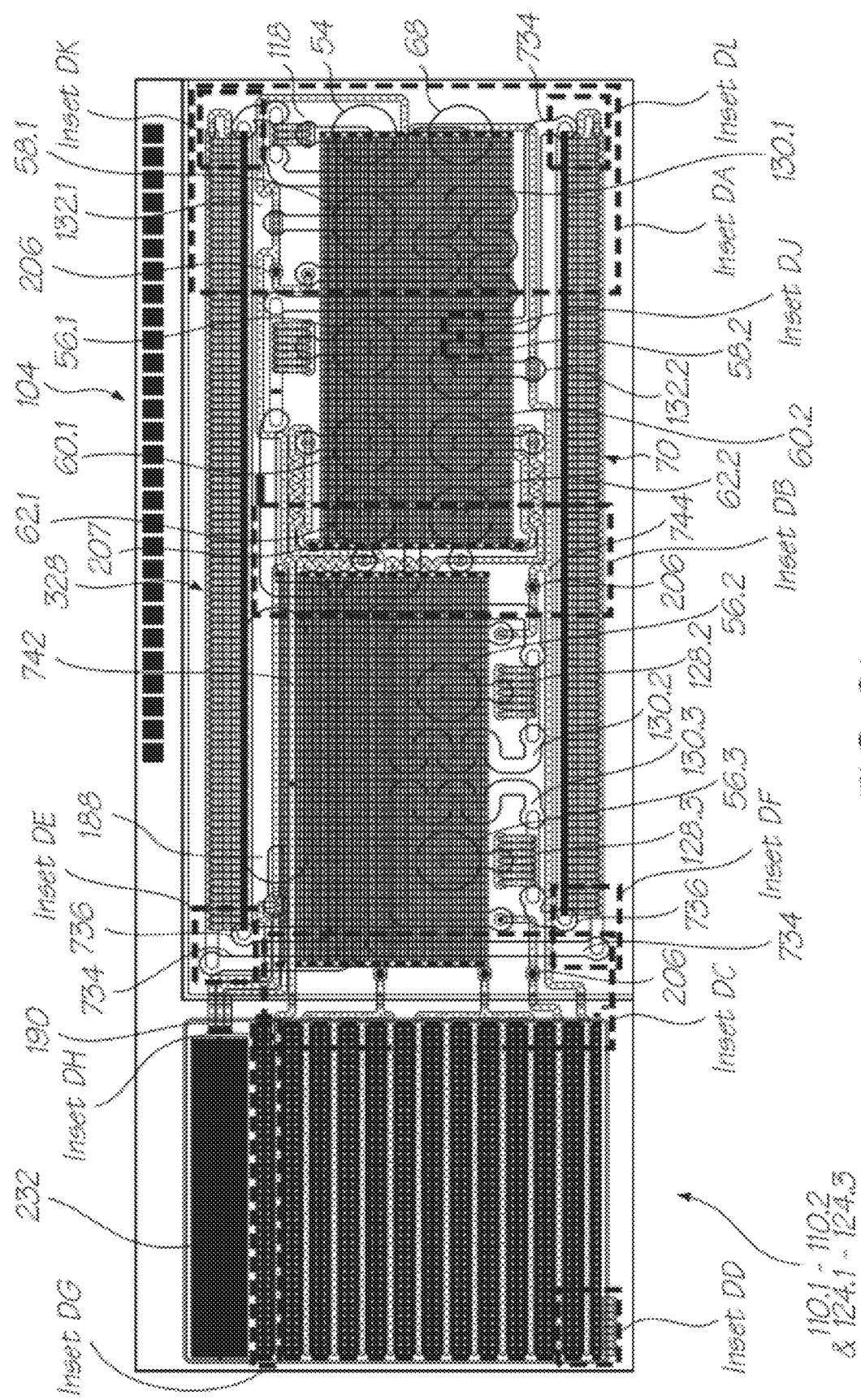
FIG. 81 is a plan view showing all the features superimposed on each other, and showing the location of Insets DA to DK.

Some LOC variants, such as LOC variant L 729, are configured to perform homogeneous protein assays on crude cell lysates within proteomic assay chamber arrays (see for example 124.1 to 124.3 of FIGS. 116 and 120) for the detection of host cell and/or pathogenic proteins. The proteomic assay chamber arrays 124.1-124.3 are manufactured and configured in exactly the same manner as the hybridization chamber arrays 110 (see FIGS. 52, 53, 54 and 56). Each proteomic assay chamber has a diffusion barrier 175 at the entrance to prevent diffusion of sample and reagents between chambers, thus avoiding an erroneous result (see FIGS. 84 and 85, which are insets DC and DD of FIG. 81). Where required for protein hybridization or conjugation, thermal energy is provided by CMOS-controlled heaters 182 in each chamber. In some embodiments, an end-point liquid sensor 178 is used to indicate when the proteomic assay chambers are filled with sample so that the heaters 182 can be activated. After sufficient time has elapsed, the fluorescent or electrochemiluminescent signal generated following protein recognition is detected by the photosensor 44.

Humidifier and Humidity Sensor

Inset AG of FIG. 6 indicates the position of the humidifier 196. The humidifier prevents evaporation of the reagents and probes during operation of the LOC device 301. As best shown in the enlarged view of FIG. 55, a water reservoir 188 is fluidically connected to three evaporators 190. The water reservoir 188 is filled with molecular biology-grade water and sealed during manufacturing. As best shown in FIGS. 55 and 61, water is drawn into three downtakes 194 and along respective water supply channels 192 by capillary action to a set of three uptakes 193 at the evaporators 190. A meniscus pins at each uptake 193 to retain the water. The evaporators have annular shaped heaters 191 which encircle the uptakes 193. The annular heaters 191 are connected to the CMOS circuitry 86 by the conductive columns 376 to the top metal layer 195 (see FIG. 37). Upon activation, the annular heaters 191 heat the water causing evaporation and humidifying the device surrounds.

The position of the humidity sensor 232 is also shown in FIG. 6. However, as best shown in the enlarged view of Inset AH in FIG. 58, the humidity sensor has a capacitive comb structure. A lithographically etched first electrode 296 and a lithographically etched second electrode 298 face each other such that their teeth are interleaved. The opposed electrodes form a capacitor with a capacitance that can be monitored by the CMOS circuitry 86. As the humidity increases, the permittivity of the air gap between the electrodes increases, so that the capacitance also increases. The humidity sensor 232 is adjacent the hybridization chamber array 110 where humidity measurement is most important to slow evaporation from the solution containing the exposed probes.

Feedback Sensors

Figure 35:
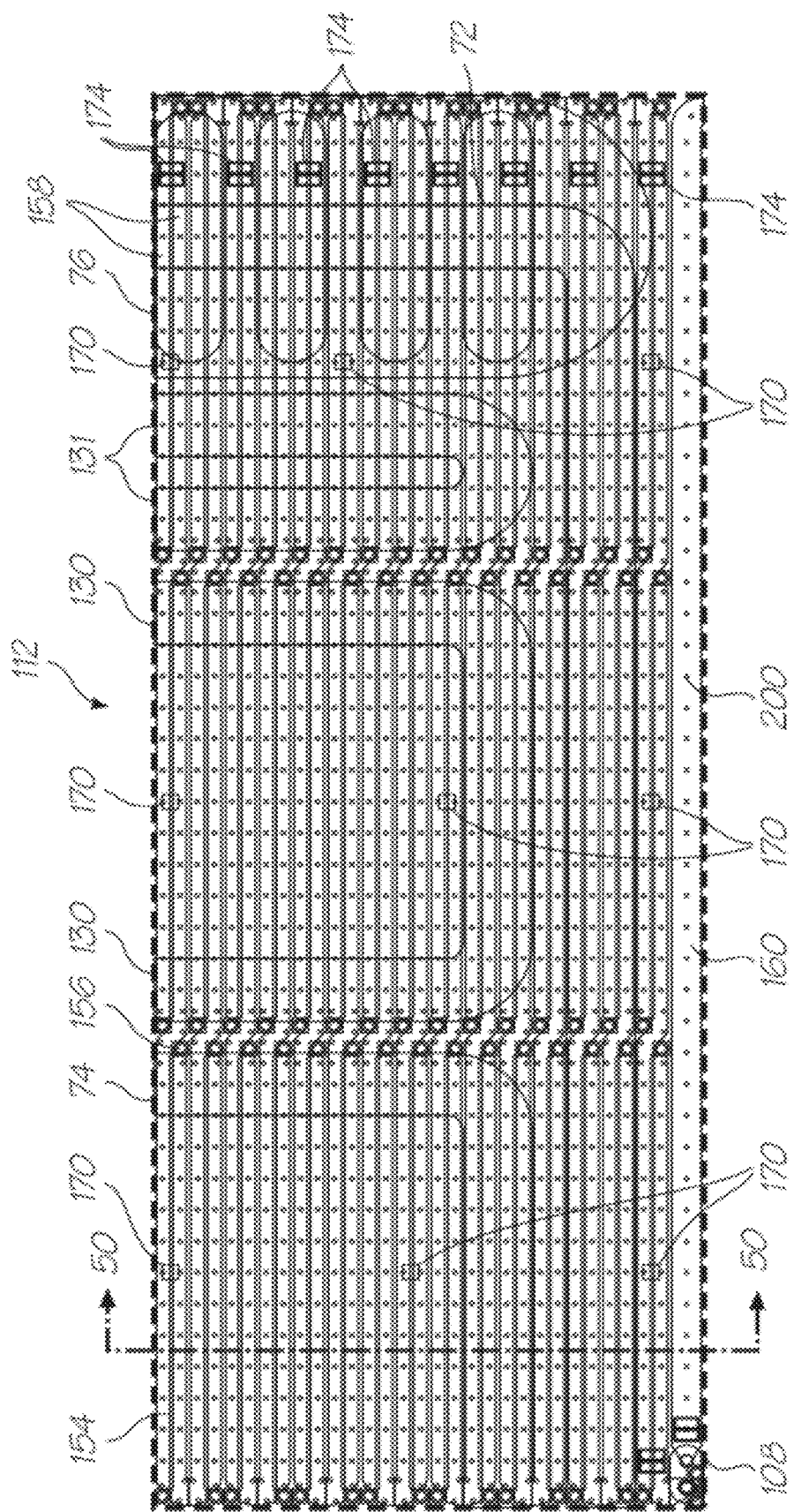
FIG. 35 is an enlarged view of Inset AC shown in FIG. 6.
Figure 36:
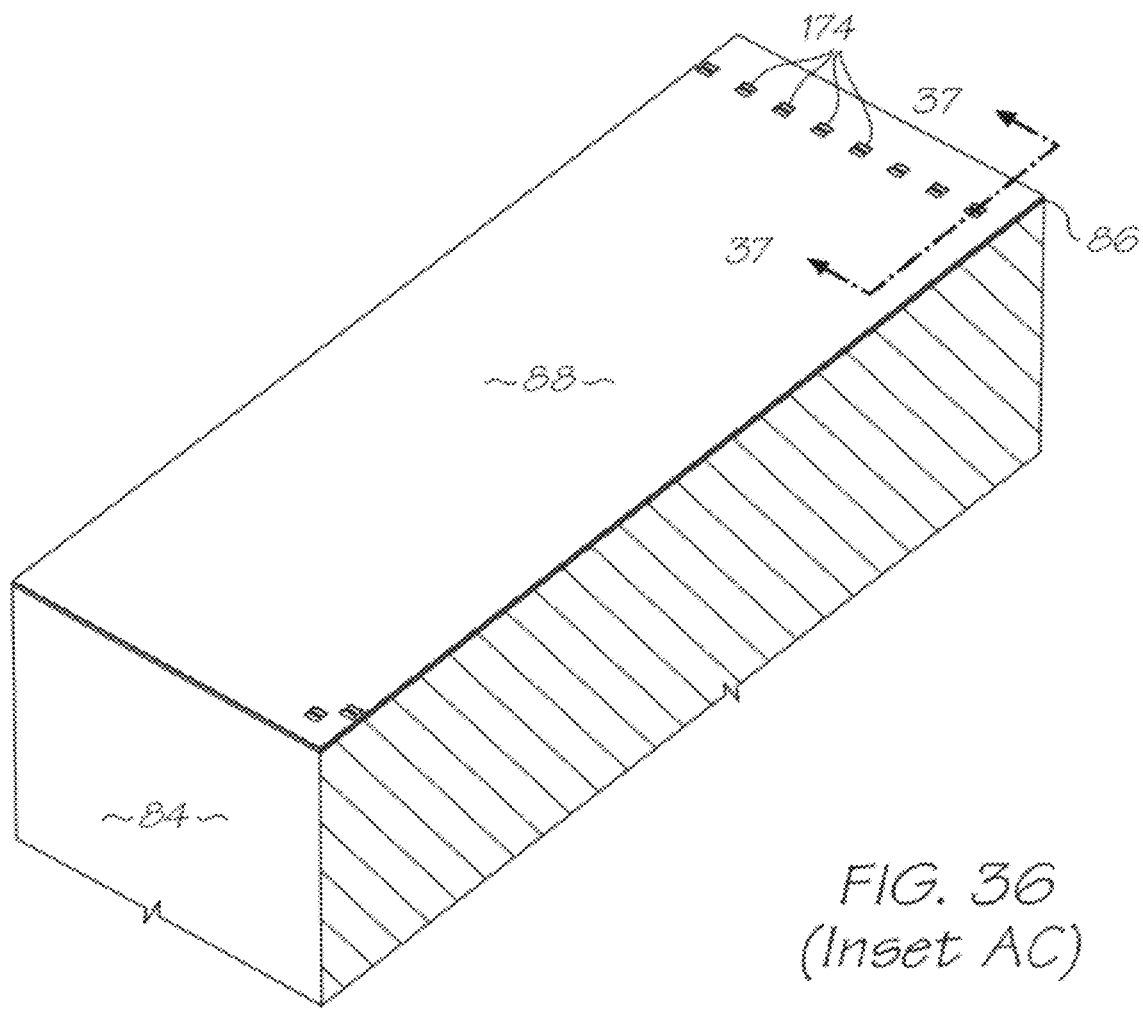
FIG. 36 is a further enlarged view within Inset AC showing the amplification section.

Temperature and liquid sensors are incorporated throughout the LOC device 301 to provide feedback and diagnostics during device operation. Referring to FIG. 35, nine temperature sensors 170 are distributed throughout the amplification section 112. Likewise, the incubation section 114 also has nine temperature sensors 170. These sensors each use a 2×2 array of bipolar junction transistors (BJTs) to monitor the fluid temperature and provide feedback to the CMOS circuitry 86. The CMOS circuitry 86 uses this to precisely control the thermal cycling during the nucleic acid amplification process and any heating during thermal lysis and incubation.

In the hybridization chambers 180, the CMOS circuitry 86 uses the hybridization heaters 182 as temperature sensors (see FIG. 56). The electrical resistance of the hybridization heaters 182 is temperature dependent and the CMOS circuitry 86 uses this to derive a temperature reading for each of the hybridization chambers 180.

Figure 37:
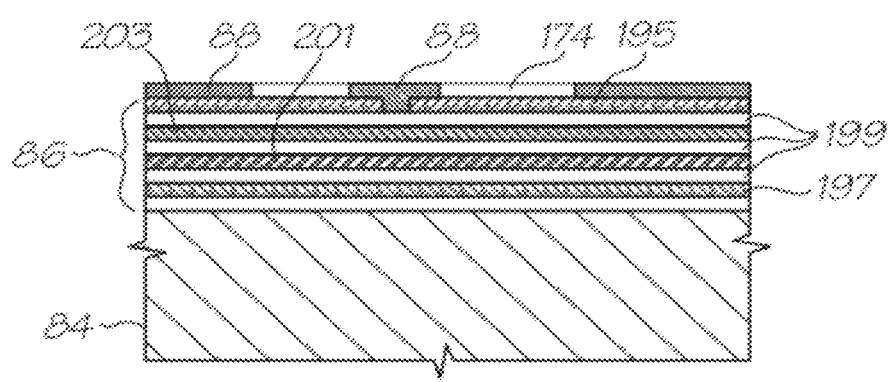
FIG. 37 is a further enlarged view within Inset AC showing the amplification section.
Figure 38:
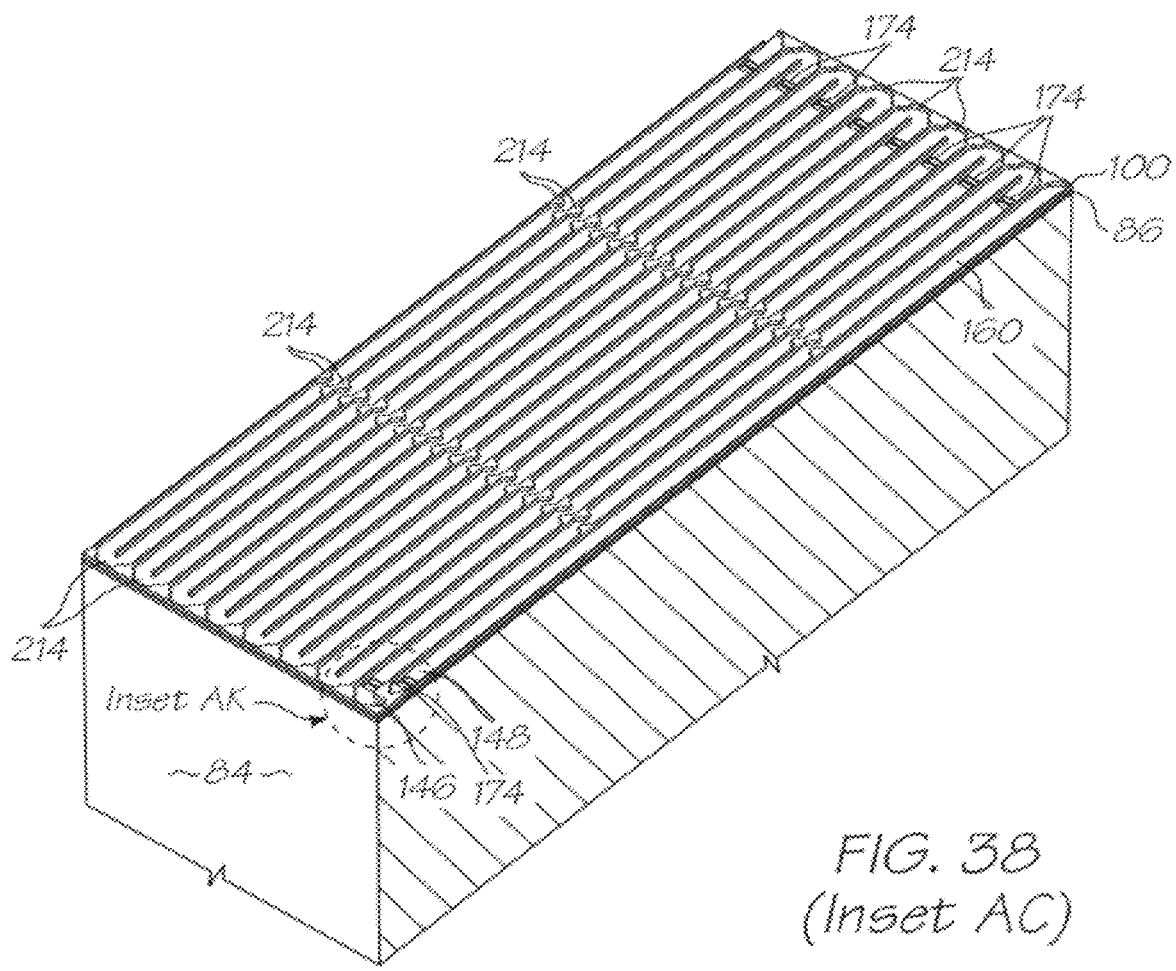
FIG. 38 is a further enlarged view within Inset AC showing the amplification section.
Figure 39:
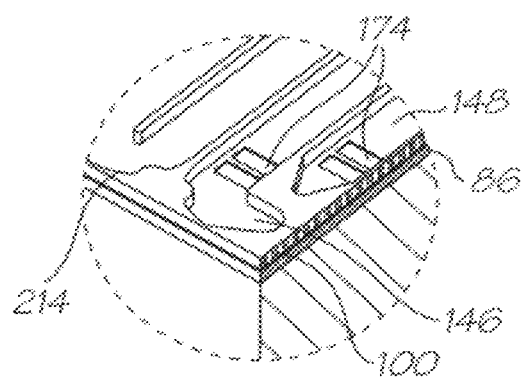
FIG. 39 is a further enlarged view within Inset AK shown in FIG. 38.
Figure 40:
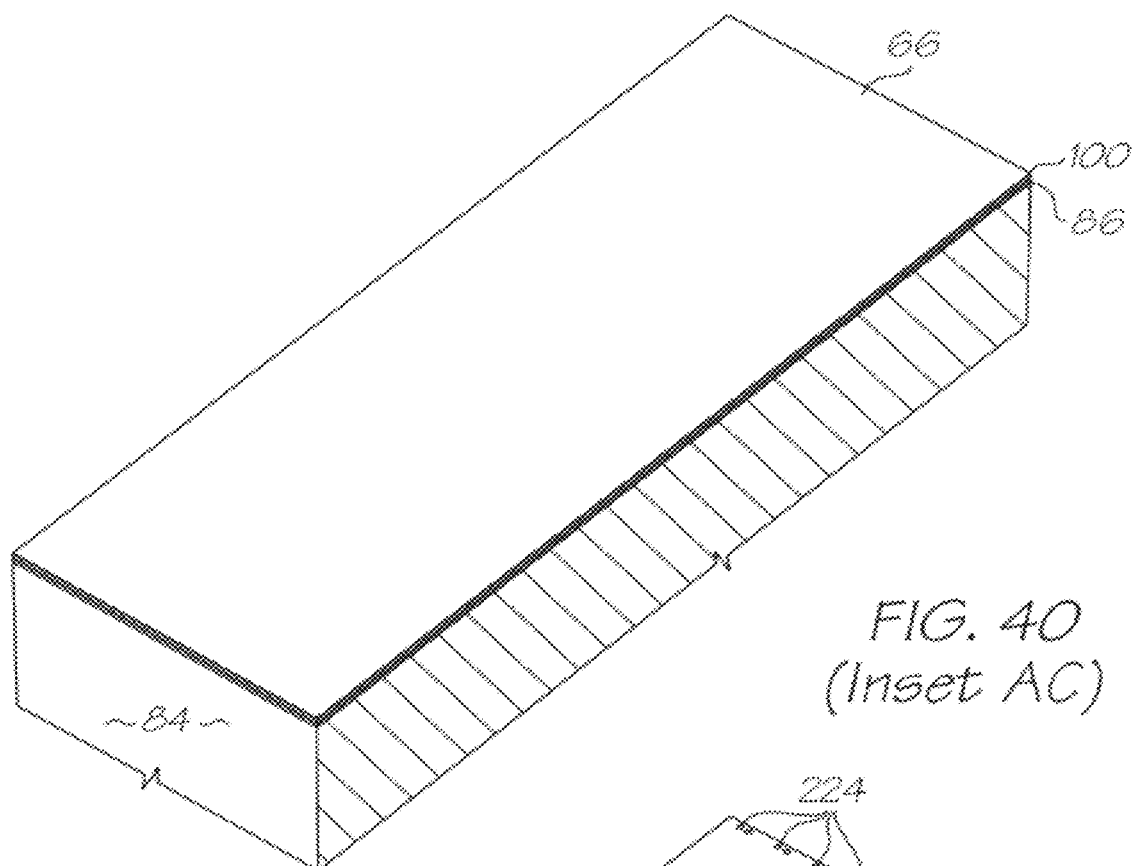
FIG. 40 is a further enlarged view within Inset AC showing the amplification chamber.
Figure 41:
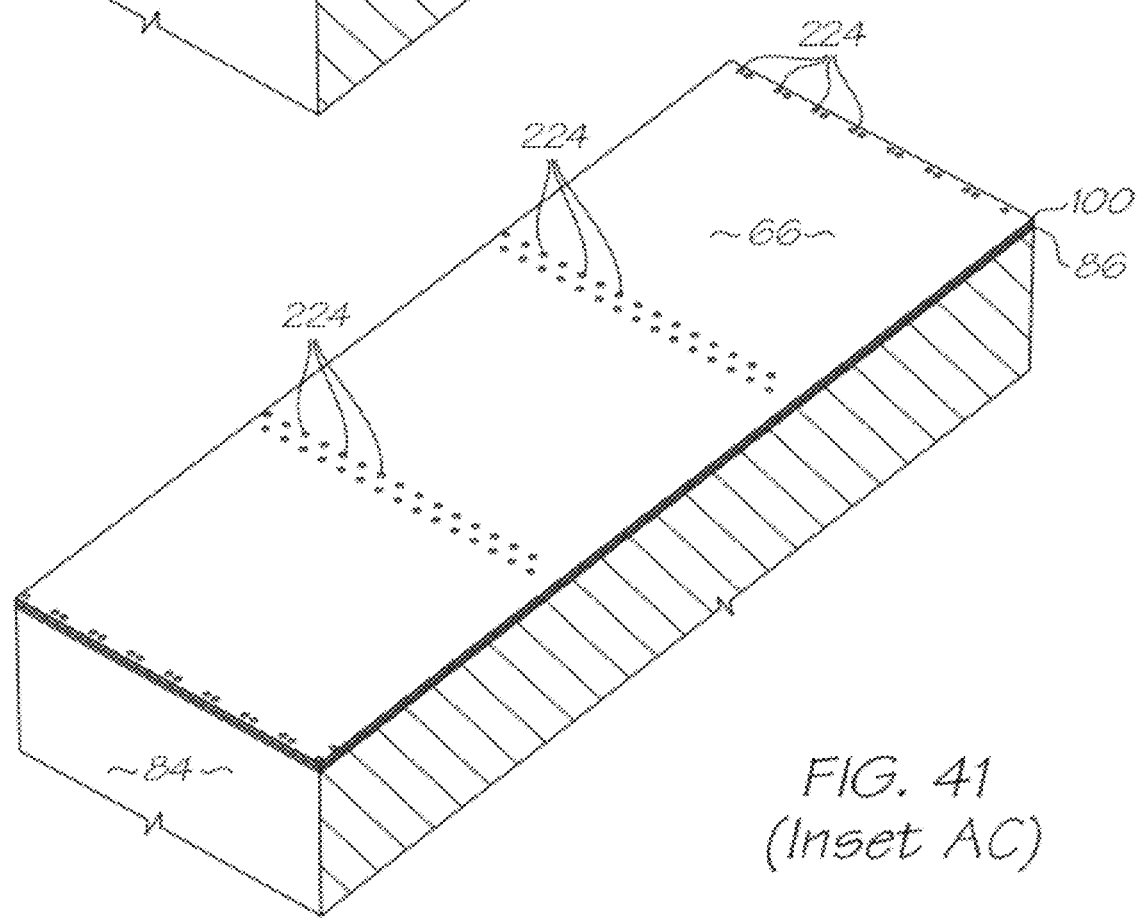
FIG. 41 is a further enlarged view within Inset AC showing the amplification section.
Figure 42:
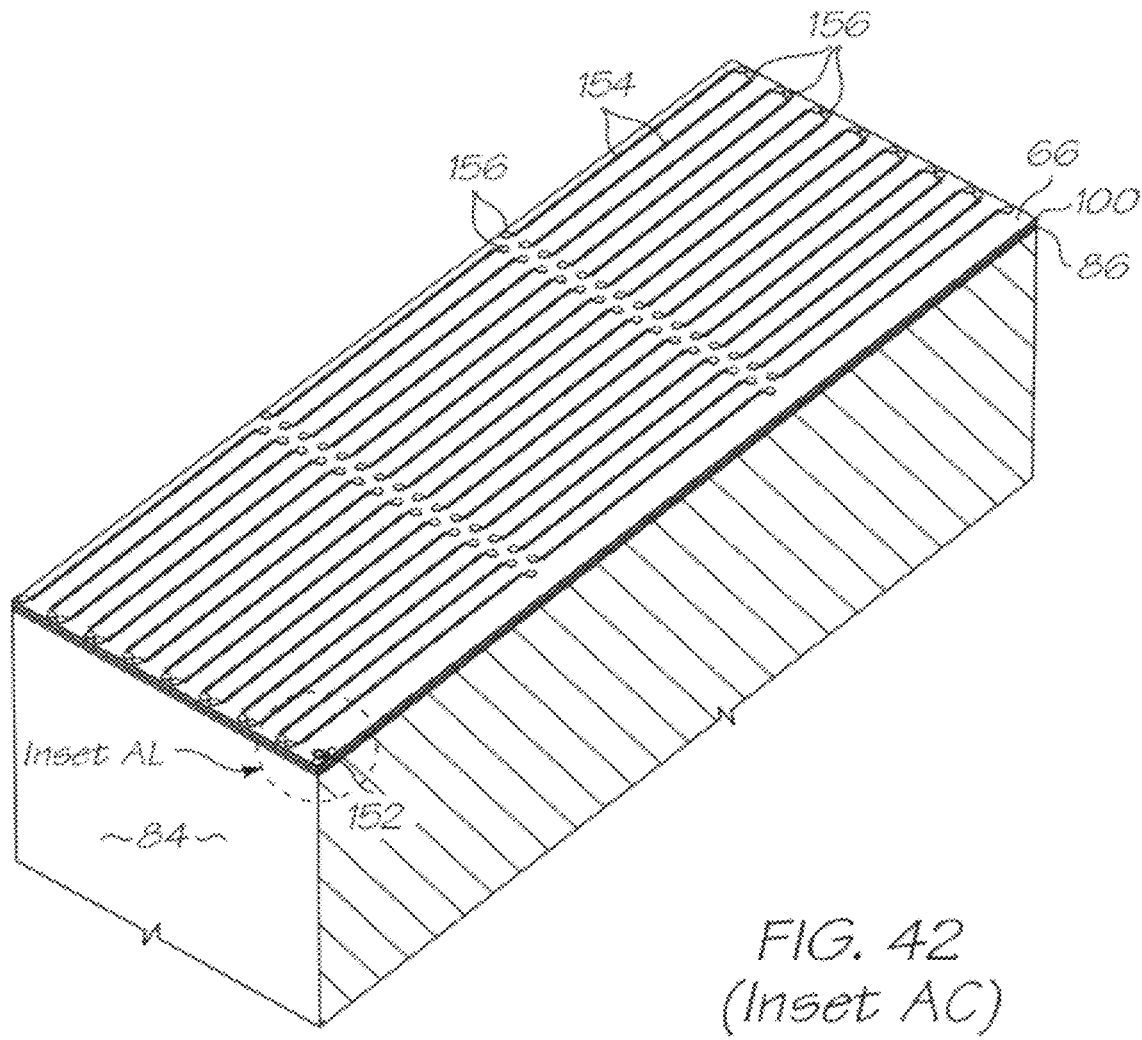
FIG. 42 is a further enlarged view within Inset AC showing the amplification chamber.
Figure 43:
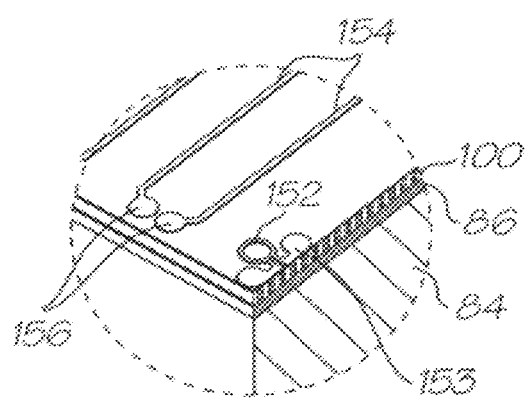
FIG. 43 is a further enlarged view within Inset AL shown in FIG. 42.
Figure 44:
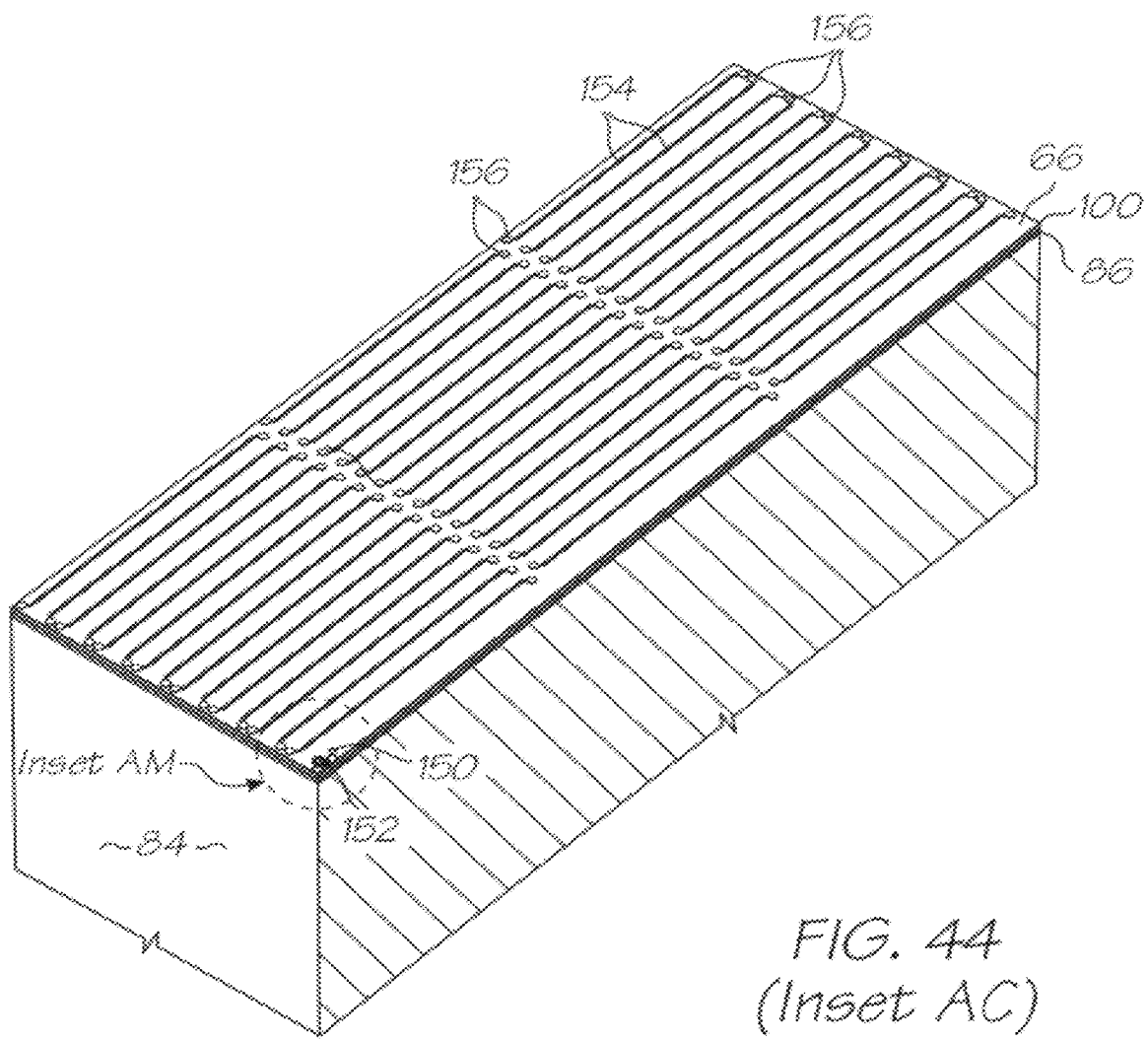
FIG. 44 is a further enlarged view within Inset AC showing the amplification section.
Figure 45:
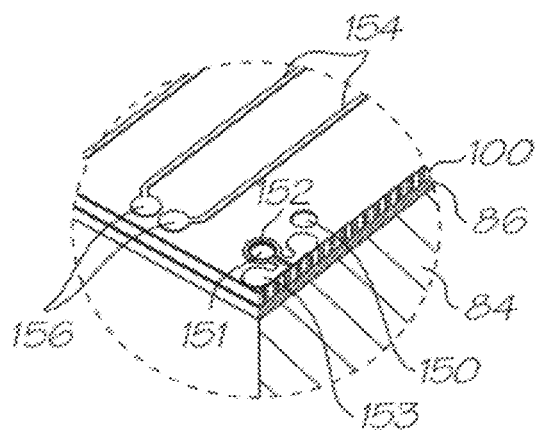
FIG. 45 is a further enlarged view within Inset AM shown in FIG. 44.
Figure 46:
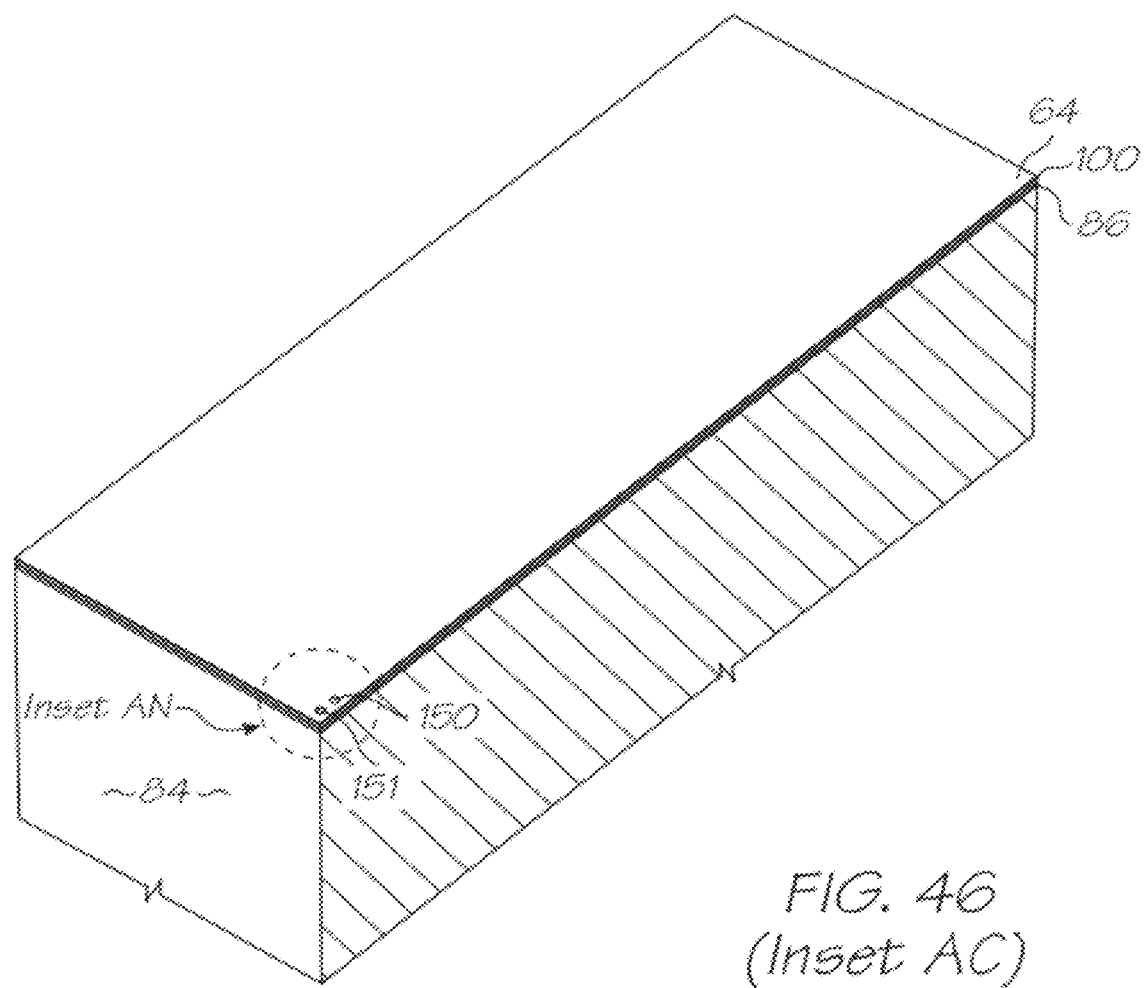
FIG. 46 is a further enlarged view within Inset AC showing the amplification chamber.
Figure 47:
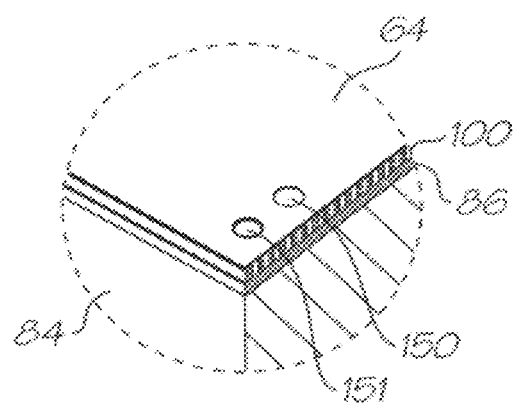
FIG. 47 is a further enlarged view within Inset AN shown in FIG. 46.
Figure 48:
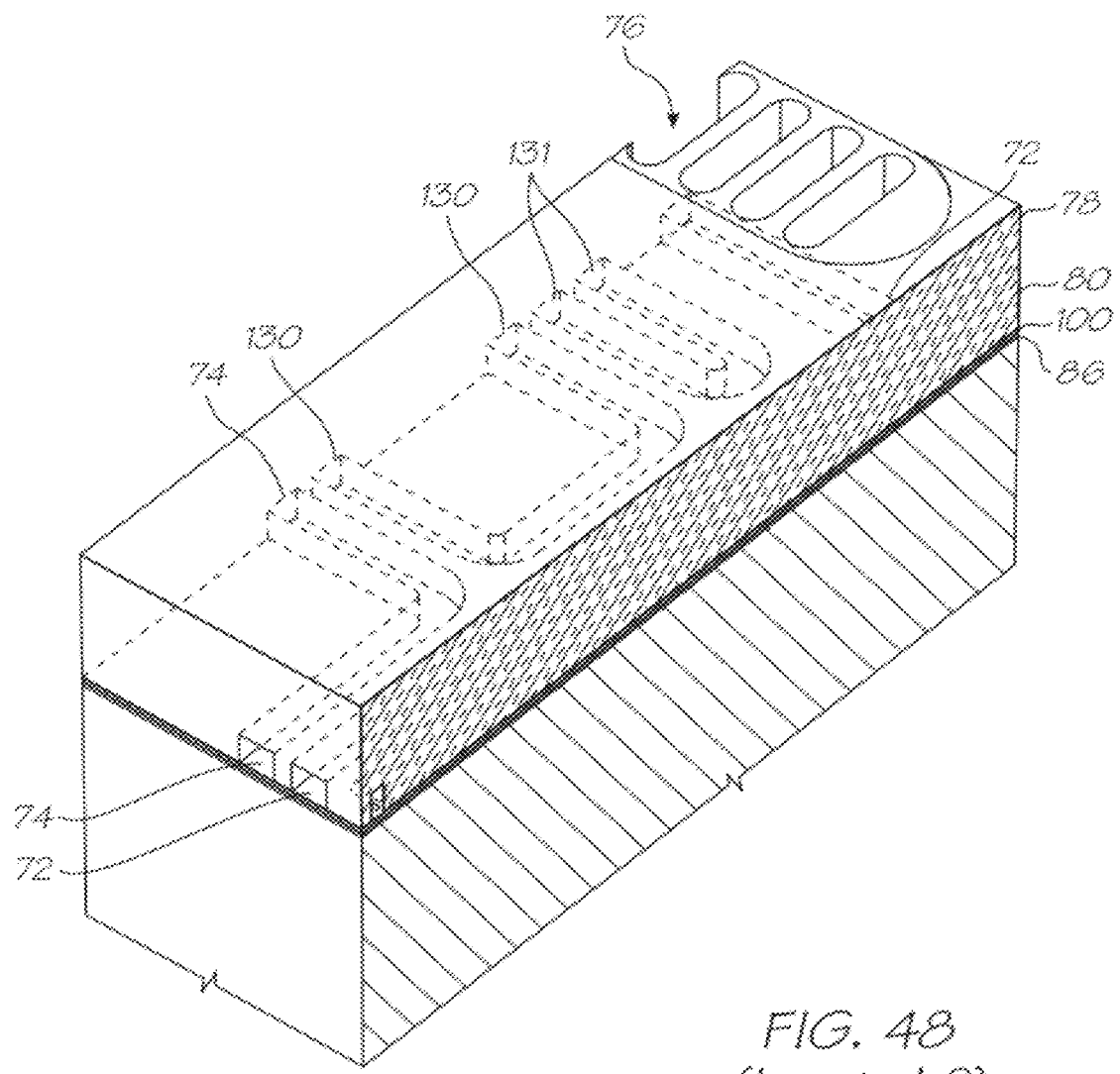
FIG. 48 is a further enlarged view within Inset AC showing the amplification chamber.
Figure 49:
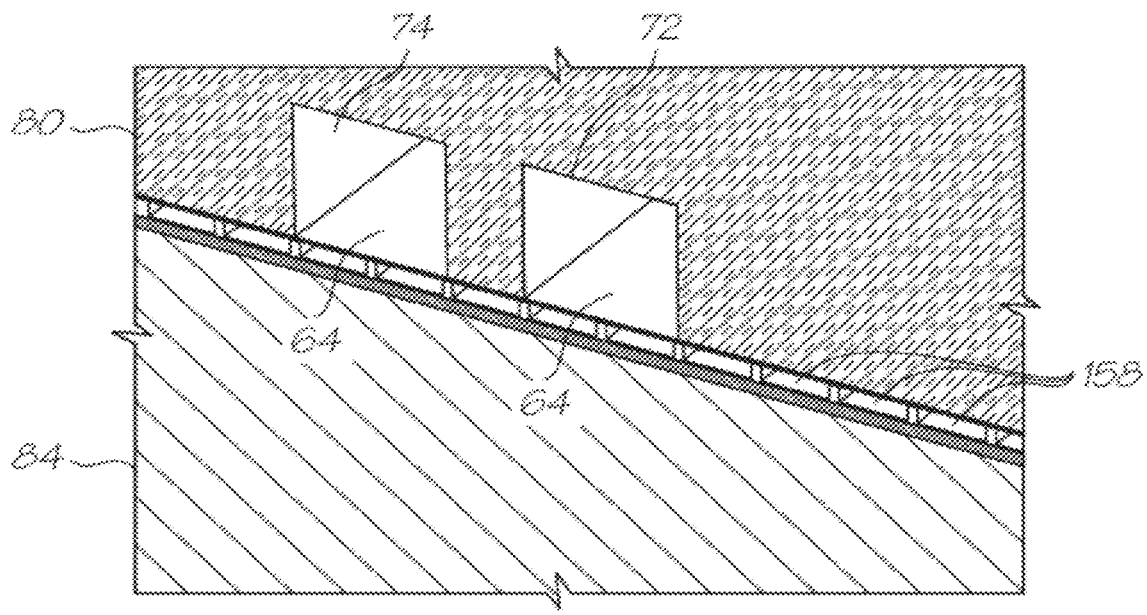
FIG. 49 is a further enlarged view within Inset AC showing the amplification chamber.
Figure 50:
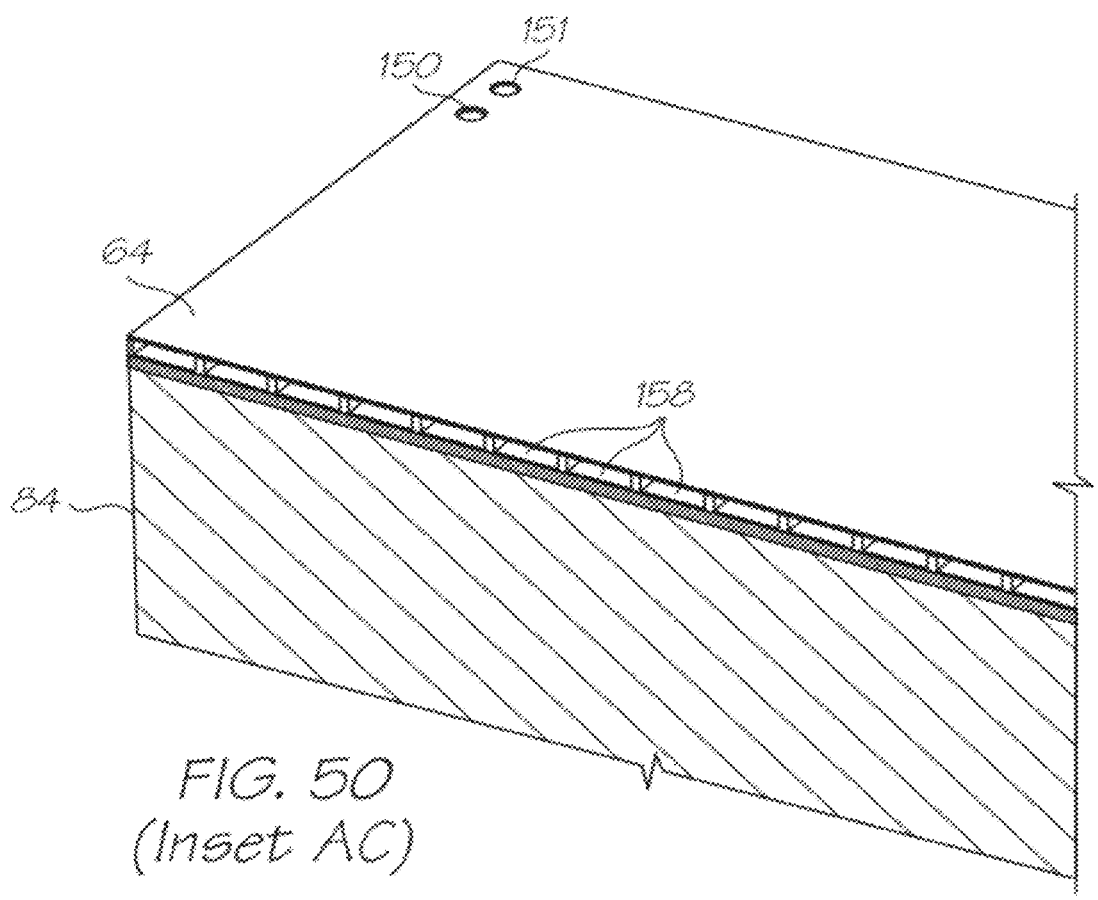
FIG. 50 is a further enlarged view within Inset AC showing the amplification section.

The LOC device 301 also has a number of MST channel liquid sensors 174 and cap channel liquid sensors 208. FIG. 35 shows a line of MST channel liquid sensors 174 at one end of every other meander in the heated microchannel 158. As best shown in FIG. 37, the MST channel liquid sensors 174 are a pair of electrodes formed by exposed areas of the top metal layer 195 in the CMOS structure 86. Liquid closes the circuit between the electrodes to indicate its presence at the sensor's location.

Figure 25:
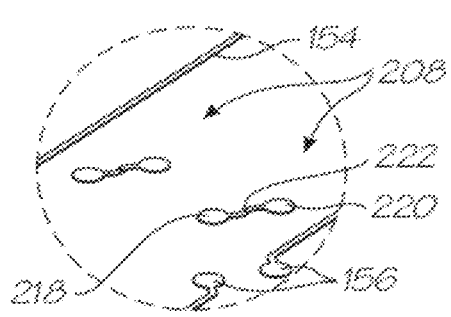
FIG. 25 is a partial perspective illustrating the laminar structure of the LOC device within Inset AI.
Figure 26:
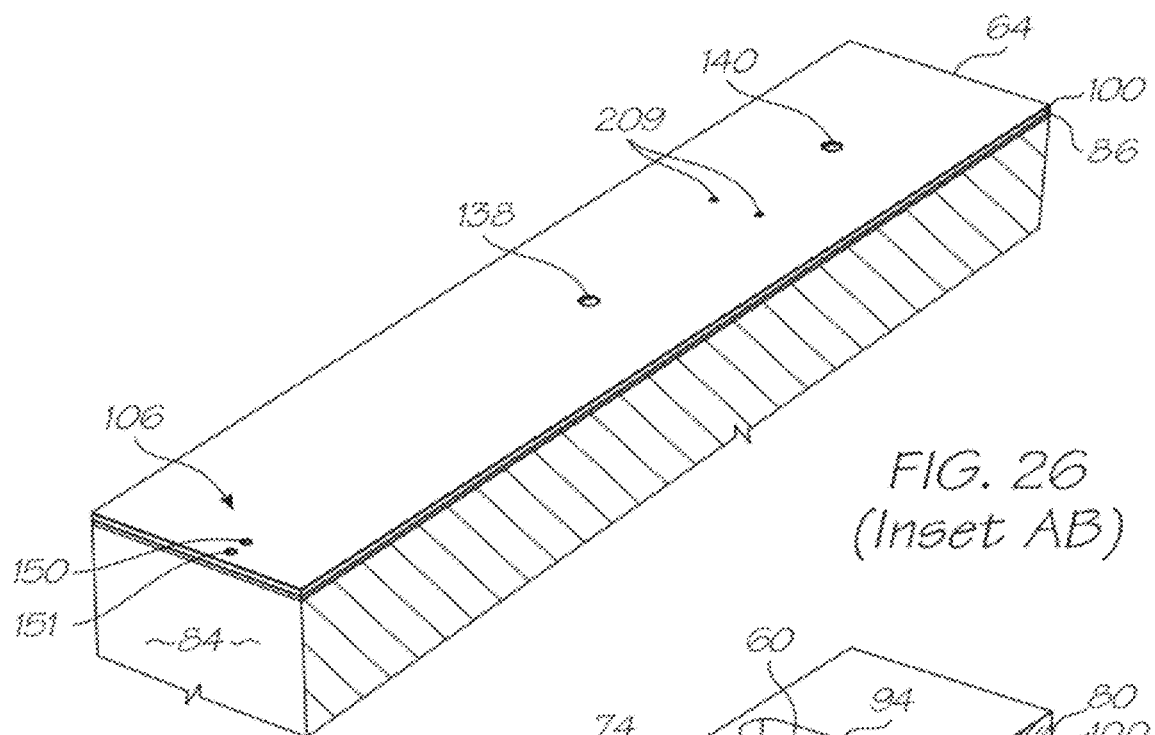
FIG. 26 is a partial perspective illustrating the laminar structure of the LOC device within Inset AB.
Figure 27:
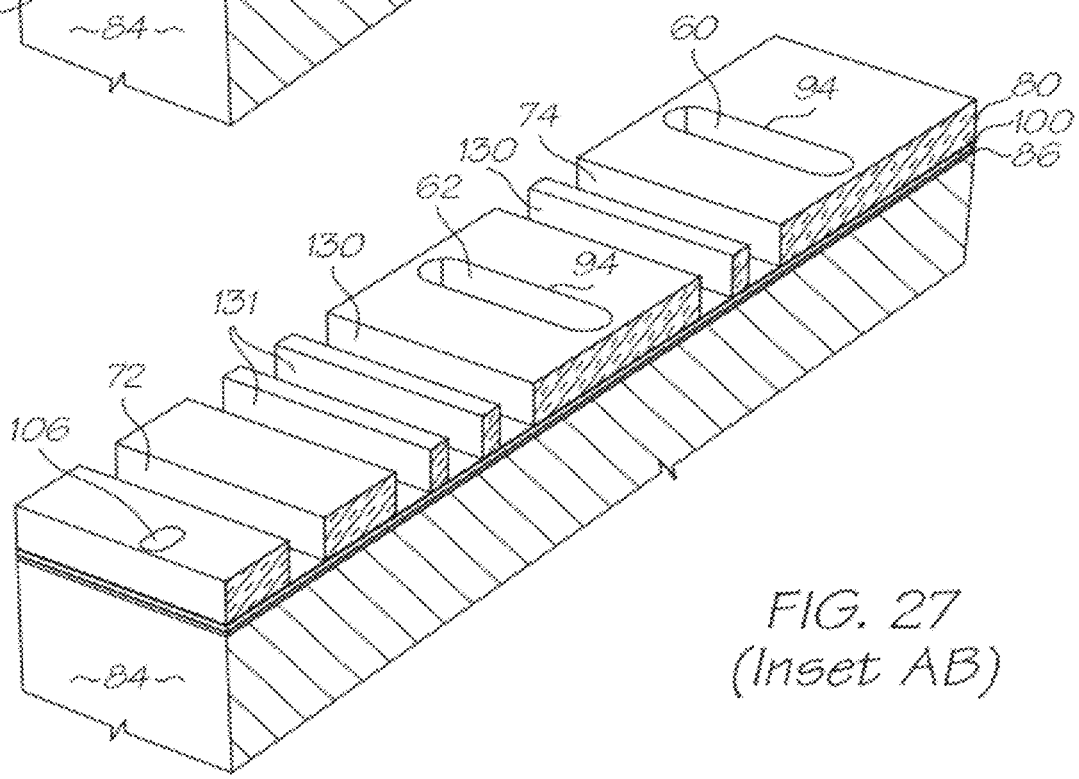
FIG. 27 is a partial perspective illustrating the laminar structure of the LOC device within Inset AB.
Figure 28:
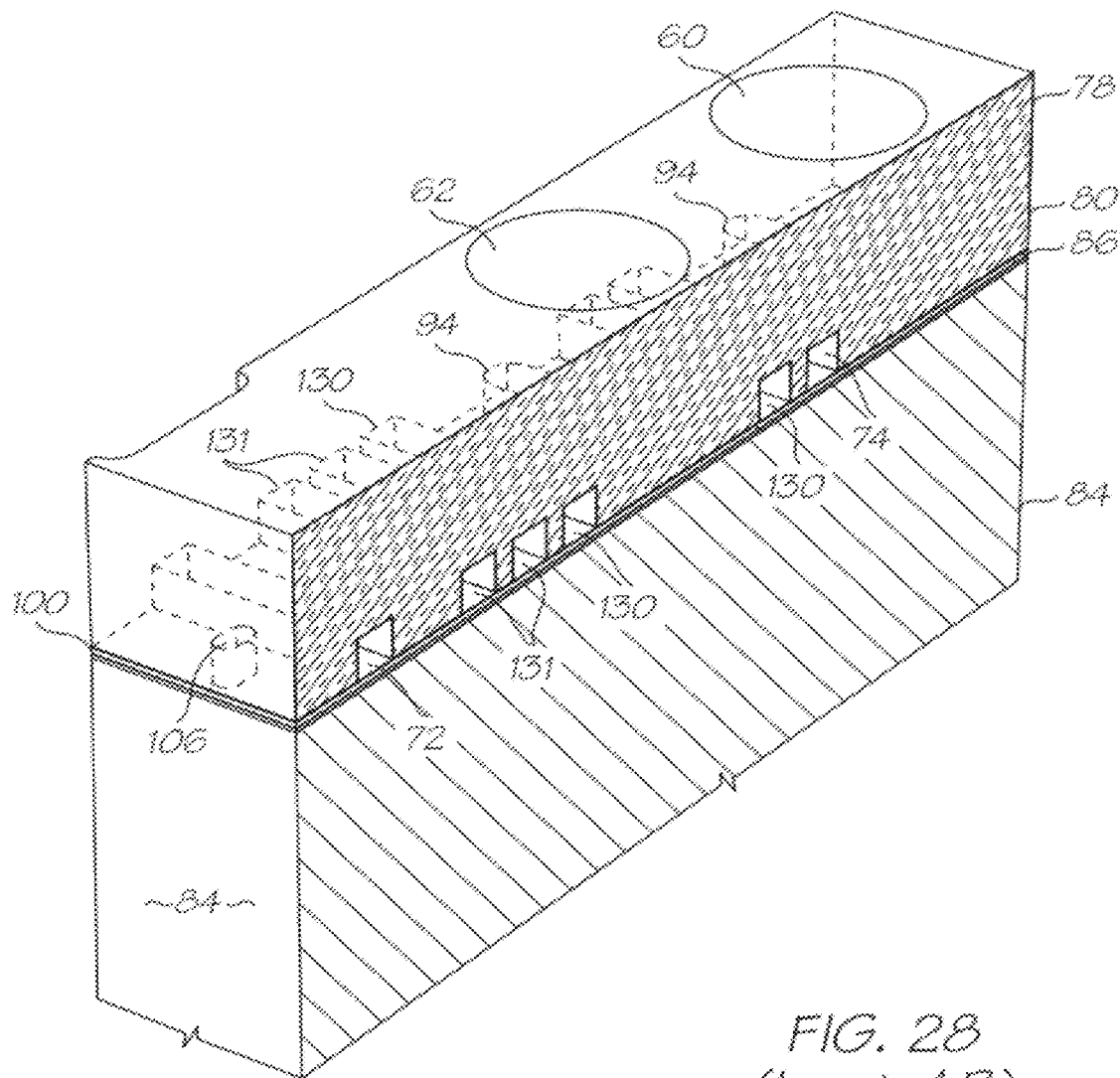
FIG. 28 is a partial perspective illustrating the laminar structure of the LOC device within Inset AB.
Figure 29:
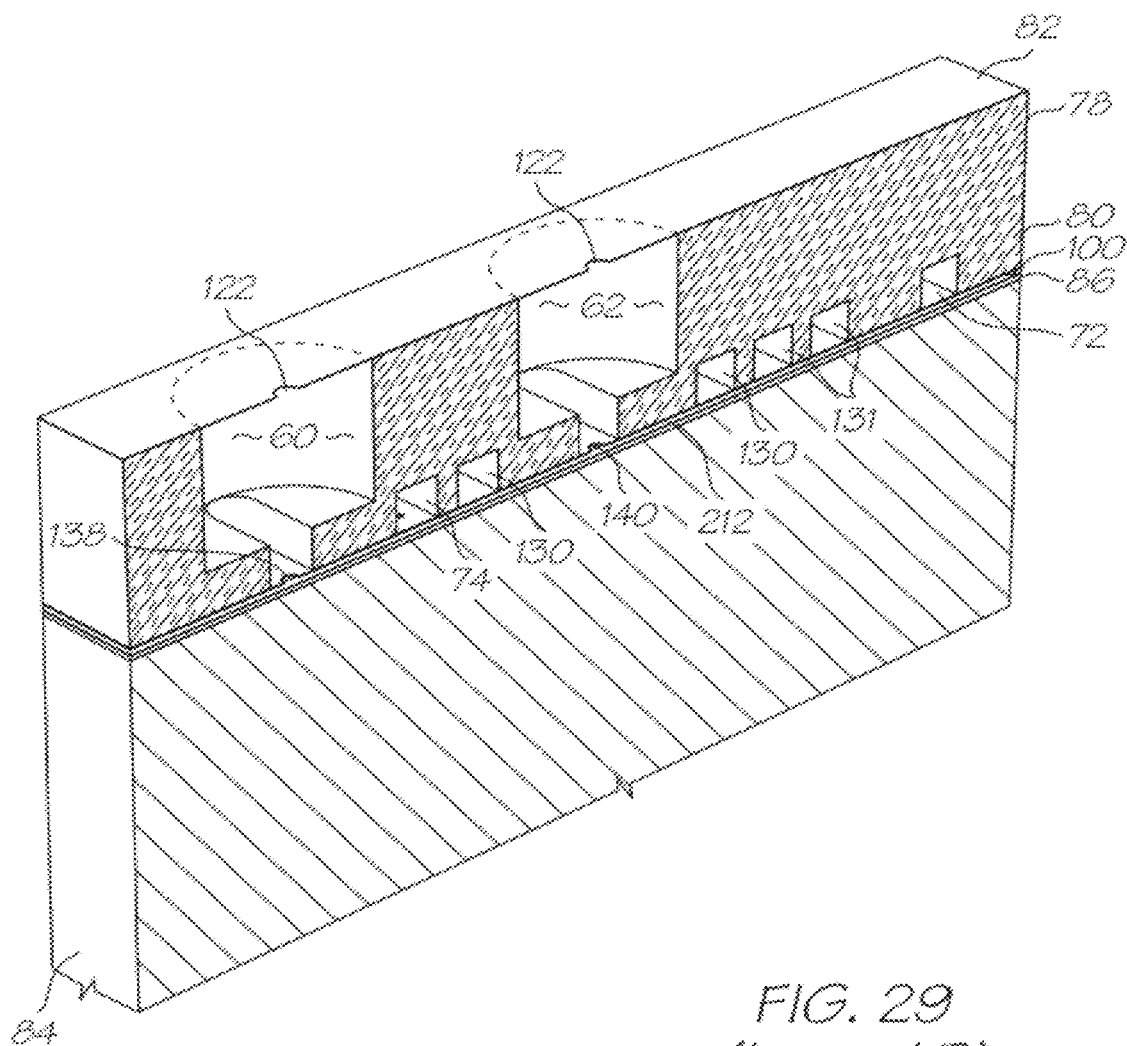
FIG. 29 is a partial perspective illustrating the laminar structure of the LOC device within Inset AB.
Figure 30:
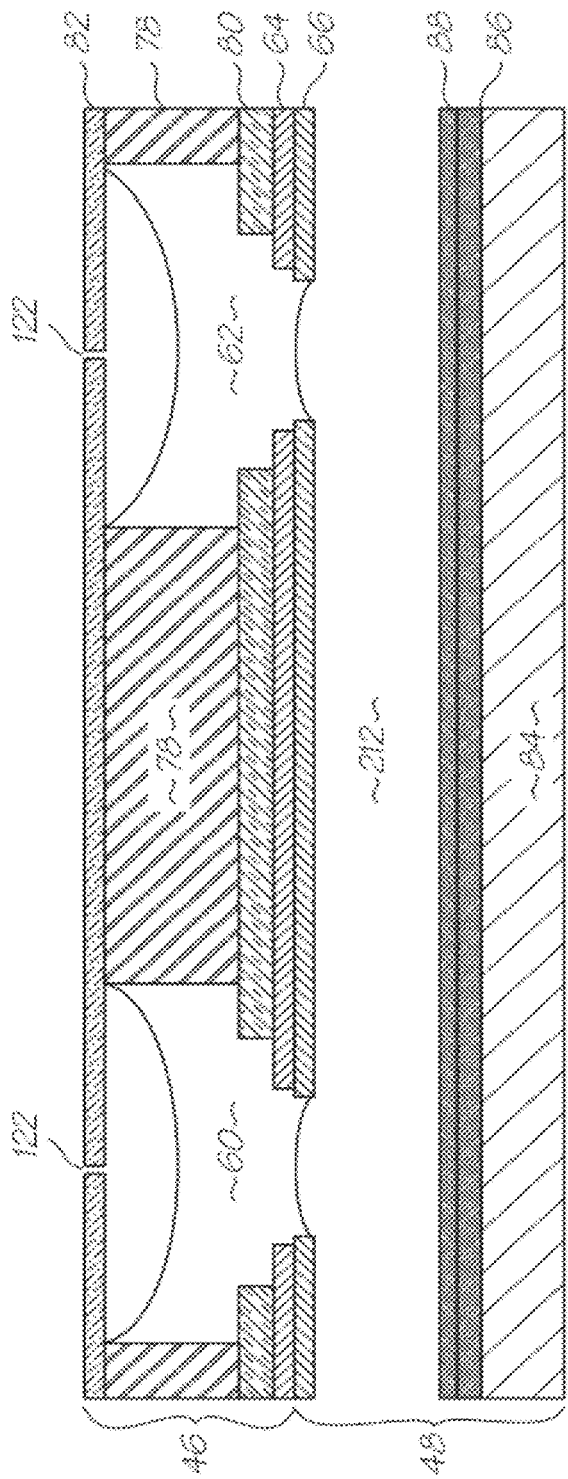
FIG. 30 is a schematic section view of the amplification mix reservoir and the polymerase reservoir.

FIG. 25 shows an enlarged perspective of cap channel liquid sensors 208. Opposing pairs of TiAl electrodes 218 and 220 are deposited on the roof layer 66. Between the electrodes 218 and 220 is a gap 222 to hold the circuit open in the absence of liquid. The presence of liquid closes the circuit and the CMOS circuitry 86 uses this feedback to monitor the flow.

Gravitational Independence

The test modules 10 are orientation independent. They do not need to be secured to a flat stable surface in order to operate. Capillary driven fluid flows and a lack of external plumbing into ancillary equipment allow the modules to be truly portable and simply plugged into a similarly portable hand held reader such as a mobile telephone. Having a gravitationally independent operation means the test modules are also accelerationally independent to all practical extents. They are resistant to shock and vibration and will operate on moving vehicles or while the mobile telephone is being carried around.

Dialysis Variants

Leukocyte Target

Figure 59:
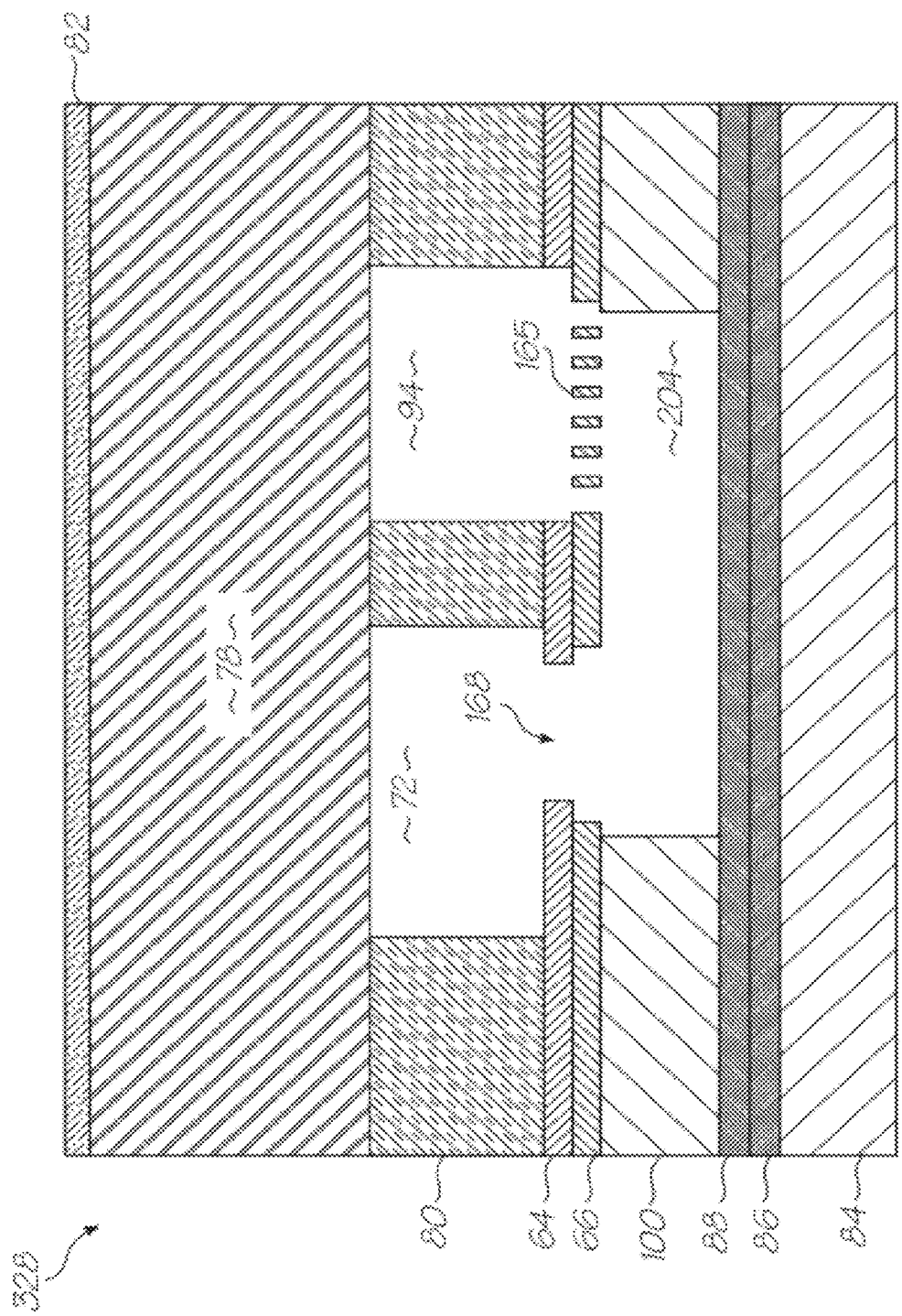
FIG. 59 is a schematic section view of a leukocyte target dialysis section.

The dialysis design described above in the LOC device 301 targets pathogens. FIG. 59 is a schematic section view of a dialysis section 328 designed to concentrate leukocytes from a blood sample for human DNA analysis. It will be appreciated that the structure is essentially the same as that of the pathogen target dialysis section 70 described above with the exception that apertures in the form of 7.5 micron diameter holes 165 restrict leukocytes from passing from the cap channel 94 to the dialysis MST channels 204. In situations where the sample being analysed is a blood sample, and the presence of haemoglobin from the erythrocytes interferes with the subsequent reaction steps, addition of an erythrocyte lysis buffer along with the anticoagulant in the reservoir 54 (see FIG. 22), will ensure that the majority of the lysed erythrocytes (and hence haemoglobin) will be removed from the sample during this dialysis step. A commonly used erythrocyte lysis buffer is 0.15M $NH_4CL$, 10 mM $KHCO_3$, 0.1 mM EDTA, pH 7.2-7.4, but a person skilled in the art will recognise that any buffer which efficiently lyses erythrocytes can be used.

Downstream of the leukocyte dialysis section 328, the cap channel 94 becomes the target channel 74 such that the leukocytes continue as part of the assay. Furthermore, in this case, the dialysis uptake holes 168 lead to a waste channel 72 so that all smaller cells and components in the sample are removed. It should be noted that this dialysis variant only reduces the concentration of the unwanted specimens in the target channel 74.

Figure 72:
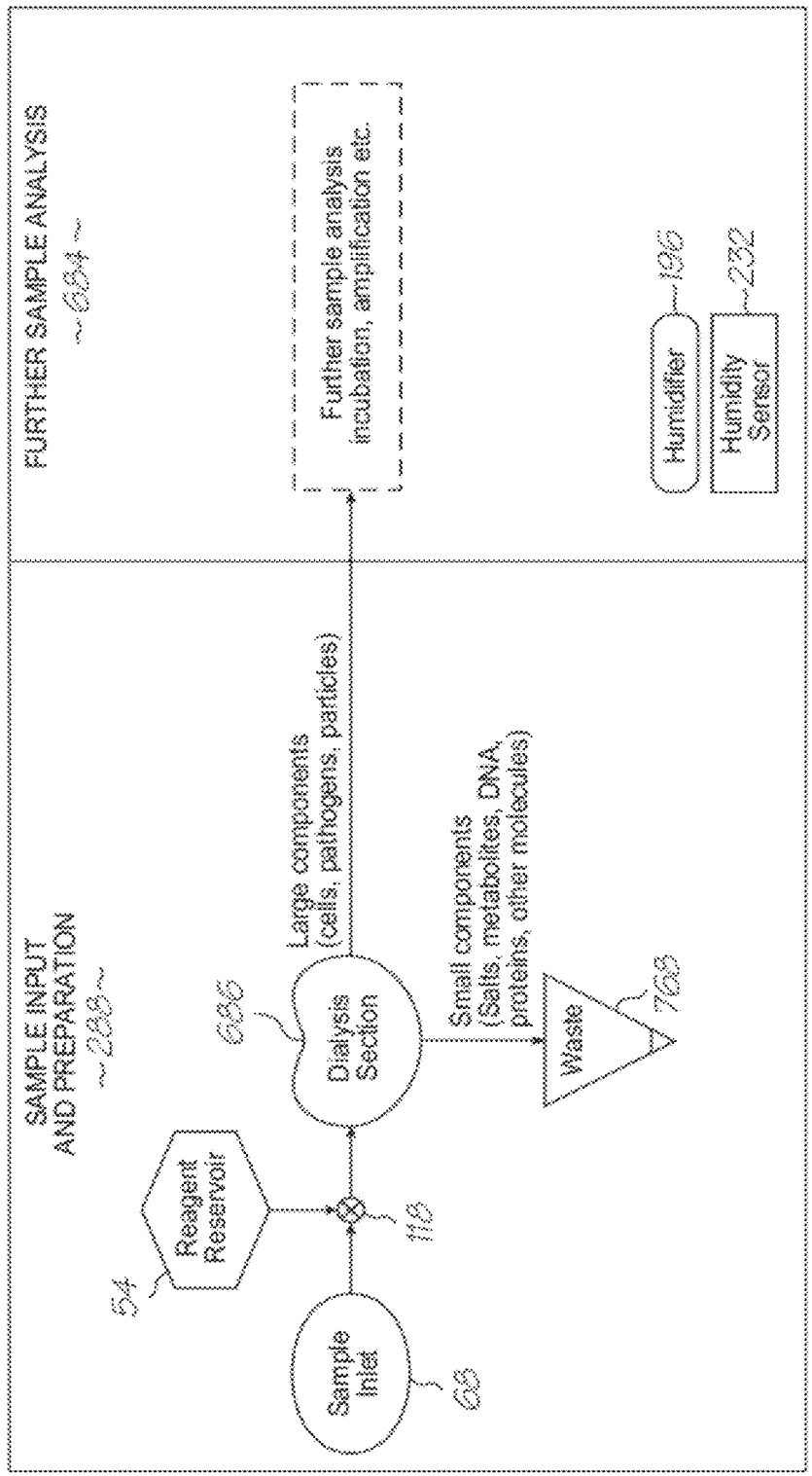
FIG. 72 is a schematic illustration of the architecture of LOC variant XLII.

FIG. 72 schematically illustrates a large constituents dialysis section 686 which also separates any large target constituents from a sample. The apertures in this dialysis section are fabricated with a size and shape tailored to withhold the large target constituents of interest in the target channel for further analysis. As with the leukocyte dialysis section described above, most (but not all) smaller sized cells, organisms or molecules flow to a waste reservoir 768. Thus, other embodiments of the LOC device are not limited to separating leukocytes that are larger than 7.5 μm in size, but can be used to separate cells, organisms or molecules of any size desired.

Dialysis Section with Flow Channel to Prevent Trapped Air Bubbles

Described below is an embodiment of the LOC device referred to as LOC variant VIII 518 and shown in FIGS. 65, 66, 67 and 68. This LOC device has a dialysis section that fills with the fluid sample without leaving air bubbles trapped in the channels. LOC variant VIII 518 also has an additional layer of material referred to as an interface layer 594. The interface layer 594 is positioned between the cap channel layer 80 and the MST channel layer 100 of the CMOS+MST device 48. The interface layer 594 allows a more complex fluidic interconnection between the reagent reservoirs and the MST layer 87 without increasing the size of the silicon substrate 84.

Figure 66:
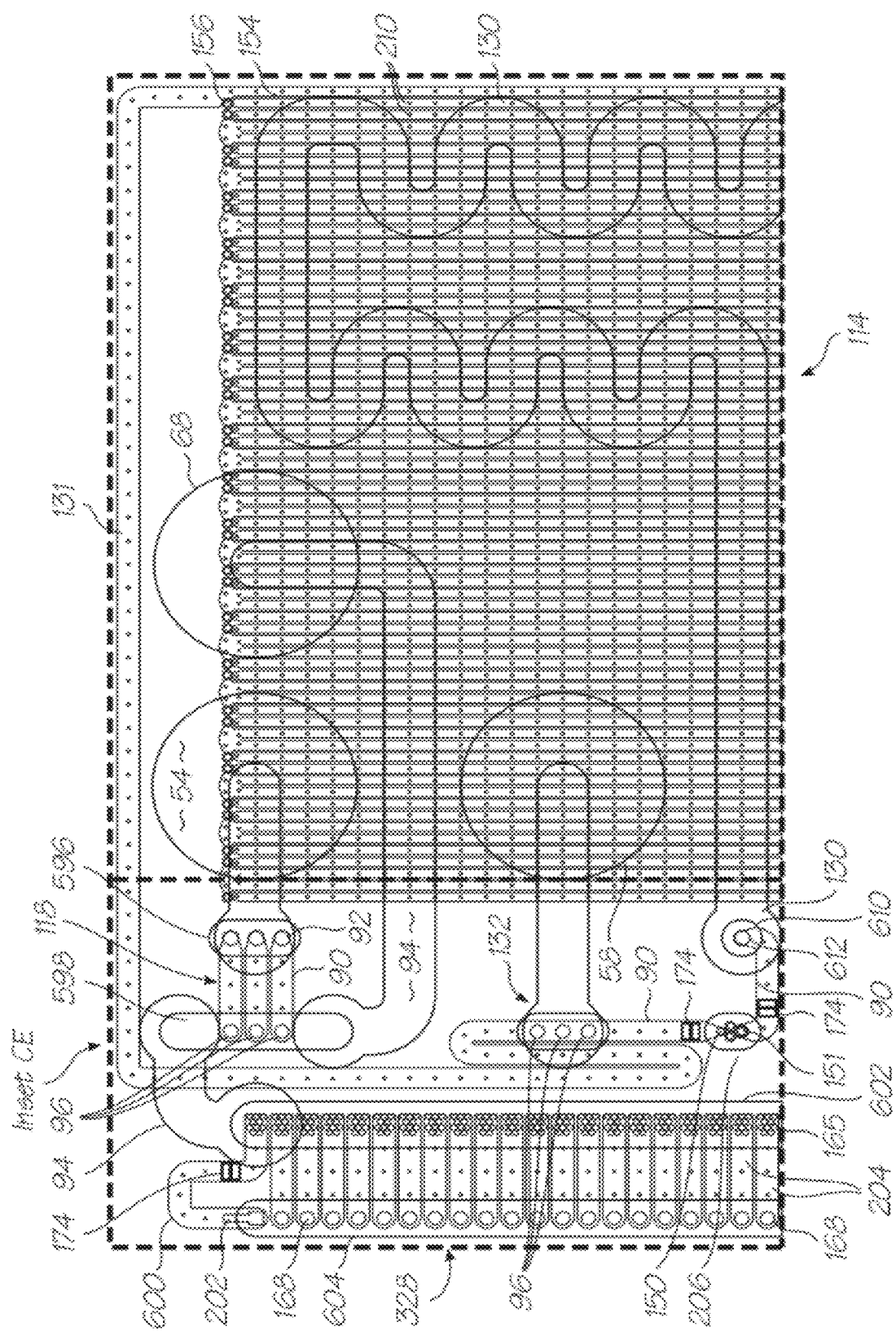
FIG. 66 is an enlarged view of Inset CA shown in FIG. 65.
Figure 67:
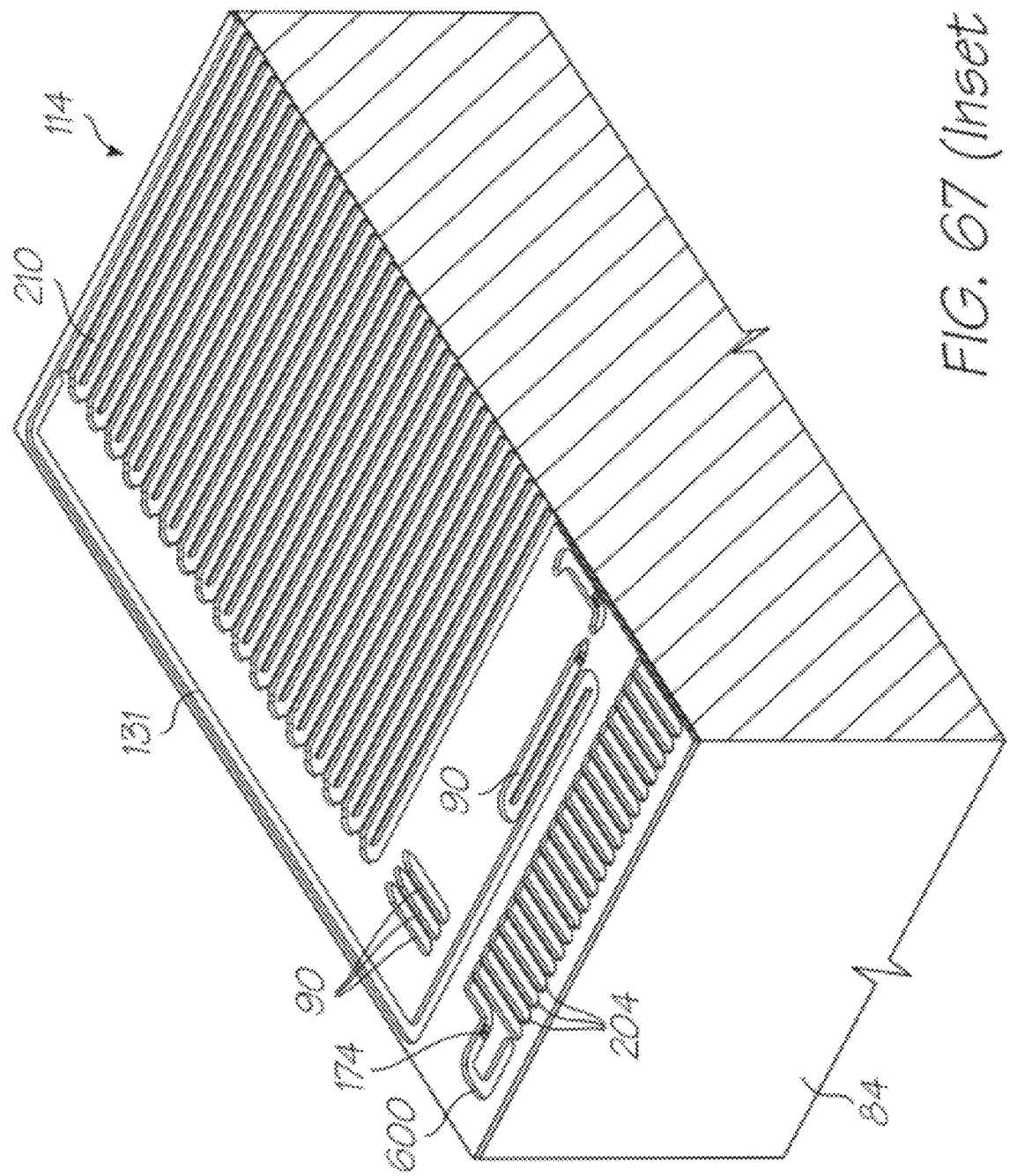
FIG. 67 is a partial perspective illustrating the laminar structure of LOC variant VIII within Inset CA shown in FIG. 65.
Figure 68:
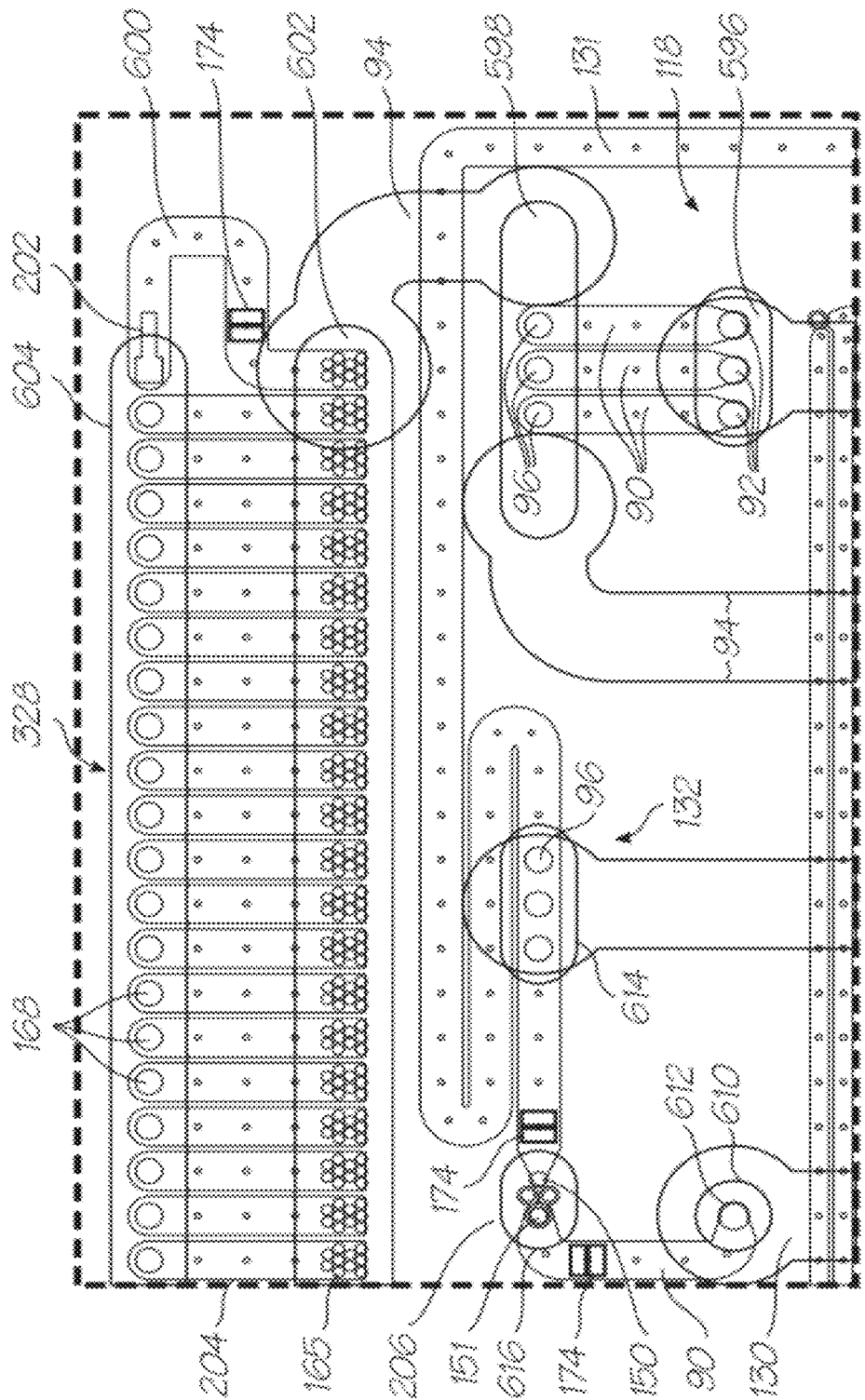
FIG. 68 is an enlarged view of Inset CE shown in FIG. 66.

Referring to FIG. 66, the bypass channel 600 is designed to introduce a time delay in the fluid sample flow from the interface waste channel 604 to the interface target channel 602. This time delay allows the fluid sample to flow through the dialysis MST channel 204 to the dialysis uptake 168 where it pins a meniscus. With a capillary initiation feature (CIF) 202 at the uptake from the bypass channel 600 to the interface target channel 602, the sample fluid fills the interface target channel 602 from a point upstream of all the dialysis uptakes 168 from the dialysis MST channels 204.

Without the bypass channel 600, the interface target channel 602 still starts filling from the upstream end, but eventually the advancing meniscus reaches and passes over an uptake belonging to an MST channel that has not yet filled, leading into air entrapment at that point. Trapped air reduces the sample flow rate through the leukocyte dialysis section 328.

Nucleic Acid Amplification Variants
Direct PCR

Traditionally, PCR requires extensive purification of the target DNA prior to preparation of the reaction mixture. However, with appropriate changes to the chemistry and sample concentration, it is possible to perform nucleic acid amplification with minimal DNA purification, or direct amplification. When the nucleic acid amplification process is PCR, this approach is called direct PCR. In LOC devices where nucleic acid amplification is performed at a controlled, constant temperature, the approach is direct isothermal amplification. Direct nucleic acid amplification techniques have considerable advantages for use in LOC devices, particularly relating to simplification of the required fluidic design. Adjustments to the amplification chemistry for direct PCR or direct isothermal amplification include increased buffer strength, the use of polymerases which have high activity and processivity, and additives which chelate with potential polymerase inhibitors. Dilution of inhibitors present in the sample is also important.

To take advantage of direct nucleic acid amplification techniques, the LOC device designs incorporate two additional features. The first feature is reagent reservoirs (for example reservoir 58 in FIG. 8) which are appropriately dimensioned to supply a sufficient quantity of amplification reaction mix, or diluent, so that the final concentrations of sample components which might interfere with amplification chemistry are low enough to permit successful nucleic acid amplification. The desired dilution of non-cellular sample components is in the range of 5× to 20×. Different LOC structures, for example the pathogen dialysis section 70 in FIG. 4, are used when appropriate to ensure that the concentration of target nucleic acid sequences is maintained at a high enough level for amplification and detection. In this embodiment, further illustrated in FIG. 6, a dialysis section which effectively concentrates pathogens small enough to be passed into the amplification section 292 is employed upstream of the sample extraction section 290, and rejects larger cells to a waste receptacle 76. In another embodiment, a dialysis section is used to selectively deplete proteins and salts in blood plasma while retaining cells of interest.

The second LOC structural feature which supports direct nucleic acid amplification is design of channel aspect ratios to adjust the mixing ratio between the sample and the amplification mix components. For example, to ensure dilution of inhibitors associated with the sample in the preferred 5×-20× range through a single mixing step, the length and cross-section of the sample and reagent channels are designed such that the sample channel, upstream of the location where mixing is initiated, constitutes a flow impedance 4×-19× higher than the flow impedance of the channels through which the reagent mixture flows. Control over flow impedances in microchannels is readily achieved through control over the design geometry. The flow impedance of a microchannel increases linearly with the channel length, for a constant cross-section. Importantly for mixing designs, flow impedance in microchannels depends more strongly on the smallest cross-sectional dimension. For example, the flow impedance of a microchannel with rectangular cross-section is inversely proportional to the cube of the smallest perpendicular dimension, when the aspect ratio is far from unity.

Reverse-Transcriptase PCR (RT-PCR)

Where the sample nucleic acid species being analysed or extracted is RNA, such as from RNA viruses or messenger RNA, it is first necessary to reverse transcribe the RNA into complementary DNA (cDNA) prior to PCR amplification. The reverse transcription reaction can be performed in the same chamber as the PCR (one-step RT-PCR) or it can be performed as a separate, initial reaction (two-step RT-PCR). In the LOC variants described herein, a one-step RT-PCR can be performed simply by adding the reverse transcriptase to reagent reservoir 62 along with the polymerase and programming the heaters 154 to cycle firstly for the reverse transcription step and then progress onto the nucleic acid amplification step. A two-step RT-PCR could also be easily achieved by utilizing the reagent reservoir 58 to store and dispense the buffers, primers, dNTPs and reverse transcriptase and the incubation section 114 for the reverse transcription step followed by amplification in the normal way in the amplification section 112.

Isothermal Nucleic Acid Amplification

For some applications, isothermal nucleic acid amplification is the preferred method of nucleic acid amplification, thus avoiding the need to repetitively cycle the reaction components through various temperature cycles but instead maintaining the amplification section at a constant temperature, typically around 37° C. to 41° C. A number of isothermal nucleic acid amplification methods have been described, including Strand Displacement Amplification (SDA), Transcription Mediated Amplification (TMA), Nucleic Acid Sequence Based Amplification (NASBA), Recombinase Polymerase Amplification (RPA), Helicase-Dependent isothermal DNA Amplification (HDA), Rolling Circle Amplification (RCA), Ramification Amplification (RAM) and Loop-mediated Isothermal Amplification (LAMP), and any of these, or other isothermal amplification methods, can be employed in particular embodiments of the LOC device described herein.

In order to perform isothermal nucleic acid amplification, the reagent reservoirs 60 and 62 adjoining the amplification section will be loaded with the appropriate reagents for the specified isothermal method instead of PCR amplification mix and polymerase. For example, for SDA, reagent reservoir

60 contains amplification buffer, primers and dNTPs and reagent reservoir 62 contains an appropriate nickase enzyme and Exo-DNA polymerase. For RPA, reagent reservoir 60 contains the amplification buffer, primers, dNTPs and recombinase proteins, with reagent reservoir 62 containing a strand displacing DNA polymerase such as Bsu. Similarly, for HDA, reagent reservoir 60 contains amplification buffer, primers and dNTPs and reagent reservoir 62 contains an appropriate DNA polymerase and a helicase enzyme to unwind the double stranded DNA strand instead of using heat. The skilled person will appreciate that the necessary reagents can be split between the two reagent reservoirs in any manner appropriate for the nucleic acid amplification process.

For amplification of viral nucleic acids from RNA viruses such as HIV or hepatitis C virus, NASBA or TMA is appropriate as it is unnecessary to first transcribe the RNA to cDNA. In this example, reagent reservoir 60 is filled with amplification buffer, primers and dNTPs and reagent reservoir 62 is filled with RNA polymerase, reverse transcriptase and, optionally, RNase H.

For some forms of isothermal nucleic acid amplification it may be necessary to have an initial denaturation cycle to separate the double stranded DNA template, prior to maintaining the temperature for the isothermal nucleic acid amplification to proceed. This is readily achievable in all embodiments of the LOC device described herein, as the temperature of the mix in the amplification section 112 can be carefully controlled by the heaters 154 in the amplification microchannels 158 (see FIG. 14).

Figure 73:
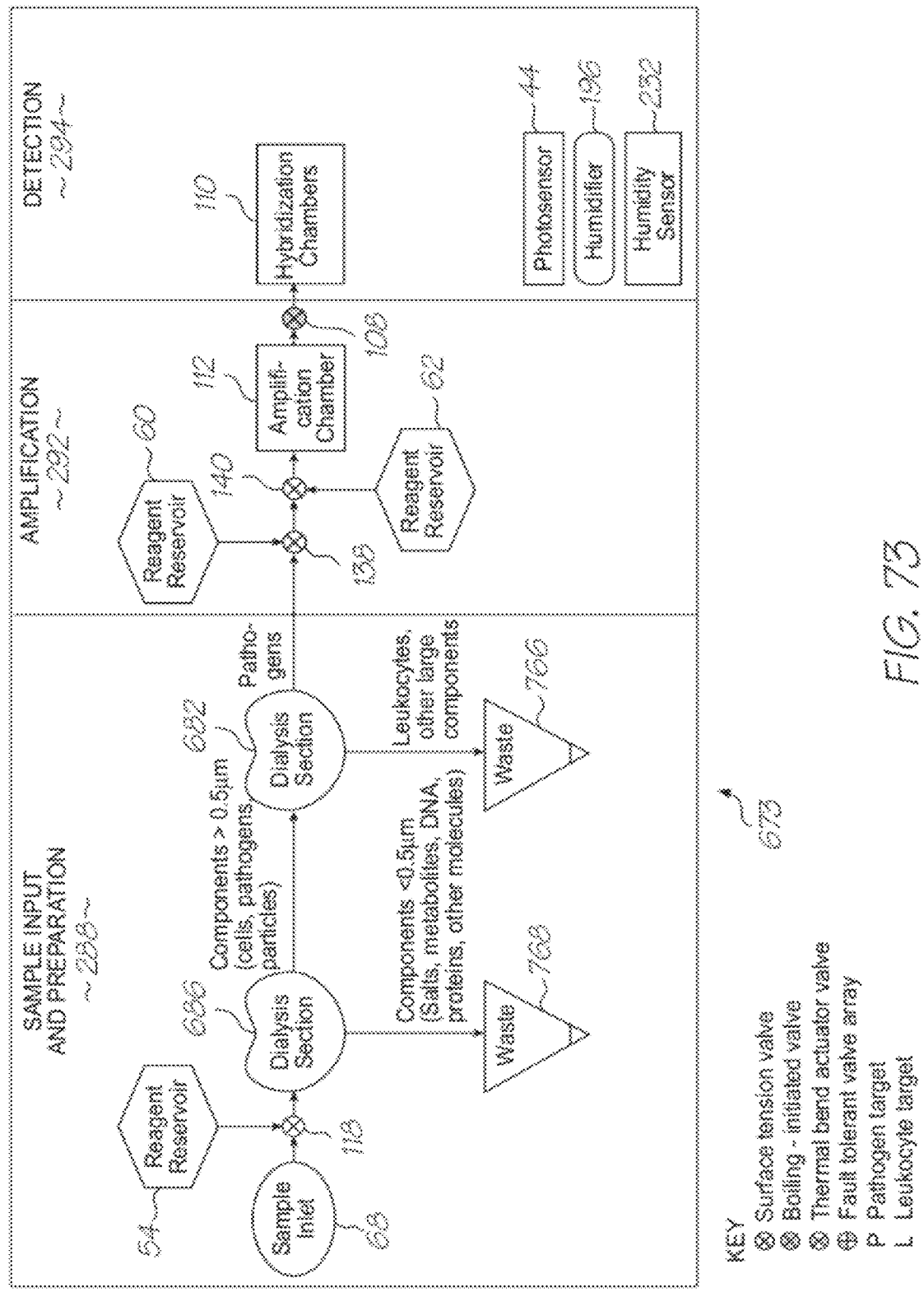
FIG. 73 is a schematic illustration of the architecture of LOC variant XLIII.
Figure 74:
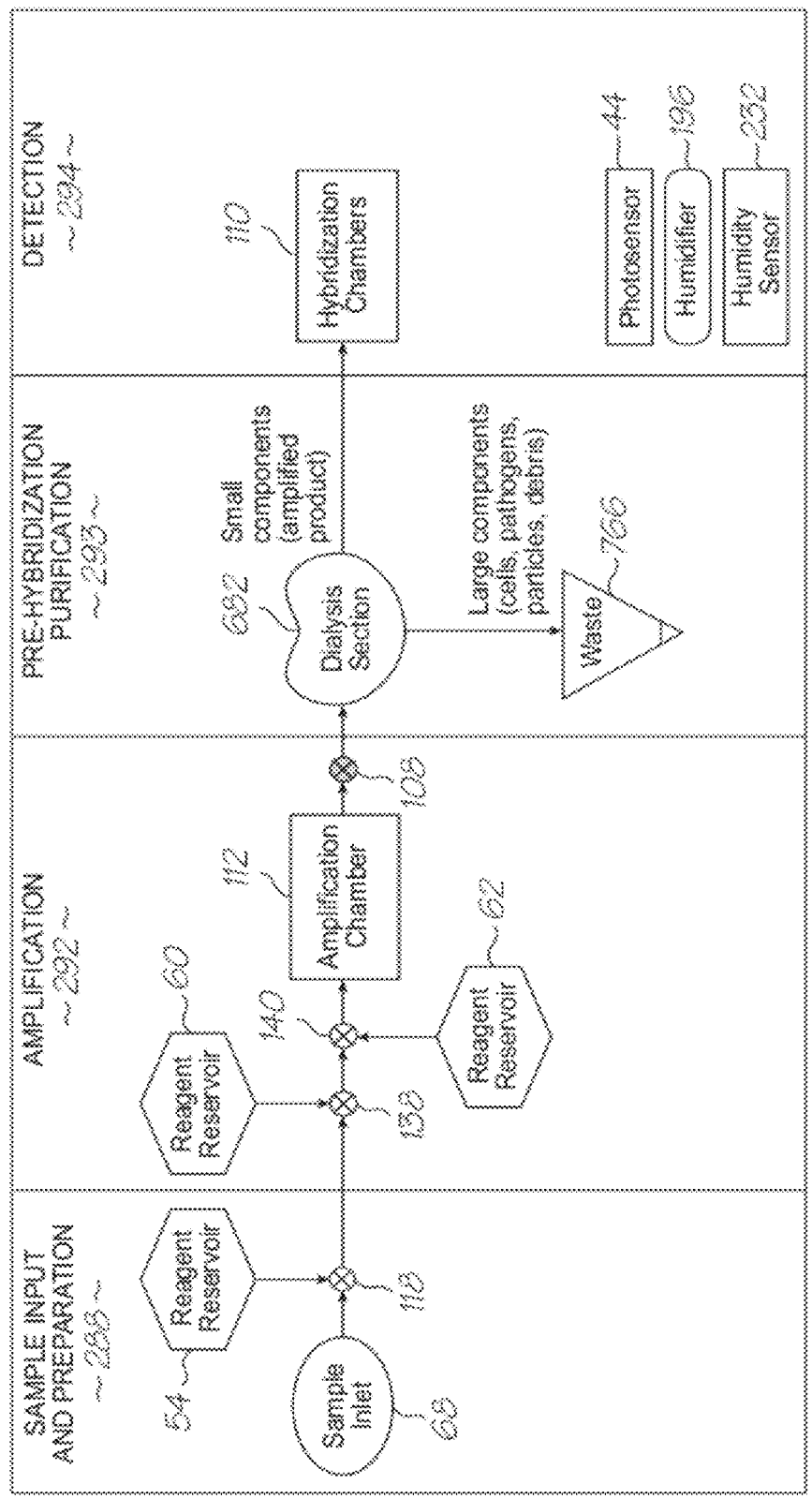
FIG. 74 is a schematic illustration of the architecture of LOC variant XLIV.
Figure 75:
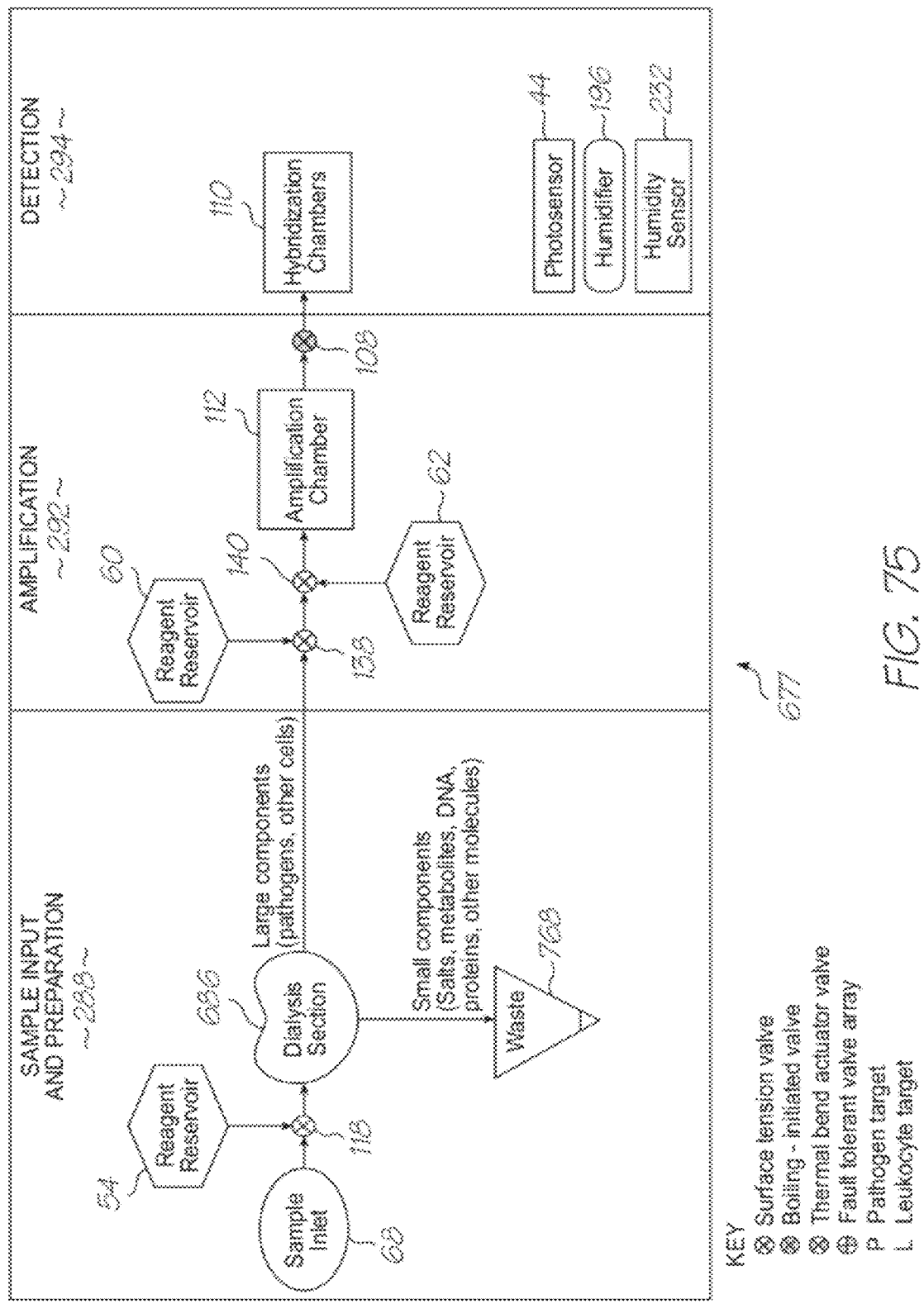
FIG. 75 is a schematic illustration of the architecture of LOC variant XLVII.
Figure 76:
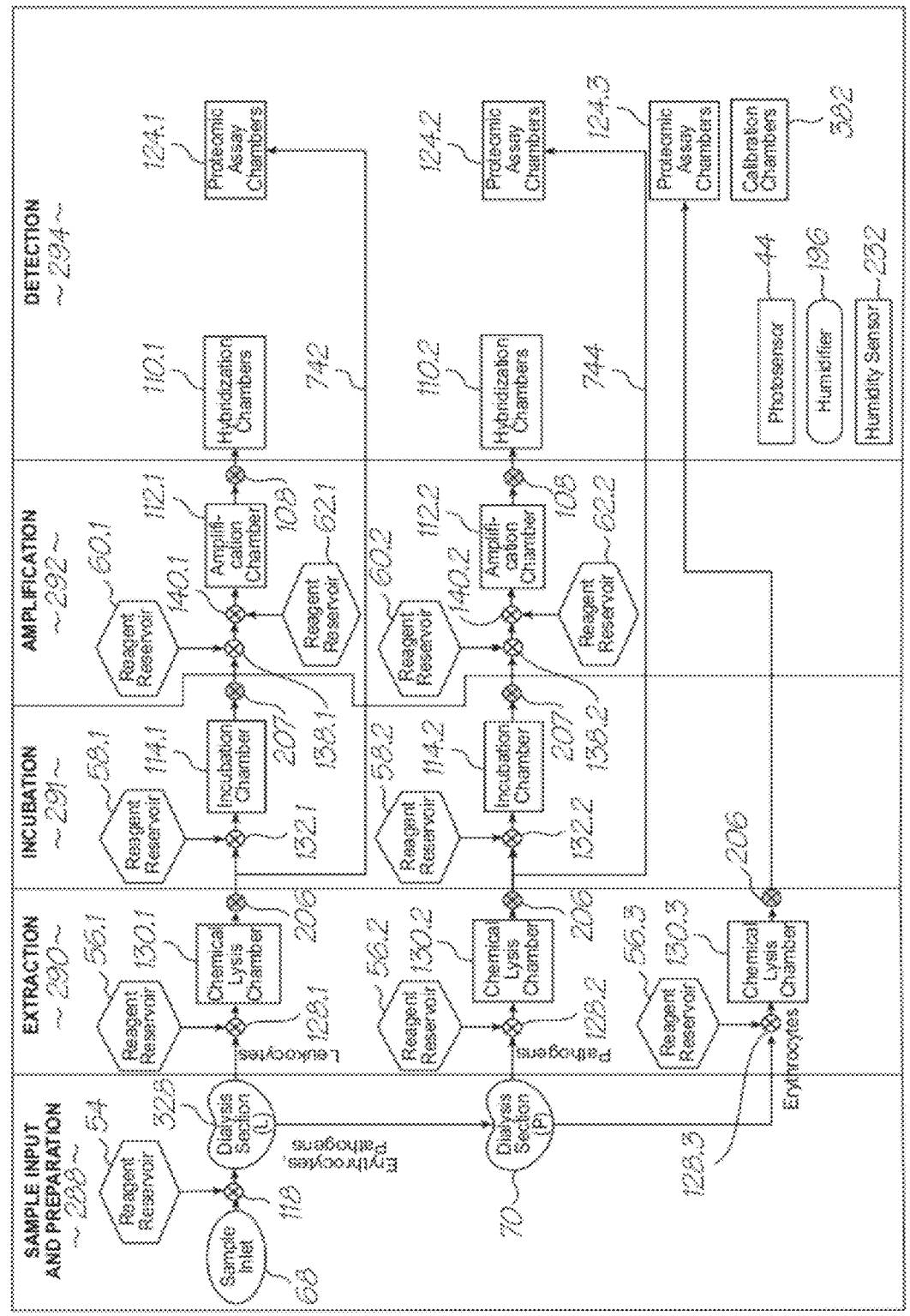
FIG. 76 is a diagrammatic representation of the architecture of LOC variant X.
Figure 77:
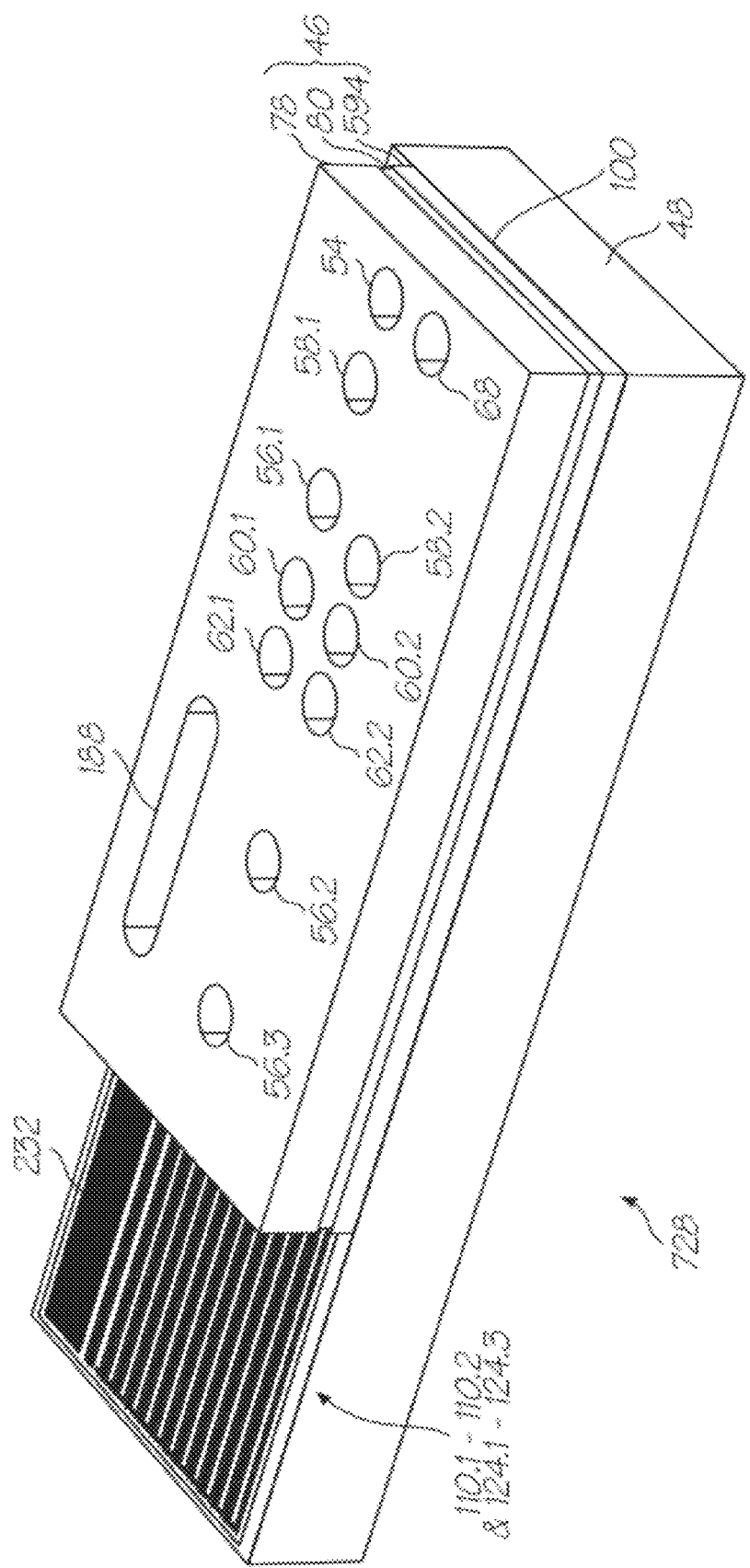
FIG. 77 is a perspective view of LOC variant X.
Figure 7B:
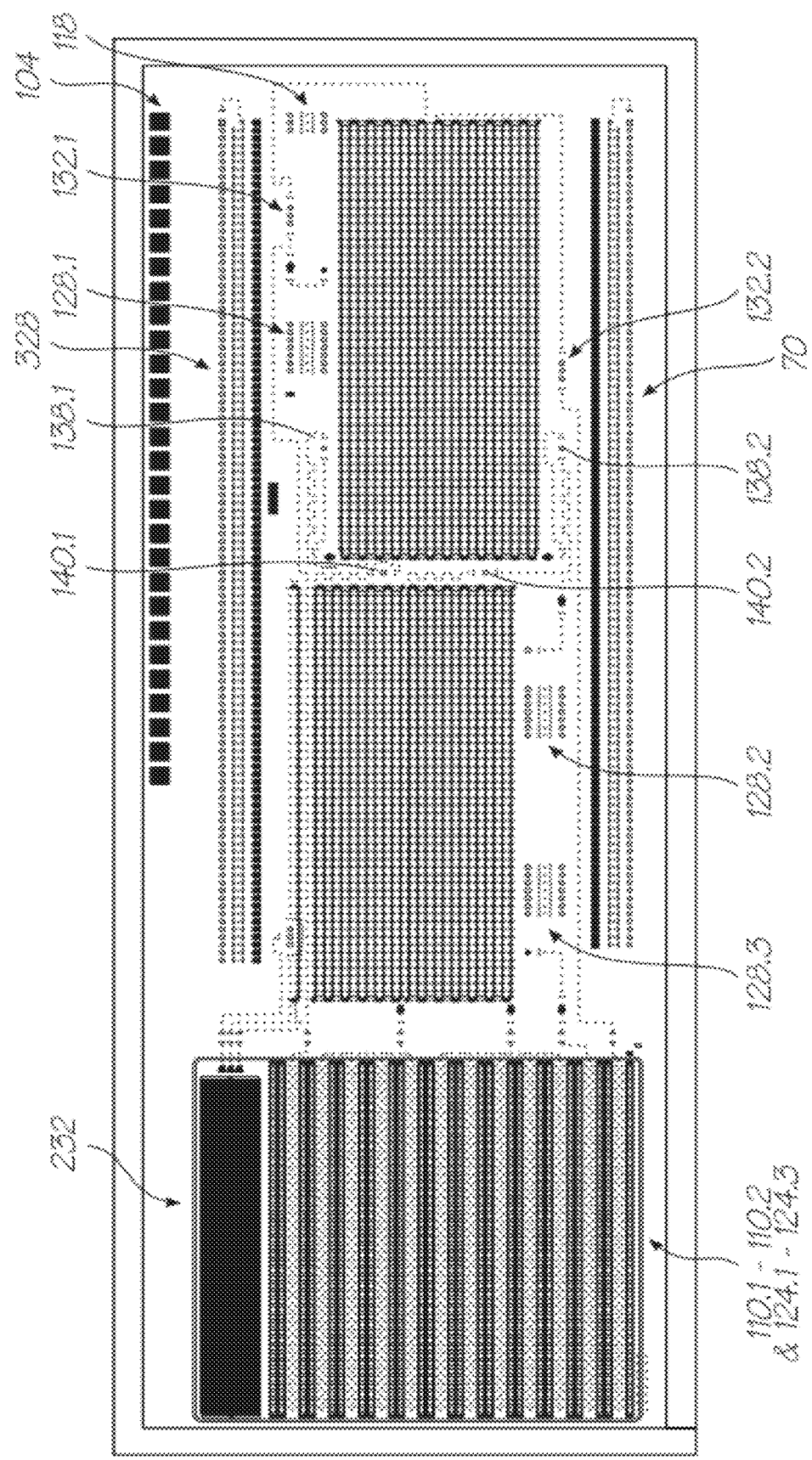
Figure 79:
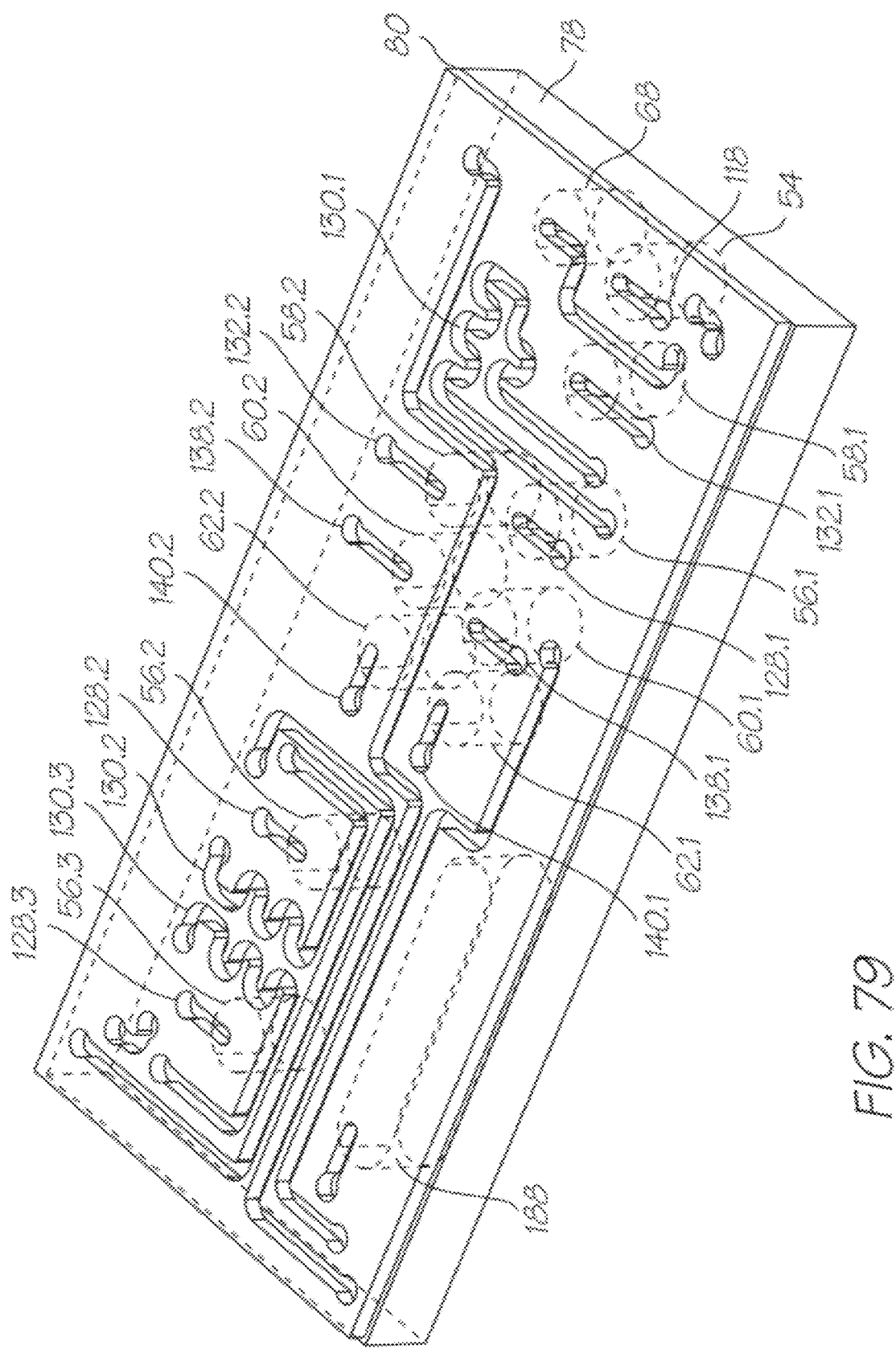
FIG. 79 is a perspective view of the underside of the cap with the reagent reservoirs shown in dotted line.
Figure 80:
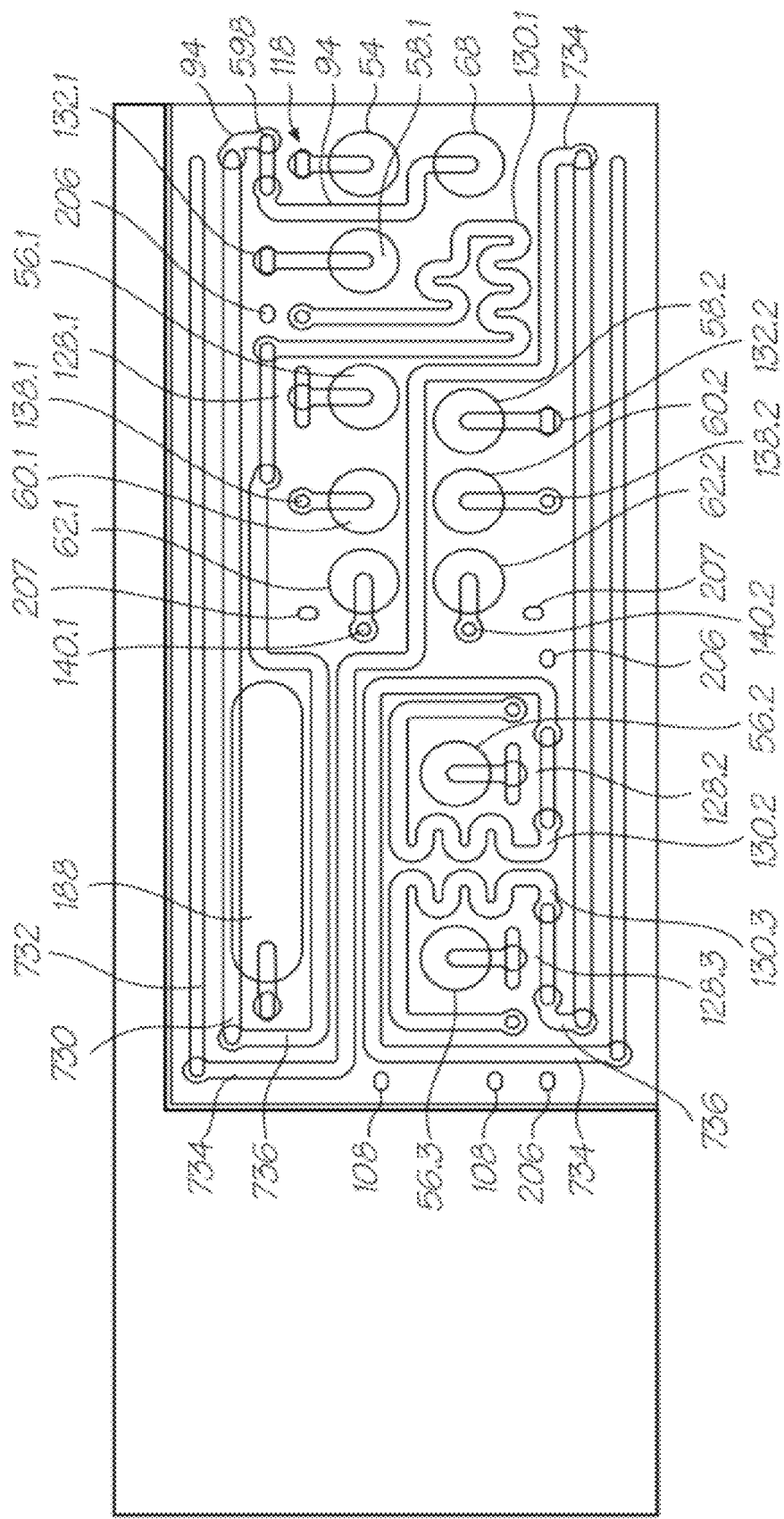
FIG. 80 is a plan view showing only the features of the cap in isolation.

Isothermal nucleic acid amplification is more tolerant of potential inhibitors in the sample and, as such, is generally suitable for use where direct nucleic acid amplification from the sample is desired. Therefore, isothermal nucleic acid amplification is sometimes useful in LOC variant XLIII 673, LOC variant XLIV 674 and LOC variant XLVII 677, amongst others, shown in FIGS. 73, 74 and 75, respectively. Direct isothermal amplification may also be combined with one or more pre-amplification dialysis steps 70, 686 or 682 as shown in FIGS. 73 and 75 and/or a pre-hybridization dialysis step 682 as indicated in FIG. 74 to help partially concentrate the target cells in the sample before nucleic acid amplification or remove unwanted cellular debris prior to the sample entering the hybridization chamber array 110, respectively. The person skilled in the art will appreciate that any combination of pre-amplification dialysis and pre-hybridization dialysis can be used.

Figure 64:
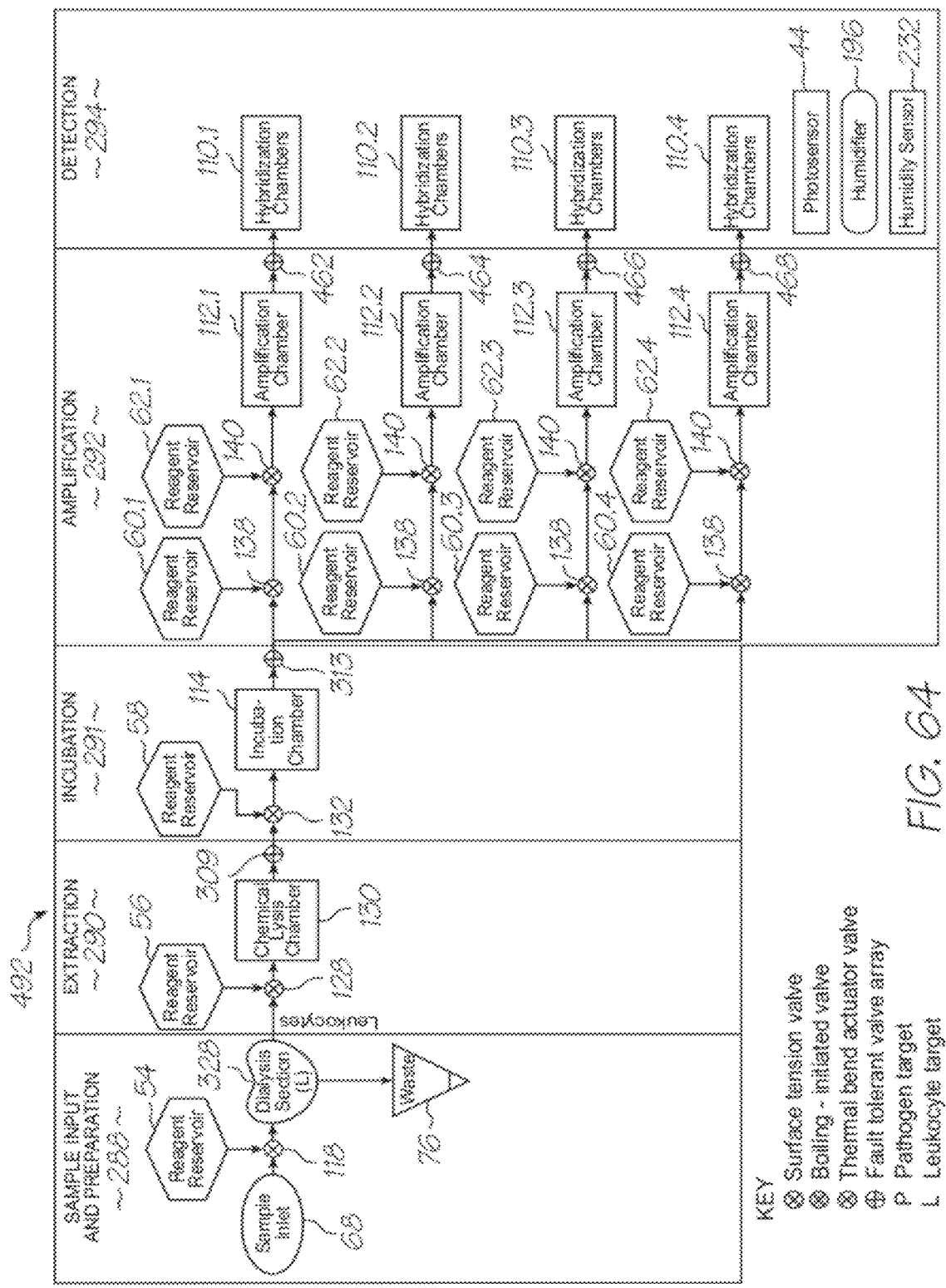
FIG. 64 is a diagrammatic representation of the architecture of LOC variant VII.
Figure 65:
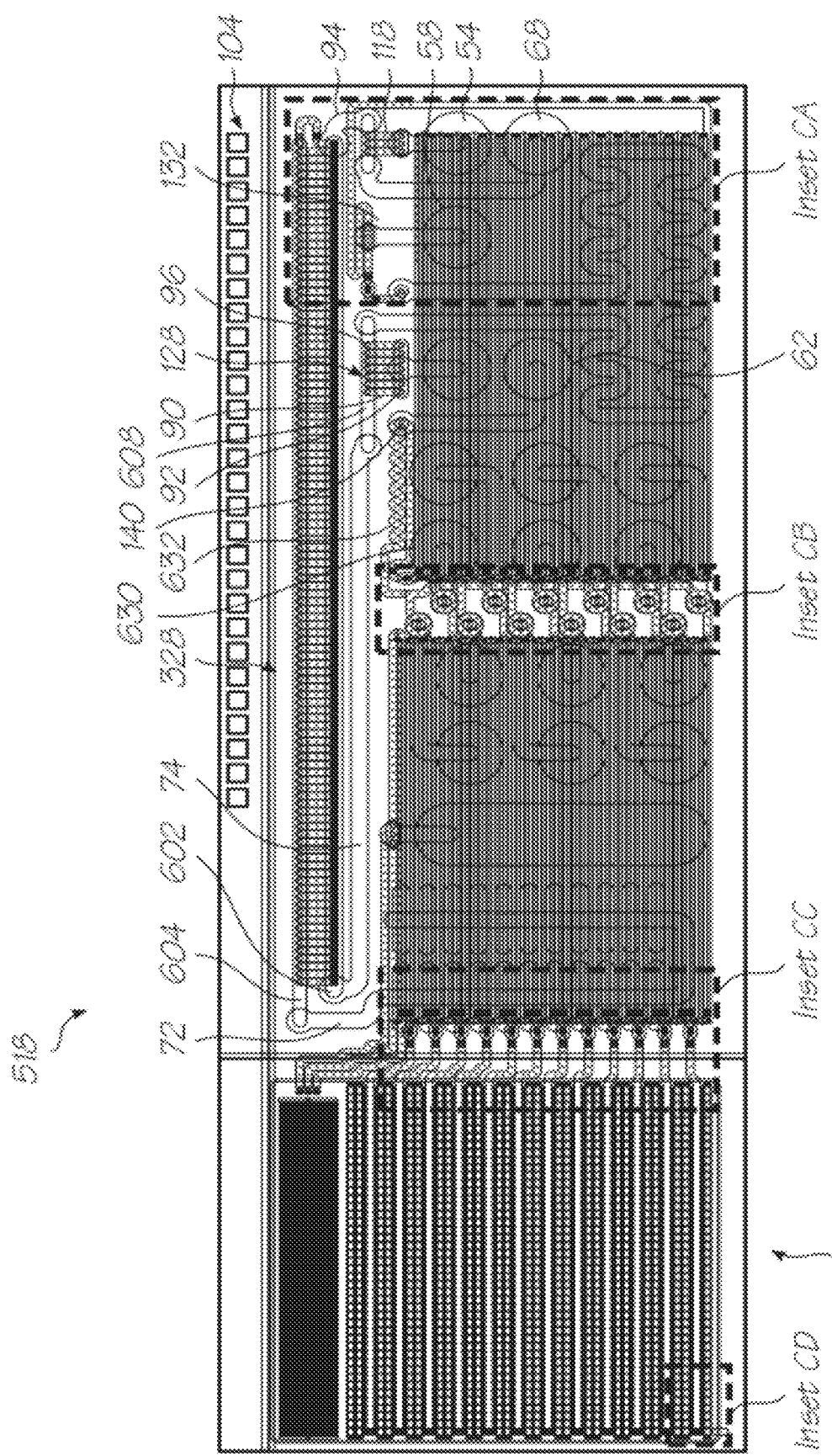
FIG. 65 is a plan view of LOC variant VIII with features and structures from all layers superimposed on each other.
Figure 69:
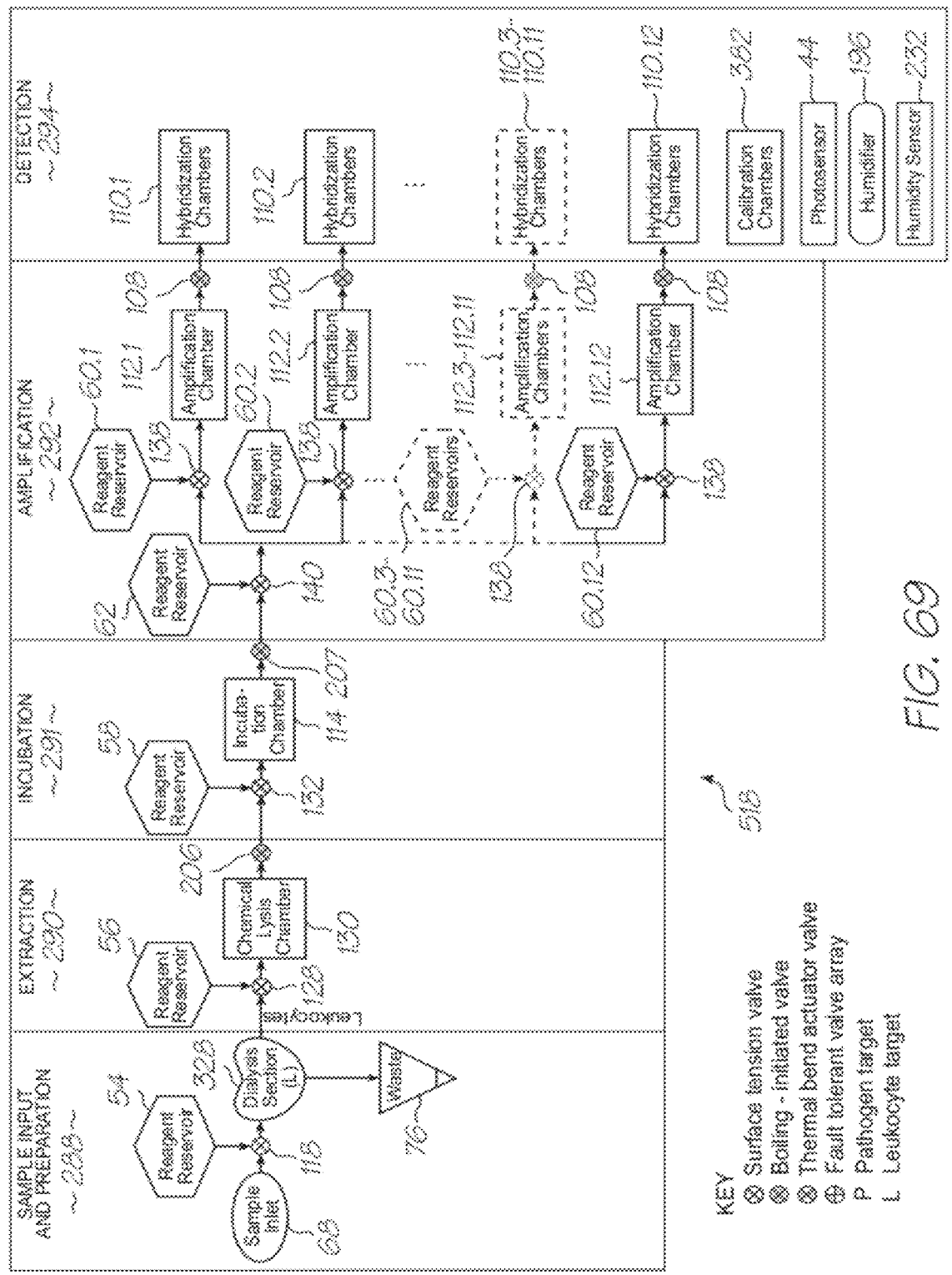
FIG. 69 is a diagrammatic representation of the architecture of LOC variant VIII.
Figure 70:
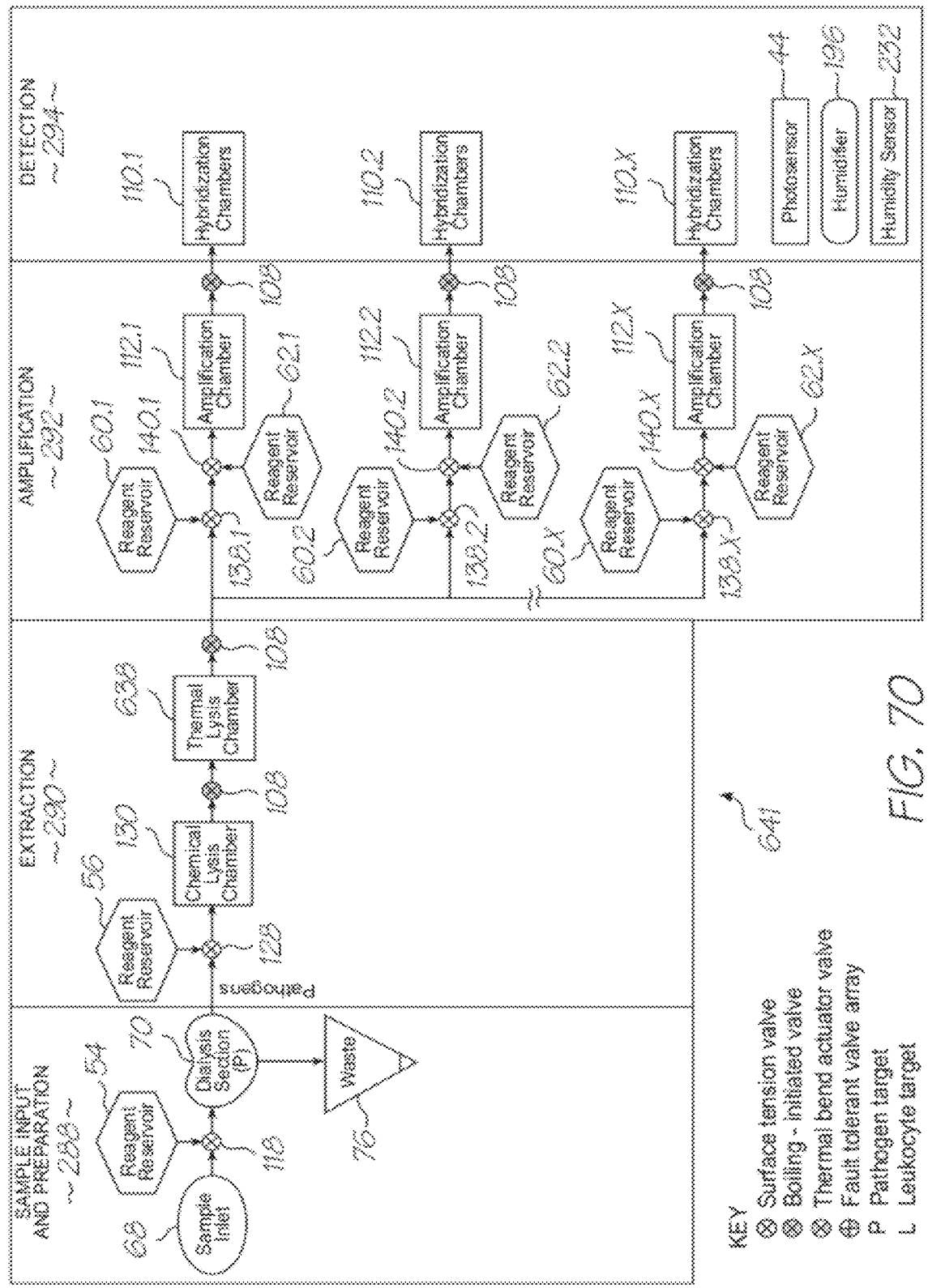
FIG. 70 is a schematic illustration of the architecture of LOC variant XIV.

Isothermal nucleic acid amplification can also be performed in parallel amplification sections such as those schematically represented in FIGS. 64, 69 and 70, multiplexed and some methods of isothermal nucleic acid amplification, such as LAMP, are compatible with an initial reverse transcription step to amplify RNA.

Other Design Variants
Flow Rate Sensor

Figure 94:
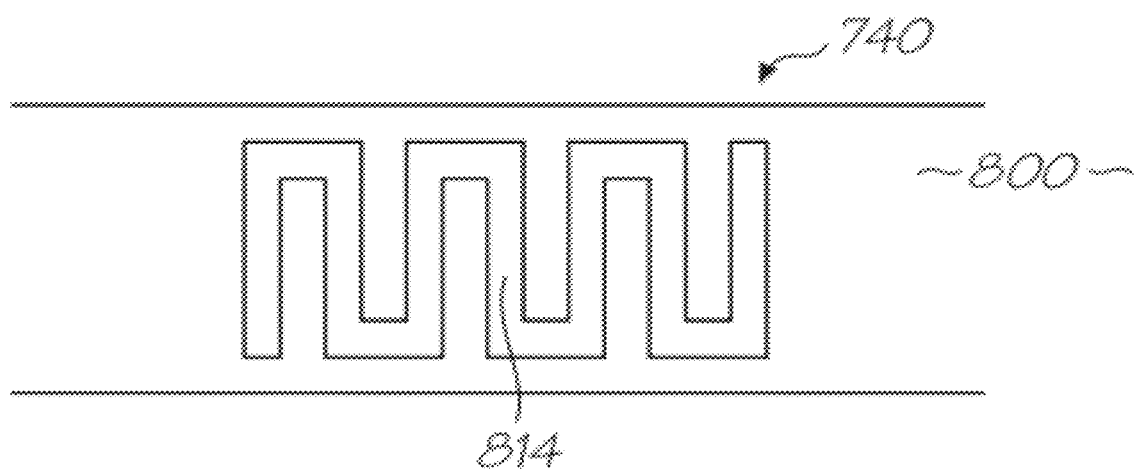
FIG. 94 schematically illustrates a CMOS-controlled flow rate sensor.

In addition to temperature and liquid sensors, the LOC device can also incorporate CMOS-controlled flow rate sensors 740, as schematically illustrated in FIG. 94 and in LOC Variant X 728 (see FIGS. 76 to 92). The sensors are used to determine the flow rate in two steps. In the first step, the temperature of the serpentine heater element 814 is determined by applying a low current and measuring the voltage to determine the resistance of the serpentine heater element 814, and therefore the temperature of the element 814 using the known relationship between resistance and the temperature of the heater element. At this stage, minimal heat is being dissipated in the element 814 and the temperature of the liquid in the channel is equal to the calculated temperature of the element 814. In the second step, a higher current is applied to the serpentine heater element 814 such that the temperature of the element 814 increases and some heat is lost to the flowing liquid. By again measuring the voltage across the element 814 while the higher current is being applied, the new resistance of the element 814 is determined and the increased temperature is again calculated by the CMOS circuitry 86. Using the new temperature of the serpentine heater element 814 and the known temperature of sample liquid calculated in the first step, the flow speed of the liquid is determined. From the known channel cross sectional geometry and the flow speed, the flow rate of the liquid in the channel is calculated.

Protein Detection Variants

Some embodiments of the LOC device use a homogeneous protein detection assay to detect specific proteins within a crude cell lysate. Numerous homogeneous protein detection assays have been developed for use in these embodiments of the LOC device. Commonly, these assays utilize antibodies or aptamers to capture the target protein.

Figure 108B:
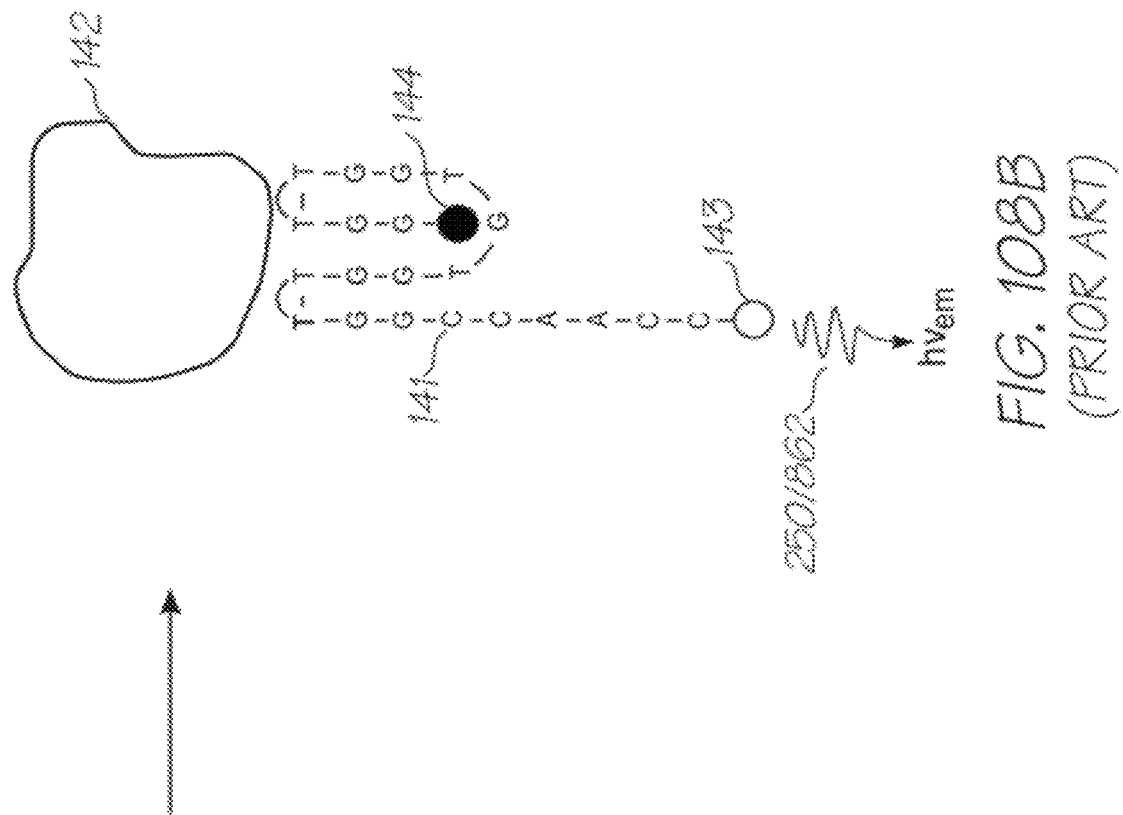
FIGS. 108A and 108B is a diagram illustrating binding of an aptamer to a protein to produce a detectable signal.
Figure 108A:
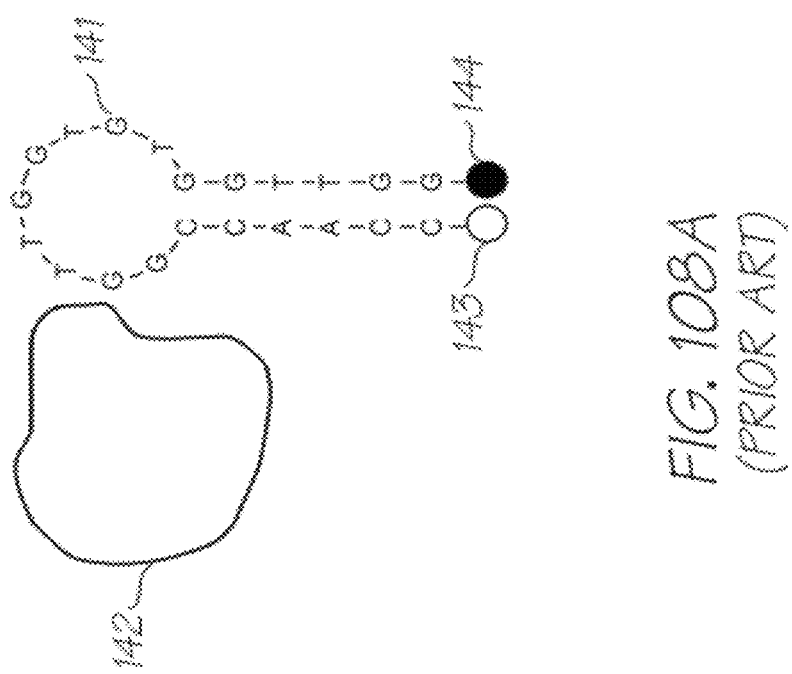
Figure 111:
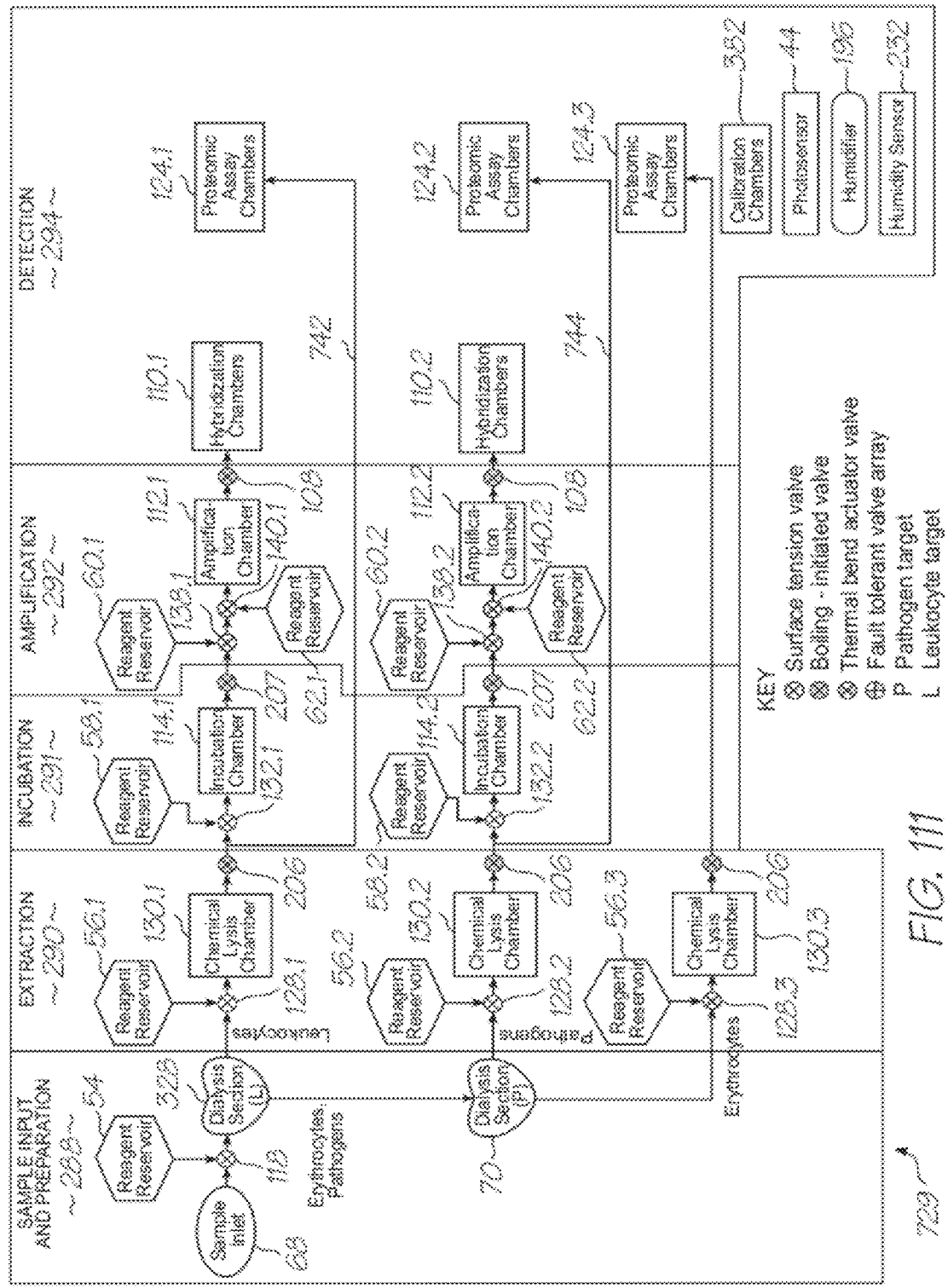
FIG. 111 is a diagrammatic representation of the architecture of LOC variant L with ECL detection.
Figure 112:
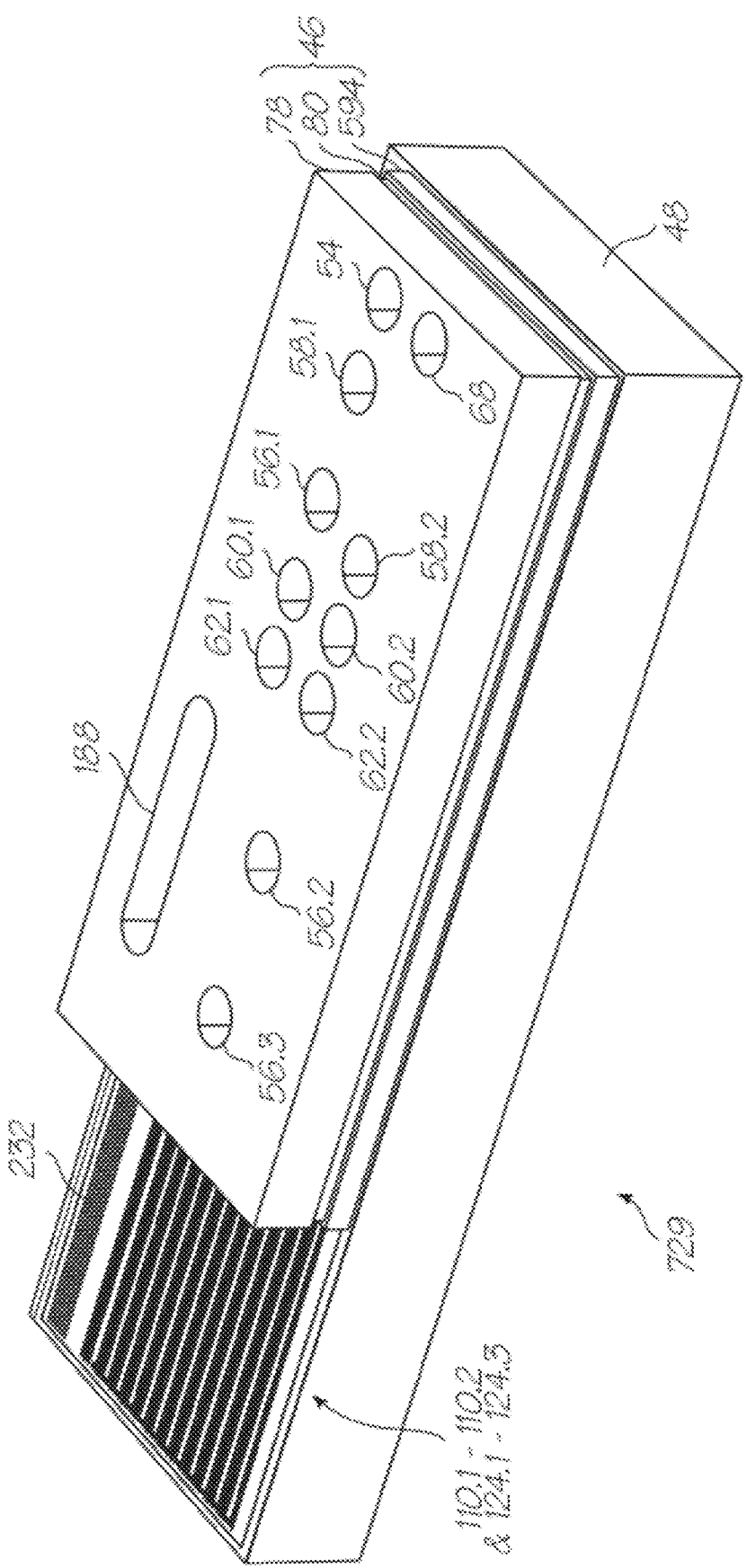
FIG. 112 is a perspective view of LOC variant L.

In one type of assay, an aptamer 141 which binds to a particular protein 142 is labelled with two different fluorophores or luminophores 143 and 144 which can function as a donor and an acceptor in a fluorescence resonance energy transfer (FRET) or electrochemiluminescence resonance energy transfer (ERET) reaction (see FIGS. 108A and 108B). Both donor 143 and acceptor 144 are linked to the same aptamer 141, and the change in separation is caused by a change in conformation upon binding to the target protein 142. For example, an aptamer 141 in the absence of the target forms a conformation where the donor and acceptor are in close proximity (see FIG. 108A); upon binding to the target, the new conformation results in a larger separation between the donor and acceptor (see FIG. 108B). When the acceptor is a quencher and the donor is a luminophore, the effect of binding to the target is an increase in light emission 250 or 862 (see FIG. 108B).

A second type of assay uses two antibodies 145 or two aptamers 141 that must independently bind to different, non-overlapping epitopes or regions of the target protein 142 (see FIGS. 109A, 109B, 110A and 110B). These antibodies 145 or aptamers 141 are labelled with different fluorophores or luminophores 143 and 144 which can function as a donor and an acceptor in a fluorescence resonance energy transfer (FRET) or electrochemiluminescence resonance energy transfer (ERET) reaction. The fluorophores or luminophores 143 and 144 form part of a pair of short complementary oligonucleotides 147 attached to the antibodies or aptamers via long, flexible linkers 149 (see FIGS. 109A and 110A). Once the antibodies 145 or aptamers 141 bind to the target protein 142, the complementary oligonucleotides 147 find each other and hybridize to one another (see FIGS. 109B and 110B). This brings the donors and acceptors 143 and 144 in close proximity to one another resulting in efficient FRET 250 or ERET 862 that is used as a signal for target protein detection.

To ensure there is no, or very little, background signal as a result of the oligonucleotides 147 attached to the two antibodies 145 or aptamers 141 hybridizing to one another in the absence of their binding to the protein 142, it is necessary to carefully choose the length and sequence of the complementary oligonucleotides 147 so that the dissociation constant ($k_d$) for the duplex is relatively high (~5 μM). Thus when free antibodies or aptamers labelled with these oligonucleotides are mixed at nanomolar concentrations, well below that of their $k_d$, the likelihood of duplex formation and a FRET 250 or ERET 862 signal being generated is negligible. However, when both antibodies 145 or both aptamers 141 bind to the target protein 142, the local concentration of the oligonucleotides 147 will be much higher than their $k_d$ resulting in almost complete hybridization and generation of a detectable FRET 250 or ERET 862 signal.

The choice of fluorophores and luminophores is an important consideration when designing a homogeneous protein detection assay. Crude cell lysates are often turbid and may contain substances which autofluoresce. In such cases, the use of molecules with long-lasting fluorescence or electrochemiluminescence and donor-acceptor pairs 143 and 144 which are optimized to give maximal FRET 250 or ERET 862 is desired. One such pair is europium chelate and Cy5, which has previously been shown to significantly improve signal-to-background ratio in such a system when compared with other donor-acceptor pairs, by allowing the signal to be read after interfering background fluorescence, electrochemiluminescence or scattered light has decayed. Europium chelate and AlexaFluor 647 or terbium chelate and Fluorescein FRET or ERET pairs also work well. The sensitivity and specificity of this approach is similar to that of enzyme-linked immunosorbent assays (ELISAs), but no sample manipulation is required.

In some embodiments of the LOC device, one of the antibodies 145 or one of the aptamers 141 is attached to the base of the proteomic assay chamber 124 (see for example FIGS. 116 and 120) and the protein lysate is combined with the other antibody 145 or aptamer 141 during lysis within the chemical lysis section 130 to facilitate binding to the first antibody 145 or aptamer 141 prior to entering the proteomic assay chamber 124. This increases the subsequent speed with which a detectable signal is generated as only one conjugation or hybridization event is required within the proteomic assay chamber.

Photodiode

FIG. 54 shows the photodiode 184 integrated into the CMOS circuitry 86 of the LOC device 301. The photodiode 184 is fabricated as part of the CMOS circuitry 86 without additional masks or steps. This is one significant advantage of a CMOS photodiode over a CCD, an alternate sensing technology which could be integrated on the same chip using non-standard processing steps, or fabricated on an adjacent chip. On-chip detection is low cost and reduces the size of the assay system. The shorter optical path length reduces noise from the surrounding environment for efficient collection of the fluorescence signal and eliminates the need for a conventional optical assembly of lenses and filters.

Quantum efficiency of the photodiode 184 is the fraction of photons impinging on its active area 185 that are effectively converted to photo-electrons. For standard silicon processes, the quantum efficiency is in the range of 0.3 to 0.5 for visible light, depending on process parameters such as the amount and absorption properties of the cover layers.

The detection threshold of the photodiode 184 determines the smallest intensity of the fluorescence signal that can be detected. The detection threshold also determines the size of the photodiode 184 and hence the number of hybridization chambers 180 in the hybridization and detection section 52 (see FIG. 52). The size and number of chambers are technical parameters that are limited by the dimensions of the LOC device (in the case of the LOC device 301, the dimensions are 1760 µm×5824 µm) and the real estate available after other functional modules such as the pathogen dialysis section 70 and amplification section(s) 112 are incorporated.

For standard silicon processes, the photodiode 184 detects a minimum of 5 photons. However, to ensure reliable detection, the minimum can be set to 10 photons. Therefore with the quantum efficiency range being 0.3 to 0.5 (as discussed above), the fluorescence emission from the probes should be a minimum of 17 photons but 30 photons would incorporate a suitable margin of error for reliable detection.

Electrochemiluminescence as an Alternative Detection Method

Electrochemiluminescence (ECL) involves the generation of species at electrode surfaces that then undergo electron-transfer reactions to form excited states that emit light. Electrochemiluminescence differs from normal chemiluminescence in that formation of the excited species relies on oxidation or reduction of the luminophore or a coreactant at an electrode. Coreactants, in this context, are additional reagents added to the ECL solution which enhance the efficiency of ECL emission. In normal chemiluminescence, the excited species form purely through mixing of suitable reagents. The emitting atom or complex is traditionally referred to as a luminophore. In brief, ECL relies on generating an excited state of the luminophore, at which point a photon will be emitted. As with any such process, it is possible for an alternate path to be taken from the excited state which does not lead to the desired light emission (i.e. quenching).

Embodiments of the test module that use ECL instead of fluorescence detection do not require an excitation LED. Electrodes are fabricated within the hybridization chambers to provide the electrical pulse for ECL generation and the photons are detected using the photosensor 44. The duration and voltage of the electrical pulse are controlled; in some embodiments, control over the current is used as an alternative to controlling the voltage.

Luminophore and Quencher

The ruthenium complex, $[Ru(bpy)_3]^{2+}$, described previously for use as a fluorescent reporter in the probes, can also be used as a luminophore in an ECL reaction in the hybridization chambers, with TPrA (tri-n-propylamine ($CH_3CH_2$—$CH_2)_3N$) as the coreactant. Coreactant ECL has the benefit that luminophores are not consumed after photon emission and the reagents are available for the process to repeat. Furthermore, the $[Ru(bpy)_3]^{2+}$/TPrA ECL system provides good signal levels at physiologically relevant conditions of pH in aqueous solutions. Alternative coreactants which can produce equivalent or better results than TPrA with ruthenium complexes are N-butyldiethanolamine and 2-(dibutylamino)ethanol.

Figure 95:
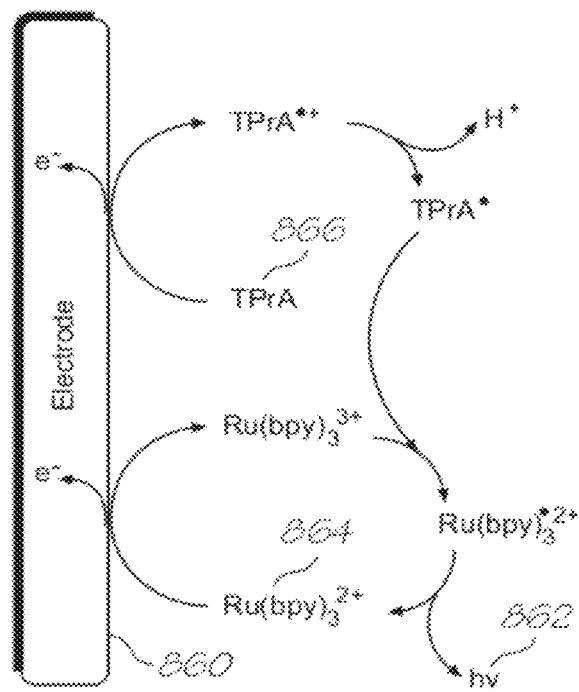
FIG. 95 illustrates the reactions occurring during an electrochemiluminescence (ECL) process.

FIG. 95 illustrates the reactions occurring during an ECL process in which $[Ru(bpy)_3]^{2+}$ is the luminophore 864 and TPrA is the coreactant 866. ECL emission 862 in the $[Ru(bpy)_3]^{2+}$/TPrA ECL system follows the oxidation of both $Ru(bpy)_3^{2+}$ and TPrA at the anode 860. The reactions are as follows:

  (1)

  (2)

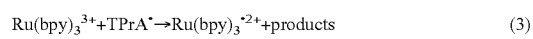  (3)

  (4)

The wavelength of the emitted light 862 is around 620 nm and the anode potential is around 1.1 V with respect to a Ag/AgCl reference electrode. For the $[Ru(bpy)_3]^{2+}$/TPrA ECL system, either the Black Hole Quencher, BHQ 2, or Iowa Black RQ described previously, would be a suitable quencher. In the embodiments described here, the quencher is a functional moiety which is initially attached to the probe, but other embodiments are possible in which the quencher is a separate molecule free in solution.

Hybridization Probes for ECL Detection

Figure 129:
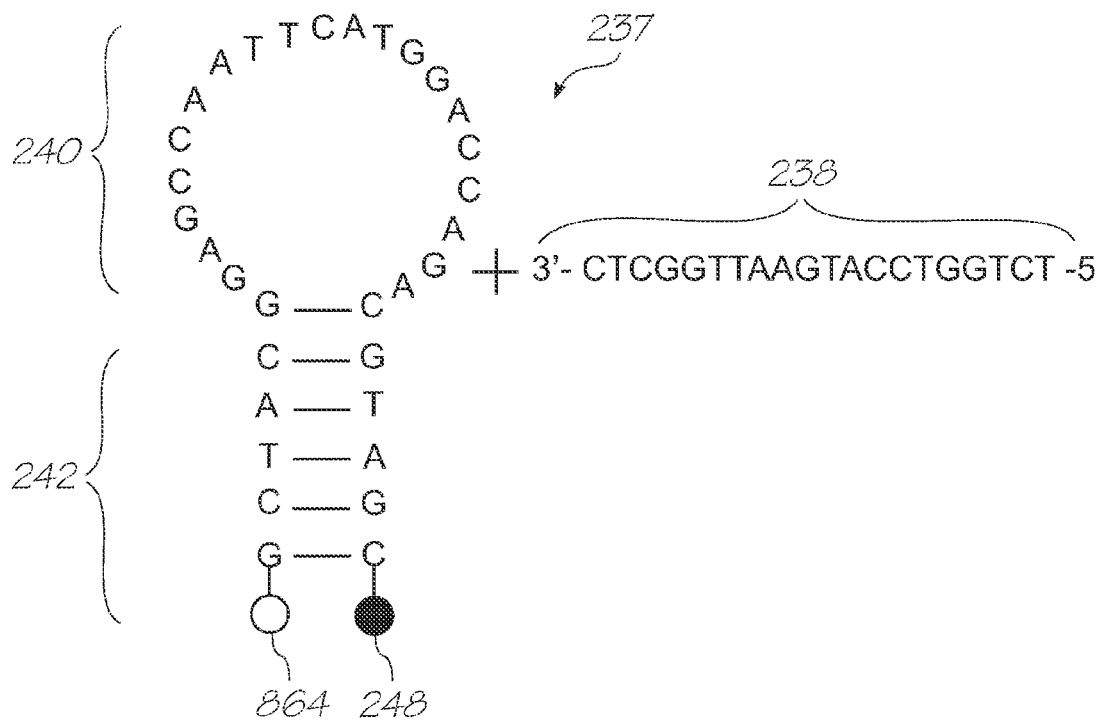
FIG. 129 is a diagram of an electrochemiluminescence resonance energy transfer probe in a closed configuration.
Figure 130:
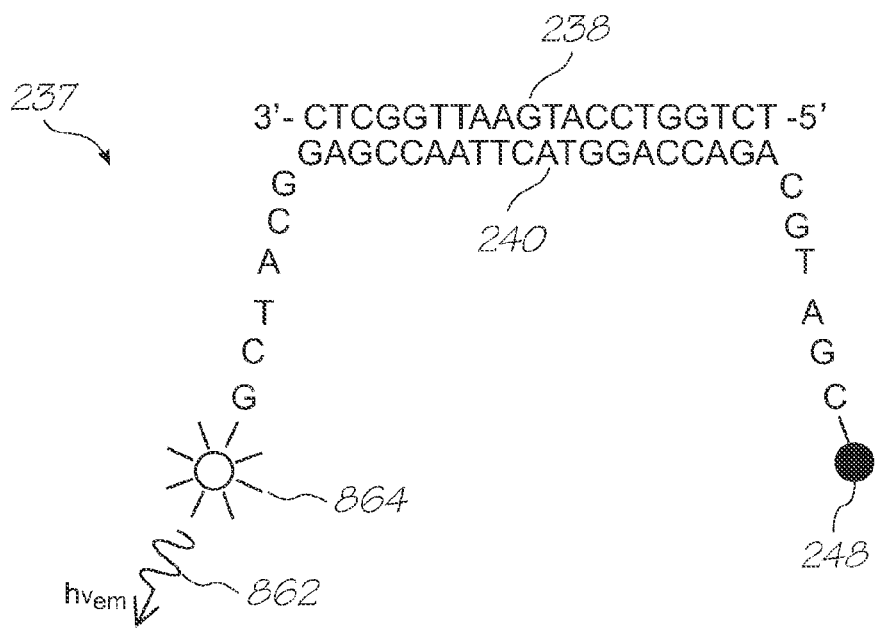
FIG. 130 is a diagram of an electrochemiluminescence resonance energy transfer probe in an open and hybridized configuration.

FIGS. 129 and 130 show the hybridization-responsive ECL probes 237. These are often referred to as molecular beacons and are stem-and-loop probes, generated from a single strand of nucleic acid, that luminesce upon hybridization to complementary nucleic acids. FIG. 129 shows a single ECL probe 237 prior to hybridization with a target nucleic acid sequence 238. The probe has a loop 240, stem 242, a luminophore 864 at the 5' end, and a quencher 248 at the 3' end. The loop 240 consists of a sequence complementary to the target nucleic acid sequence 238. Complementary sequences on either side of the probe sequence anneal together to form the stem 242.

In the absence of a complementary target sequence, the probe remains closed as shown in FIG. 129. The stem 242 keeps the luminophore-quencher pair in close proximity to each other, such that significant resonant energy transfer can occur between them, substantially eliminating the ability of the luminophore to emit light after electrochemical excitation.

FIG. 130 shows the ECL probe 237 in an open or hybridized configuration. Upon hybridization to a complementary target nucleic acid sequence 238, the stem-and-loop structure is disrupted, the luminophore 864 and quencher 248 are spatially separated, thus restoring the ability of the luminophore 864 to emit light. The ECL emission 862 is optically detected as an indication that the probe has hybridized.

The probes hybridize with very high specificity with complementary targets, since the stem helix of the probe is designed to be more stable than a probe-target helix with a single nucleotide that is not complementary. Since double-stranded DNA is relatively rigid, it is sterically impossible for the probe-target helix and the stem helix to coexist.

Primer-Linked ECL Probes

Primer-linked stem-and-loop probes and primer-linked linear probes, otherwise known as scorpion probes, are an alternative to molecular beacons and can be used for real-time and quantitative nucleic acid amplification in the LOC device. Real-time amplification is performed directly in the hybridization chambers of the LOC device. The benefit of using primer-linked probes is that the probe element is physically linked to the primer, thus only requiring a single hybridization event to occur during the nucleic acid amplification rather than separate hybridizations of the primers and probes being required. This ensures that the reaction is effectively instantaneous and results in stronger signals, shorter reaction times and better discrimination than when using separate primers and probes. The probes (along with polymerase and the amplification mix) would be deposited into the hybridization chambers 180 during fabrication and there would be no need for an amplification section on the LOC device. Alternatively, the amplification section is left unused or used for other reactions.

Primer-Linked Linear ECL Probes

Figure 131:
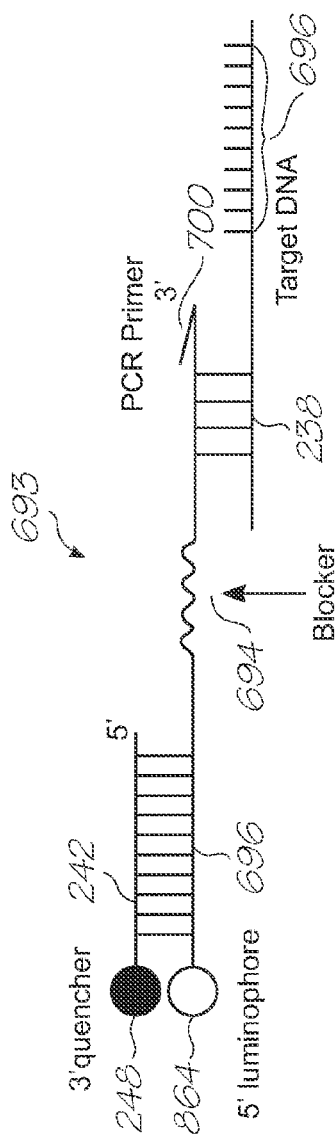
FIG. 131 is a diagram of a primer-linked, luminescent linear probe during the initial round of amplification.
Figure 132:
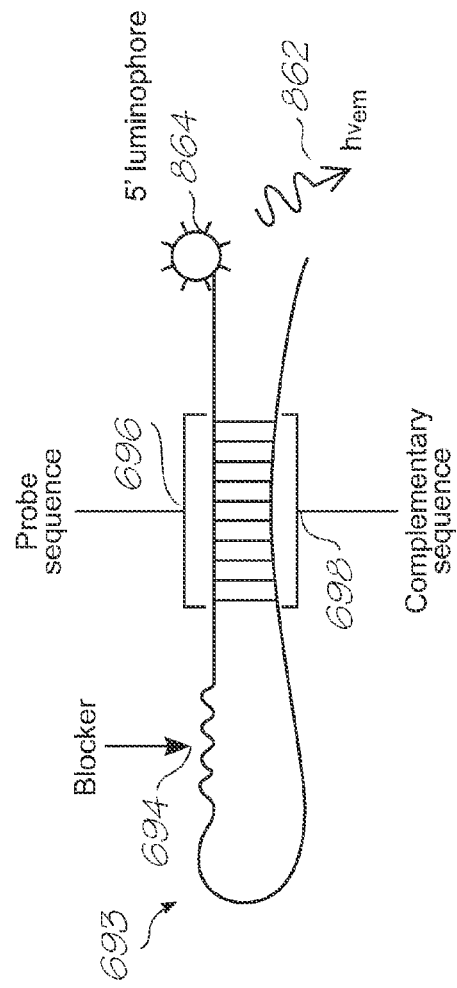
FIG. 132 is a diagram of a primer-linked, luminescent linear probe during a subsequent amplification cycle.

FIGS. 131 and 132 show a primer-linked linear ECL probe 693 during the initial round of nucleic acid amplification and in its hybridized configuration during subsequent rounds of nucleic acid amplification, respectively. Referring to FIG. 131, the primer-linked linear ECL probe 693 has a double-stranded stem segment 242. One of the strands incorporates the primer linked probe sequence 696 which is homologous to a region on the target nucleic acid 696 and is labelled on its 5' end with luminophore 864, and linked on its 3' end to an oligonucleotide primer 700 via an amplification blocker 694. The other strand of the stem 242 is labelled at its 3 end with a quencher molecule 248. After the initial round of nucleic acid amplification has completed, the probe can loop around and hybridize to the extended strand with the, now, complementary sequence 698. During the initial round of nucleic acid amplification, the oligonucleotide primer 700 anneals to the target DNA 238 (see FIG. 131) and is then extended, forming a DNA strand containing both the probe sequence and the amplification product. The amplification blocker 694 prevents the polymerase from reading through and copying the probe region 696. Upon subsequent denaturation, the extended oligonucleotide primer 700/template hybrid is dissociated and so is the double stranded stem 242 of the primer-linked linear probe, thus releasing the quencher 248. Once the temperature decreases for the annealing and extension steps, the primer linked probe sequence 696 of the primer-linked linear ECL probe curls around and hybridizes to the amplified complementary sequence 698 on the extended strand and light emission is detected indicating the presence of the target DNA. Non-extended primer-linked linear ECL probes retain their double-stranded stem and light emission remains quenched. This detection method is particularly well suited for fast detection systems as it relies on a single-molecule process.

Primer-Linked Stem-and-Loop ECL Probes

Figure 133:
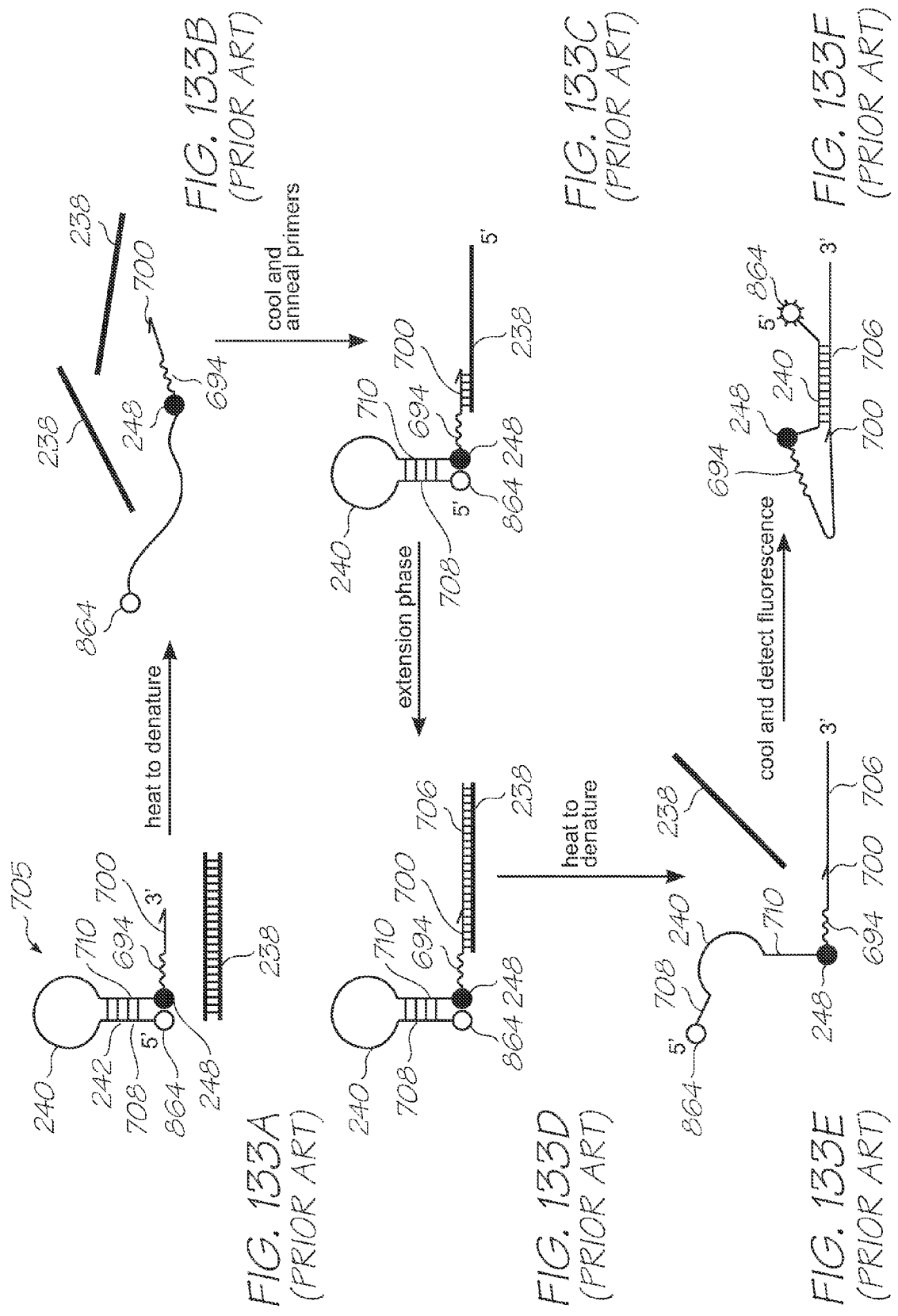
FIGS. 133A to 133F diagrammatically illustrate thermal cycling of a luminescent primer-linked stem-and-loop probe.

FIGS. 133A to 133F show the operation of a primer-linked stem-and-loop ECL probe 705. Referring to FIG. 133A, the primer-linked stem-and-loop ECL probe 705 has a stem 242 of complementary double-stranded DNA and a loop 240 which incorporates the probe sequence. One of the stem strands 708 is labelled at its 5' end with luminophore 864. The other strand 710 is labelled with a 3'-end quencher 248 and carries both the amplification blocker 694 and oligonucleotide primer 700. During the initial denaturation phase (see FIG. 133B), the strands of the target nucleic acid 238 separate, as does the stem 242 of the primer-linked stem-and-loop ECL probe 705. When the temperature cools for the annealing phase (see FIG. 133C), the oligonucleotide primer 700 on the primer-linked stem-and-loop ECL probe 705 hybridizes to the target nucleic acid sequence 238. During extension (see FIG. 133D), the complement 706 to the target nucleic acid sequence 238 is synthesized forming a DNA strand containing both the probe sequence 705 and the amplified product. The amplification blocker 694 prevents the polymerase from reading through and copying the probe region 705. When the probe next anneals, following denaturation (see FIG. 133E), the probe sequence of the loop segment 240 of the primer-linked stem-and-loop probe (see FIG. 133F) anneals to the complementary sequence 706 on the extended strand. This configuration leaves the luminophore 864 relatively remote from the quencher 248, resulting in a significant increase in light emission.

ECL Control Probes

Figure 134:
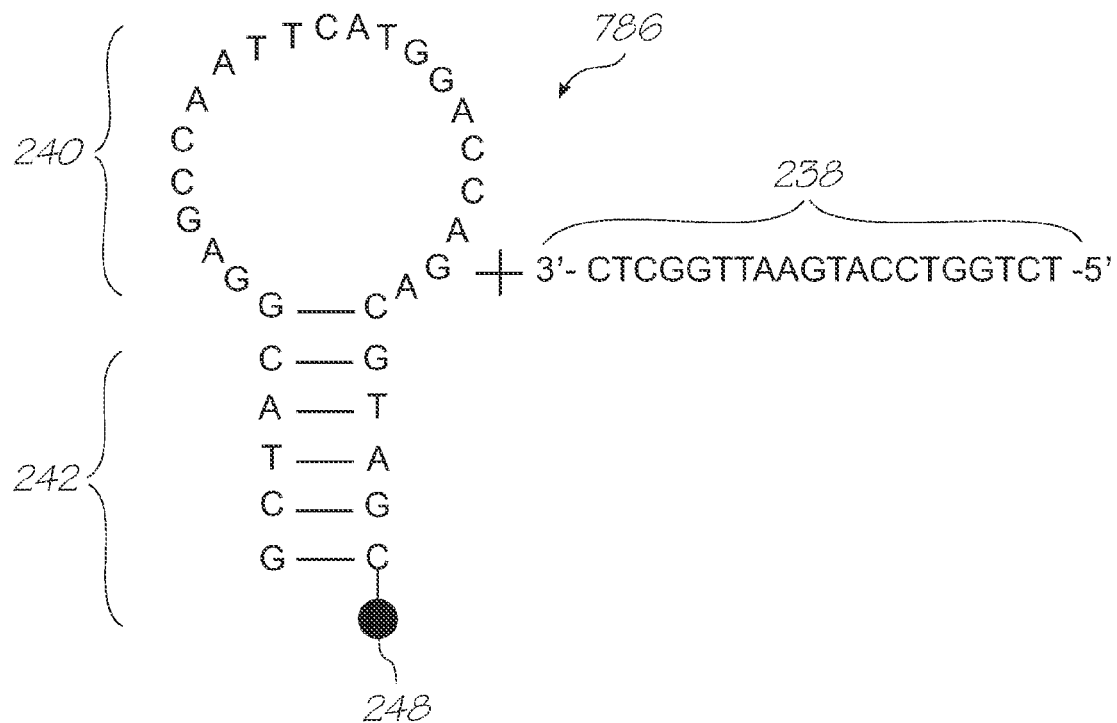
FIG. 134 schematically illustrates a negative control luminescent probe in its stem-and-loop configuration.
Figure 135:
FIG. 135 schematically illustrates the negative control luminescent probe of FIG. 134 in its open configuration.
Figure 136:
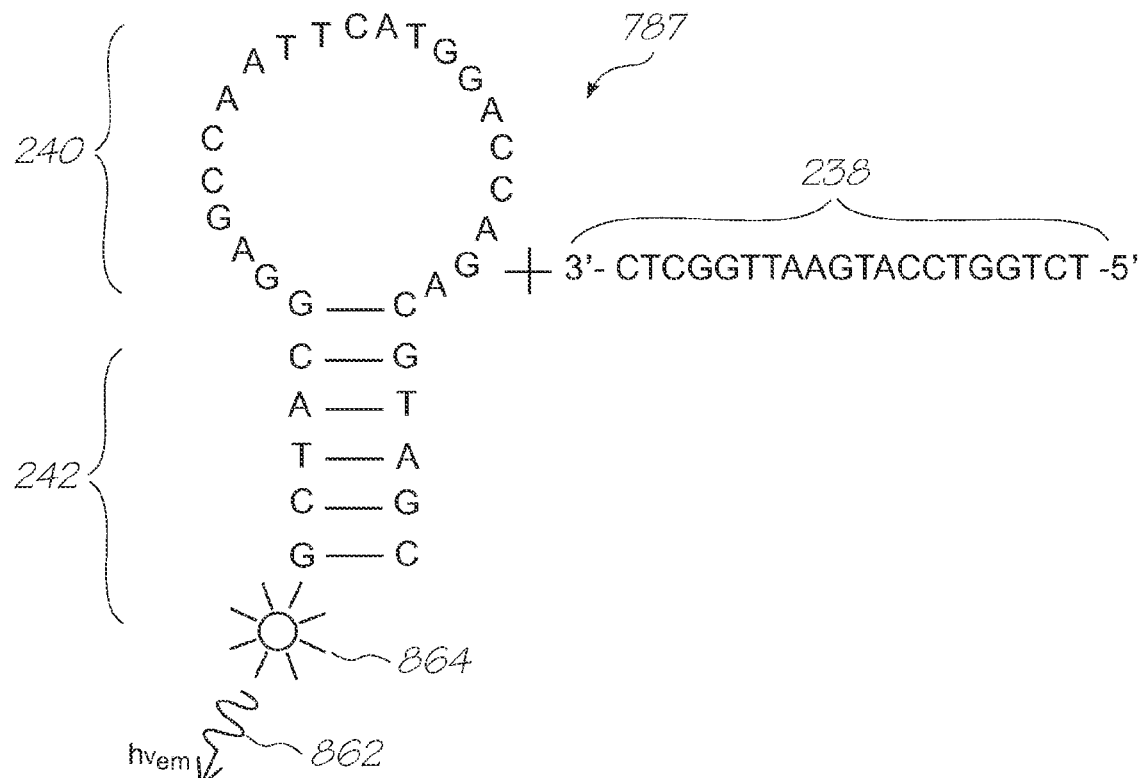
FIG. 136 schematically illustrates a positive control luminescent probe in its stem-and-loop configuration.
Figure 137:
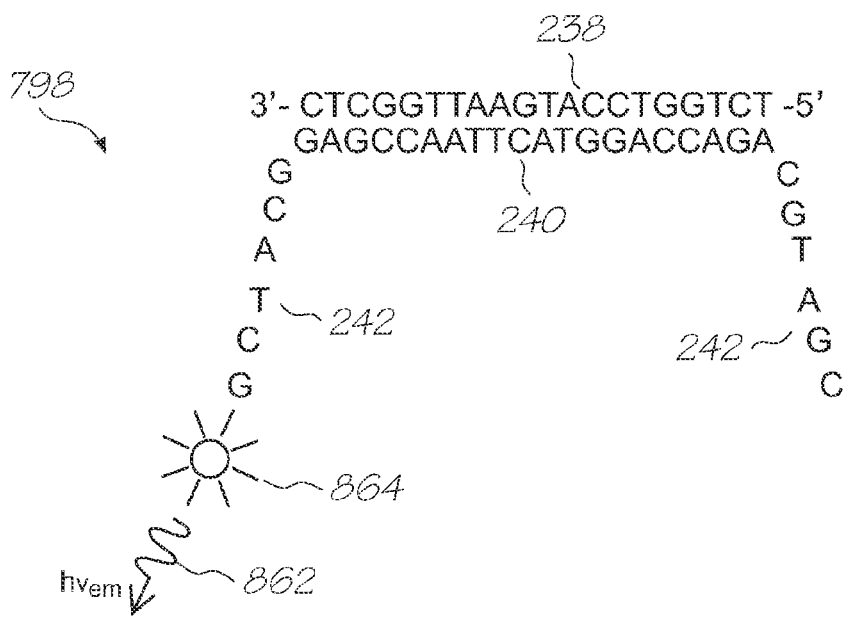
FIG. 137 schematically illustrates the positive control luminescent probe of FIG. 136 in its open configuration.
Figure 136:
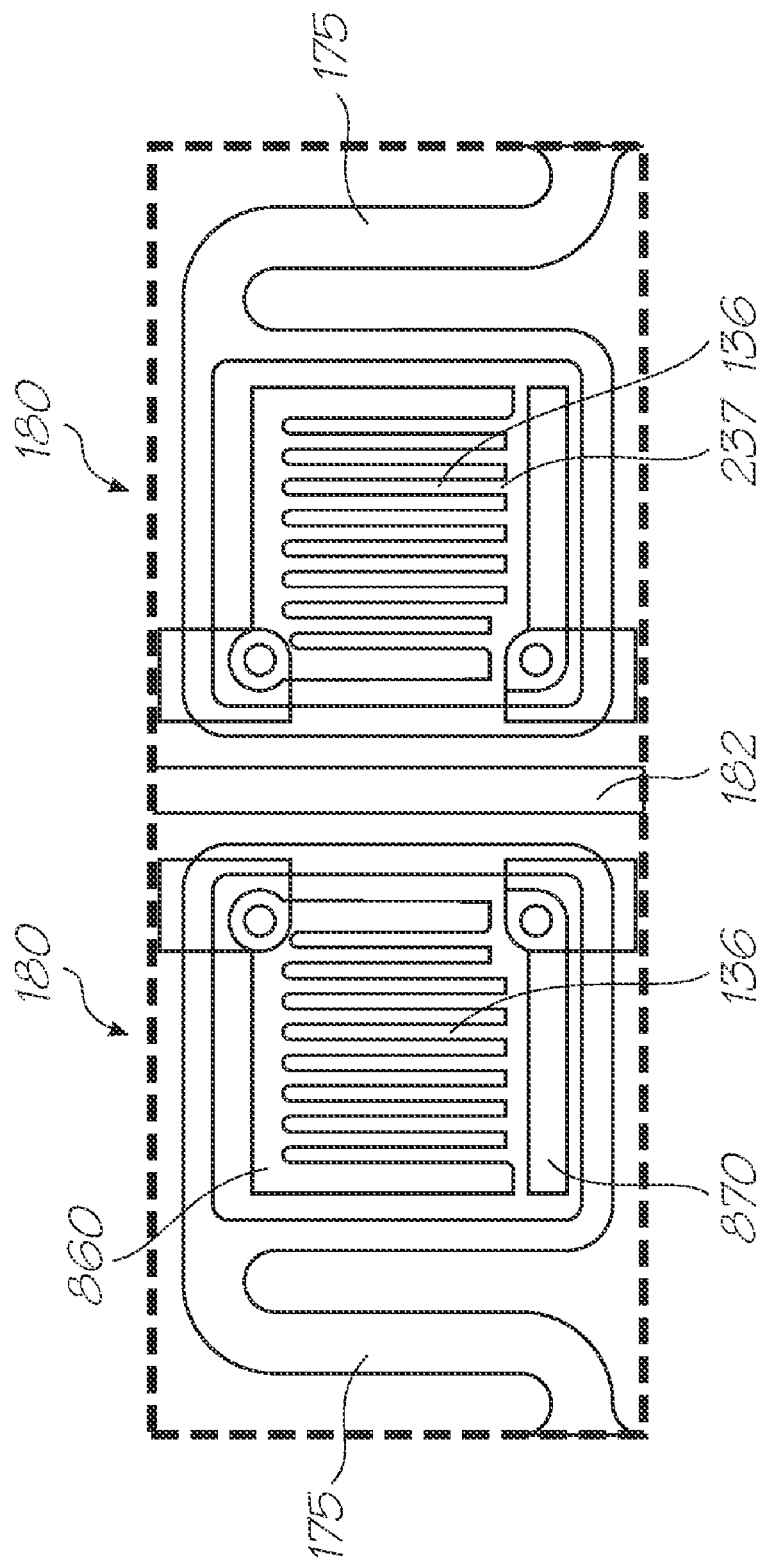

The hybridization chamber array 110 includes some hybridization chambers 180 with positive and negative ECL control probes used for assay quality control. FIGS. 134 and 135 schematically illustrate negative control ECL probes 786 without a luminophore, and FIGS. 136 and 137 are sketches of positive control ECL probes 787 without a quencher. The positive and negative control ECL probes have a stem-and-loop structure like the ECL probes described above. However, an ECL signal 862 (see FIG. 130) will always be emitted from positive control ECL probes 787 and no ECL signal 862 is ever emitted from negative control ECL probes 786, regardless of whether the probes hybridize into an open configuration or remain closed.

Referring to FIGS. 134 and 135, the negative control ECL probe 786 has no luminophore (and may or may not have a quencher 248). Hence, whether the target nucleic acid sequence 238 hybridizes with the probe as shown in FIG. 135, or the probe remains in its stem 242 and loop 240 configuration as shown in FIG. 134, the ECL signal is negligible. Alternatively, the negative control ECL probe could be designed so that it always remains quenched. For example, by having an artificial probe (loop) sequence 240 that will not hybridize to any nucleic acid sequence within the sample under investigation, the stem 242 of the probe molecule will re-hybridize to itself and the luminophore and quencher will remain in close proximity and no appreciable ECL signal will be detected. This negative control would account for any low level emission that may occur if the quenching is not complete.

Conversely, the positive control ECL probe 787 is constructed without a quencher as illustrated in FIGS. 136 and 137. Nothing quenches the ECL emission 862 from the luminophore 864 regardless of whether the positive control probe 787 hybridizes with the target nucleic acid sequence 238.

FIGS. 123 and 124 show another possibility for constructing a positive control chamber. In this case, the calibration chambers 382 which are sealed from the amplicon (or any flow containing target molecules) can be filled with the ECL luminophore solution such that a positive signal is always detected at the electrode Similarly, the control chambers can be negative control chambers because the lack of inlets prevents any targets from reaching the probes such that an ECL signal is never detected.

FIG. 52 shows a possible distribution of the positive and negative control probes (378 and 380 respectively) throughout the hybridization chamber array 110. For ECL, positive and negative control ECL probes 786 and 787 would replace control fluorescent probes 378 and 380, respectively. The control probes are placed in hybridization chambers 180 along a line extending diagonally across the hybridization chamber array 110. However, the arrangement of the control probes within the array is arbitrary (as is the configuration of the hybridization chamber array 110).

Calibration Chambers for ECL Detection

The non-uniformity of the electrical characteristic of the photodiode 184, response to any ambient light present at the sensor array, and light originating at other locations in the array, introduce background noise and offset into the output signal. This background is removed from each output signal by calibration chambers 382 in the hybridization chamber array 110 which either do not contain any probes, contain probes that have no ECL luminophore, or contain probes with a luminophore and quencher configured such that quenching is always expected to occur. The number and arrangement of the calibration chambers 382 throughout the hybridization chamber array is arbitrary. However, the calibration is more accurate if photodiodes 184 are calibrated by a calibration chamber 382 that is relatively proximate. Referring to FIG. 139, the hybridization chamber array 110 has one calibration chamber 382 for every eight hybridization chambers 180. That is, a calibration chamber 382 is positioned in the middle of every three by three square of hybridization chambers 180. In this configuration, the hybridization chambers 180 are calibrated by a calibration chamber 382 that is immediately adjacent.

Figure 93:
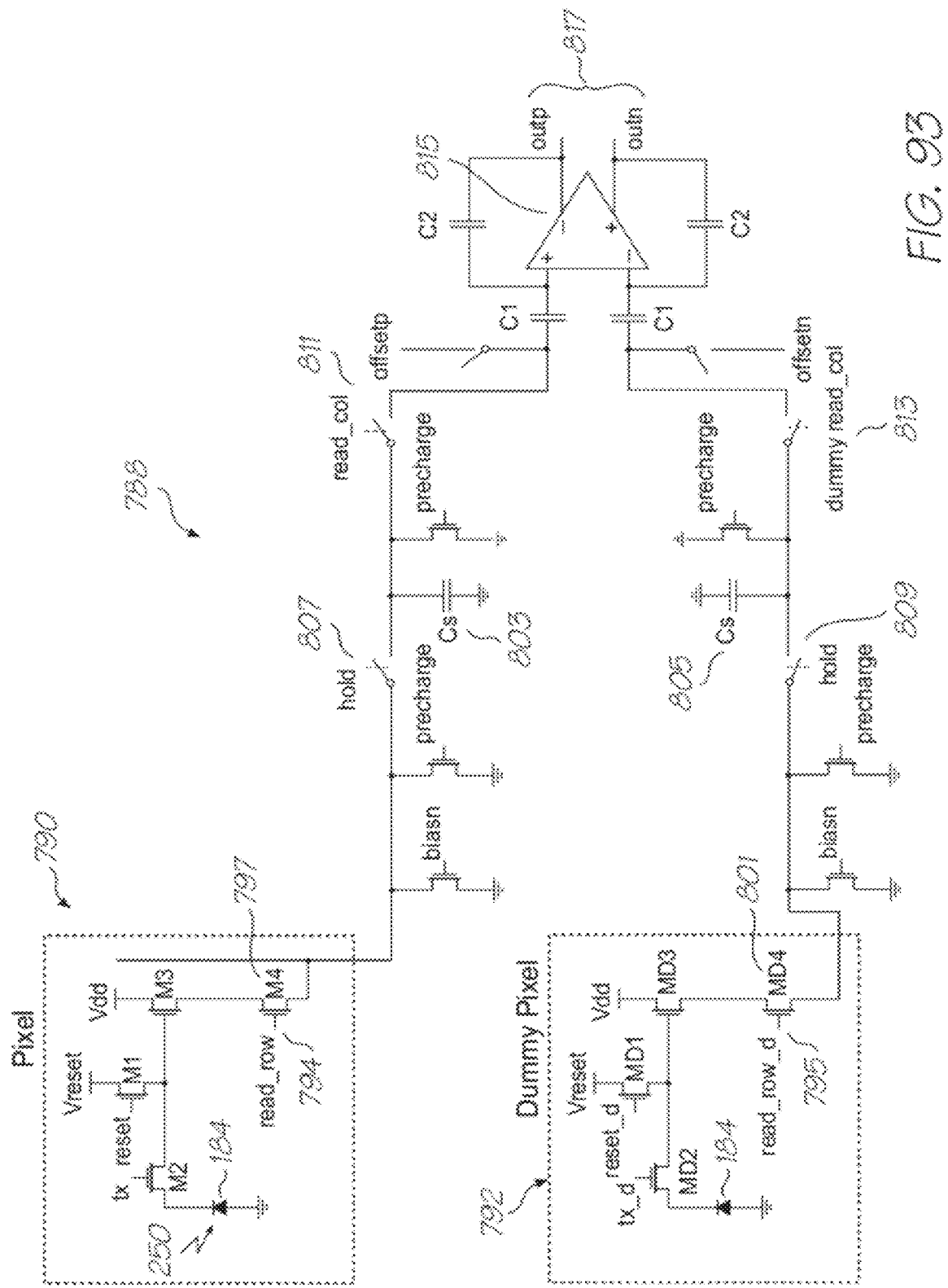
FIG. 93 is a circuit diagram of the differential imager.

FIG. 93 shows a differential imager circuit 788 used to substract the signal from the photodiode 184 corresponding to the calibration chamber 382 as a result of the applied electrical pulse, from the ECL signal from the surrounding hybridization chambers 180. The differential imager circuit 788 samples the signal from the pixel 790 and a "dummy" pixel 792. Signals arising from ambient light in the region of the chamber array are also subtracted. The signals from the pixel 790 are small (i.e. close to dark signal), and without a reference to a dark level it is hard to differentiate between the background and a very small signal.

During use, the "read_row" 794 and "read_row_d" 795 are activated and M4 797 MD4 801 transistors are turned on. Switches 807 and 809 are closed such that the outputs from the pixel 790 and "dummy" pixel 792 are stored on pixel capacitor 803 and dummy pixel capacitor 805 respectively. After the pixel signals have been stored, switches 807 and 809 are deactivated. Then the "read_col" switch 811 and dummy "read_col" switch 813 are closed, and the switched capacitor amplifier 815 at the output amplifies the differential signal 817.

ECL Levels and Signal Efficiency

The normal metric of efficiency in ECL is the number of photons obtained per "Faradaic" electron, i.e. per electron which participates in the electrochemistry. The ECL efficiency is denoted $\phi_{ECL}$:

$$\phi_{ECL} = \frac{\int_0^t I d\tau}{\left(\frac{N_A}{F}\right)\int_0^t i d\tau} \tag{5}$$

where I is the intensity in photons per second, i is the current in amperes, F is Faraday's constant, and $N_A$ is Avogadro's constant.

Efficiency of Coreactant ECL

Annihilation ECL in deoxygenated, aprotic solutions (e.g. nitrogen-flushed acetonitrile solutions) is simple enough to allow efficiency measurements, and the consensus value of $\phi_{ECL}$ is around 5%. Coreactant systems, however, have been generally declared to be beyond meaningful direct measurements of efficiency. Instead, emission intensity is related by scaling to easily-prepared standard solutions such as Ru(bpy)$_3^{2+}$, measured in the same format. The literature (see for example J. K. Leland and M. J. Powell, J. Electrochem. Soc., 137, 3127 (1990), and R. Pyati and M. M. Richter, Annu. Rep. Prog. Chem. C, 103, 12-78 (2007)) indicates that (without enhancers such as surfactants), the efficiency of Ru(bpy)$_3^{2+}$ ECL with TPrA coreactants peaks at levels comparable to the 5% seen for annihilation ECL in acetonitrile (e.g. 2% efficiency; see I. Rubinstein & A. J. Bard, J. Am. Chem. Soc., 103 512-516 (1981)).

ECL Potentials

The voltage at the working electrode for the Ru(bpy)$_3^{2+}$/TPrA system is approximately +1.1 V (generally measured in the literature with respect to a reference Ag/AgCl electrode). Voltages this high shorten electrode lifetimes but this is not an issue for single-use devices such as the LOC device used in the present diagnostic system.

The ideal voltage between the anode and cathode depends on the combination of solution components and electrode materials. Selecting the correct voltage can require compromising between the highest signal levels, reagent and electrode stability, and the activation of undesired side reactions such as electrolysis of the water in the chamber. In tests on buffered aqueous Ru(bpy)$_3$]$^{2+}$/coreactant solution and platinum electrodes, the ECL emission is maximized at 2.1-2.2 V (depending on the coreactant choice). Emission intensities drop to <75% of the peak values for voltages below 1.9 V and above 2.6 V, and to <50% of the peak values for voltages below 1.7 V and above 2.8 V. A preferred anode-cathode voltage difference for ECL operation in such systems is therefore 1.7-2.8 V, with the range 1.9-2.6 V being particularly preferred. This allows maximization of the emission intensity as a function of voltage, while avoiding voltages at which significant gas evolution at the electrodes is observed.

ECL Emission Wavelength

The wavelength of the emitted light 862 from ECL has an intensity peak at around 620 nm (measured in air or vacuum), and the emission spans a relatively broad wavelength range. Significant emission occurs at wavelengths from around 550 nm to 700 nm. Furthermore, the peak emission wavelength can vary by ~10% due to changes in the chemical environment around the active species. The LOC device embodiments described here, which incorporate no wavelength-specific filters, have two advantages for capturing signals with such a broad and variable spectrum. The first advantage is sensitivity: any wavelength filter reduces light transmission, even within its pass band, so efficiency is improved by not including a filter. The second advantage is flexibility: adjustment of filter pass bands is not required after minor reagent changes, and the signals are less dependent on minor differences in non-target components of the input sample.

Solution Volume Participating in ECL

ECL relies on the availability of luminophore (and coreactant) in solution. However, as illustrated in FIG. 97, the excited species 868 are generated only in the solution 872 near the electrodes 860 and 870. The parameter boundary layer depth in the models presented here, is the depth of the layer of solution 872 around the electrode 860 in which the excited species 868 are generated.

This is a simplification, since solution dynamics can drive the available concentration upward or downward:
Increased availability: diffusion and electrophoretic effects will allow exchange with more of the solution.
Decreased availability: reagents can adsorb onto the electrodes and may become unavailable to the ECL process.

For a boundary layer depth value of 0.5 µm, the following observations are made: ECL is observed in experiments where conjugation to magnetic beads with diameters up to 4.5 µm is used to attract the luminophore 864 to the anode 860.

$Ru(bpy)_3^{2+}$/TPrA ECL emission 862 as a function of electrode spacing, for interdigitated electrode arrays, was found to be maximised at a 0.8 µm electrode spacing. The requirement for a coreactant 866 in aqueous solutions 872 can be lifted when electrode spacings are ~2 µm. This indicates that the excited species 868 diffuse multiple microns, which implies diffusive exchange on a similar scale for the species in the ground state.

Steady State and Pulsed Operation

During pulsed activation of the electrodes 860 and 870, the intensity of the ECL emission 862 (see FIG. 130) is generally higher than the intensity of the emission 862 from steady-state activation of the electrodes. Accordingly, the activation signal to the electrodes 860 and 870 is pulse-width modulated (PWM) by the CMOS circuitry 86 (see FIG. 102).

Reagent Recycling and Species Lifetime

The Ru complex is not consumed in the $Ru(bpy)_3^{2+}$/TPrA ECL system, so the intensity of emission 862 does not reduce with successive reaction cycles. The lifetime of the rate-limiting step is approximately 0.2 milliseconds giving a total reaction recycling time of approximately 1 millisecond.

Electrophoretic Effects and Other Constraints

Given the complexity of the solutions in the hybridization chamber, a large number of phenomena take place when the ECL voltage is turned on. Electrophoresis of macromolecules, ohmic conduction, and capacitive effects from small ion migration occur simultaneously.

Electrophoresis of the oligonucleotides (probes and amplicon) can complicate the detection of probe-target hybrids, as DNA is highly negatively charged and attracted to the anode 860. The time scale for this motion is typically short (in the order of milliseconds). Electrophoretic effects are strong even though the voltages are moderate (~1 V), because the separation between the anode 860 and cathode 870 is small.

Electrophoresis enhances the ECL emission 862 in some embodiments of the LOC device and degrades the emission in others. This is addressed by increasing or decreasing the electrode spacing to get the associated increases or decreases in electrophoretic effect. Interdigitation of the anode 860 and the cathode 870 above the photodiode 184 represents the extreme case of minimizing this separation. Such an arrangement produces ECL, even in the absence of a coreactant 866 at carbon electrodes 860 and 870.

Ohmic Heating (DC Current)

The current required to maintain an ECL voltage of ~2.2 V, is determined as follows with reference to the ECL cell 874 schematically illustrated in FIG. 98.

The DC current through the chamber is determined by two resistances: the interface resistance $R_i$ between the electrodes 860 and 870 and the bulk of the solution, and the solution resistance $R_s$ which is derived from the bulk solution resistivity and conduction path geometry. For solutions with ionic strengths relevant to the conditions in LOC devices, the chamber resistance is dominated by interfacial resistances at the electrodes 860 and 870, and $R_s$ can be neglected.

The effect of the interfacial resistance is estimated by scaling measurements of macroscopic current flow through similar solutions for the electrode geometries in the LOC devices.

Macroscopic measurements of current density through a similar solution, at platinum electrodes, were taken. Consistent with the worst-case (high current) approach being taken, overall ionic strength and ECL reactant concentrations in the test solution were higher than those used in the LOC devices. The anode area was smaller than the cathode area, and was surrounded by a cathode with comparable area in a ring geometry. For an anode consisting of a circle 2 mm in diameter, the current measured was 1.1 mA, giving a current density of 350 $A/m^2$.

Figure 98:
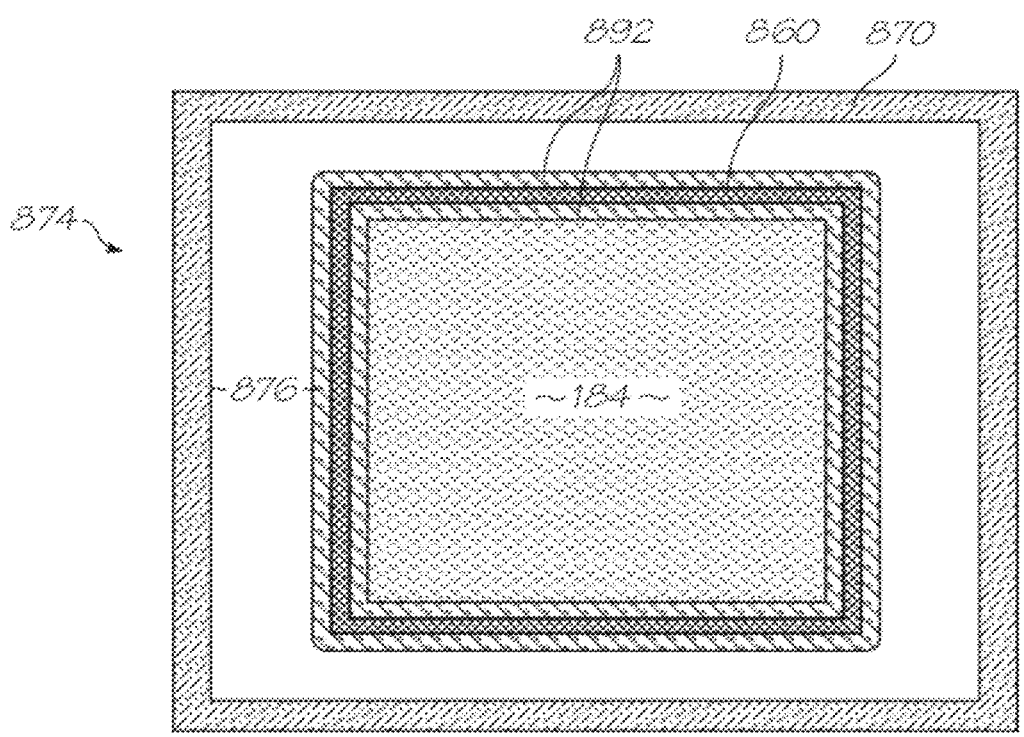
FIG. 98 schematically illustrates an anode in a ring geometry around the peripheral edge of a photodiode.

In the heating model, the electrode area is for the square ring geometry schematically illustrated in FIG. 98. The anode is a ring with width 1 µm and thickness 1 µm. The surface area is 196 square microns, and therefore the calculated current I=69 nA.

The heating (power=$V^2/R$) was modelled for the worst case in which all the heat goes into raising the temperature of the water in the chamber. This leads to heating of chamber contents at 5.8° C./s, at a voltage difference of 2.2 V, if no allowance for heat removal by the bulk of the LOC device is made.

Heating of the chambers by ~20° C. can cause denaturation of most hybridization probes. For highly specific probes intended for mutation detection, it is preferable to further restrict heating to 4° C. or less. With this level of temperature stability, single base mismatch-sensitive hybridization, using appropriately designed sequences, becomes feasible. This allows the detection of mutations and allelic differences at the level of single nucleotide polymorphisms. Hence the DC current is applied to the electrodes 860 and 870 for 0.69 s, to limit the heating to 4° C.

A current of ~69 nA passing through the chamber is far more than can be accommodated as Faradaic current by the ECL species at micromolar concentrations. Therefore, low-duty-cycle pulsing of the electrodes 860 and 870 to further reduce heating (to 1° C. or less) while maintaining sufficient ECL emission 862, does not introduce complications associated with reagent depletion. In other embodiments, the current is reduced to 0.1 nA which removes the need for pulsed activation of the electrodes. Even at currents as low as 0.1 nA, the ECL emission 862 is luminophore-limited.

Chamber and Electrode Geometry

Maximizing Optical Coupling Between ECL Luminescence and Photosensor

The immediate chemical precursors of ECL luminescence are generated within nanometers of the working electrode. Referring again to FIG. 97, light emission (the excited species 868) generally occurs within microns or less of that location. Hence the volume immediately adjacent to the working electrode (anode 860) is visible to the corresponding photodiode 184 of the photosensor 44. Accordingly, the electrodes 860 and 870 are directly adjacent the active surface area 185 of the corresponding photodiode 184 in the photosensor 44. Furthermore, the anode 860 is shaped to increase the length of its lateral periphery 'seen' by the photodiode 184. This aims to maximize the volume of excited species 868 that can be detected by the underlying photodiode 184.

Figure 96:
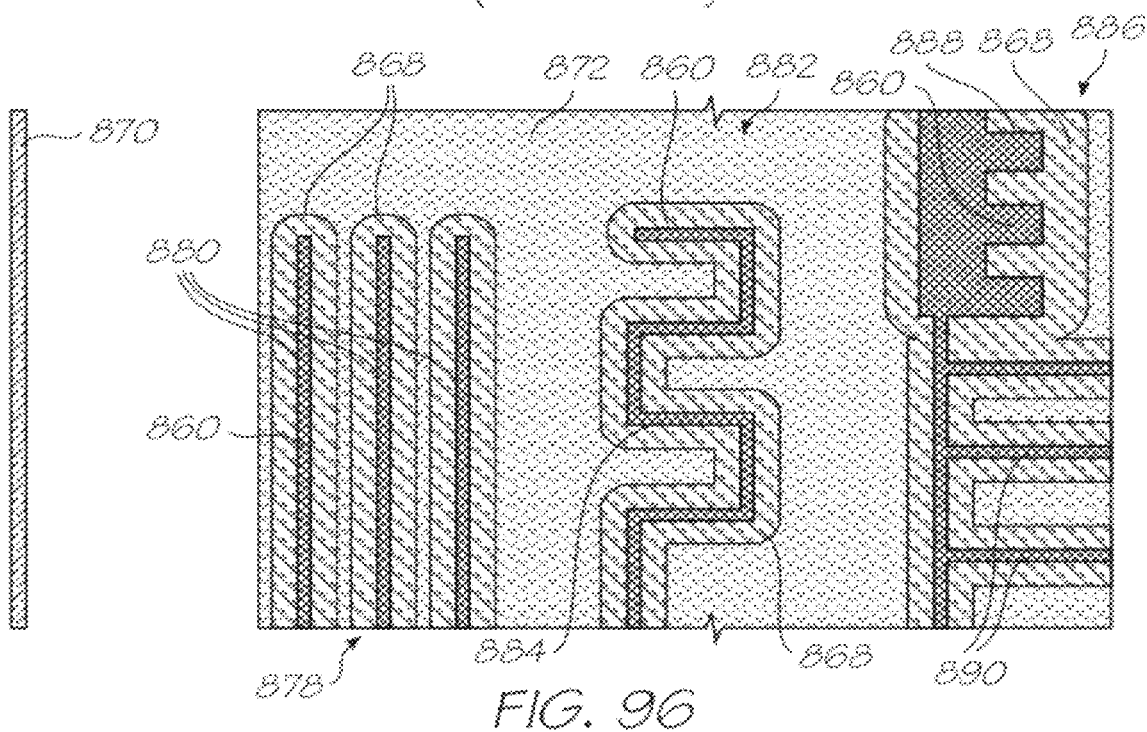
FIG. 96 schematically illustrates three different anode configurations.
Figure 103:
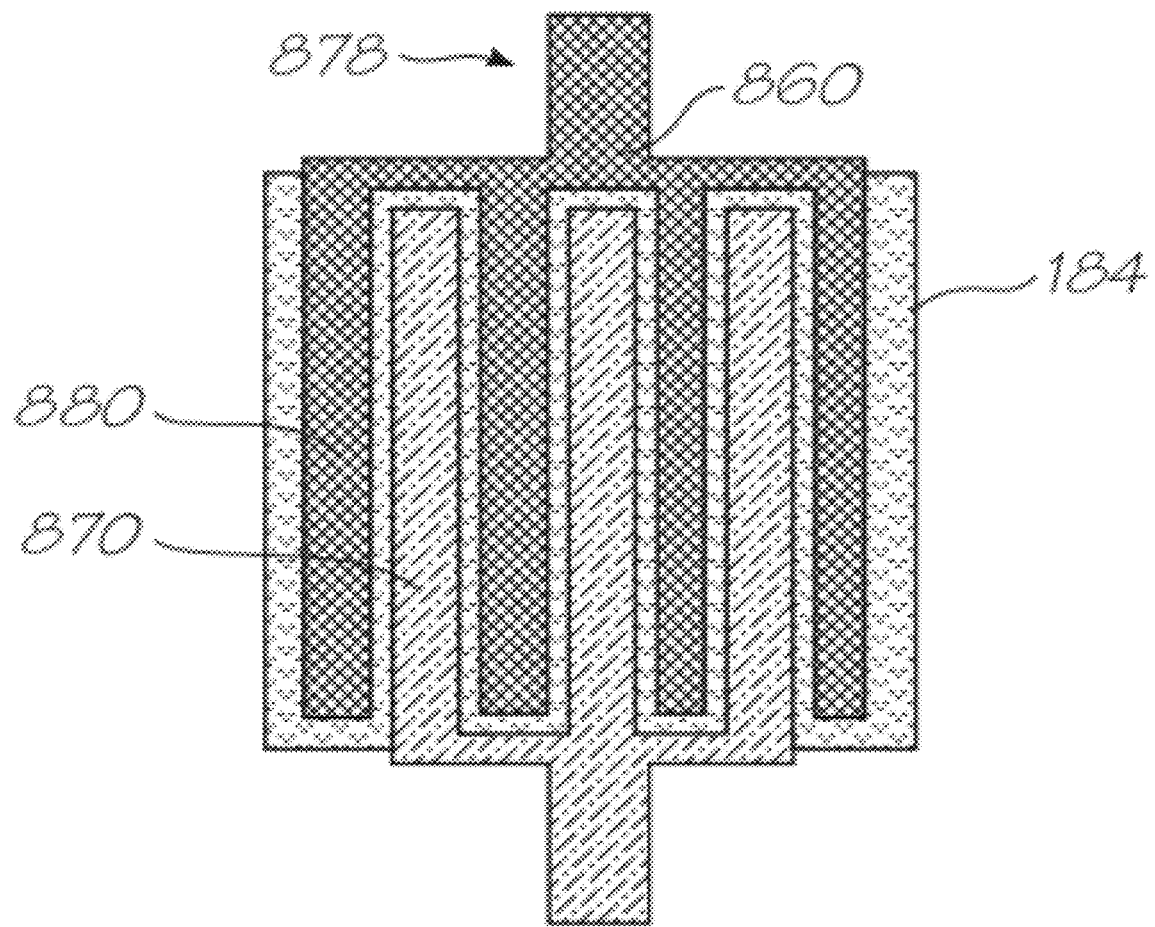
FIG. 103 schematically illustrates an anode interdigitated with a cathode.

FIG. 96 schematically illustrates three embodiments of the anode 860. A comb structure anode 878 has the advantage that the parallel fingers 880 can be interdigitated with the fingers of a cathode 870. The interdigitated configuration is shown in FIG. 103, and in a partial view of a LOC layout in FIGS. 120 and 124. The interdigitated configuration provides a uniform dielectric gap 876 (see FIG. 97) that is relatively narrow (1 to 2 microns) and the interdigitated comb structure is relatively simple for the lithographic fabrication process. As discussed above, a relatively narrow dielectric gap 876 between the electrodes 860 and 870 obviates the need for a coreactant in some solutions 872, as the excited species 868 will diffuse between anode and cathode. The removal of the requirement for a coreactant removes the potential chemical impact of the coreactant on the various assay chemistries and provides a wider range of possible assay options.

Referring again to FIG. 96, some embodiments of the anode 860 have a serpentine configuration 882. To achieve high periphery length while maintaining tolerance against fabrication errors, it is convenient to form wide, rectangular meanders 884.

The anode may have a more complex configuration 886 if necessary or desirable. For example, it may have a crenulated section 888, a branched structure 890, or a combination of the two. Partial views of LOC designs incorporating a branched structure 890 are shown in FIGS. 138 and 139. The more complicated configurations such as 886 provide a long length of lateral periphery, and are best suited to solution chemistries where a coreactant is employed since patterning a closely-spaced opposing cathode is more difficult.

Electrode Thickness

Generally, ECL cells involve a planar working electrode which is viewed externally. Also, traditional microfabrication techniques for metal layers tend to lead to planar structures with metal thicknesses of approximately 1 micron. As has been indicated earlier, and shown schematically in FIGS. 96, 99 and 100, increasing the length of lateral periphery enhances the coupling between the ECL emission and the photodiode 184.

A second strategy to further increase the efficiency of collection of emitted light 862 (see FIG. 130) by the photodiode 184 is to increase the thickness of the anode 860. This is shown schematically in FIG. 97. The part of the participating volume 892 adjacent to the walls of the working electrode is the region most efficiently coupled to the photodiode 184. Therefore, for a given width of working electrode 860, the overall collection efficiency of the emitted light 862 can be improved by increasing the thickness of the electrodes. Further, since high current carrying capacity is not required, the width of the working electrode 860 is reduced as far as is practical. The thickness of the electrodes 860 and 870 can not increase without restrictions. Noting that the feature and separation sizes of the electrodes are likely to be of the order of 1 micron, and that liquid filling makes gaps which are wider than they are deep unfavourable, the optimum practical thickness for the electrodes is 0.25 micron to 2 microns.

Electrode Spacing

Figure 100:
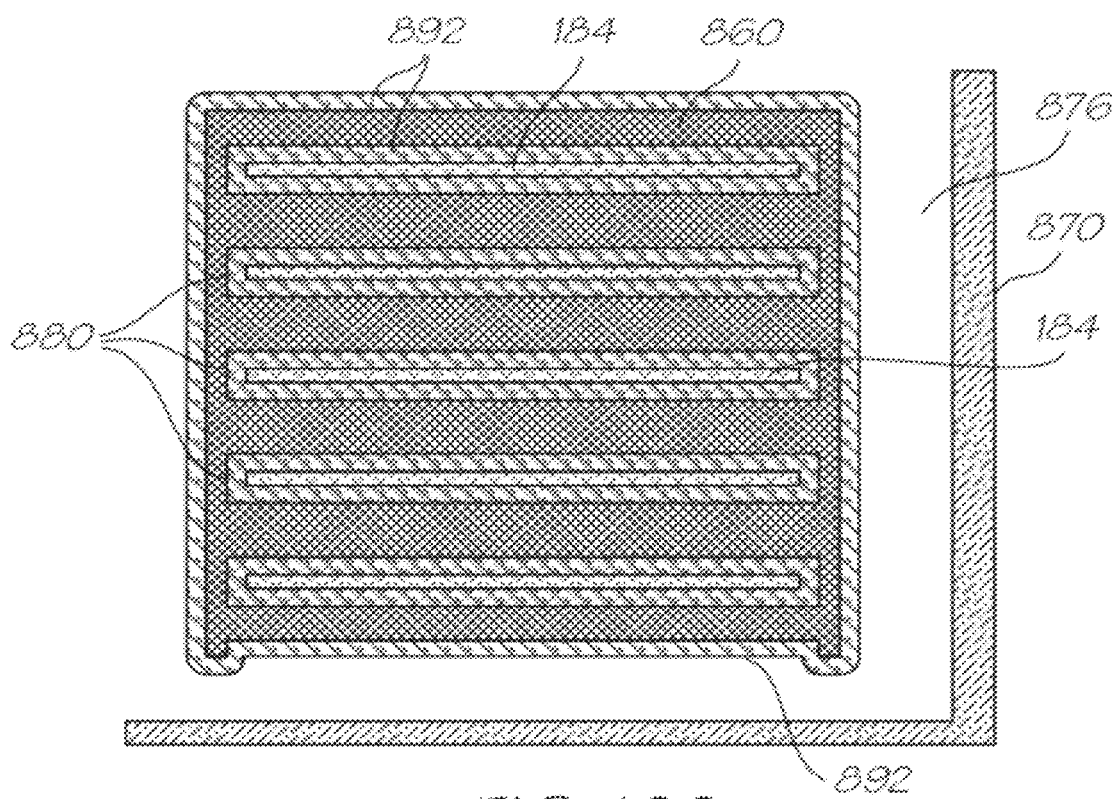
FIG. 100 schematically illustrates an anode with a series of fingers to increase the length of its lateral edges.

The spacing between the electrodes 860 and 870 is important for the quality of signals in LOC devices, particularly in embodiments where the electrodes are interdigitated. In embodiments where the anode 860 is a branched structure such as shown in FIG. 96 and FIG. 100, the spacing between adjacent elements can also be important. ECL emission efficiency, and the collection efficiency of the emitted light, should both be maximised.

Generation of ECL emission tends to favour electrode spacings on the order of one micron or less. Small spacings are particularly attractive when performing ECL in the absence of a coreactant. The fact that the spacing can be comparable to the wavelength of the emitted light 862 is of limited importance. Therefore, in many embodiments where the emitted light 862 (see FIG. 130) is measured at a location which does not require that the light have passed between the electrodes 860 and 870, making the electrode spacing as small as practical is often the goal. In embodiments where the emitted light 862 must pass between the electrodes 860 and 870, however, it becomes necessary to move beyond considering just the ECL emission process, and consider the wave properties of light.

The wavelength of the emitted light 862 from ECL of $Ru(bpy)_3^{2+}$ is around 620 nm, and therefore 460 nm (0.46 microns) in water. In embodiments where the photodiode 184 and the ECL excited species 868 are on different sides of the electrode structure, and the electrode structure is metallic, the emitted light 862 must pass through a gap between elements of the metallic structures. If this gap is comparable to the wavelength of the light, diffraction generally reduces the intensity of propagating light which reaches the photodiode 184. In cases where the emitted light 862 is incident on the gap at large angles, however, evanescent mode coupling can be harnessed to improve the strength of collected signals. Two measures are taken in the LOC devices to enhance the efficiency of coupling between the photodiode 184 and the emitted light 862.

First, the separation between metallic elements is not reduced below approximately the wavelength of the emitted light in water, i.e. approximately 0.4 microns. When combined with other observations regarding small separations between interdigitated electrodes, this indicates an optimal range for the electrode spacing of 0.4 to 2 microns.

Second, the distance from the gap between elements to the photodiode 184 is minimised. In the LOC device embodiments described here, this indicates that the total thickness of layers between the electrodes 860 and 870 and the photodiode 184 be one micron or less. In embodiments where multiple layers are present between the electrodes and the photodiode, arranging their thicknesses to be quarter-wave or three-quarter wave layers has the further benefit of suppressing reflection of the emitted light 862.

Electrode Models

FIG. 97 is a schematic partial cross-section of the electrodes 860 and 870 in the hybridization chamber. The volume around the lateral periphery of the anode 860 occupied by the excited species 868, is sometimes referred to as the participating volume 892. The occluded region 894 above the anode 860 is ignored because its optical coupling to the photodiode 184 is negligible.

A technique for determining whether a particular electrode configuration provides a foundation for the level of ECL emission 862 for the underlying photodiode 184 is set out below with reference to FIGS. 98, 99 and 100.

FIG. 98 is a ring geometry in which the anode 860 is around the edge of photodiode 184. In FIG. 99, the anode 860 is positioned within the periphery of the photodiode 184. FIG. 100 shows a more complex configuration in which the anode 860 has a series of parallel fingers 880 to increase the length of its lateral edges.

For all of the above configurations, the model calculations are as follows. For a participating volume 892 of solution $V_{ECL}$, the total effective number of emitters $N_{em}$ is:

$$N_{em} = N_{lum} \tau_p / \tau_{ECL} = V_{ECL} C_L N_A \tau_p / \tau_{ECL} \quad (6)$$

where the participating number of luminophores $N_{lum} = V_{ECL} C_L N_A$, $\tau_{ECL}$ is the lifetime of the ECL process, $C_L$ is the luminophore concentration, $\tau_p$ is the pulse duration, and $N_A$ is Avogadro's number.

The number of isotropically emitted photons $N_{phot}$ is:

$$N_{phot} = \phi_{ECL} N_{em} \quad (7)$$

where $\phi_{ECL}$ is the ECL efficiency, defined as the average number of photons emitted by the ECL reaction of a single luminophore.

The signal count of electrons, S, from the photodiode is then $$S = N_{phot} \phi_o \phi_q, \quad (8)$$

where $\phi_o$ is the optical coupling efficiency (the number of photons absorbed by the photodiode 184) and $\phi_q$ is the photodiode quantum efficiency. The signal is therefore:

$$S = V_{ECL} C_L N_A \frac{\tau_p}{\tau_{ECL}} \phi_{ECL} \phi_o \phi_q \quad (9)$$

Figure 99:
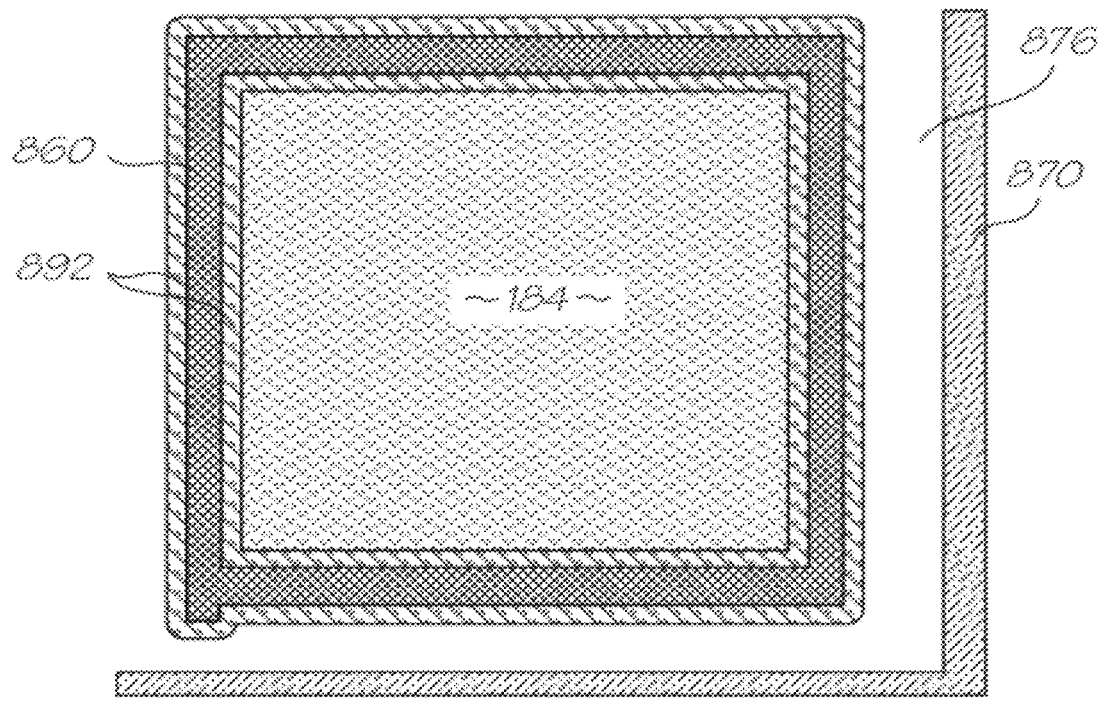
FIG. 99 schematically illustrates an anode in a ring geometry within the peripheral edge of a photodiode.

For FIGS. 98 and 99 electrode configurations, $\phi_o$ is:

$\phi_o$=(25% photons which are directed towards the photodiode 184)×(10% of photons which are not reflected)

i.e., $\phi_o$=2.5% for configurations shown in FIGS. 98 and 99

For the electrode configuration of FIG. 100, 50% of photons are emitted in a direction pointing towards the photodiode 184, but the absorption efficiency as a function of angle is unchanged, so $\phi_o$=(50% photons which are directed towards the photodiode)×(10% of photons which are not reflected)

i.e., $\phi_o$=5% for the configuration of FIG. 100.

The participating volume 892 depends on the electrode configuration, and details are presented in the corresponding sections.

The input parameters for the calculations are listed in the following:

TABLE 5

Input Parameters

| Parameter | Value | Comment |
|---|---|---|
| Luminophore concentration $C_L$ | 2.89 μM | Probe concentration calculated previously |
| ECL recycling period | 1 ms | Combined lifetimes of |

TABLE 5-continued

Input Parameters

| Parameter | Value | Comment |
|---|---|---|
| (lifetime) $\tau_{ECL}$ | | reaction steps for luminophore. |
| Boundary layer depth D | 0.5 μm | Effective volume (including diffusion and electrophoresis) of solution participating in ECL |
| Duration of current application $\tau_p$ | 0.69 s | Chosen to limit ohmic heating to 4° C. (as described previously) |
| Chamber X dimension | 28 μm | |
| Chamber Y dimension | 28 μm | |
| Chamber height Z | 8 μm | |
| Photodiode X dimension | 16 μm | |
| Photodiode Y dimension | 16 μm | |
| Electrode thickness (i.e., exposed edge height) | 1 μm | |
| Electrode layer minimum width and gap | 1 μm | Process critical dimension |
| Electrode interfacial current density | 350 A/m² | For ohmic heating |
| Solution volume resistivity | 0.5 Ω·m | For ohmic heating |
| Voltage difference applied (working – counter electrode) | 2.2 V | |

Ring Geometry Around Periphery of Photodiode

Referring to FIG. 98, the anode 860 is a ring around the edge of the photodiode 184. In this configuration, the participating volume 892 is:

$V_{ECL}$=4×[(layer beside the electrode wall)+(quarter-cylinder above the electrode wall)]

Calculation Results:

Photons generated from a 0.5 μm boundary layer: 3.1×10⁵
Electron counts in photodiode: 2.3×10³

This signal is readily detectable by the underlying photodiode 184 of the LOC device photosensor 44.

Additional Fingers to Increase Edge Length

Referring to FIG. 100, parallel fingers 880 are added across the anode 860. Only horizontal edges shown in figure contribute to the participating volume 892, to avoid double-counting the perpendicular edges. The participating volume 892 is then:

$V_{ECL}$=(8×2)×[(layer beside the electrode wall)+(quarter-cylinder above the electrode wall)]

Calculation Results for FIG. 100 Configuration:

Photons generated from a 0.5 μm boundary layer: 1.1×10⁶
Electron counts in photodiode 184: 8.0×10³

This signal is easily detectable in the photodiode 184.

Complete Overlay

Figure 101:
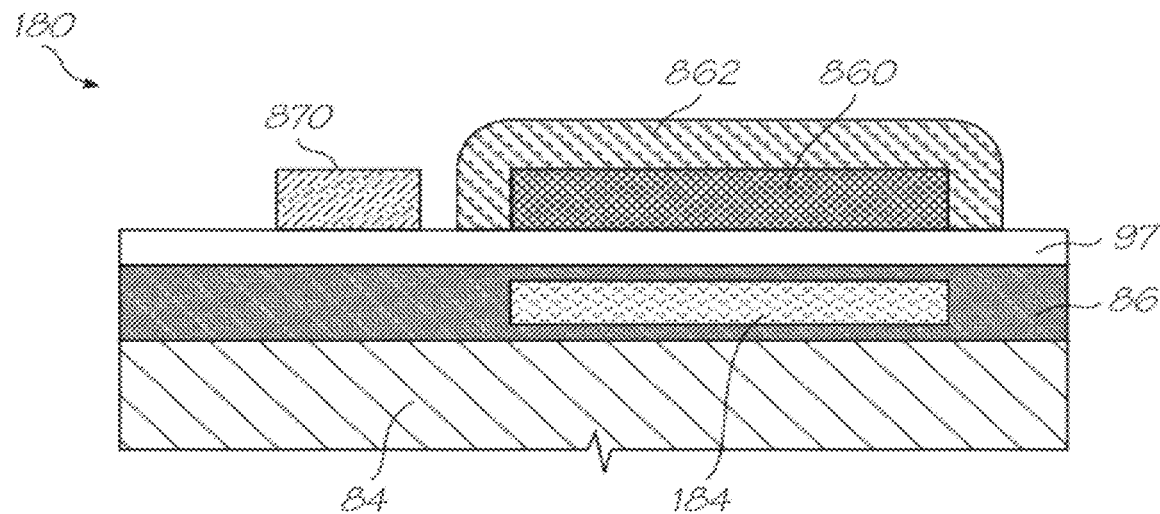
FIG. 101 schematically illustrates the use of a transparent anode to maximise surface area coupling and ECL signal detection.
Figure 102:
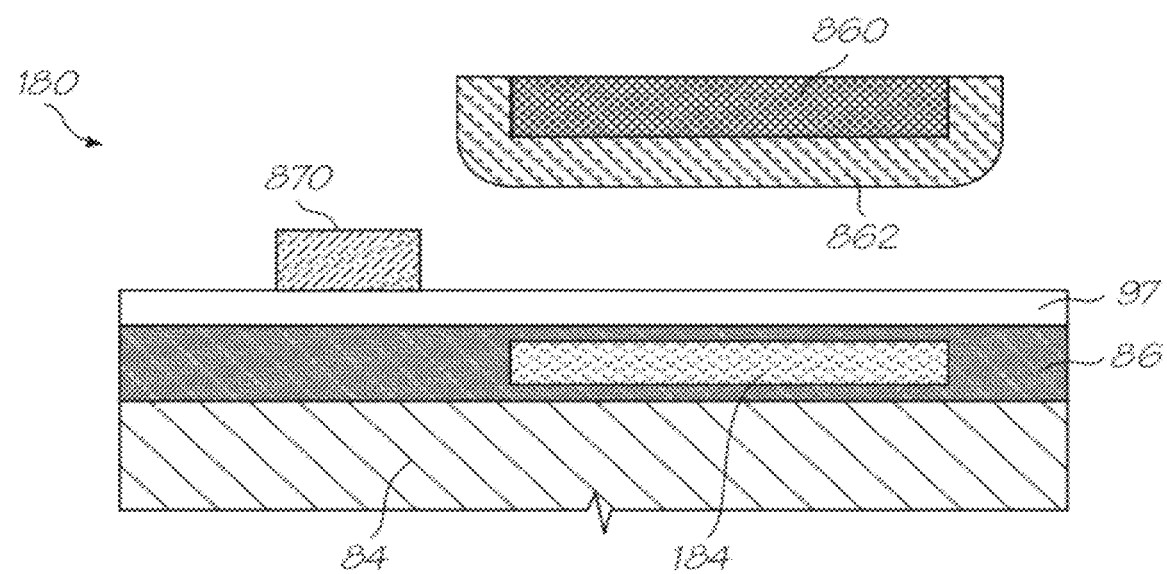
FIG. 102 schematically illustrates the use of an anode affixed to the roof of the hybridization chamber to maximise surface area coupling and ECL signal detection.

This configuration shown in FIG. 101 and FIG. 102 is included as a limiting case of maximum surface area coupling. In practice, 90% or better coupling between the electrode surface area and the active surface area 185 of the photodiode 184 achieves a nearly optimal result, and even coupling of 50% of the photodiode active surface area 185 to the electrode surface area provides most of the benefit of the complete overlay configuration. Complete overlay can be achieved in two embodiments: first, as indicated schematically in FIG. 101, by employing a transparent anode 860, in a plane parallel with that of the photodiode 184 and with an area matched to that of the photodiode, and arranging the anode in immediate proximity to the photodiode 184, such that emitted light 862 passes through the anode and onto the photodiode. In a second embodiment shown schematically in FIG. 102, the anode 860 is again parallel to and registered with the photodiode area, but the solution 872 fills a void between the anode 860 and the photodiode 184. For signal modelling of a complete overlay configuration, the anode is assumed to be a complete layer above the photodiode 184, with half of the photons directed toward the photodiode 184 (absorption efficiency still 10%).

Photons generated from a 0.5 µm boundary layer: $7.7\times10^5$
Electron counts in photodiode: $1.2\times10^4$ It is possible to improve the signal and assay beyond the above models by using surfactants and probe immobilization at the anode.

Maximum Spacing Between ECL Probes and Photodiode

The on-chip detection of hybridization avoids the needs for detection via confocal microscopy (see Background of the Invention). This departure from traditional detection techniques is a significant factor in the time and cost savings associated with this system. Traditional detection requires imaging optics which necessarily uses lenses or curved mirrors. By adopting non-imaging optics, the diagnostic system avoids the need for a complex and bulky optical train. Positioning the photodiode very close to the probes has the advantage of extremely high collection efficiency: when the thickness of the material between the probes and the photodiode is on the order of 1 micron, the angle of collection of emission light is up to 174°. This angle is calculated by considering light emitted from a probe at the centroid of the face of the hybridization chamber closest to the photodiode, which has a planar active surface parallel to that chamber face. The cone of emission angles within which light is able to be absorbed by the photodiode is defined as having the emitting probe at its vertex and the corner of the sensor on the perimeter of its planar face. For a 16 micron×16 micron sensor, the vertex angle of this cone is 170°; in the limiting case where the photodiode is expanded so that its area matches that of the 28 micron×26.5 micron hybridization chamber, the vertex angle is 174°. A separation between the chamber face and the photodiode active surface of 1 micron or less is readily achievable.

Employing a non-imaging optics scheme does require the photodiode 184 to be very close to the hybridization chamber in order to collect sufficient photons of fluorescence emission. The maximum spacing between the photodiode and probes is determined as follows.

Utilizing a ruthenium chelate luminophore and the electrode configuration of FIG. 100, we calculated 27,000 photons being absorbed by our 16 micron×16 micron sensor from the respective hybridization chamber, to generate 8000 electrons assuming a sensor quantum efficiency of 30%. In performing this calculation we assumed that the light-collecting region of our hybridization chamber has a base area which is the same as our sensor area, one quarter of the total number of the hybridization photons is angled so as to reach the sensor, and a conservative 10% estimate for the proportion of photons which do not scatter away from the sensor-dielectric interface. That is, the light gathering efficiency of the optical system is $\phi_0=0.025$.

More accurately we can write $\phi_0=$[(base area of the light-collecting region of the hybridization chamber)/(photodetector area)][$\Omega/4\pi$][10% absorbed], where $\Omega=$solid angle subtended by the photodetector at a representative point on the base of the hybridization chamber. For a right square pyramid geometry:

$$\Omega = 4\arcsin(a^2/(4d_0^2+a^2)), \text{ where } d_0=\text{distance between the chamber and the photodiode, and } a \text{ is the photodiode dimension.}$$

Each hybridization chamber releases $1.1\times10^6$ photons. The selected photodetector has a detection threshold of 17 photons, and for values of $d_0$ greater than ten times the sensor size (i.e., essentially normal incidence) the proportion of photons not reflected at the sensor surface can be increased from 10% to 90%. Therefore, the minimum optical efficiency required is:

$$\phi_0=17/(1.1\times10^6\times0.9)=1.72\times10^{-5}$$

The base area of the light-emitting region of the hybridization chamber 180 is 29 micron×19.75 micron.

Solving for $d_0$, we will get the maximum limiting distance between the bottom of our hybridization chamber and our photodetector to be $d_0=1600$ microns. In this limit, the collection cone angle as defined above is only 0.8°. It should be noted this analysis ignores the negligible effect of refraction.

LOC Variants

The LOC device 301 described and illustrated above in full is just one of many possible LOC device designs. Variations of the LOC device that use different combinations of the various functional sections described above will now be described and/or shown as schematic flow-charts, from sample inlet to detection, to illustrate some of the combinations possible. The flow-charts have been divided, where appropriate, into sample input and preparation stage 288, extraction stage 290, incubation stage 291, amplification stage 292, pre-hybridization stage 293 and detection stage 294. For all the LOC variants that are briefly described or shown only in schematic form, the accompanying full layouts are not shown for reasons of clarity and succinctness. Also in the interests of clarity, smaller functional units such as liquid sensors and temperature sensors are not shown but it will be appreciated that these have been incorporated into the appropriate locations in each of the following LOC device designs.

LOC Device with ECL Detection

FIGS. 111 to 127 show a LOC variant 729 with electrochemiluminescence (ECL) detection. This LOC device prepares 288, extracts 290, incubates 291, amplifies 292 and detects 294 both human and pathogen nucleic acids, as well as human and pathogen protein detection. ECL is used in the hybridization chamber arrays and proteomic assay chamber arrays for target detection.

As best shown in FIG. 117, a biological sample (for example, whole blood) is added to the sample inlet 68. The sample flows through the cap channel 94 to the anticoagulant surface tension valve 118. The cap 46 is fabricated with an interface layer 594 positioned between the cap channel layer 80 and the MST channel layer 100 of the CMOS+MST device 48 (see FIG. 112). The interface layer 594 allows a more complex fluidic interconnection between the reagent reservoirs and the MST layer 87 without increasing the size of the silicon substrate 84.

Figure 113:
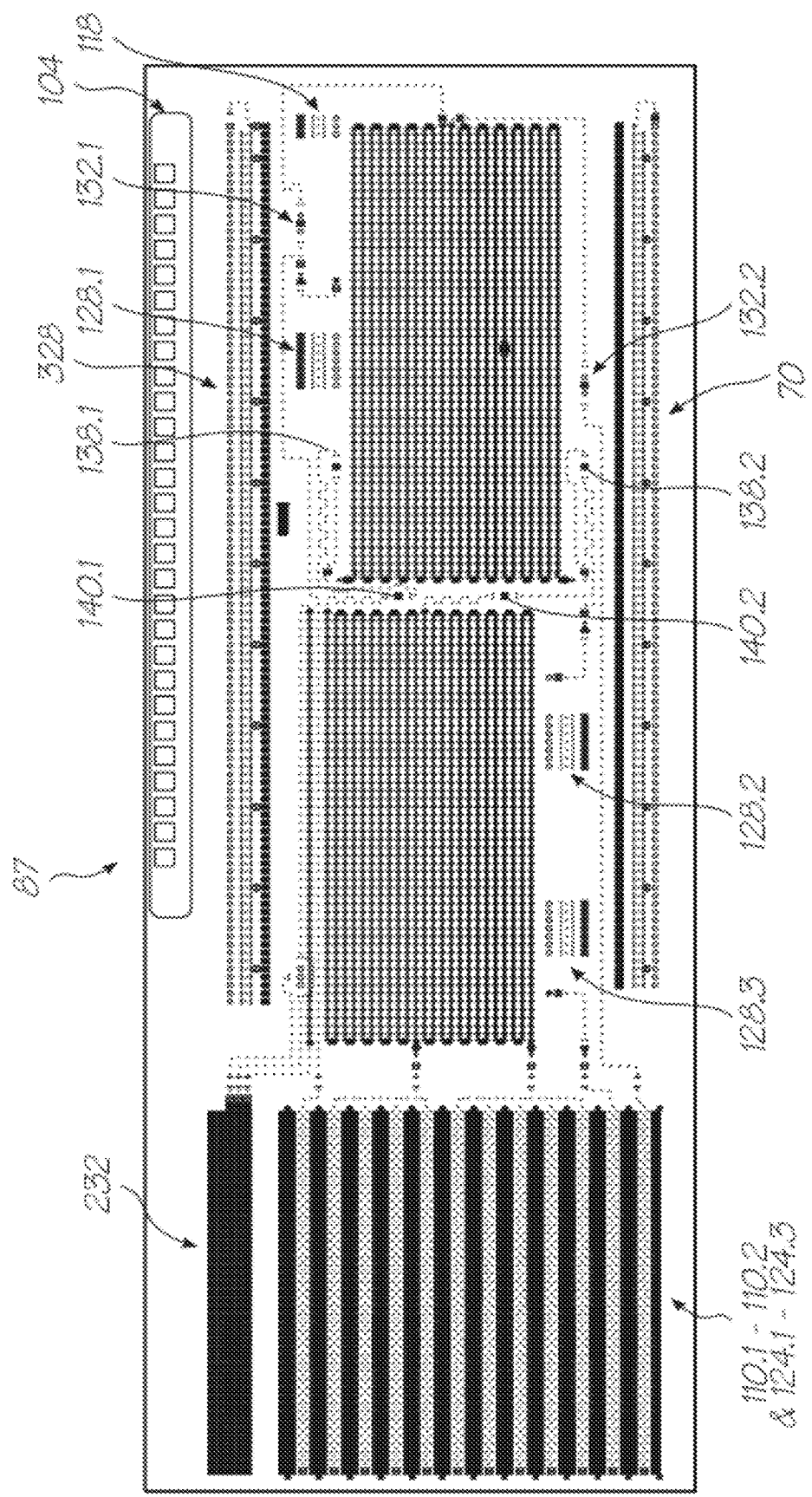
FIG. 113 is a plan view of LOC variant L showing the structures of the CMOS+MST device in isolation.
Figure 114:
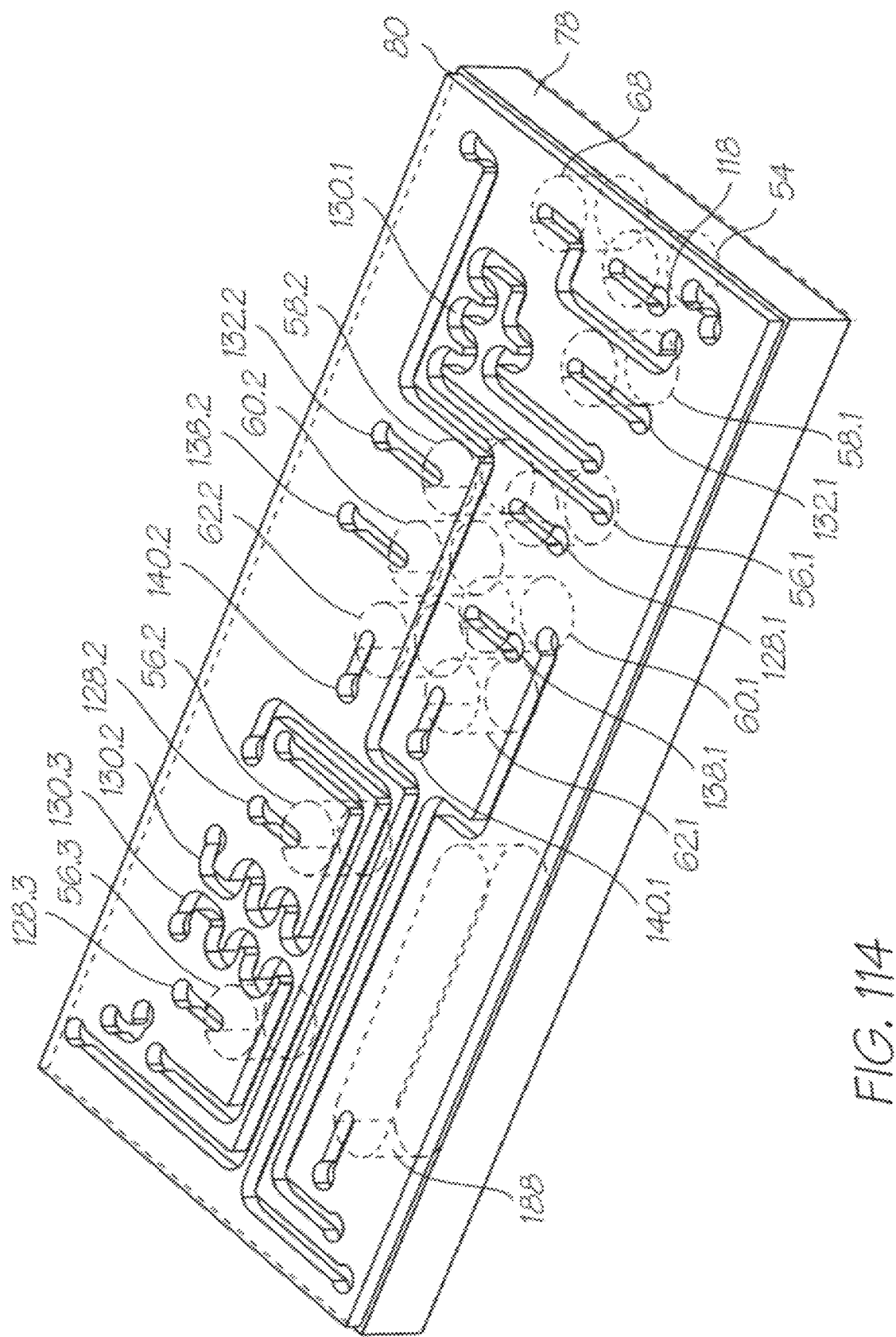
FIG. 114 is a perspective view of the underside of the cap of LOC variant L with the reagent reservoirs shown in dotted lines.
Figure 115:
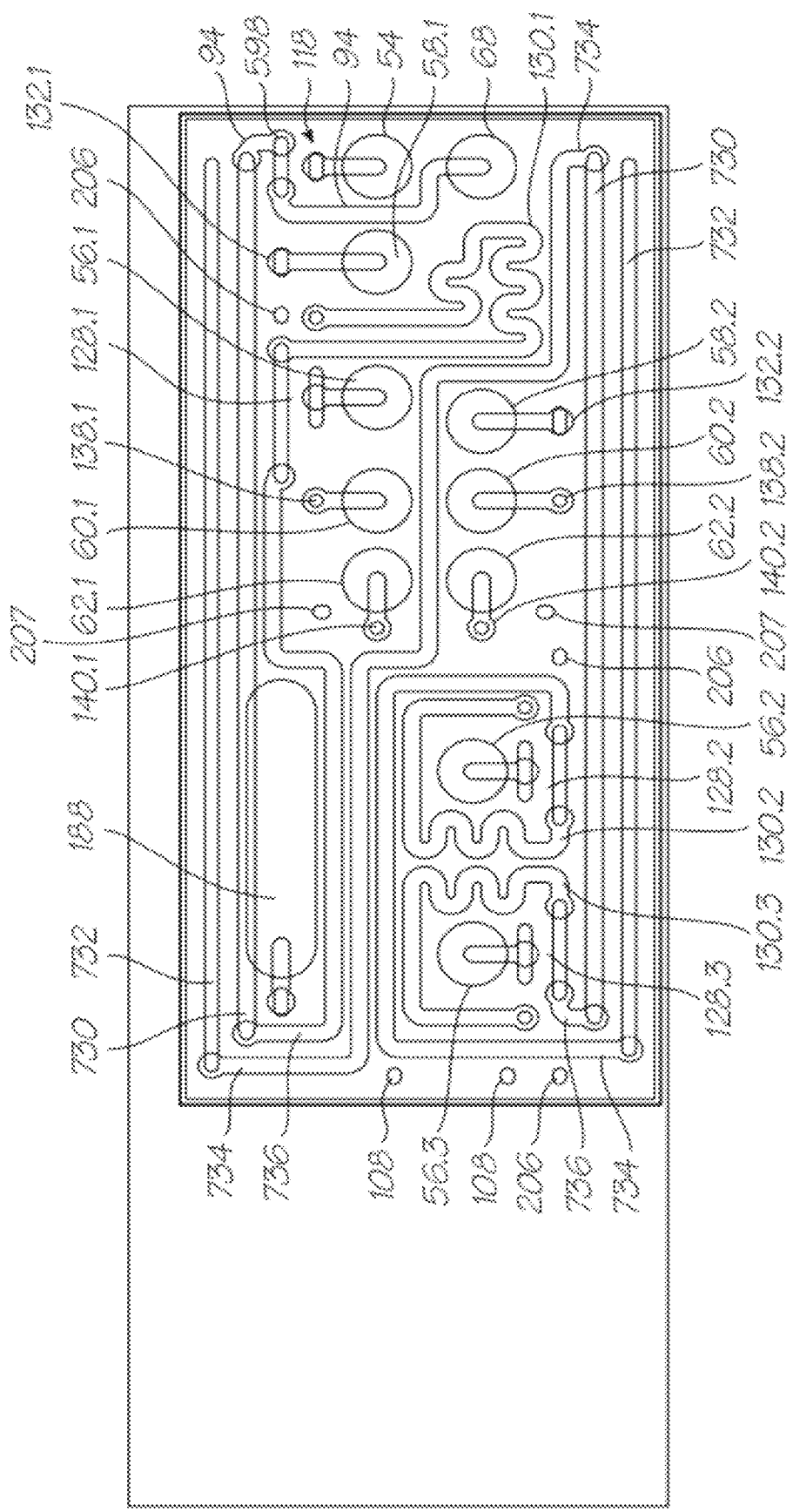
FIG. 115 is a plan view of LOC variant L showing the features of the cap in isolation.

FIG. 113 shows the MST layer 87 visible on the top surface of the CMOS+MST device 48. FIG. 114 shows the cap channel layer 80 on the underside of the cap 46. FIG. 115 superimposes the reservoirs, the cap channels 94 and the interface channels to illustrate the more sophisticated plumbing achieved with a cap 46 incorporating an interface layer 594.

As best shown in FIG. 117, the interface layer 594 requires the anticoagulant surface tension valve 118 to have two interface channels 596 and 598. A reservoir-side interface channel 596 connects the reservoir outlet with the downtakes 92 and a sample-side interface channel 598 connects the uptakes 96 with the cap channel 94.

Anticoagulant from the reservoir 54 flows through the MST channels 90 via the reservoir-side interface channel 596 to pin a meniscus at the uptakes 96. The sample flow along the cap channel 94 dips into the sample-side interface channel 598 to remove the meniscus so that the anticoagulant combines with the blood sample as it continues onto the leukocyte dialysis section 328.

The leukocyte dialysis section 328 incorporates a bypass channel 600 for filling the flow channel structures without trapped air bubbles (see FIGS. 117 and 126). The blood sample flows through cap channel 94 to the upstream end of the large constituents interface channel 730. The large constituents interface channel 730 is in fluid communication with the dialysis MST channels 204 via apertures in the form of 7.5 micron diameter holes 165 (see FIG. 126).

Referring to FIG. 126, each of the dialysis MST channels 204 lead from the 7.5 micron diameter holes 165 to respective dialysis uptakes 168. The dialysis uptake holes 168 are open to the small constituents interface channel 732. However the uptakes are configured to pin a meniscus rather than allow capillary driven flow to continue. The uptake belonging to the bypass channel 600 has a capillary initiation feature 202 configured to initiate capillary driven flow into the small constituents interface channel 732. This ensures the flow begins at the upstream end of the small constituents interface channel 732 and sequentially unpins the menisci at the dialysis uptakes 168 as the flow progresses downstream.

FIG. 121 shows the downstream end of the leukocyte dialysis section 328. The large constituents interface channel 730 feeds into the large constituents cap channel 736 and the small constituents interface channel 732 feeds the small constituents cap channel 734. As best shown in FIG. 115, the large constituents cap channel 736 feeds the leukocytes (and any other large constituents) into the chemical lysis section 130.1 via the lysis surface tension valve 128.1 where lysis reagent from reservoir 56.1 is added. The chemical lysis section 130.1 has a 3 micron filter downtake 738 at the outlet (see FIG. 117). The filter downtake ensures that no large constituents reach the lysis chamber exit boiling-initiated valve 206. After sufficient time, the boiling-initiated valve 206 opens the chemical lysis section 130.1 outlet and the sample flow is split into two streams. As best shown in FIG. 117, one stream flows to the surface tension valve 132.1 for the first restriction enzyme, ligase and linker reservoir 58.1 and the other stream is drawn along a lysed leukocyte bypass channel 742 directly to the proteomic assay chamber array 124.1 in the hybridization and detection section 294. Here the sample fills the proteomic assay chamber array 124.1 (see FIG. 119) containing probes for hybridization with target human proteins. Probe-target hybrids are detected with a photosensor 44 (see FIG. 111). The other stream flows into the leukocyte incubation section 114.1 together with restriction enzymes, ligase and linker primers from reservoir 58.1.

Referring to FIG. 118, after restriction enzyme digestion and linker ligation, the incubator outlet valve 207 (also a boiling-initiated valve) opens and flow continues into the leukocyte DNA amplification section 112.1. The amplification mix and polymerase in reservoirs 60.1 and 62.1 are added via surface tension valves 138.1 and 140.1 respectively. Referring to FIG. 119, after thermal cycling, the boiling-initiated valve 108 opens for the amplicon to enter the hybridization chamber array 110.1 containing probes for human DNA targets. Probe-target hybrids are detected with the photosensor 44.

The erythrocytes and pathogens from the leukocyte dialysis section 328 are fed to the pathogen dialysis section 70 via the cap channel 734 (see FIGS. 117 and 127). This operates in the same manner as the leukocyte dialysis section 328 with the exception that the filter downtakes have 3 micron holes 164 instead of the 7.5 micron holes 165 used for leukocyte dialysis. The erythrocytes remain in the large constituents interface channel 730 while the pathogens diffuse to the small constituents interface channel 732.

Figure 116:
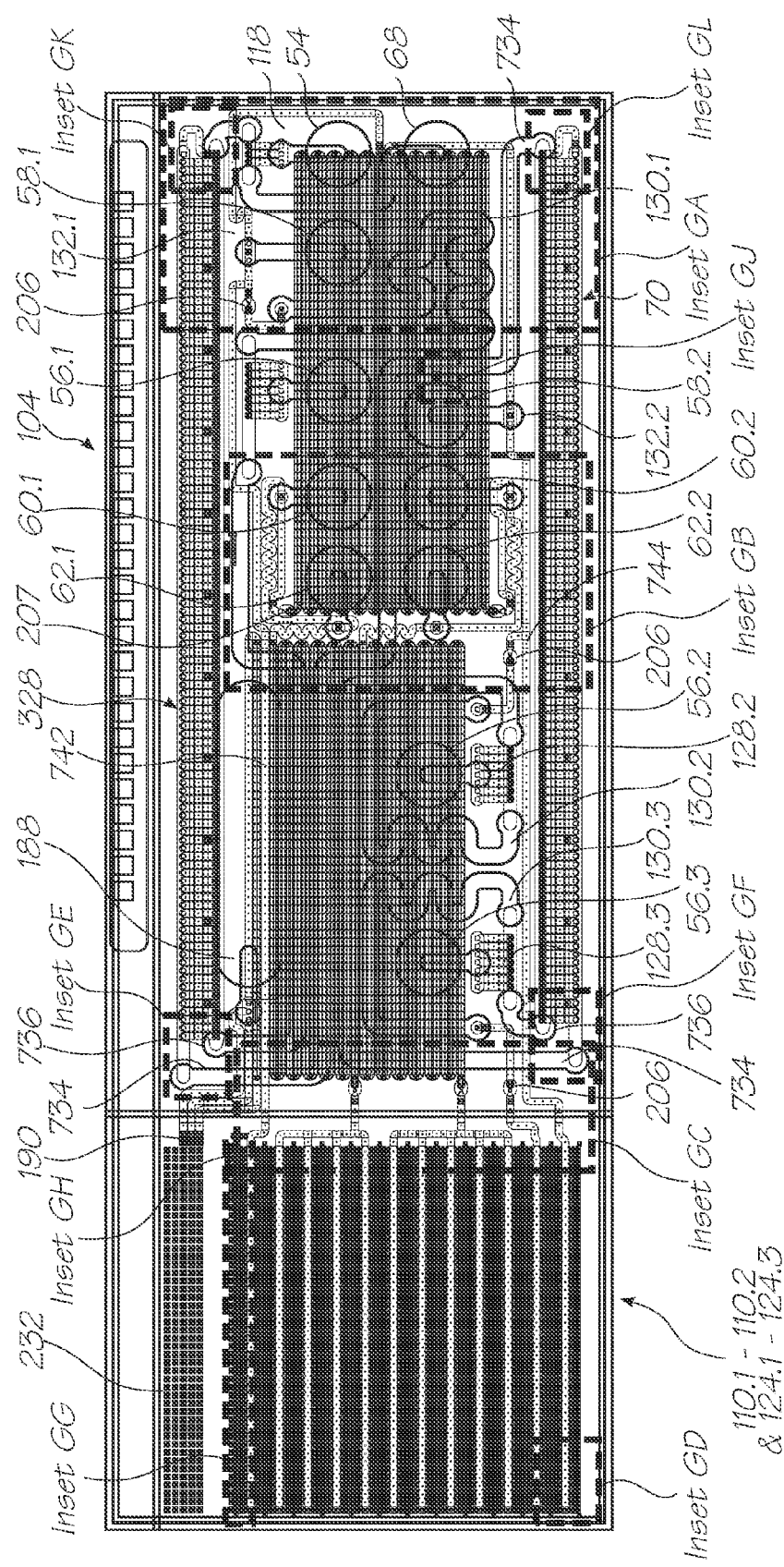
FIG. 116 is a plan view of LOC variant L showing all the features superimposed on each other and showing the locations of Insets GA to GL.

FIG. 122 shows the downstream end of the pathogen dialysis section 70. The erythrocytes flow into the large constituents cap channel 736 and the pathogens fill the small constituents cap channel 734. It will be appreciated that 'large constituents' and 'small constituents' are used in a relative sense as the large constituents output of the pathogen dialysis section is part of the small constituents output of the leukocyte dialysis section. The constituents in the large constituents cap 736 or interface channels are simply larger than the constituents in the small constituents cap 734 or interface channels within that particular dialysis section. As best shown in FIGS. 115 and 116, the erythrocytes in the large constituents cap channel 736 are directed to the surface tension valve 128.3 for the lysis reagent reservoir 56.3. The lysis reagent combines with the erythrocytes as the sample fluid fills the chemical lysis section 130.3. Boiling-initiated valve 206 at the outlet of the third chemical lysis section 130.3 retains the pathogens until lysis is complete. When the boiling-initiated valve 206 opens, the erythrocyte DNA flows directly into the proteomic assay chamber array 124.3 for protein analysis and detection by the photosensor 44 (see FIG. 119).

The pathogens in the small constituents cap channel 734 are directed to the surface tension valve 128.2 of the second lysis reagent reservoir 56.2. The lysis reagent combines with the pathogens as the sample fluid fills the second chemical lysis section 130.2. After sufficient time, the boiling-initiated valve 206 opens the chemical lysis section 130.2 outlet and the sample flow is split into two streams. As best shown in FIGS. 116 and 118, one stream flows to the surface tension valve 132.2 for the second restriction enzyme, ligase and linker reservoir 58.2 and the other stream is drawn along a bypass channel 744 directly to the hybridization and detection section 294. Here the sample fills the proteomic assay chamber array 124.2 (see FIG. 119) containing probes for hybridization with target pathogen proteins or other biomolecules. Probe-target hybrids are detected with the photosensor 44 (see FIG. 111).

The other stream flows into the pathogen incubation section 114.2 together with restriction enzymes, ligase and linker primers from reservoir 58.2. After restriction digestion and linker ligation, the incubator exit valve 207 (also a boiling-initiated valve) opens and flow continues into the pathogenic DNA amplification section 112.2 (see FIG. 118). As the chamber fills, the amplification mix and polymerase in reservoirs 60.2 and 62.2 are added via surface tension valves 138.2 and 140.2 respectively. After thermal cycling, the boiling-initiated valve 108 opens for the amplicon to flow into the second hybridization chamber array 110.2 containing probes for pathogenic DNA targets. Probe-target hybrids are detected with the photosensor 44 (see FIG. 119).

Referring to FIG. 120, the hybridization chamber arrays 110.1 and 110.2 and proteomic assay chamber arrays 124.1 to 124.3 have heater elements 182 made from strips of titanium nitride. There are end-point liquid sensors 178 that detect when the flow has reached the end of the hybridization chamber array or proteomic assay chamber array and the heaters 182 are then activated after a time delay. The flow rate sensor 740 (see FIG. 125) is included in the pathogen incubation section 114.2 to determine the time delay.

FIGS. 123 and 124 show the calibration chambers 382. They are used to calibrate the photodiodes 184 to adjust for system noise and background levels. The photodiode's response and electrical noise characteristics can vary with location and due to thermal variations. The output signal from calibration chambers 382, which do not contain any probes, closely approximates the noise and background in the output signal from all the chambers. Subtracting the calibration signal from the output signals generated by the other hybridization chambers substantially removes the noise and leaves the signal generated by the electrochemiluminescence (if any). Also, positive and negative control ECL probes 786 and 787 can be placed in some of the hybridization chambers 180 for assay quality control.

Referring to FIG. 116, a humidifier 196, composed of the water reservoir 188 and evaporators 190, is located in the top left of the device. The position of the humidity sensor 232 is adjacent to the hybridization chamber array 110 where humidity measurement is most important to slow evaporation from the solution containing the exposed probes.

By combining the leukocyte and pathogen output dialysis sections, three output streams are produced (leukocytes, erythrocytes, and pathogens and other biomolecules) which are processed separately to enable higher sensitivity and parallel analysis. The output from each stream is lysed and separately directed to the proteomic assay chamber arrays for protein detection. The lysed leukocytes and pathogens are also separately directed to the incubation 114 and amplification 112 sections for amplification, followed by hybridization for nucleic acid detection.

LOC Device with Thermal Insulation Trench

Figure 128:
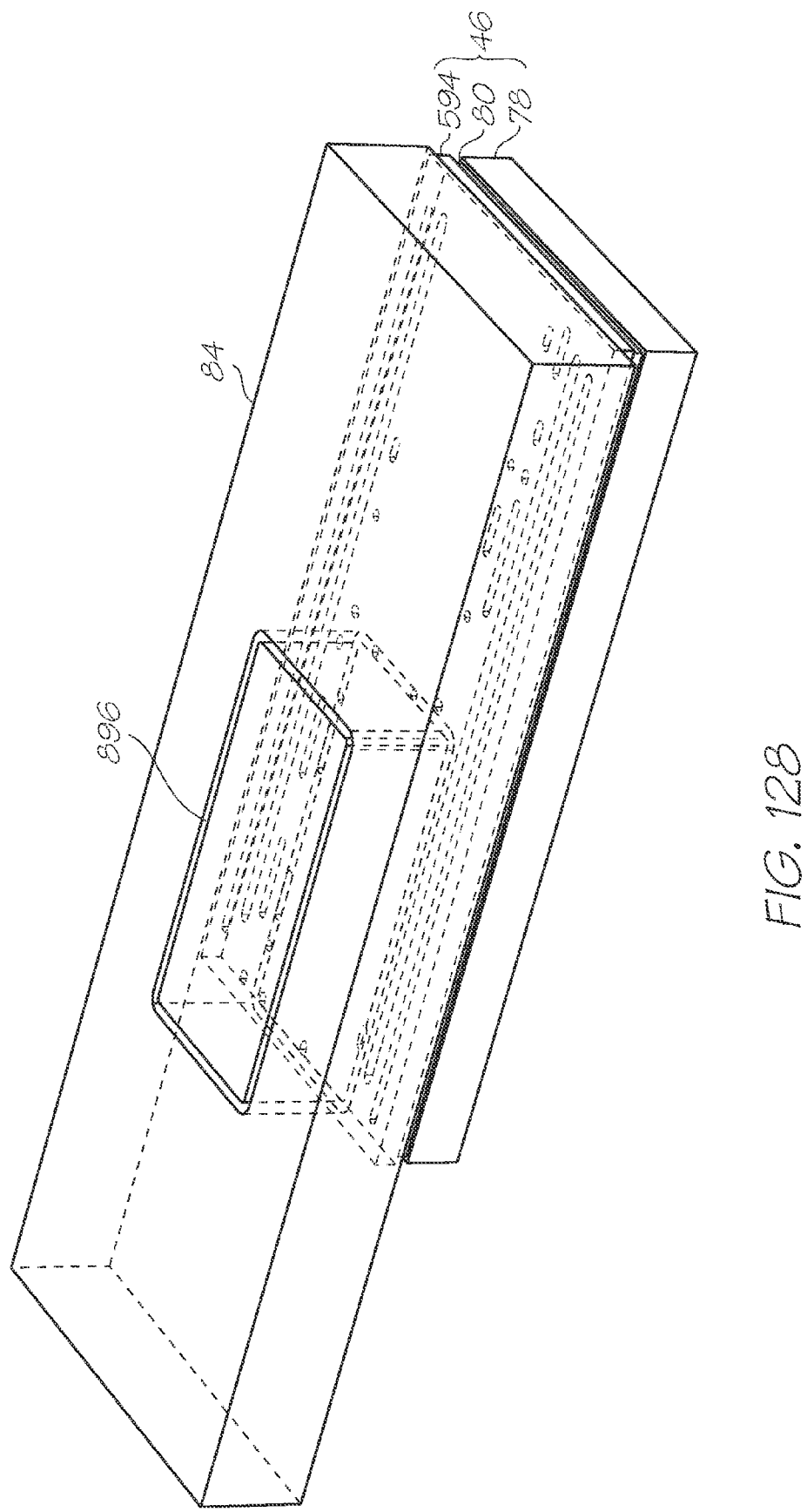
FIG. 128 is a diagrammatic representation of a LOC device with thermal insulation trench.

As best depicted in FIG. 128, a trench 896 is etched into the back of the silicon substrate 84. The purpose of the trench is to thermally insulate the amplification section 112 from the hybridization chamber array 110. The hybridization array contains detection probes that can degrade at high temperatures. The trench, when filled with air, has a thermal conductivity of the order of 6000 times less than that of the silicon substrate, thereby significantly reducing the heat flux into adjacent parts of the LOC device.

This provides two main advantages: an increase in the heating efficiency in the amplification section 112; and a reduction in the undesirable temperature rise of the adjacent hybridization section 110. Improved heating efficiency means less power is required to heat the amplification section 112 and the temperature reaches its desired end-point temperature faster and with better spatial uniformity within the amplification section. A reduction in the temperature rise in the hybridization section 110 allows for a wider range of probe chemistries and superior signal quality.

The trench can be placed around any region on the LOC device to thermally insulate the components in that region. The width and depth of the trench 896 are variable to suit the specific application.

Conclusion

The devices, systems and methods described here facilitate molecular diagnostic tests at low cost with high speed and at the point-of-care.

The system and its components described above are purely illustrative and the skilled worker in this field will readily recognize many variations and modifications which do not depart from the spirit and scope of the broad inventive concept.

The invention claimed is:

1. A test module for detecting target nucleic acid sequences in a fluid, the test module comprising:
   an outer casing having a receptacle for receiving the fluid containing the target nucleic acid sequences;
   electrochemiluminescent (ECL) probes having an ECL luminophore for emitting photons when in an excited state and a functional moiety for quenching photon emission from the ECL luminophore by resonant energy transfer;
   electrodes for receiving an electrical pulse to excite the ECL luminophores;
   a detection photosensor for exposure to the photons emitted by the ECL luminophores;
   an array of hybridization chambers containing the ECL probes for different target nucleic acid sequences; and,
   a plurality of calibration sources each configured to provide a calibration emission, the calibration sources being distributed throughout the array of hybridization chambers such that each of the calibration sources are surrounded by a three-by-three square of the hybridization chambers.

2. A test module according to claim 1 further comprising a lab-on-a-chip (LOC) device with circuitry for providing the electrical pulse to the electrodes wherein the detection photosensor is incorporated into the circuitry and the ECL probes, the electrodes, and the control circuitry are integrated into the LOC device.

3. A test module according to claim 2 wherein the LOC device has a supporting substrate for supporting the circuitry which in turn supports the electrodes and the ECL probes.

4. A test module according to claim 2 wherein the circuitry has layers of CMOS circuitry deposited on the supporting substrate for providing the electrodes with an electrical pulse.

5. A test module according to claim 4 wherein the electrical pulse has duration less than 0.69 seconds.

6. A test module according to claim 5 wherein the electrical pulse has a current of 0.1 nanoamperes to 69.0 nanoamperes.

7. A test module according to claim 6 further comprising:
   a communication interface for the circuitry to transmit data to an external device.

8. A test module according to claim 7 wherein the CMOS circuitry has memory for storing the identity data relating to the ECL probes in each of the hybridization chambers.

9. A test module according to claim 8 wherein the hybridization chambers have a volume less than 900,000 cubic microns.

10. A test module according to claim 9 wherein the hybridization chambers have a volume less than 200,000 cubic microns.

11. A test module according to claim 7 wherein the communication interface is a universal serial bus (USB) connection such that the outer casing is configured as a USB drive.

12. A test module according to claim 8 wherein the detection photosensor is an array of detection photodiodes positioned in registration with the hybridization chambers.

13. The test module according to claim 12 further comprising a calibration photosensor for sensing the calibration emissions, wherein the CMOS circuitry has a differential circuit for subtracting the calibration photosensor output from the output of one or more of the detection photodiodes.

14. The test module according to claim 13 wherein the calibration photosensor is a plurality of calibration photodiodes in registration with the calibration sources respectively.

15. The test module according to claim 14 wherein the calibration sources are calibration probes without an ECL luminophore.

16. The test module according to claim 14 further comprising a plurality of calibration chambers containing the calibration sources distributed throughout the array of hybridization chambers, wherein during use, output from any one of the detection photodiodes is compared to output from the calibration photodiode most proximate to that detection photodiode.

17. The test module according to claim 16 wherein the calibration sources are calibration probes and the calibration chambers are configured to seal the calibration probes from the fluid containing the target nucleic acid sequences.

18. The test module according to claim 12 wherein the detection photodiodes are less than 1600 microns from the hybridization chambers.

19. The test module according to claim 1 wherein the ECL probes have a stem-and-loop structure with a loop portion containing the sequence complementary to the target nucleic acid sequence, the loop portion being positioned between the functional moiety for quenching photon emission from the ECL luminophore, and the ECL luminophore, such that hybridization with the target nucleic acid sequence opens the loop portion and moves the ECL luminophore away from the functional moiety.

* * * * *